(12) United States Patent
Schug et al.

(10) Patent No.: US 12,281,084 B2
(45) Date of Patent: Apr. 22, 2025

(54) ACETYL-CoA SYNTHETASE 2 (ACSS2) INHIBITORS AND METHODS USING SAME

(71) Applicant: The Wistar Institute, Philadelphia, PA (US)

(72) Inventors: Zachary Schug, Philadelphia, PA (US); Joseph Salvino, Philadelphia, PA (US); Valli Venkata Srikanth Yellamelli, Philadelphia, PA (US)

(73) Assignee: The Wistar Institute, Philadelphia, PA (US)

( * ) Notice: Subject to any disclaimer, the term of this patent is extended or adjusted under 35 U.S.C. 154(b) by 728 days.

(21) Appl. No.: 17/618,397

(22) PCT Filed: Jun. 12, 2020

(86) PCT No.: PCT/US2020/037626
§ 371 (c)(1),
(2) Date: Dec. 10, 2021

(87) PCT Pub. No.: WO2020/252407
PCT Pub. Date: Dec. 17, 2020

(65) Prior Publication Data
US 2022/0281826 A1 Sep. 8, 2022

Related U.S. Application Data

(60) Provisional application No. 62/860,691, filed on Jun. 12, 2019.

(51) Int. Cl.
| | |
|---|---|
| *C07D 235/12* | (2006.01) |
| *A61K 31/4184* | (2006.01) |
| *A61K 31/437* | (2006.01) |
| *A61K 31/4545* | (2006.01) |
| *A61K 31/496* | (2006.01) |
| *A61K 31/5377* | (2006.01) |
| *A61P 35/00* | (2006.01) |
| *C07D 235/04* | (2006.01) |
| *C07D 401/12* | (2006.01) |
| *C07D 403/12* | (2006.01) |
| *C07D 471/04* | (2006.01) |
| *C07D 471/10* | (2006.01) |

(52) U.S. Cl.
CPC ........ *C07D 235/12* (2013.01); *A61K 31/4184* (2013.01); *A61K 31/437* (2013.01); *A61K 31/4545* (2013.01); *A61K 31/496* (2013.01); *A61K 31/5377* (2013.01); *A61P 35/00* (2018.01); *C07D 235/04* (2013.01); *C07D 401/12* (2013.01); *C07D 403/12* (2013.01); *C07D 471/04* (2013.01); *C07D 471/10* (2013.01)

(58) Field of Classification Search
None
See application file for complete search history.

(56) References Cited

U.S. PATENT DOCUMENTS

2014/0309261 A1 * 10/2014 Alford ................. C07D 235/12
514/394
2019/0062284 A1 2/2019 Hulme et al.

FOREIGN PATENT DOCUMENTS

| WO | WO-2007087518 A2 * | 8/2007 | ......... A61K 31/4184 |
|---|---|---|---|
| WO | 2015066241 A1 | 5/2015 | |
| WO | WO-2015175845 A1 * | 11/2015 | ......... A61K 31/4184 |
| WO | 2019097515 A1 | 5/2019 | |

OTHER PUBLICATIONS

International Search Report and Written Opinion, PCT/US2020/037626, dated Oct. 26, 2020.
Comerford, et al., "Acetate Dependence of Tumors", Cell, Dec. 18, 2014; 159(7): 1591-1602. doi:10.1016/j.cell.2014.11.020. PMCID: PMC4272450. NIHMSID: NIHMS642906. PMID: 25525877.
Gulick, et al., "The 1.75 Å crystal structure of acetyl-CoA synthetase bound to adenosine-5'-propylphosphate and coenzyme A†", Biochemistry, Mar. 18, 2003, 42(10), 2866-2873. PMID: 12627952. DOI: 10.1021/bi0271603 (Abstract only).
Staeben, et al., "Development and validation of a transcreener assay for detection of AMP- and GMP-producing enzymes", Assay Drug Dev Technol., Jun. 2010;8(3):344-55. doi: 10.1089/adt.2009.0254. PMID: 20158441. PMCID: PMC2894640.
Huang, et al., "Decade Progress of Organic Fluorine Chemistry in China", Higher Education Press, p. 94, Aug. 31, 1999.
European Search Report, EP Application No. 20821577, dated May 30, 2023.

* cited by examiner

*Primary Examiner* — Danah Al-Awadi
*Assistant Examiner* — Donna M Nestor
(74) *Attorney, Agent, or Firm* — Saul Ewing LLP; Kathryn Doyle; Domingos J. Silva

(57) ABSTRACT

The present disclosure provides compounds, which in certain embodiments are ACSS2 inhibitors. In certain embodiments, the compounds of the disclosure are useful for treating, ameliorating, and/or preventing certain types of cancer.

20 Claims, 30 Drawing Sheets
Specification includes a Sequence Listing.

FIG. 1D
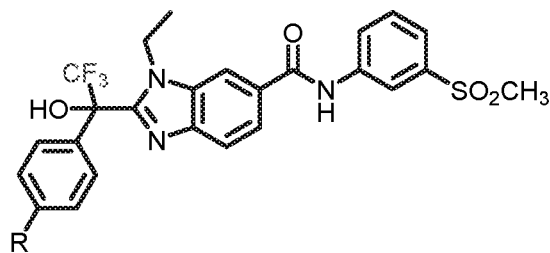
| R= F | Cmpd 1 | $IC_{50}$ = 164.1 nM |
| R= H | Cmpd 2 | $IC_{50}$ = 91.5 nM |
| R= OMe | Cmpd 3 | $IC_{50}$ = 411 nM |
| R= tBu | Cmpd 4 | $IC_{50}$ = 5944 nM |
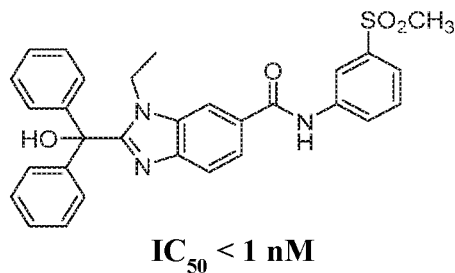
$IC_{50}$ < 1 nM
FIG. 1E
|  | Microsomal Stability Mouse Compound Conc=0.5μM n=1 | Microsomal Stability Human Compound Conc=0.5μM n=1 |
| --- | --- | --- |
| Control | Midazolam | Midazolam |
| Test Compound | Half life ($t_{1/2}$) (min) | Half life ($t_{1/2}$) (min) |
| Cmpd 1 | 62.2 | 288.8 |
| Cmpd 2 | 94.9 | 353.8 |

BT474

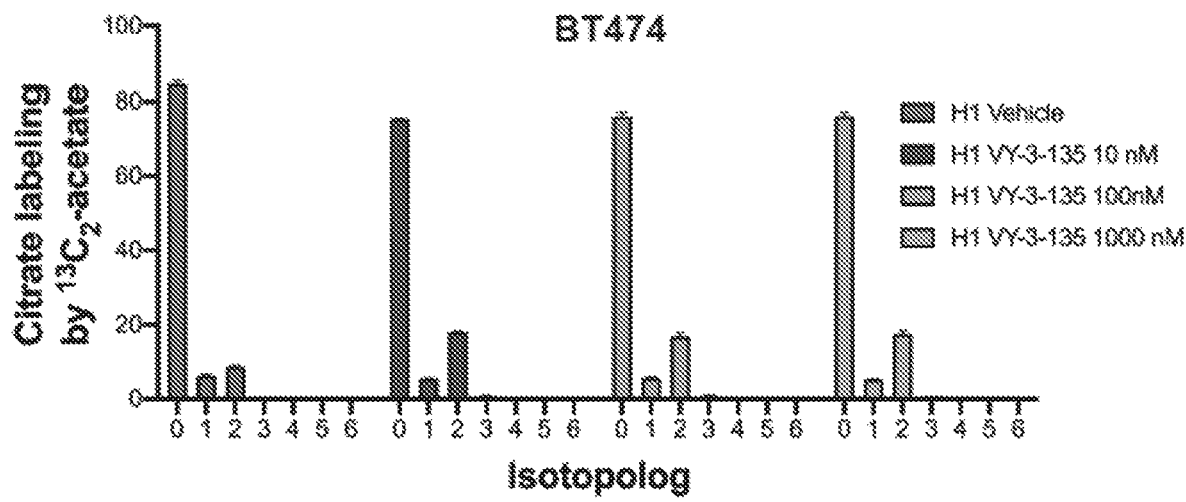

| H1/N10 | | N10 | | H1 | | Gene |
|---|---|---|---|---|---|---|
| fold | FDR | 1 | 2 | 1 | 2 | |
|  | 0% |  |  |  |  | MVD |
|  | 0% |  |  |  |  | HMGCS1 |
|  | 0% |  |  |  |  | LSS |
|  | 0% |  |  |  |  | FDFT1 |
|  | 0% |  |  |  |  | MSMO1 |
|  | 0% |  |  |  |  | FDPS |
|  | 0% |  |  |  |  | DHCR7 |
|  | 0% |  |  |  |  | HMGCR |
|  | 0% |  |  |  |  | HSD17B7 |
|  | 0% |  |  |  |  | TM7SF2 |
|  | 0% |  |  |  |  | CYP51A1 |
|  | 0% |  |  |  |  | IDI1 |
|  | 0% |  |  |  |  | ACAT2 |
|  | 0% |  |  |  |  | EBP |
|  | 0% |  |  |  |  | NSDHL |
|  | 0% |  |  |  |  | SQLE |
|  | 0% |  |  |  |  | SC5D |
| 1.6 | 2% |  |  |  |  | MVK |
| 1.4 | 2% |  |  |  |  | HMGCS2 |
| 1.4 | 0% |  |  |  |  | DHCR24 |
| -1.5 | 3% |  |  |  |  | ACAT1 |

FIG. 3B

| H1/N10 | | N10 | | H1 | | Gene |
|---|---|---|---|---|---|---|
| fold | FDR | 1 | 2 | 1 | 2 | |
|  | 0% |  |  |  |  | PFKP |
|  | 0% |  |  |  |  | PGK1 |
|  | 0% |  |  |  |  | ALDOA |
|  | 0% |  |  |  |  | GPI |
|  | 0% |  |  |  |  | ENO1 |
|  | 0% |  |  |  |  | PGAM1 |
|  | 0% |  |  |  |  | GAPDH |
|  | 0% |  |  |  |  | TPI1 |
|  | 0% |  |  |  |  | PKM |
| 1.4 | 3% |  |  |  |  | PFKL |

| H1/N10 fold | FDR | N10 1 | N10 2 | H1 1 | H1 2 | Gene |
|---|---|---|---|---|---|---|
| | 0% | | | | | ACSS2 |
| | 0% | | | | | PTGS1 |
| | 0% | | | | | VEGFA |
| | 0% | | | | | INSIG1 |
| | 0% | | | | | FASN |
| | 0% | | | | | FADS2 |
| | 0% | | | | | FADS1 |
| | 0% | | | | | ACSL1 |
| | 0% | | | | | EGFR |
| | 0% | | | | | ACLY |
| | 0% | | | | | INSIG2 |
| | 2% | | | | | PTGES |
| | 0% | | | | | ELOVL6 |
| | 0% | | | | | LDLR |
| | 0% | | | | | PRKAA2 |
| | 1% | | | | | ACSM3 |
| | 0% | | | | | ERBB4 |
| | 0% | | | | | SREBF1 |
| | 0% | | | | | ALOX15B |
| | 0% | | | | | PKM |
| | 0% | | | | | FOXO3 |
| | 1% | | | | | NPC1 |
| | 0% | | | | | MIF |
| | 0% | | | | | ACACA |
| | 0% | | | | | XBP1 |
| | 2% | | | | | MAP2K1 |
| 1.4 | 5% | | | | | ACSS1 |
| | 0% | | | | | ACSL3 |
| 1.3 | 4% | | | | | ACADVL |
| | 3% | | | | | SLC25A1 |

FIG. 3E

| H1/N10 | | H1/KD | H1/VY | N10 | | H1 | | KD | | VY | | Gene |
| fold | FDR | FDR | pv | 1 | 2 | 1 | 2 | 1 | 2 | 1 | 2 | |
|---|---|---|---|---|---|---|---|---|---|---|---|---|
| -1.6 | 0% | 3% | 9E-06 | | | | | | | | | RBM3 |
| -1.6 | 0% | 0% | 4E-04 | | | | | | | | | MCM7 |
| -1.7 | 0% | 0% | 0.002 | | | | | | | | | HIST1H2BC |
| -1.8 | 0% | 0% | 0.002 | | | | | | | | | HIST2H2AC |
| -2.0 | 0% | 0% | 0.003 | | | | | | | | | CENPH |
| -1.6 | 4% | 1% | 0.003 | | | | | | | | | HIST1H4C |
| -1.7 | 0% | 0% | 0.004 | | | | | | | | | HIST1H2BE |
| -1.5 | 0% | 0% | 0.004 | | | | | | | | | HIST1H2BG |
| -1.5 | 1% | 0% | 0.005 | | | | | | | | | MAD2L1 |
| -2.1 | 0% | 1% | 0.006 | | | | | | | | | FBXO5 |
| -1.5 | 0% | 0% | 0.012 | | | | | | | | | PCNA |
| -1.5 | 0% | 1% | 0.016 | | | | | | | | | NCAPG2 |
| -1.3 | 3% | 3% | 0.023 | | | | | | | | | DHX15 |
| -1.5 | 0% | 4% | 0.026 | | | | | | | | | RFWD3 |
| -1.6 | 1% | 0% | 0.027 | | | | | | | | | ODC1 |
| -1.7 | 0% | 0% | 0.041 | | | | | | | | | FIGNL1 |
| -1.5 | 0% | 2% | 0.047 | | | | | | | | | KNTC1 |
| 1.3 | 0% | 3% | 0.028 | | | | | | | | | DYNC1H1 |
| 1.4 | 1% | 1% | 0.023 | | | | | | | | | RP11-206M11.7 |
| 1.9 | 0% | 0% | 0.01 | | | | | | | | | LRP2 |
| 1.4 | 0% | 4% | 0.007 | | | | | | | | | MACF1 |

FIG. 3F

| Canonical Pathways | N | FDR | % up | Z |
|---|---|---|---|---|
| Cell Cycle Control of Chromosomal Replication | 6 | 5x10⁻⁵ | | na |
| Mitotic Roles of Polo-Like Kinase | 6 | 7x10⁻⁵ | | 1.0 |
| Cell Cycle: G2/M DNA Damage Checkpoint Regulation | 5 | 0.0002 | | |
| DNA Methylation and Transcriptional Repression Signaling | 4 | 0.0009 | | na |
| GADD45 Signaling | 3 | 0.0029 | | na |
| Transcriptional Regulatory Network in Embryonic Stem Cells | 4 | 0.0034 | | na |
| Sirtuin Signaling Pathway | 7 | 0.013 | 43% | -0.4 |
| ATM Signaling | 4 | 0.025 | | na |
| RAN Signaling | 2 | 0.045 | | na |

FIG. 7C
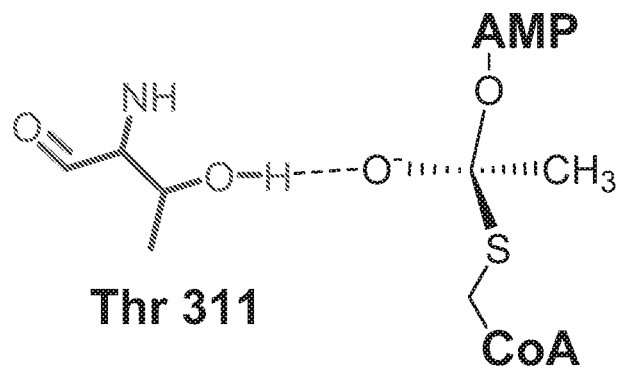
Putative Tetrahedral Transition State Stabilized by Thr 416
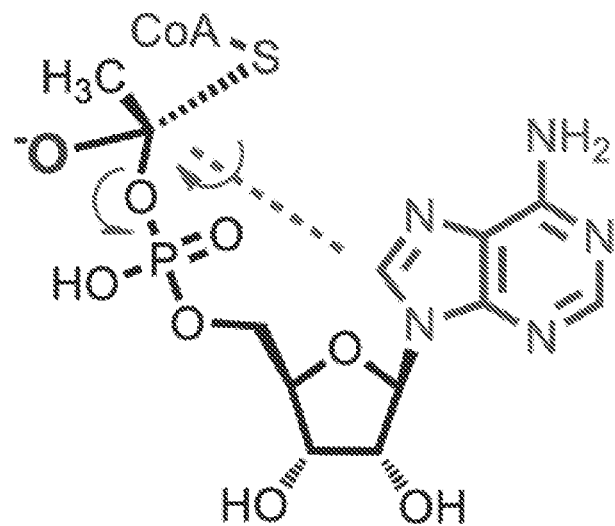
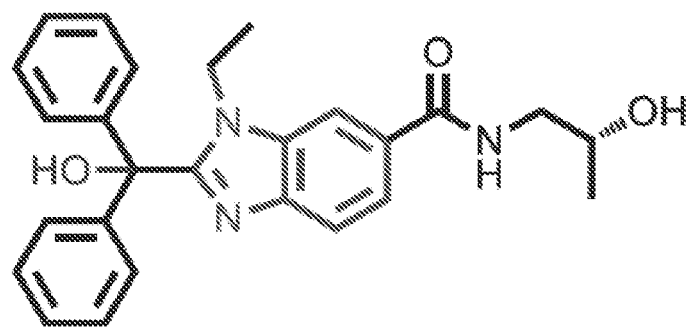

| H1/N10 fold | H1/KD FDR | H1/VY FDR | pv | N10 1 | 2 | H1 1 | 2 | KD 1 | 2 | VY 1 | 2 | Gene |
|---|---|---|---|---|---|---|---|---|---|---|---|---|
|  | 0% | 0% | 0.68 |  |  |  |  |  |  |  |  | ACSS2 |
|  | 0% | 0% | 0.05 |  |  |  |  |  |  |  |  | RP11-809N8.5 |
|  | 0% | 2% | 0.50 |  |  |  |  |  |  |  |  | CNTN1 |
|  | 0% | 0% | 0.23 |  |  |  |  |  |  |  |  | AGPAT5 |
| 1.4 | 0% | 0% | 0.25 |  |  |  |  |  |  |  |  | ESYT2 |
| 1.4 | 2% | 2% | 0.29 |  |  |  |  |  |  |  |  | HMGCS2 |
| 1.4 | 0% | 0% | 0.88 |  |  |  |  |  |  |  |  | IGFBP5 |
| 1.4 | 0% | 1% | 0.08 |  |  |  |  |  |  |  |  | P4HB |
| 1.3 | 1% | 0% | 0.75 |  |  |  |  |  |  |  |  | CLCA2 |

FIG. 13

| Tukey's multiple comparisons test | Mean Diff. | 95.00% CI of diff. | Summary | Adjusted P Value |
|---|---|---|---|---|
| Basal vs. HER2 | -0.2026 | -0.3428 to -0.06238 | *** | 0.0006 |
| Basal vs. LumA | -0.09967 | -0.2152 to 0.01585 | ns | 0.1363 |
| Basal vs. LumB | 0.08455 | -0.03701 to 0.2061 | ns | 0.3518 |
| Basal vs. Normal-like | -0.3718 | -0.5299 to -0.2137 | **** | <0.0001 |
| Basal vs. Claudin-low | 0.0197 | -0.1240 to 0.1634 | ns | 0.9968 |
| HER2 vs. LumA | 0.1029 | -0.008265 to 0.2141 | ns | 0.0882 |
| HER2 vs. LumB | 0.2871 | 0.1697 to 0.4046 | **** | <0.0001 |
| HER2 vs. Normal-like | -0.1692 | -0.3241 to -0.01428 | * | 0.0229 |
| HER2 vs. Claudin-low | 0.2223 | 0.08208 to 0.3625 | **** | <0.0001 |
| LumA vs. LumB | 0.1842 | 0.09773 to 0.2707 | **** | <0.0001 |
| LumA vs. Normal-like | -0.2721 | -0.4051 to -0.1391 | **** | <0.0001 |
| LumA vs. Claudin-low | 0.1194 | 0.003849 to 0.2349 | * | 0.0381 |
| LumB vs. Normal-like | -0.4563 | -0.5946 to -0.3180 | **** | <0.0001 |
| LumB vs. Claudin-low | -0.06484 | -0.1864 to 0.05671 | ns | 0.6502 |
| Normal-like vs. Claudin-low | 0.3915 | 0.2334 to 0.5496 | **** | <0.0001 |

FIG. 14A

| FC | p | fdr | Vehicle 1 | 2 | 3 | 4 | VY-3-135 1 | 2 | 3 | 4 | Gene Name |
|---|---|---|---|---|---|---|---|---|---|---|---|
| | 2E-05 | 13% | | | | | | | | | PDE2A |
| | 0.004 | 100% | | | | | | | | | MCTP2 |
| | 0.004 | 100% | | | | | | | | | MIR210HG |
| | 0.001 | 100% | | | | | | | | | TNFAIP3 |
| | 0.004 | 100% | | | | | | | | | TCN1 |
| | 0.001 | 100% | | | | | | | | | CTD-2619J13.14 |
| | 0.01 | 100% | | | | | | | | | HIST2H4A |
| | 0.001 | 100% | | | | | | | | | SNRK |
| | 0.014 | 100% | | | | | | | | | GJB1 |
| | 0.008 | 100% | | | | | | | | | RP11-227G15.8 |
| | 0.02 | 100% | | | | | | | | | SCD5 |
| | 0.015 | 100% | | | | | | | | | TMPRSS11E |
| | 0.003 | 100% | | | | | | | | | CTD-2033D15.2 |
| | 0.017 | 100% | | | | | | | | | CFD |
| | 0.007 | 100% | | | | | | | | | C10orf35 |
| | 0.01 | 100% | | | | | | | | | CACNB1 |
| | 0.015 | 100% | | | | | | | | | RNY1P9 |
| | 0.031 | 100% | | | | | | | | | AQP1 |
| | 0.022 | 100% | | | | | | | | | WNT2B |
| | 0.018 | 100% | | | | | | | | | PACSIN1 |
| | 0.023 | 100% | | | | | | | | | SYNE3 |
| | 0.028 | 100% | | | | | | | | | ENDOU |
| | 0.033 | 100% | | | | | | | | | DTX1 |
| | 0.012 | 100% | | | | | | | | | LIN37 |
| | 3E-04 | 100% | | | | | | | | | RAB11FIP5 |

FIG. 14B

| FC | p | fdr | \multicolumn{8}{c|}{BT474 tumors} | Gene Name |
| --- | --- | --- | --- | --- | --- | --- | --- | --- | --- | --- | --- |
| | | | \multicolumn{4}{c|}{Vehicle} | \multicolumn{4}{c|}{VY-3-135} | |
| | | | 1 | 2 | 3 | 4 | 1 | 2 | 3 | 4 | |
| 2.17 | 4E-04 | 100% | | | | | | | | | RP11-11N7.5 |
| 2.06 | 0.004 | 100% | | | | | | | | | VMAC |
| -1.92 | 0.014 | 100% | | | | | | | | | RP11-619I22.1 |
| 1.85 | 0.008 | 100% | | | | | | | | | RNU6-549P |
| 1.83 | 0.024 | 100% | | | | | | | | | ZNF337-AS1 |
| -1.80 | 0.015 | 100% | | | | | | | | | SCML1 |
| -1.74 | 0.023 | 100% | | | | | | | | | ENO1-IT1 |
| -1.73 | 0.014 | 100% | | | | | | | | | ZNF93 |
| -1.72 | 0.006 | 100% | | | | | | | | | C18orf54 |
| -1.69 | 0.007 | 100% | | | | | | | | | TMEM220 |
| 1.69 | 0.031 | 100% | | | | | | | | | MAP3K12 |
| -1.68 | 0.037 | 100% | | | | | | | | | ZNF333 |
| -1.67 | 0.027 | 100% | | | | | | | | | ACYP1 |
| 1.67 | 0.02 | 100% | | | | | | | | | TFAP2A-AS1 |
| -1.67 | 0.002 | 100% | | | | | | | | | RNASEH1-AS1 |
| 1.63 | 0.003 | 100% | | | | | | | | | HSD17B7 |
| -1.63 | 0.049 | 100% | | | | | | | | | LINC00630 |
| -1.60 | 0.027 | 100% | | | | | | | | | RP11-319F12.2 |
| -1.57 | 0.044 | 100% | | | | | | | | | AL133243.1 |
| 1.57 | 0.018 | 100% | | | | | | | | | KRT17 |
| -1.57 | 0.037 | 100% | | | | | | | | | KBTBD11 |
| -1.56 | 0.005 | 100% | | | | | | | | | WARS2 |
| 1.55 | 0.022 | 100% | | | | | | | | | CTB-178M22.2 |
| -1.55 | 0.006 | 100% | | | | | | | | | ZNF678 |
| -1.55 | 0.005 | 100% | | | | | | | | | AC007191.4 |

FIG. 14C

| Type | Regulator | p | % Up | State | z |
| --- | --- | --- | --- | --- | --- |
| ligand-dependent nuclear receptor | ESR1 | 7E-06 | | Inhibited | |
| chemical drug | imipramine blue | 0.0003 | | Activated | |
| transcription regulator | KDM5B | 0.0451 | | Activated | |
| chemical drug | imatinib | 0.0042 | | Activated | |
| transcription regulator | TP53 | 0.0064 | | Activated | |

FIG. 15
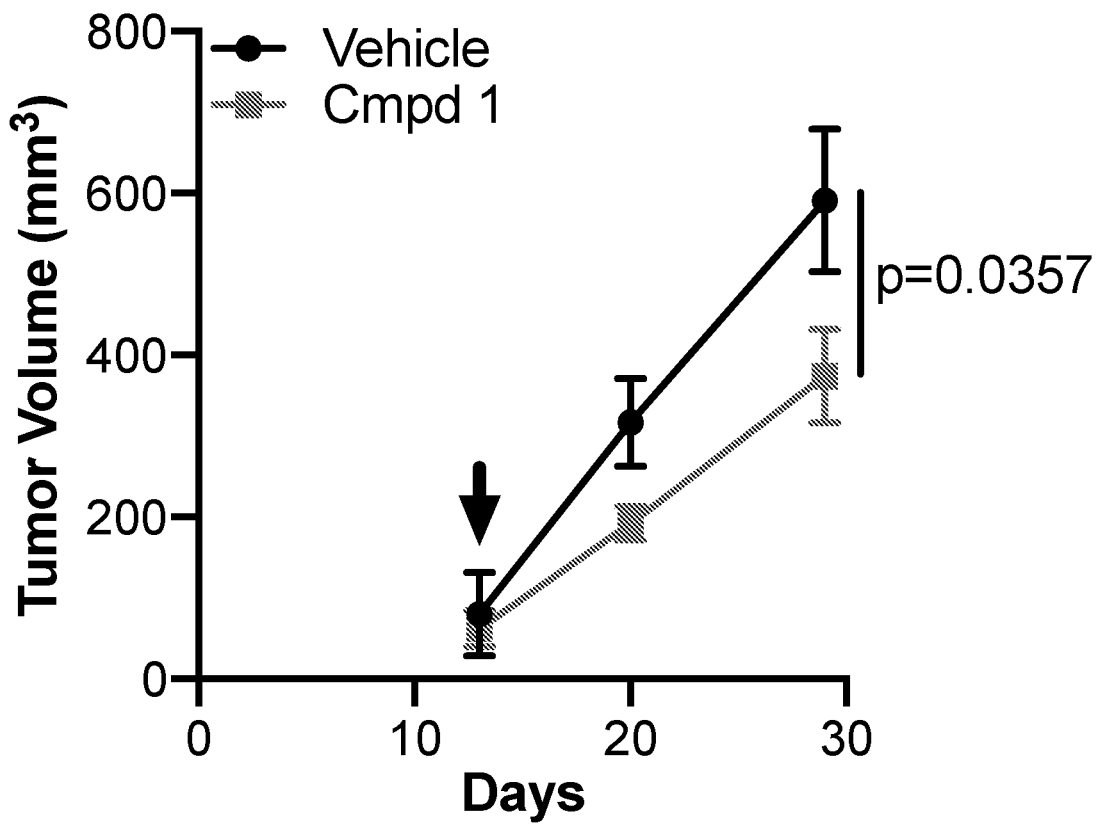
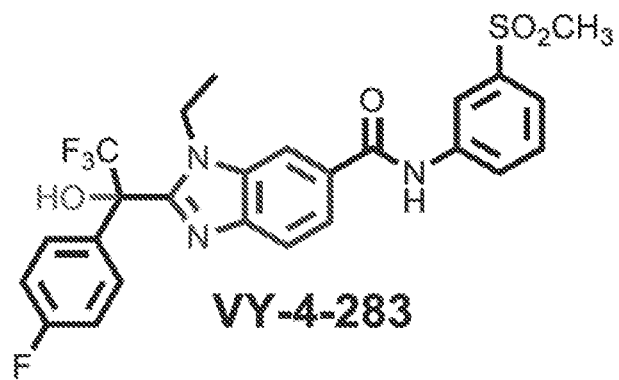
VY-4-283

FIG. 16A
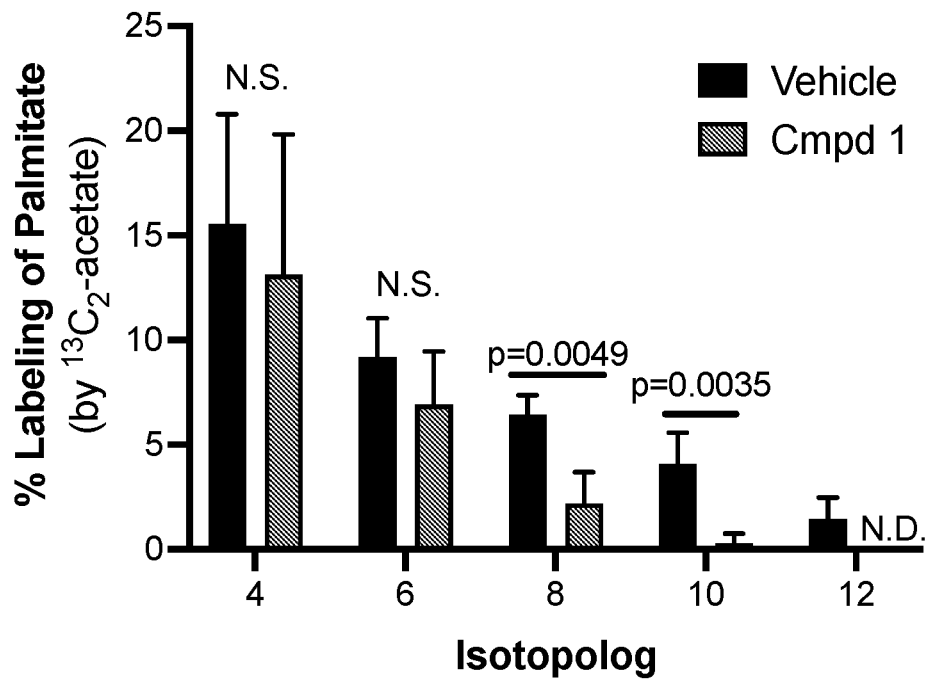
FIG. 16B
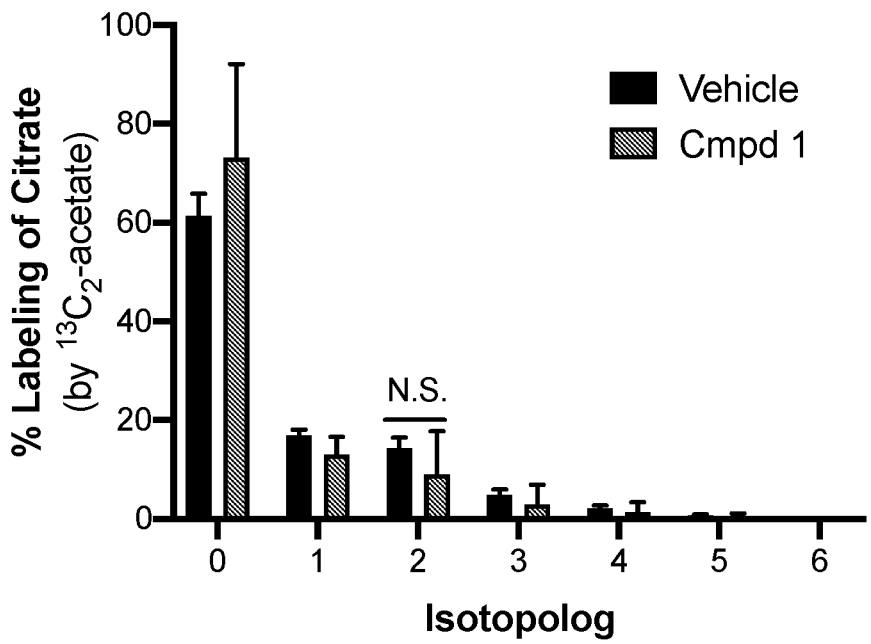
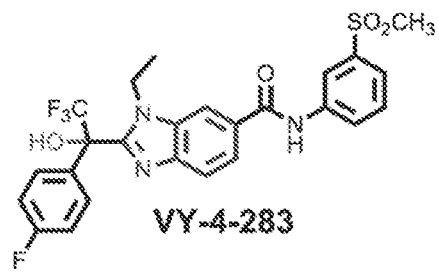

FIG. 17A
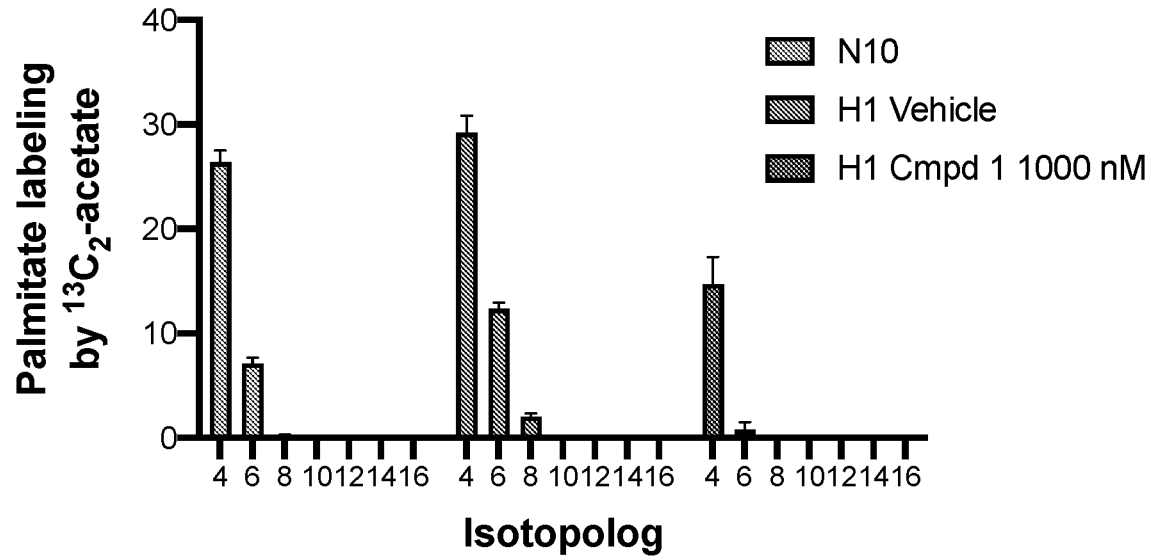
FIG. 17B
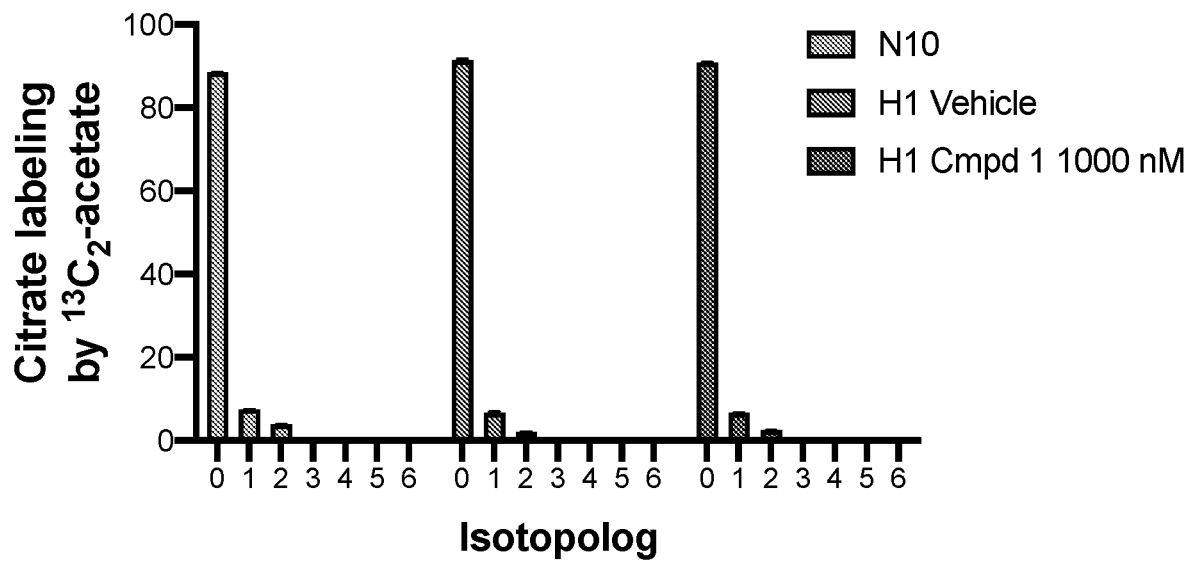
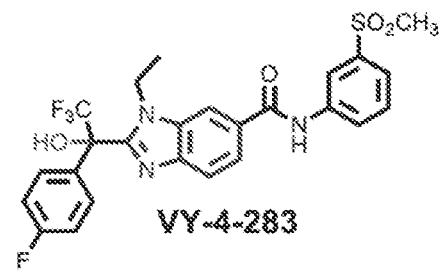

ACETYL-CoA SYNTHETASE 2 (ACSS2) INHIBITORS AND METHODS USING SAME

CROSS-REFERENCE TO RELATED APPLICATIONS

The present application is a 35 U.S.C. § 371 national phase application from, and claiming priority to, International Application No. PCT/US2020/037626, filed Jun. 12, 2020, which claims priority under 35 U.S.C. § 119 (e) to U.S. Provisional Application No. 62/860,691, filed Jun. 12, 2019, all of which are hereby incorporated by reference in their entireties.

STATEMENT REGARDING FEDERALLY SPONSORED RESEARCH OR DEVELOPMENT

This invention was made with government support under P30 CA010815-51 and DP2 CA249950-01 awarded by National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM

This invention contains sequences in a computer readable format in an accompanying text file titled "368530-7024US1", which is 11.7 KB in size and was created Dec. 10, 2021, the contents of which are incorporated herein by reference in their entirety.

BACKGROUND OF THE DISCLOSURE

Autopsy and clinical data indicate that nearly 100,000 cancer patients will develop brain metastases (mets) this year. This statistic clearly demonstrates that the magnitude of the problem is substantial, affecting patients in numbers that approach the incidence rates of some of the most common primary cancer types. Unfortunately for these patients, there are no specific therapeutic options for treating brain mets and, as such, there is an unmet need for novel targeted therapies.

The tumor microenvironment is a dynamic, ever-changing landscape that rapidly evolves as the tumor progresses. Solid tumors often contain regions where oxygen and other nutrients are highly restricted due to inadequate tumor vascularization and/or rapid cancer cell proliferation. Cancer cells can adapt to these hypoxic, nutrient-poor regions by altering their metabolism. Such metabolically-adapted tumor cells are often more invasive, more metastatic, and more drug resistant, and as a result, they are more likely to cause relapse after treatment.

Altered metabolism has thus recently emerged as an exciting cancer research field and is now recognized as one of the hallmarks of cancer. Many (if not all) brain mets, regardless of the primary tumor site, undergo a metabolic switch in the brain microenvironment and obtain about 50% of their energy from the oxidation of the nutrient acetate. Acetate satisfies several needs for cancer cells during hypoxic stress. In one aspect, acetyl-CoA synthetases (ACSSs) capture and convert acetate into acetyl-CoA, which is then used for histone acetylation. The subsequent epigenetic changes activate genes associated with therapy resistance (BCL2, PD-L1, and fatty acid metabolism) and metastasis (MMP9 and interferon stimulated genes). In another aspect, acetate is used to synthesize a number of macromolecules for cancer cell growth such as fatty acids, cholesterols, and hexosamines. In yet another aspect, acetate is oxidized by mitochondria to produce ATP.

This unique capture and metabolism of acetate by tumors supports their growth. In fact, the enzyme acetyl-CoA synthetase 2 (ACSS2) is critical for the capture and utilization of acetate as a nutritional source by the tumor. Silencing ACSS2 expression by inducible shRNAs or CRISPR-Cas9 sgRNAs in breast, prostate, and colorectal cancer cell lines inhibits tumor xenograft growth. Consistently, crossing $Acss2^{-/-}$ mice into two different genetically engineered mouse models of hepatocellular carcinoma significantly reduced tumor burden and promoted well-differentiated tumors. Knockdown of ACSS2 in a melanoma xenograft also strongly inhibited tumor growth. Multiple tissue microarrays in breast, ovarian, and lung cancer demonstrated that ACSS2 is highly expressed in cancerous tissue compared to normal adjacent tissue. High ACSS2 expression also correlates with poorer outcome in triple negative breast cancer and glioblastoma patients.

Expression of ACSS2 is emerging as one of the key factors in the regulation of acetate metabolism: ACSS2 expression endows cancer cells with the ability to maximally utilize acetate as a nutritional source. Interestingly, ACSS2 is strongly upregulated by hypoxia and low nutrient availability, suggesting that it is an important enzyme for coping with the typical stresses within the tumor microenvironment and, as such, a potential Achilles heel. Moreover, highly stressed regions of tumors select for apoptotic resistance and promote aggressive behavior, treatment resistance, and relapse.

There is thus a need in the art for novel compounds that inhibit ACSS2. Such compounds should be useful for treating and/or preventing cancers which growth is at least partially supported by acetate metabolism. The present disclosure fulfills this need.

BRIEF SUMMARY OF THE DISCLOSURE

The disclosure provides certain compound of Formula (I), or an enantiomer, diastereoisomer, tautomer, salt, and/or solvate thereof:

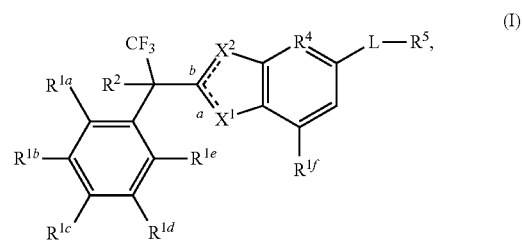

wherein variables $R^{1a}$-$R^{1f}$, $R^2$, $R^4$, $R^5$, a, b, $X^1$, $X^2$, and L are defined elsewhere herein.

The disclosure further provides a method of treating, ameliorating, and/or preventing a disease or disorder that is caused, induced, or characterized by abnormal expression or activity of ACSS2 in a subject, the method comprising administering to the subject a therapeutically effective amount of at least one compound contemplated herein.

The disclosure further provides a method of reducing the rate of, reversing, and/or preventing conversion of a non-metastatic cancer cell to a metastatic cancer cell, the method comprising contacting the cell with an effective amount of at least one compound contemplated herein.

The disclosure further provides a method of reducing the rate of, reversing, and/or preventing development of a hypoxic region in a cancer in a subject, the method comprising administering to the subject a therapeutically effective amount of at least one compound contemplated herein.

The disclosure further provides a method of increasing effectiveness of chemotherapy, radiotherapy, and/or immunotherapy administered to a subject suffering from a cancer, the method comprising administering to the subject a therapeutically effective amount of at least one compound contemplated herein and at least one of chemotherapy, radiotherapy, and immunotherapy.

BRIEF DESCRIPTION OF THE DRAWINGS

For the purpose of illustrating the disclosure, there are depicted in the drawings certain embodiments of the disclosure. However, the disclosure is not limited to the precise arrangements and instrumentalities of the embodiments depicted in the drawings.

FIGS. 1A-1E depict ACSS2 inhibition. (FIG. 1A) Schematic of the forward reaction catalyzed by ACSS2, showing substrates and products. (FIG. 1B) Chemical structures of VY-3-249 and VY-3-135. (FIG. 1C) $IC_{50}$ determination for VY-3-135 and VY-3-249. Data represent mean±standard deviation (S.D.), n≥3. (FIG. 1D) Selected ACSS2 inhibitor compounds contemplated within the disclosure. (FIG. 1E) Table summarizing liver microsome stability data for certain compounds of the disclosure.

FIGS. 2A-2D depict that an illustrative ACSS2 small molecule inhibitor is a potent inhibitor of ACSS2 in cells. (FIG. 2A) Immunoblot for ACSS2 expression in a small panel of human breast cancer cell lines. (FIG. 2B) Enrichment of 100 μM $^{13}C_2$-acetate in the intracellular palmitate pool in SKBr3 cells treated with vehicle or VY-3-135 and cultured in normoxia and SMEM+10% serum (N10) or hypoxia and SMEM+1% serum (H1) over a 24 hr period. Data represent mean±S.D., n=3. (FIG. 2C) Enrichment of 100 μM $^{13}C_2$-acetate into palmitate in BT474 cells cultured in hypoxia and SMEM+1% serum (H1) over a 24 hr period using a 10-fold dilution series of VY-3-135. Data represent mean±S.D., n=3. (FIG. 2D) Enrichment of $^{13}C_2$-acetate into the intracellular citrate pool. Experimental parameters were identical to FIG. 2C.

FIGS. 3A-3F show that an illustrative ACSS2 small molecule inhibitor does not alter transcriptional responses to metabolic stress. (FIG. 3A) Top ten pathways that are most significantly enriched (FDR<5%) based on RNA sequencing of BT474 cells that were exposed to metabolic stress, defined as hypoxia and SMEM+1% serum (H1) over a 24 hr period. n=2 per condition. (FIG. 3B) Heatmap, including FDR values and fold change for the 21 genes within the Superpathway of Cholesterol Biosynthesis from FIG. 3A. (FIG. 3C) Heatmap, including FDR values and fold change for the ten genes within the Glycolysis I pathway from FIG. 3A. (FIG. 3D) Heatmap, including FDR values and fold change for fatty acid biosynthesis genes that are induced in response to hypoxia and low lipid stress. (FIGS. 3E-3F) Heatmap showing pairwise comparisons of fold change for differentially regulated genes (FDR<5%) genes in BT474 cells after siRNA mediated knockdown of ACSS2 (KD) and VY-3-135 treatment in BT474 cells exposed to hypoxia and low lipid stress (H1). (FIG. 3F) List of the ten canonical pathways that had an FDR<5% after siRNA mediated knockdown of ACSS2.

(FIG. 4A) Immunoblot for EGFR and HER2 expression in a small panel of human breast cancer cell lines. (FIG. 4B) Box and whiskers plot showing median, $25^{th}$ to $75^{th}$ percentiles, and min to max values of ACSS2 mRNA expression in human breast cancer cell lines. mRNA expression data were obtained from the Cancer Cell Line Encyclopedia. Pos (+)=HER2 and/or EGFR amplification. Neg (−)=no amplification. Unpaired, two tailed, Mann-Whitney test. n=58 cell lines. (FIG. 4C) mRNA expression of ACSS2 in six different subtypes of breast cancer. One-way ANOVA with a Tukey's multiple comparisons test. Adjusted p values are reported on the graphs. (FIG. 4D) mRNA expression of ACSS2 in HER2+ tumors (Pos (+)) versus all other subtypes of breast cancer (Neg (−)). Mann-Whitney test, two tailed. p value is on the graph. (FIG. 4E) mRNA expression of ACSS2 in TNBC patient tumors stratified by EGFR copy number alterations. Shl Del=shallow deletion, Gain=copy number gains, and Amp=gene amplification. One-way ANOVA with a Tukey's multiple comparisons test. Adjusted p values are reported on the graphs.

(FIG. 5A) ACSS2 protein expression in cell lines derived from four different transgenic models of breast cancer. Lysates from two independent MMTV-Neu tumors (63h and 164h), two independent MMTV-Polyoma Middle T tumors (PyMT; 70g and 76g) were screened as well as syngeneic breast cancer cell lines derived from p53/Ras (A7C11) and p53/Kras/PI3K mouse tumors (Brpkp110). (FIG. 5B) Immunoblot for ACSS2 protein expression in A7C11 and Brpkp110 cells after CRISPR-Cas9 targeting of Acss2. Lysates were prepared from cells grown in normoxia and SMEM+10% serum (N10) or hypoxia and SMEM+1% serum (H1) over a 24 hr period. sgNTC=single guide RNA against non-targeting control. sgACSS2=single guide RNA against Acss2. (FIG. 5C) CRISPR-Cas9 knockout of Acss2 in A7C11 cells has a modest effect on tumor growth. Data represent mean±standard error of the means (S.E.M.) with ANOVA p value displayed, n=5. (FIG. 5D) CRISPR-Cas9 knockout of Acss2 in Brpkp110 cells causes a significant decrease in tumor growth. Data represent mean±S.E.M. with ANOVA p value displayed, n=5. (FIG. 5E) VY-3-135 treatment causes a significant decrease in Brpkp110 tumor growth. Data represent mean±S.E.M. with ANOVA p value displayed, n=5. (FIG. 5F) VY-3-135 treatment did not further affect the growth of Brpkp110 sgACSS2 tumors that lack expression of ACSS2. Data represent mean±S.E.M. with ANOVA p value displayed, n=5.

(FIG. 6A) VY-3-135 treatment causes a significant decrease in BT474+ luciferase tumor growth. Black arrow indicates start of treatment. ANOVA p value is displayed, n=5 mice per group, dual flank injection. (FIG. 6B) Bioluminescent imaging of mice from FIG. 6A on day 14. Insets above show the corresponding tumors excised at the end of the study on day 28. (FIG. 6C) Fractional labeling of intratumoral palmitate by $^{13}C_2$-acetate in BT474 tumors that were treated with vehicle or VY-3-135. N.D.=not detected by the mass spectrometer. Two-way ANOVA with Sidak's multiple comparison test, adjusted p values are shown on the graph, n≥6. (FIG. 6D) Fractional labeling of intratumoral citrate by $^{13}C_2$-acetate in BT474 tumors that were treated with vehicle or VY-3-135. Two-way ANOVA with Sidak's multiple comparison test, adjusted p values are shown on the graph, n≥6. (FIG. 6E) Volcano plot comparing log 2 fold change in metabolite abundance versus log 10(FDR) in BT474 tumors. Red dots represent metabolites that have an FDR<5% or log 10(FDR)>1.31. (FIG. 6F) Metabolites that displayed increases after VY-3-135 treatment. Data represent mean peak area, with individual data points shown, for each metabolite per mg of wet tumor weight in vehicle versus VY-3-135 treated BT474 tumors. Two tailed t test with adjusted p values are reported.

FIGS. 7A-7C illustrate certain structural considerations relating to the binding of compounds of the disclosure to ACSS2. FIG. 7A: AMP-propyl ester (in blue) bound to the ACSS2 active site (pdb: 1PG3), showing the close proximity of certain binding residues and the Thr 311 residue which stabilizes the oxyanion transition state. FIG. 7B: Schematic of the lead compound Cmpd 1 with key residues in relative positions to highlight important binding interactions for rational lead optimization. FIG. 7C: Schematic of the putative tetrahedral transition state mimicked by enzyme inhibitors. Without wishing to be limited by any theory, an illustrative ACSS2 small molecule inhibitor is a transition state mimetic of ACSS2. The adenine moiety (green) is in close proximity to the oxyanion (blue) in the reaction center which suggests that the alcohol moiety (blue) in VY-3-135 is mimicking the oxyanion and the benzimidiazole is mimicking the adenine.

FIG. 8 illustrates alignment of human and *salmonella* ACSS2, showing key conserved residues.

(FIG. 10A) AMP standard curve using a 3-fold serial dilution starting at 10 µM. (FIG. 10B) Enzyme titration in the presence and absence of 140 mM NaCl was performed using a 2-fold serial dilution starting at 100 nM. n=1. (FIGS. 10C-10D) $K_m$ and $V_{max}$ determination for coenzyme A and ATP. Concentrations of reactants ranged from 5 µM to 100 µM. n=1.

(FIG. 11A) Schematic of carbon-13 tracing with $^{13}C_2$-acetate in citrate, fatty acids, and phospholipids. (FIG. 11B) Enrichment of 100 µM $^{13}C_2$-acetate into palmitate in MDA-MB-468 cells cultured in hypoxia and SMEM+1% serum (H1) over a 24 hr period using a 10-fold serial dilution of VY-3-135. n=1. (FIGS. 11C-11D) Enrichment of $^{13}C_2$-acetate into the intracellular UDP-GlcNAc pool of BT474 cells (n=3) and MDA-MB-468 cells (n=1). Experimental parameters were identical to FIG. 11B.

Figure 12A:
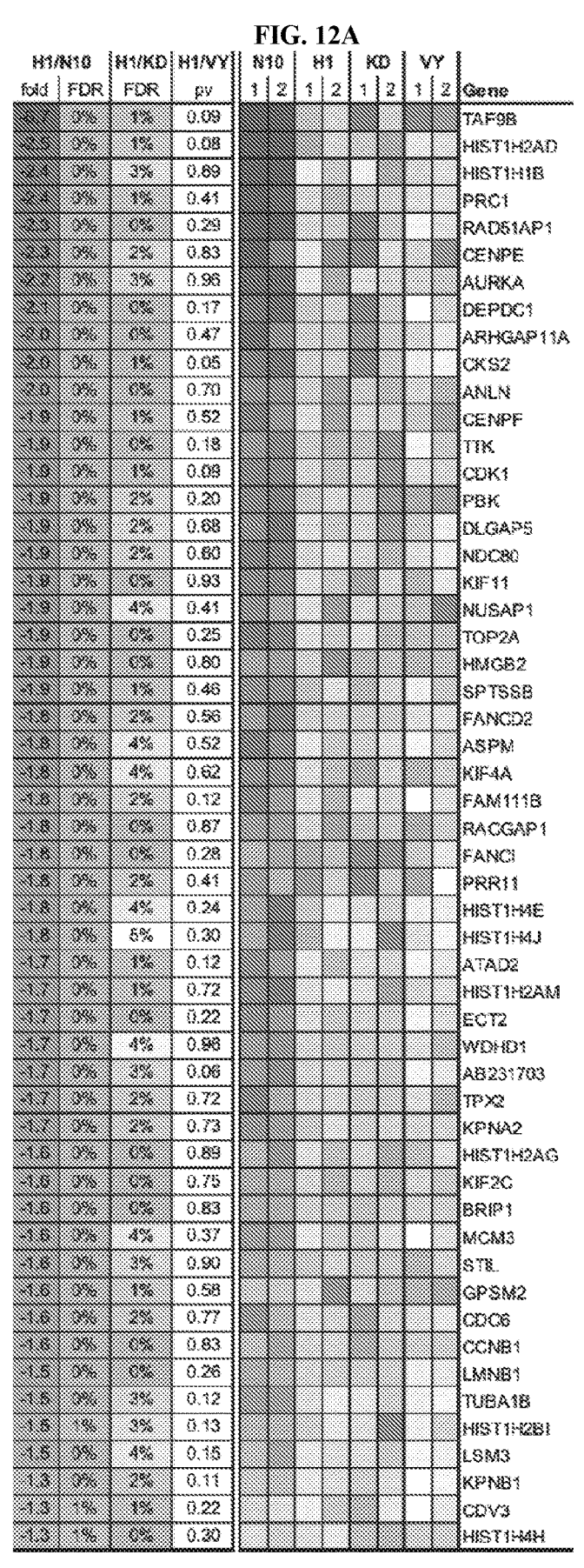

FIGS. 12A-12B depict certain genes affected by siACSS2 under hypoxia and low lipid stress conditions. (FIGS. 12A-12B) Hypoxia and low lipid stress responsive genes that are affected by siRNA mediated knockdown of ACSS2. Upregulated genes are shown in (FIG. 12A) and downregulated genes in (FIG. 12B).

FIG. 13 depicts a summary table of the ANOVA multiple comparisons test results from FIG. 4C.

FIGS. 14A-14E depict the finding that ACSS2 is predominantly found in the cytosol and the soluble nuclear fraction. (FIG. 14A) Heatmap of QuantSeq 3'mRNA sequencing data showingfold change, nominal p value (p), and adjusted p value (fdr). The 129 genes upregulated (nominal p<0.05) in BT474 tumors in response to VY-3-135 treatment. n=4 tumors per treatment group. (FIG. 14B) Same as FIG. 15A, except the 119 genes downregulated (nominal p<0.05) in BT474 tumors in response to VY-3-135 treatment are displayed. n=4 tumors per treatment group. (FIG. 14C) List of the transcriptional regulators affected by VY-3-135 as predicted by IPA. p<0.05 and a Z score >2 or <−2. (FIG. 14D) Immunohistochemical staining of ACSS2 in a BT474 tumor. The enlarged inset shows both nuclear and cytosolic localization. (FIG. 14E) Nuclear fractionation of BT474 cells grown in normoxia and SMEM+10% serum (N10) or hypoxia and SMEM+1% serum (H1) in vitro growth conditions.

FIG. 15 depicts a graph illustrating that Cmpd 1 (40 mg/kg) once daily IP dosing causes a significant decrease in BT474 tumor growth. Black arrow indicates start of treatment. 2-way ANOVA p value is displayed, n≥4 mice per group, dual flank injection.

FIGS. 16A-16B illustrate in vivo tumor metabolomic analysis of Cmpd 1. FIG. 16A: Enrichment of $^{13}C_2$-acetate in palmitate in BT474 tumors treated with vehicle or Cmpd 1. Data represent mean S.D., n≥4. Welch's t test. N.D.=not detected. N.S.=not significant (p>0.0500). FIG. 16B: Enrichment of $^{13}C_2$-acetate into citrate in tumors in vivo. Experimental parameters were identical to FIG. 16A.

FIGS. 17A-17B illustrate in vitro metabolomic analysis of Cmpd 1. FIG. 17A: Enrichment of 100 µM $^{13}C_2$-acetate in the intracellular palmitate pool in BT474 cells treated with vehicle or Cmpd 1 and cultured in normoxia and SMEM+10% serum (N10) or hypoxia and SMEM+1% serum (H1) over a 24 hr period. Data represent mean±S.D., n 3. FIG. 17B: Enrichment of $^{13}C_2$-acetate into the intracellular citrate pool. Experimental parameters were identical to FIG. 17A.

DETAILED DESCRIPTION OF THE DISCLOSURE

Figure 1A:
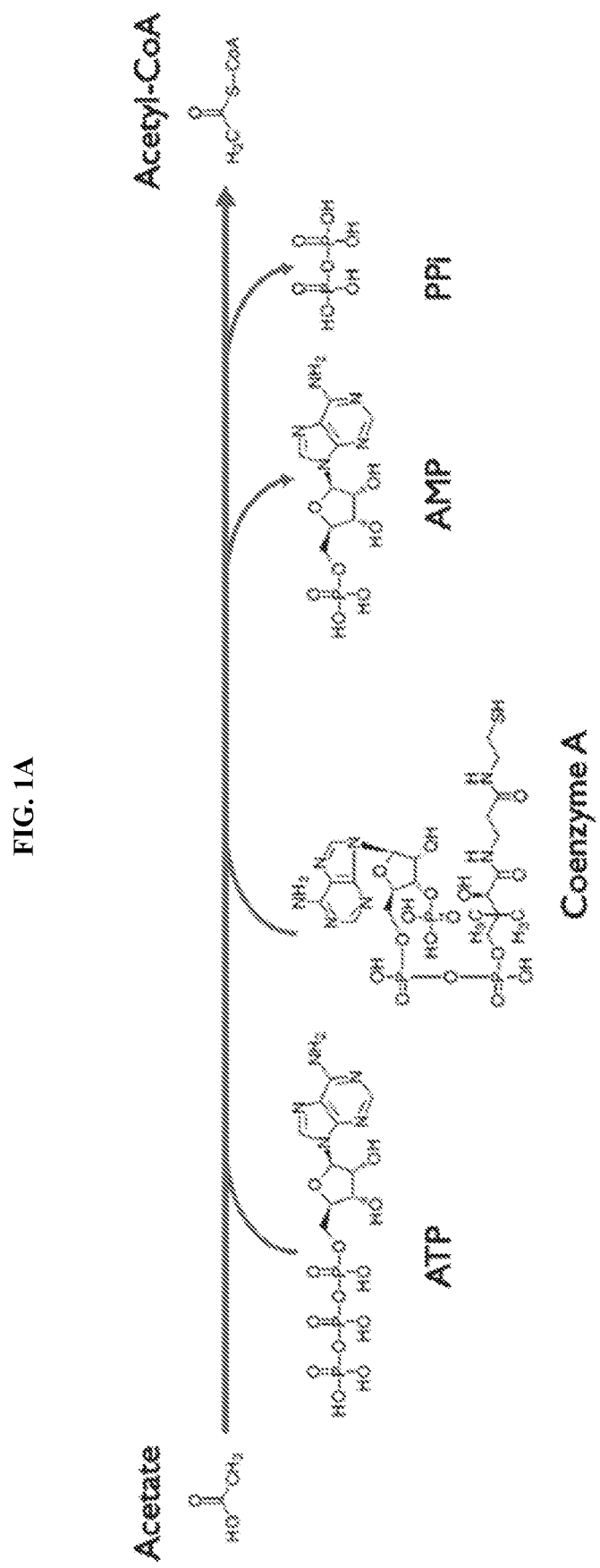
Figure 1B:
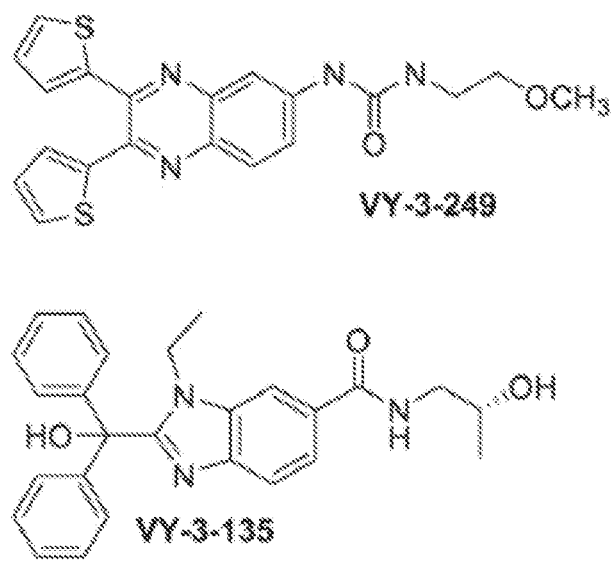

This disclosure relates in part to the discovery that targeting acetate metabolism prevents cancer cells from developing metastatic properties. In certain embodiments, targeting acetate metabolism in extant metastases represents a therapeutic opportunity to treat cancer. In other embodiments, inhibition of acetate metabolism is therapeutically useful for treating and/or preventing metastatic breast cancer. In yet other embodiments, inhibition of ACSS2 reduces the rate of, reverses, and/or prevents development of hypoxic regions. In yet other embodiments, anti-ACSS2 therapy improves effectiveness of chemotherapy, radiotherapy, and/or immunotherapy. As shown herein, in vivo inhibition of ACSS2 with a small molecule inhibitor strongly impedes tumor growth, and can induce tumor regression.

In order to validate ACSS2 as a target for pharmacological modulation, compounds were designed based on the X-ray crystal structure of acetyl-coenzyme A synthetase (*Salmonella typhimurium*) complexed with adenosine-5'-propylphosphate and CoA (Gulick, et al., 2003, Biochemistry 42:2866-2873). Without wishing to be limited by any theory, the nucleoside binding site between human ACSS2 and *salmonella* are almost identical, the only difference being an aromatic Trp residue in *salmonella* vs an aromatic Phe residue in human. This structure is helpful in depicting the geometry of the transition state of this enzyme-catalyzed reaction, where the sulfur of the CoA attacks the carbonyl carbon of the acetate group of the acetyl-adenosine monophosphate to form a tetrahedral intermediate. In certain non-limiting embodiments, a compound that mimics the tetrahedral transition state can be useful as a "transition state analog" inhibitor of ACCSS2.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.10% to about 5%" or "about 0.10% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, $-CH=C=CCH_2$, $-CH=CH(CH_3)$, $-CH=C(CH_3)_2$, $-C(CH_3)=CH_2$, $-C(CH_3)=CH(CH_3)$, $-C(CH_2CH_3)=CH_2$, cyclohexenyl, cyclopentenyl, cyclohexadienyl, butadienyl, pentadienyl, and hexadienyl among others.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to $-C\equiv CH$, $-C\equiv C(CH_3)$, $-C\equiv C(CH_2CH_3)$, $-CH_2C\equiv CH$, $-CH_2C\equiv C(CH_3)$, and $-CH_2C\equiv C(CH_2CH_3)$ among others.

The term "amine" as used herein refers to primary, secondary, and tertiary amines having, e.g., the formula $N(group)_3$ wherein each group can independently be H or non-H, such as alkyl, aryl, and the like. Amines include but are not limited to $R-NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

As used herein, the term "composition" or "pharmaceutical composition" refers to a mixture of at least one compound described herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system.

An appropriate therapeutic amount in any individual case may be determined by one of ordinary skill in the art using routine experimentation.

As used herein, the term "efficacy" refers to the maximal effect ($E_{max}$) achieved within an assay.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heteroarylalkyl" as used herein refers to alkyl groups as defined herein in which a hydrogen or carbon bond of an alkyl group is replaced with a bond to a heteroaryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl $(C_1)$, ethyl $(C_2)$, propyl $(C_3)$, or butyl $(C_4)$, and $(C_0-C_b)$hydrocarbyl means in certain embodiments there is no hydrocarbyl group.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "monovalent" as used herein refers to a substituent connecting via a single bond to a substituted molecule. When a substituent is monovalent, such as, for example, F or Cl, it is bonded to the atom it is substituting by a single bond.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" or "pharmaceutically acceptable excipient" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound described herein within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound(s) described herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound(s) described herein, and are physiologically acceptable to the patient. Supplementary active compounds may also be incorporated into the compositions. The "pharmaceutically acceptable carrier" may further include a pharmaceutically acceptable salt of the compound(s) described herein. Other additional ingredients that may be included in the pharmaceutical compositions used with the methods or compounds described herein are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds described herein include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "potency" refers to the dose needed to produce half the maximal response ($ED_{50}$).

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

The term "room temperature" as used herein refers to a temperature of about 15° C. to about 28° C.

The term "solvent" as used herein refers to a liquid that can dissolve a solid, liquid, or gas. Non-limiting examples of solvents are silicones, organic compounds, water, alcohols, ionic liquids, and supercritical fluids.

The term "standard temperature and pressure" as used herein refers to 20° C. and 101 kPa.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

As used herein, the term "substituted" means that an atom or group of atoms has replaced hydrogen as the substituent attached to another group.

As used herein, the term "substituted alkyl" or "substituted cycloalkyl" means alkyl or cycloalkyl, as defined above, substituted by one, two or three substituents selected from the group consisting of halogen, alkoxy, tetrahydro-2-H-pyranyl, —NH$_2$, —N(CH$_3$)$_2$, (1-methyl-imidazol-2-yl), pyridin-2-yl, pyridin-3-yl, pyridin-4-yl, —C(=O)OH, trifluoromethyl, —C≡N, —C(=O)O(C$_1$-C$_4$)alkyl, —C(=O)NH$_2$, —C(=O)NH(C$_1$-C$_4$)alkyl, —C(=O)N((C$_1$-C$_4$)alkyl)$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound or compounds as described herein (alone or in combination with another pharmaceutical agent), to a patient, or application or administration of a therapeutic agent to an isolated tissue or cell line from a patient (e.g., for diagnosis or ex vivo applications), who has a condition contemplated herein and/or a symptom of a condition contemplated, with the purpose to cure, heal, alleviate, relieve, alter, remedy, ameliorate, improve, or affect a condition contemplated herein and/or the symptoms of a condition contemplated herein. Such treatments may be specifically tailored or modified, based on knowledge obtained from the field of pharmacogenomics.

Non-limiting abbreviations used herein include: ACSS, acetyl-CoA synthetase; mets, metastases.

Ranges: throughout this disclosure, various aspects can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The compounds described herein can be prepared by the general schemes described herein, and/or using synthetic methods known by those skilled in the art. The following examples illustrate non-limiting embodiments of the compound(s) described herein and their preparation.

In certain embodiments, the compound is a compound of Formula (I), or an enantiomer, diastereoisomer, tautomer, salt, and/or solvate thereof:

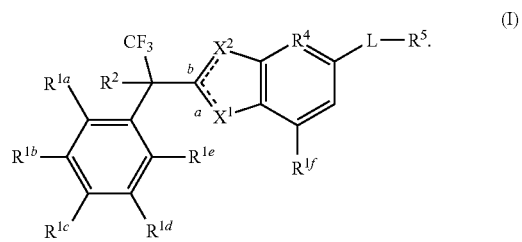

In the compound of Formula (I),
one of the following applies:
(a) $X^1$ is N, $X^2$ is N($CH_2$—$R^3$), bond a is a double bond, and bond b is a single bond; or
(b) $X^1$ is N($CH_2$—$R^3$), $X^2$ is N, bond a is a single bond, and bond b is a double bond;
  each occurrence of $R^{1a}$, $R^{1b}$, $R^{1c}$, $R^{1d}$, $R^{1e}$, $R^{1f}$, and $R^{1g}$ is independently selected from the group consisting of: H; $C_1$-$C_6$ alkyl; $C_3$-$C_8$ cycloalkyl; $C_1$-$C_6$ haloalkyl (such as, but not limited to, trifluoromethyl); —OH; $C_1$-$C_6$ alkoxy; halogen; —C≡N; —NR'R'; —C(=O)OR'; —C(=O)NR'R'; —S($C_1$-$C_6$ alkyl); —S(=O)($C_1$-$C_6$ alkyl); —S(=O)$_2$($C_1$-$C_6$ alkyl); —SO$_2$NR'R'; —C(=NR')—NR'R'; —NO$_2$; and $C_1$-$C_6$ alkyl optionally substituted with at least one selected from halogen, —OH, $C_1$-$C_6$ alkoxy, and —NR'R';
    wherein each occurrence of R' is independently H, $C_1$-$C_6$ alkyl, or $C_3$-$C_8$ cycloalkyl;
  $R^2$ is selected from the group consisting of —OH, —CN, and —SO$_2$($C_1$-$C_6$ alkyl);
  $R^3$ is selected from the group consisting of H, $C_1$-$C_6$ alkyl, $C_3$-$C_8$ cycloalkyl, —OH, $C_1$-$C_6$ haloalkyl, $C_1$-$C_6$ alkoxy, and $C_1$-$C_6$ haloalkoxy;
  $R^4$ is selected from the group consisting of $CR^{1g}$ and N;
  L is selected from the group consisting of —O—*, —C(=O)NR—*, and —NR$^c$—(C=O)—NR—*,
    wherein each occurrence of R is independently selected from the group consisting of H, $C_1$-$C_6$ alkyl, and $C_3$-$C_8$ cycloalkyl, and
    wherein each occurrence of R$^c$ is independently selected from the group consisting of H, $C_1$-$C_6$ alkyl, and $C_3$-$C_8$ cycloalkyl, and
    wherein the bond marked as * is to $R^5$;
  $R^5$ is selected from the group consisting of $C_1$-$C_{10}$ alkyl, phenyl, and heteroaryl, any of each optionally independently substituted with at least one substituent independently selected from the group consisting of: H; $C_1$-$C_6$ alkyl; $C_3$-$C_8$ cycloalkyl; $C_1$-$C_6$ haloalkyl (such as, but not limited to, trifluoromethyl); optionally substituted phenyl; optionally substituted heterocyclyl; optionally substituted heteroaryl; —OH; $C_1$-$C_6$ alkoxy; heterocyclyl; halogen; —C≡N; —NR"R"; —C(=O)OR"; —C(=O)NR"R"; —S($C_1$-$C_6$ alkyl); —S(=O)($C_1$-$C_6$ alkyl); —S(=O)$_2$($C_1$-$C_6$ alkyl); —SO$_2$NR"R"; —C(=NR")—NR"R"; —NO$_2$; and $C_1$-$C_6$ alkyl optionally substituted with at least one selected from halogen, —OH, $C_1$-$C_6$ alkoxy, and —NR"R";
    wherein each occurrence of R" is independently H, $C_1$-$C_6$ alkyl, or $C_3$-$C_8$ cycloalkyl;
  or -L-$R^5$ is optionally substituted heterocyclyl or —C(=O)(optionally substituted heterocyclyl).

In certain embodiments, the heteroaryl is pyrrolyl. In certain embodiments, the heteroaryl is pyrazolyl. In certain embodiments, the heteroaryl is triazolyl. In certain embodiments, the heteroaryl is tetrazolyl. In certain embodiments, the heteroaryl is oxazolyl. In certain embodiments, the heteroaryl is isoxazolyl. In certain embodiments, the heteroaryl is thiazolyl. In certain embodiments, the heteroaryl is pyridinyl. In certain embodiments, the heteroaryl is thiophenyl. In certain embodiments, the heteroaryl is benzothiophenyl. In certain embodiments, the heteroaryl is benzofuranyl. In certain embodiments, the heteroaryl is indolyl. In certain embodiments, the heteroaryl is azaindolyl. In certain embodiments, the heteroaryl is indazolyl. In certain embodiments, the heteroaryl is benzimidazolyl. In certain embodiments, the heteroaryl is azabenzimidazolyl. In certain embodiments, the heteroaryl is benzoxazolyl. In certain embodiments, the heteroaryl is benzothiazolyl. In certain embodiments, the heteroaryl is benzothiadiazolyl. In certain embodiments, the heteroaryl is imidazopyridinyl. In certain embodiments, the heteroaryl is isoxazolopyridinyl. In certain embodiments, the heteroaryl is thianaphthalenyl. In certain embodiments, the heteroaryl is purinyl. In certain embodiments, the heteroaryl is xanthinyl. In certain embodiments, the heteroaryl is adeninyl. In certain embodiments, the heteroaryl is guaninyl. In certain embodiments, the heteroaryl is quinolinyl. In certain embodiments, the heteroaryl is isoquinolinyl. In certain embodiments, the heteroaryl is tetrahydroquinolinyl. In certain embodiments, the heteroaryl is quinoxalinyl. In certain embodiments, the heteroaryl is quinazolinyl.

In certain embodiments, the heterocyclyl is pyrrolidinyl. In certain embodiments, the heterocyclyl is piperidinyl. In certain embodiments, the heterocyclyl is piperazinyl. In certain embodiments, the heterocyclyl is morpholinyl. In certain embodiments, the heterocyclyl is dihydroindolyl.

In certain embodiments, the heterocyclyl is optionally substituted with at least one substituent independently selected from the group consisting of: H; oxo (=O), $C_1$-$C_6$ alkyl; $C_3$-$C_8$ cycloalkyl; $C_1$-$C_6$ haloalkyl (such as, but not limited to, trifluoromethyl); —OH; $C_1$-$C_6$ alkoxy; optionally substituted phenyl; optionally substituted heteroaryl; optionally substituted heterocyclyl; halogen; —C≡N; —N"R"; —C(=O)OR"; —C(=O)N"R"; —S($C_1$-$C_6$ alkyl); —S(=O)($C_1$-$C_6$ alkyl); —S(=O)$_2$($C_1$-$C_6$ alkyl); —SO$_2$N"R"; —C(=NR")—N"R"; —NO$_2$; and $C_1$-$C_6$ alkyl optionally substituted with at least one selected from halogen, —OH, $C_1$-$C_6$ alkoxy, and —N"R".

In certain embodiments, each occurrence of alkyl, alkenyl, alkynyl, or cycloalkyl is independently optionally substituted with at least one substituent selected from the group consisting of $C_1$-$C_6$ alkyl, $C_3$-$C_8$ cycloalkyl, halo, cyano (—CN), —OR$^a$, optionally substituted phenyl (thus yielding, in non-limiting examples, optionally substituted phenyl-($C_1$-$C_3$ alkyl), such as, but not limited to, benzyl or substituted benzyl), optionally substituted heteroaryl, optionally substituted heterocyclyl, —C(=O)OR$^a$, —OC(=O)R$^a$, —SR$^a$, —S(=O)R$^a$, —S(=O)$_2$R$^a$, —S(=O)$_2$NR$^a$R$^a$, —N(R$^a$)S(=O)$_2$R$^a$, —N(R$^a$)C(=O)R$^a$, —C(=O)NR$^a$R$^a$, and —N(R$^a$)(R$^a$), wherein each occurrence of R$^a$ is independently H, optionally substituted $C_1$-$C_6$ alkyl, optionally substituted $C_3$-$C_8$ cycloalkyl, optionally substituted aryl, or optionally substituted heteroaryl, or two R$^a$ groups combine with the N to which they are bound to form a heterocycle.

In certain embodiments, each occurrence of aryl or heteroaryl is independently optionally substituted with at least one substituent selected from the group consisting of $C_1$-$C_6$ alkyl, $C_3$-$C_8$ cycloalkyl, phenyl, $C_1$-$C_6$ hydroxyalkyl, ($C_1$-$C_6$ alkoxy)-$C_1$-$C_6$ alkyl, $C_1$-$C_6$ haloalkyl, $C_1$-$C_6$ haloalkoxy, halogen, oxo, —CN, —OR$^b$, —N(R$^b$)(R$^b$), —NO$_2$, —C(=O)N(R$^b$)(R$^b$), —C(=O)OR$^b$, —OC(=O)R$^b$, —SR$^b$, —S(=O)R$^b$, —S(=O)$_2$R$^b$, —N(R$^b$)S(=O)$_2$R$^b$, —S(=O)$_2$N(R$^b$)(R$^b$), acyl, and $C_1$-$C_6$ alkoxycarbonyl, wherein each occurrence of R$^b$ is independently H, $C_1$-$C_6$ alkyl, or $C_3$-$C_8$ cycloalkyl, wherein in R$^b$ the alkyl or cycloalkyl is optionally substituted with at least one selected from the group consisting of halogen, —OH, $C_1$-$C_6$ alkoxy, and heteroaryl; or substituents on two adjacent carbon atoms combine to form —O(CH$_2$)$_{1-3}$O—.

In certain embodiments, each occurrence of aryl or heteroaryl is independently optionally substituted with at least one substituent selected from the group consisting of $C_1$-$C_6$ alkyl, $C_3$-$C_8$ cycloalkyl, phenyl, $C_1$-$C_6$ hydroxyalkyl, ($C_1$-$C_6$ alkoxy)-$C_1$-$C_6$ alkyl, $C_1$-$C_6$ haloalkyl, $C_1$-$C_6$ haloalkoxy, halogen, oxo, —OR$^b$, —C(=O)N(R$^b$)(R$^b$), —C(=O)OR$^b$, —OC(=O)R$^b$, —SR$^b$, —S(=O)R$^b$, —S(=O)$_2$R$^b$, and —N(R$^b$)S(=O)$_2$R$^b$, wherein each occurrence of R$^b$ is independently H, $C_1$-$C_6$ alkyl, or $C_3$-$C_8$ cycloalkyl, wherein in R$^b$ the alkyl or cycloalkyl is optionally substituted with at least one selected from the group consisting of halogen, —OH, $C_1$-$C_6$ alkoxy, and heteroaryl; or substituents on two adjacent carbon atoms combine to form —O(CH$_2$)$_{1-3}$O—.

In certain embodiments, the alkyl, alkenyl, alkynyl, cycloalkyl, heteroaryl, heterocyclyl, aryl, or benzyl group is optionally independently substituted with at least one group selected from the group consisting of $C_1$-$C_6$ alkyl; $C_1$-$C_6$ alkoxy; $C_1$-$C_6$ haloalkyl; $C_1$-$C_6$ haloalkoxy; —NH$_2$, —NH($C_1$-$C_6$ alkyl), —N($C_1$-$C_6$ alkyl)($C_1$-$C_6$ alkyl), halogen, —OH; —CN; phenoxy, —NHC(=O)H, —NHC(=O)$C_1$-$C_6$ alkyl, —C(=O)NH$_2$, —C(=O)NHC$_1$-$C_6$ alkyl, —C(=O)N($C_1$-$C_6$ alkyl)($C_1$-$C_6$ alkyl), tetrahydropyranyl, morpholinyl, —C(=O)CH$_3$, —C(=O)CH$_2$OH, —C(=O)NHCH$_3$, —C(=O)CH$_2$OMe, or an N-oxide thereof.

In certain embodiments, each occurrence of the heteroaryl is independently selected from the group consisting of quinolinyl, imidazo[1,2-a]pyridyl, pyridyl, pyrimidyl, pyrazinyl, imidazolyl, thiazolyl, pyrazolyl, isoxazolyl, oxadiazolyl (including 1,2,3-, 1,2,4-, 1,2,5-, and 1,3,4-oxadiazole), and triazolyl (such as 1,2,3-triazolyl and 1,2,4-triazolyl).

In certain embodiments, each occurrence of the heterocyclyl group is independently selected from the group consisting of tetrahydrofuranyl, tetrahydropyranyl, piperidinyl, piperazinyl, pyrrolidinyl, morpholinyl, thiomorpholinyl, 1-oxido-thiomorpholinyl, 1,1-dioxido-thiomorpholinyl, oxazolidinyl, azetidinyl, and the corresponding oxo analogues (where a methylene ring group is replaced with a carbonyl) thereof.

In various embodiments, in (I) $R^{1c}$ is not H. In various embodiments, in (I) $R^{1c}$ is F. In various embodiments, in (I) $R^{1c}$ is OMe. In various embodiments, in (I) $R^{1c}$ is tBu. In various embodiments, in (I) $R^{1c}$ is Cl. In various embodiments, in (I) $R^{1c}$ is $C_1$-$C_6$ alkyl.

In various embodiments, the compound is

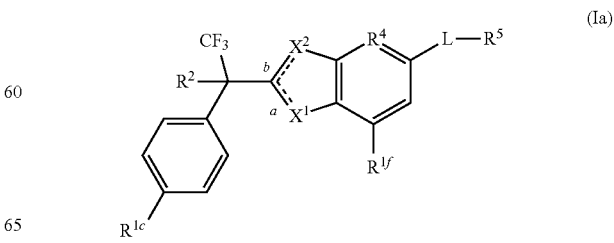

(Ia)

or an enantiomer, diastereoisomer, tautomer, salt, and/or solvate thereof. In certain embodiments, the compound is

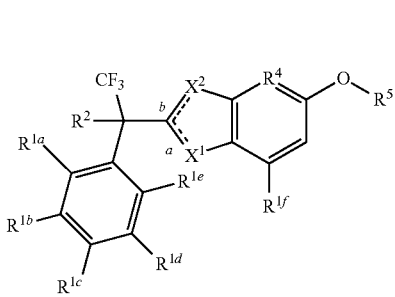
(Ib)

or an enantiomer, diastereoisomer, tautomer, salt, and/or solvate thereof. In certain embodiments, the compound is

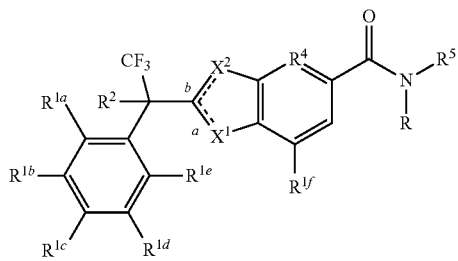
(Ic)

or an enantiomer, diastereoisomer, tautomer, salt, and/or solvate thereof. In certain embodiments, the compound is

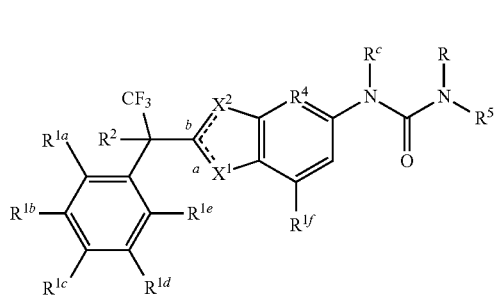
(Id)

or an enantiomer, diastereoisomer, tautomer, salt, and/or solvate thereof. In certain embodiments, the compound is

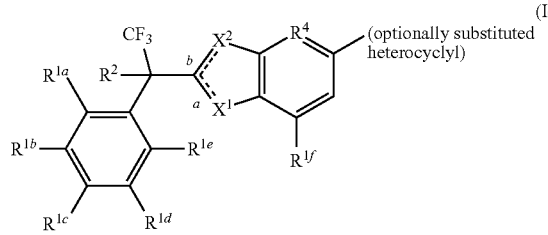
(Ie)

or an enantiomer, diastereoisomer, tautomer, salt, and/or solvate thereof. In certain embodiments, the compound is

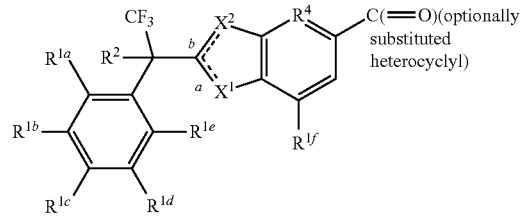
(If)

or an enantiomer, diastereoisomer, tautomer, salt, and/or solvate thereof. In certain embodiments, the compound is

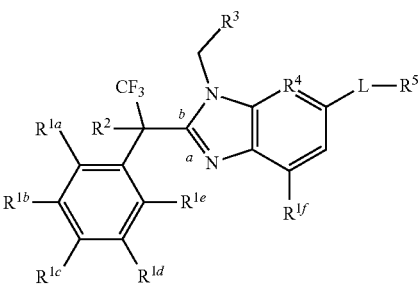
(Ig)

or an enantiomer, diastereoisomer, tautomer, salt, and/or solvate thereof. In certain embodiments, the compound is

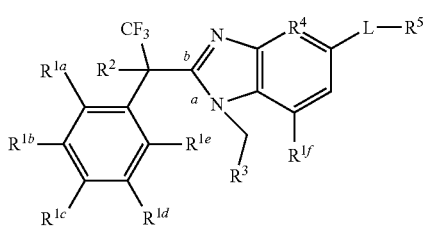
(Ih)

or an enantiomer, diastereoisomer, tautomer, salt, and/or solvate thereof. In certain embodiments, the compound is

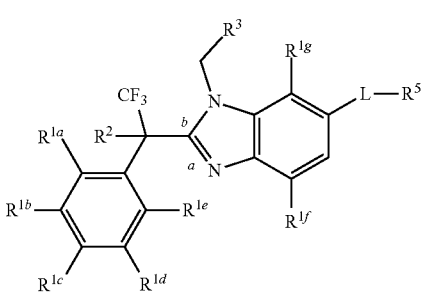
(Ii)

or an enantiomer, diastereoisomer, tautomer, salt, and/or solvate thereof. In certain embodiments, the compound is

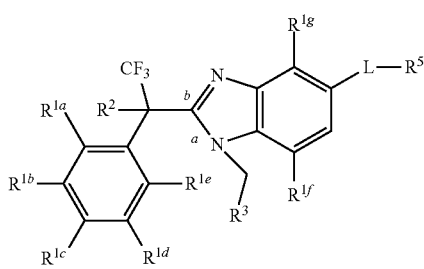

(Ij)

or an enantiomer, diastereoisomer, tautomer, salt, and/or solvate thereof. In certain embodiments, the compound is

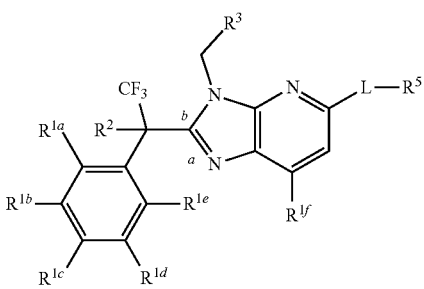

(Ik)

or an enantiomer, diastereoisomer, tautomer, salt, and/or solvate thereof. In certain embodiments, the compound is

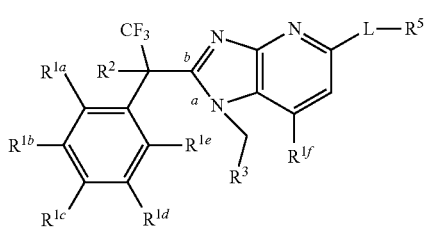

(Il)

or an enantiomer, diastereoisomer, tautomer, salt, and/or solvate thereof.

In certain embodiments, the compound is

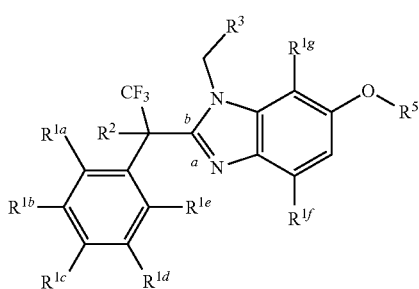

or an enantiomer, diastereoisomer, tautomer, salt, and/or solvate thereof. In certain embodiments, the compound is

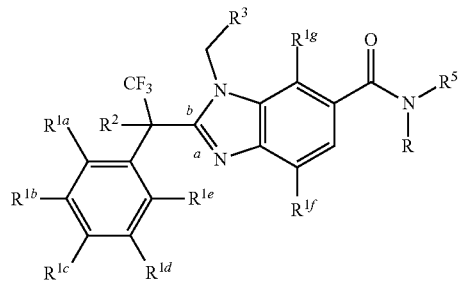

or an enantiomer, diastereoisomer, tautomer, salt, and/or solvate thereof. In certain embodiments, the compound is

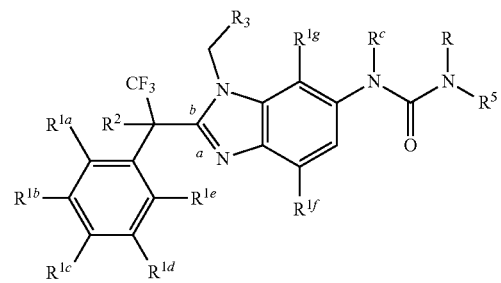

or an enantiomer, diastereoisomer, tautomer, salt, and/or solvate thereof. In certain embodiments, the compound is

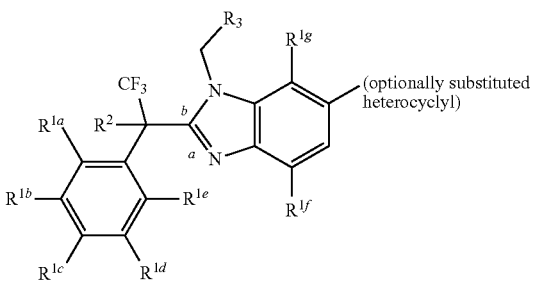

or an enantiomer, diastereoisomer, tautomer, salt, and/or solvate thereof. In certain embodiments, the compound is

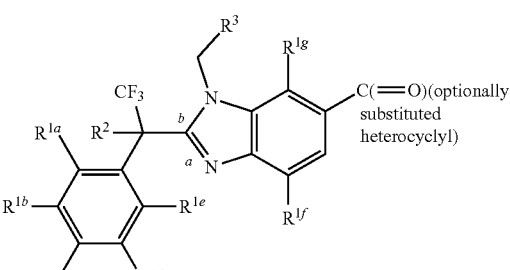

or an enantiomer, diastereoisomer, tautomer, salt, and/or solvate thereof. In certain embodiments, the compound is

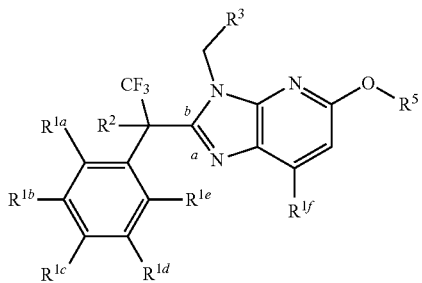

or an enantiomer, diastereoisomer, tautomer, salt, and/or solvate thereof. In certain embodiments, the compound is

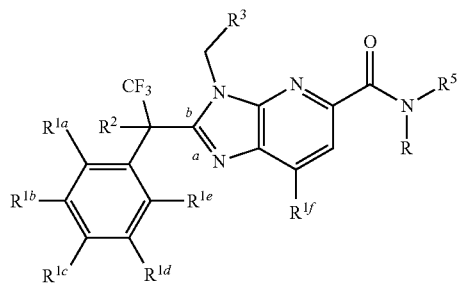

or an enantiomer, diastereoisomer, tautomer, salt, and/or solvate thereof. In certain embodiments, the compound is

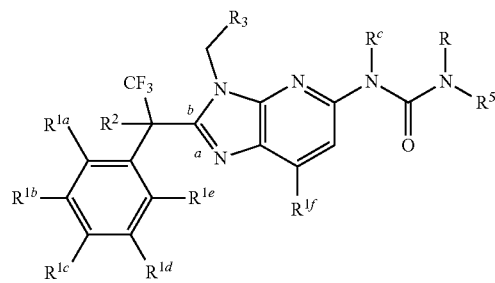

or an enantiomer, diastereoisomer, tautomer, salt, and/or solvate thereof. In certain embodiments, the compound is

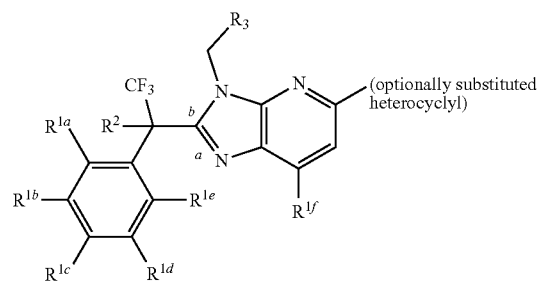

or an enantiomer, diastereoisomer, tautomer, salt, and/or solvate thereof. In certain embodiments, the compound is

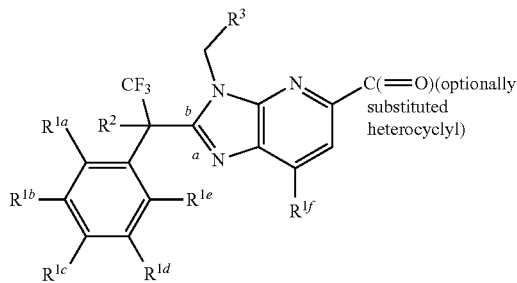

or an enantiomer, diastereoisomer, tautomer, salt, and/or solvate thereof. In certain embodiments, the compound is

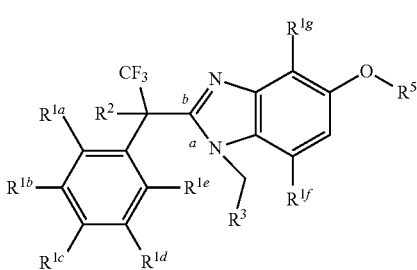

or an enantiomer, diastereoisomer, tautomer salt and/or solvate thereof. In certain embodiments, the compound is

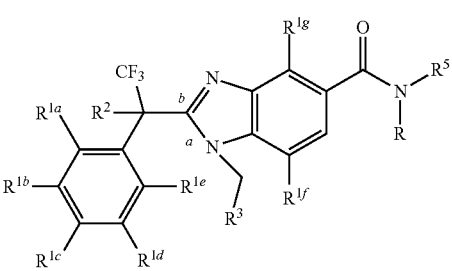

or an enantiomer, diastereoisomer, tautomer, salt, and/or solvate thereof. In certain embodiments, the compound is

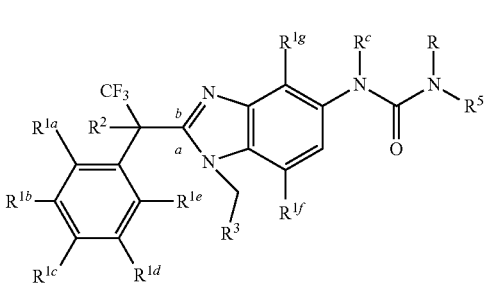

or an enantiomer, diastereoisomer, tautomer, salt, and/or solvate thereof. In certain embodiments, the compound is

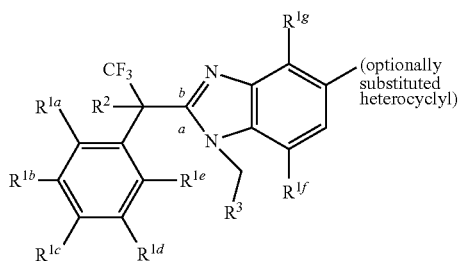

or an enantiomer, diastereoisomer, tautomer, salt, and/or solvate thereof. In certain embodiments, the compound is

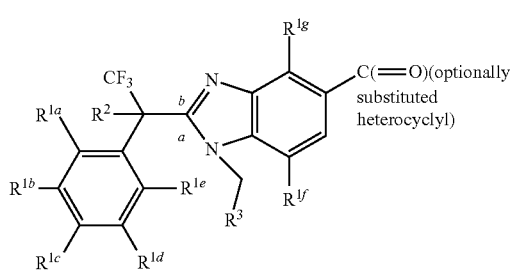

or an enantiomer, diastereoisomer, tautomer, salt, and/or solvate thereof. In certain embodiments, the compound is

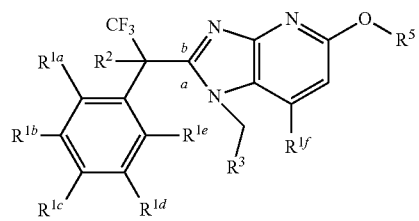

or an enantiomer, diastereoisomer, tautomer, salt, and/or solvate thereof. In certain embodiments, the compound is

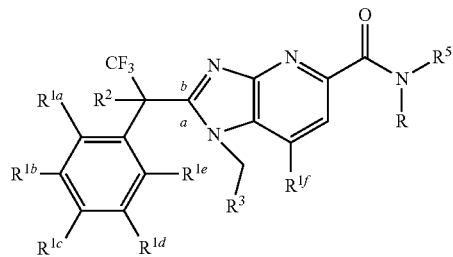

or an enantiomer, diastereoisomer, tautomer, salt, and/or solvate thereof. In certain embodiments, the compound is

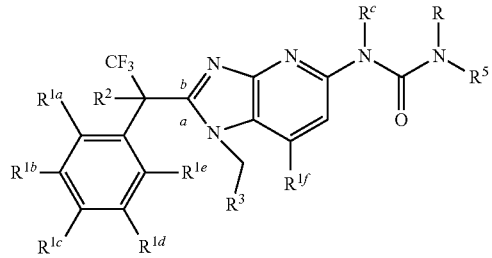

or an enantiomer, diastereoisomer, tautomer, salt, and/or solvate thereof. In certain embodiments, the compound is

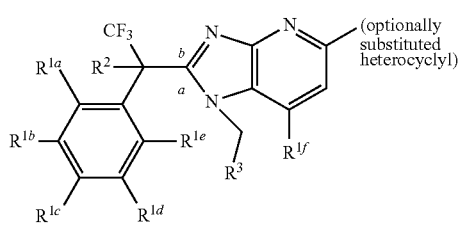

or an enantiomer, diastereoisomer, tautomer, salt, and/or solvate thereof. In certain embodiments, the compound is In certain embodiments, -L-$R^5$ is

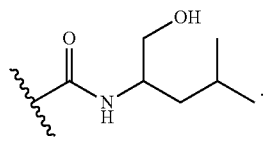 [SMILES: *C(=O)NC(CO)CC(C)C]

In certain embodiments, -L-$R^5$ is

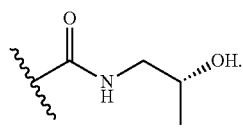 [SMILES: *C(=O)NC[C@@H](C)O]

In certain embodiments, -L-$R^5$ is

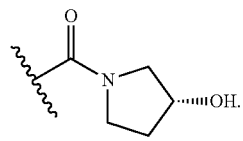 [SMILES: *C(=O)N1CC[C@@H](O)C1]

In certain embodiments, -L-R⁵ is
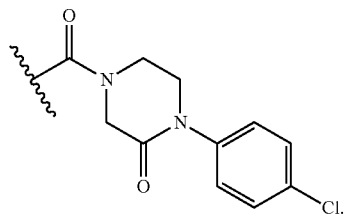 [SMILES: *C(=O)N1CCN(c2ccc(Cl)cc2)C(=O)C1]
In certain embodiments, -L-R⁵ is
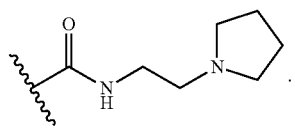 [SMILES: *C(=O)NCCN1CCCC1]
In certain embodiments, -L-R⁵ is
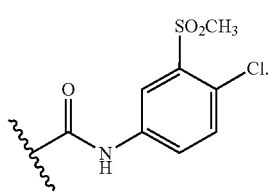 [SMILES: *C(=O)Nc1ccc(Cl)c(S(C)(=O)=O)c1]
In certain embodiments, -L-R⁵ is
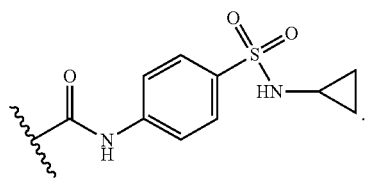 [SMILES: *C(=O)Nc1ccc(S(=O)(=O)NC2CC2)cc1]
In certain embodiments, -L-R⁵ is
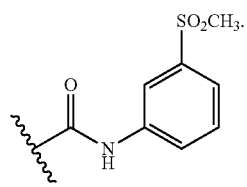 [SMILES: *C(=O)Nc1cccc(S(C)(=O)=O)c1]
In certain embodiments, -L-R⁵ is
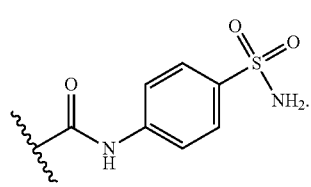 [SMILES: *C(=O)Nc1ccc(S(N)(=O)=O)cc1]
In certain embodiments, -L-R⁵ is
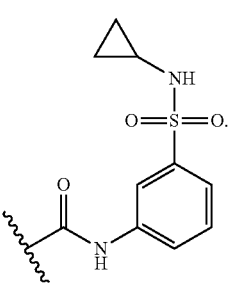 [SMILES: *C(=O)Nc1cccc(S(=O)(=O)NC2CC2)c1]
In certain embodiments, -L-R⁵ is
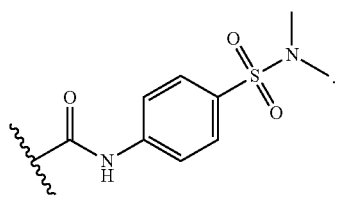 [SMILES: *C(=O)Nc1ccc(S(=O)(=O)N(C)C)cc1]
In certain embodiments, -L-R⁵ is
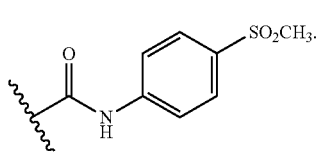 [SMILES: *C(=O)Nc1ccc(S(C)(=O)=O)cc1]
In certain embodiments, -L-R⁵ is
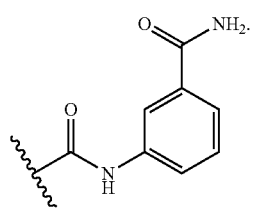 [SMILES: *C(=O)Nc1cccc(C(N)=O)c1]
In certain embodiments, -L-R⁵ is
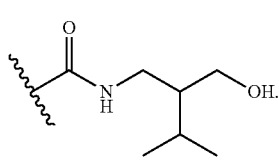 [SMILES: *C(=O)NCC(CO)C(C)C]

In certain embodiments, -L-R⁵ is

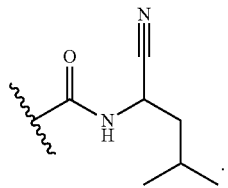 [SMILES: *C(=O)NC(C#N)CC(C)C]

In certain embodiments, -L-R⁵ is

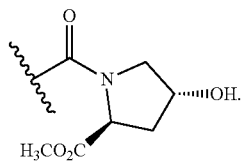 [SMILES: *C(=O)N1C[C@H](O)C[C@H]1C(=O)OC]

In certain embodiments, -L-R⁵ is

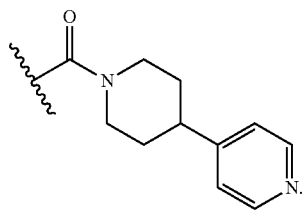 [SMILES: *C(=O)N1CCC(c2ccncc2)CC1]

In certain embodiments, -L-R⁵ is

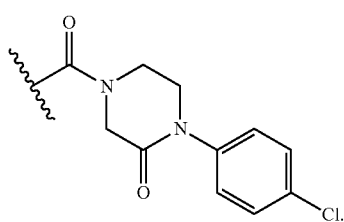 [SMILES: *C(=O)N1CCN(c2ccc(Cl)cc2)C(=O)C1]

In certain embodiments, -L-R⁵ is

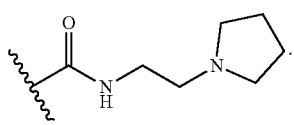 [SMILES: *C(=O)NCCN1CCCC1]

In certain embodiments, -L-R⁵ is

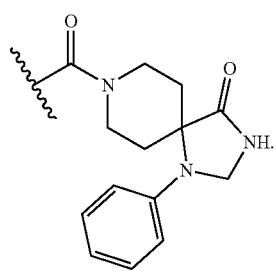 [SMILES: *C(=O)N1CCC2(CC1)C(=O)NCN2c1ccccc1]

In certain embodiments, -L-R⁵ is

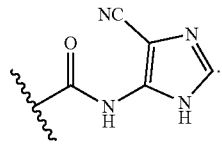 [SMILES: *C(=O)Nc1[nH]cnc1C#N]

In certain embodiments, -L-R⁵ is

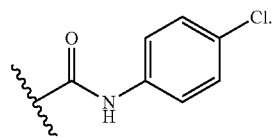 [SMILES: *C(=O)Nc1ccc(Cl)cc1]

In certain embodiments, -L-R⁵ is

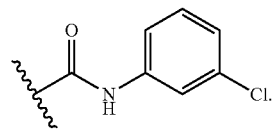 [SMILES: *C(=O)Nc1cccc(Cl)c1]

In certain embodiments, -L-R⁵ is

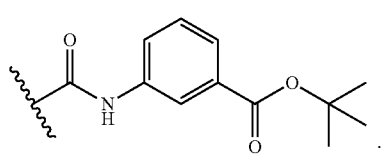 [SMILES: *C(=O)Nc1cccc(C(=O)OC(C)(C)C)c1]

In certain embodiments, -L-R⁵ is

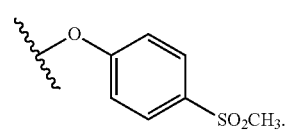

In certain embodiments, -L-R⁵ is

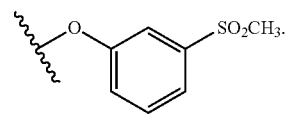 [SMILES: *Oc1cccc(S(C)(=O)=O)c1]

In certain embodiments, -L-R⁵ is

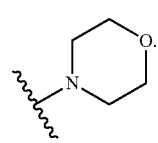 [SMILES: *N1CCOCC1]

In certain embodiments, -L-R⁵ is

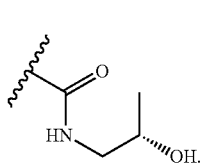 [SMILES: *C(=O)NC[C@H](C)O]

In certain embodiments, the compound is

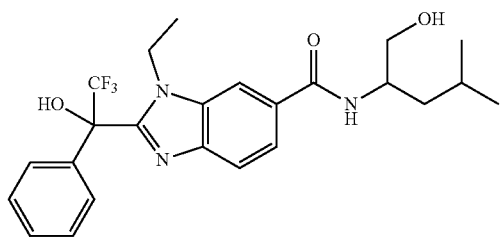

or an enantiomer, diastereoisomer, tautomer, salt, and/or solvate thereof. In certain embodiments, the compound is

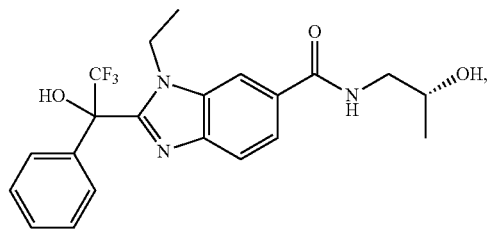 [SMILES: CCn1c(C(O)(c2ccccc2)C(F)(F)F)nc2ccc(C(=O)NC[C@@H](C)O)cc21]

or an enantiomer, diastereoisomer, tautomer, salt, and/or solvate thereof. In certain embodiments, the compound is

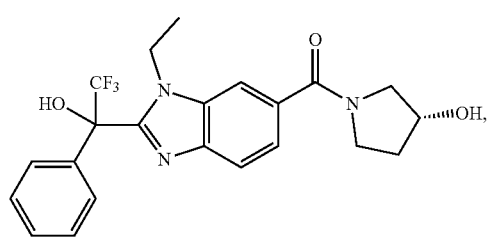 [SMILES: CCn1c(C(O)(c2ccccc2)C(F)(F)F)nc2ccc(C(=O)N3CC[C@@H](O)C3)cc21]

or an enantiomer, diastereoisomer, tautomer, salt, and/or solvate thereof. In certain embodiments, the compound is

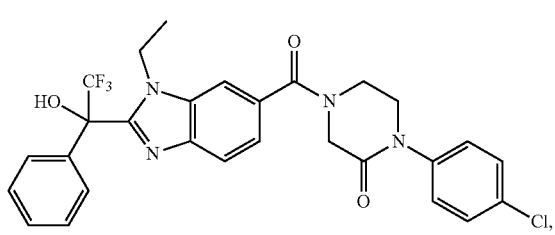 [SMILES: CCn1c(C(O)(c2ccccc2)C(F)(F)F)nc2ccc(C(=O)N3CCN(c4ccc(Cl)cc4)C(=O)C3)cc21]

or an enantiomer, diastereoisomer, tautomer, salt, and/or solvate thereof. In certain embodiments, the compound is

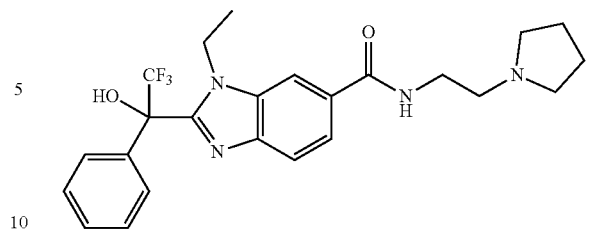

or an enantiomer, diastereoisomer, tautomer, salt, and/or solvate thereof. In certain embodiments, the compound is

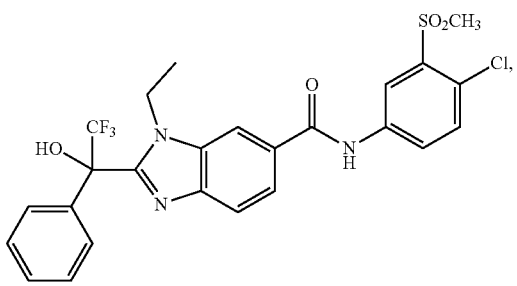 [SMILES: CCn1c(C(O)(c2ccccc2)C(F)(F)F)nc2ccc(C(=O)Nc3ccc(Cl)c(S(C)(=O)=O)c3)cc21]

or an enantiomer, diastereoisomer, tautomer, salt, and/or solvate thereof. In certain embodiments, the compound is

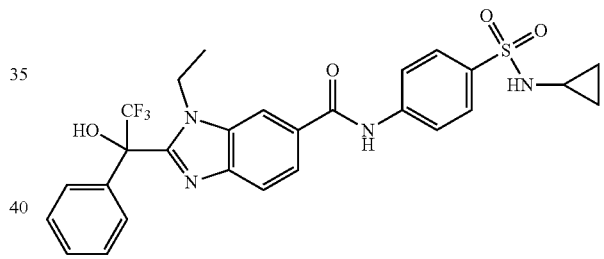

or an enantiomer, diastereoisomer, tautomer, salt, and/or solvate thereof. In certain embodiments, the compound is

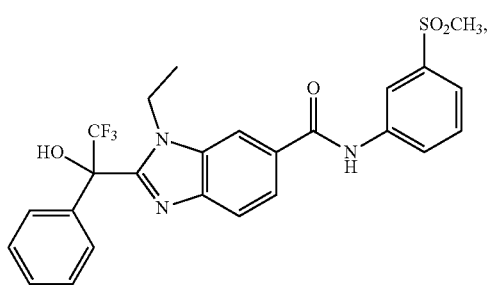 [SMILES: CCn1c(C(O)(c2ccccc2)C(F)(F)F)nc2ccc(C(=O)Nc3cccc(S(C)(=O)=O)c3)cc21]

or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is

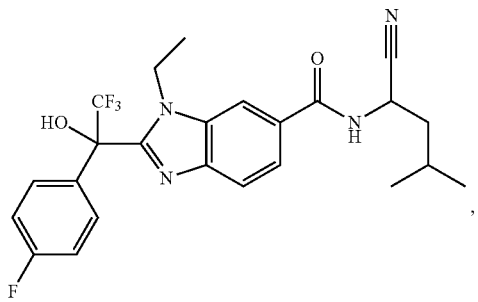 [SMILES: CCn1c(C(O)(c2ccc(F)cc2)C(F)(F)F)nc2ccc(C(=O)NC(C#N)CC(C)C)cc21]

or an enantiomer, diastereoisomer, tautomer, salt, and/or solvate thereof. In certain embodiments, the compound is

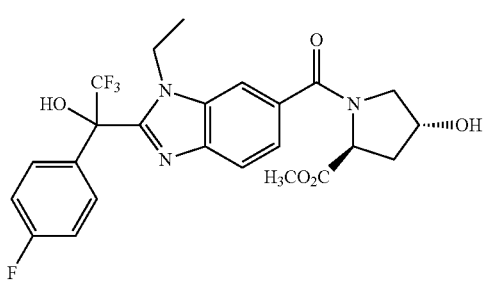 [SMILES: CCn1c(C(O)(c2ccc(F)cc2)C(F)(F)F)nc2ccc(C(=O)N3C[C@H](O)C[C@H]3C(=O)OC)cc21]

or an enantiomer, diastereoisomer, tautomer, salt, and/or solvate thereof. In certain embodiments, the compound is

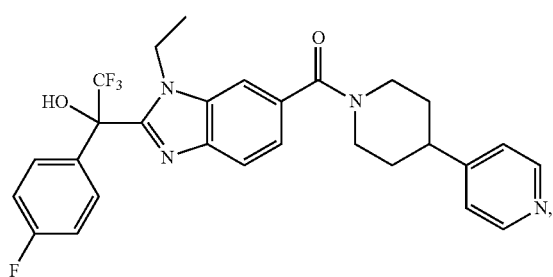

or an enantiomer, diastereoisomer, tautomer, salt, and/or solvate thereof. In certain embodiments, the compound is

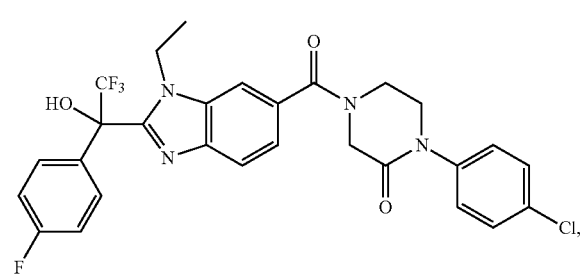 [SMILES: CCn1c(C(O)(c2ccc(F)cc2)C(F)(F)F)nc2ccc(C(=O)N3CCN(c4ccc(Cl)cc4)C(=O)C3)cc21]

or an enantiomer, diastereoisomer, tautomer, salt, and/or solvate thereof. In certain embodiments, the compound is

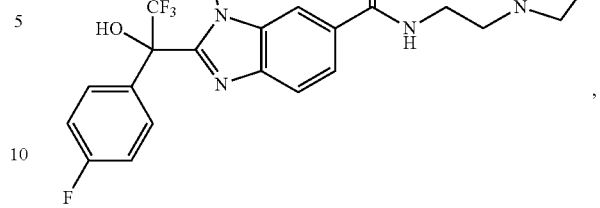

or an enantiomer, diastereoisomer, tautomer, salt, and/or solvate thereof. In certain embodiments, the compound is

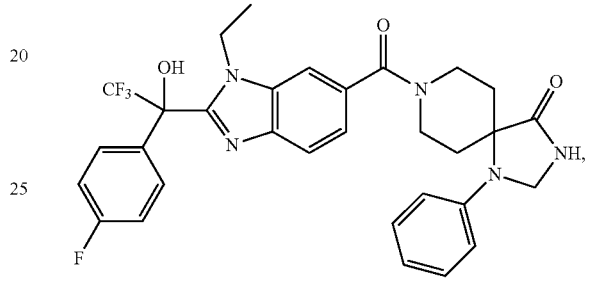

or an enantiomer, diastereoisomer, tautomer, salt, and/or solvate thereof. In certain embodiments, the compound is

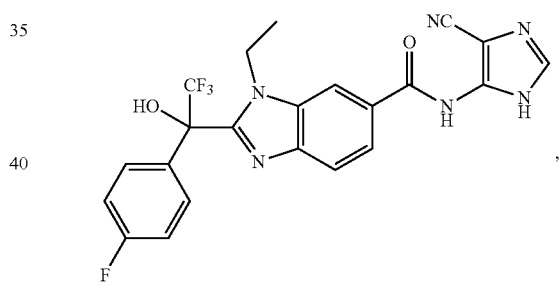

or an enantiomer, diastereoisomer, tautomer, salt, and/or solvate thereof. In certain embodiments, the compound is

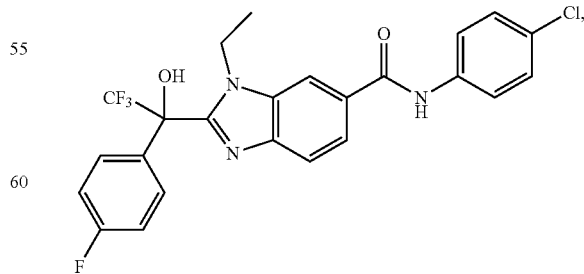

or an enantiomer, diastereoisomer, tautomer, salt, and/or solvate thereof. In certain embodiments, the compound is

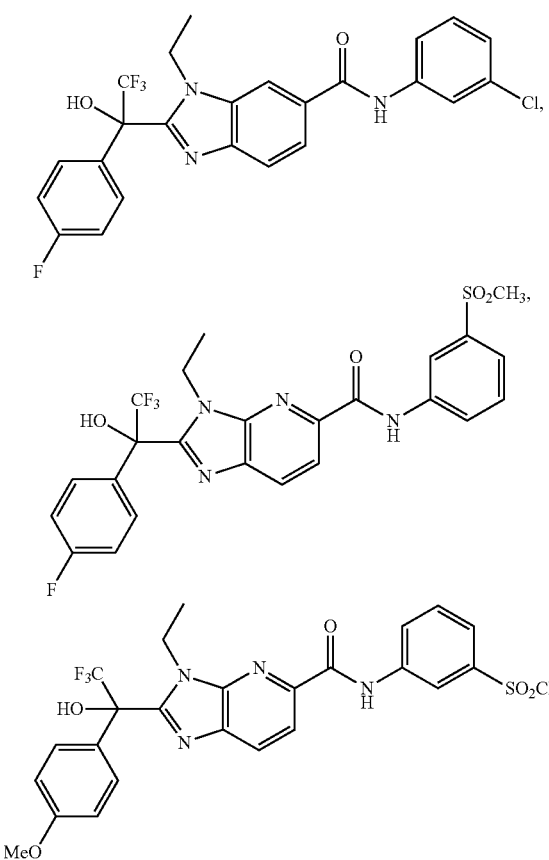

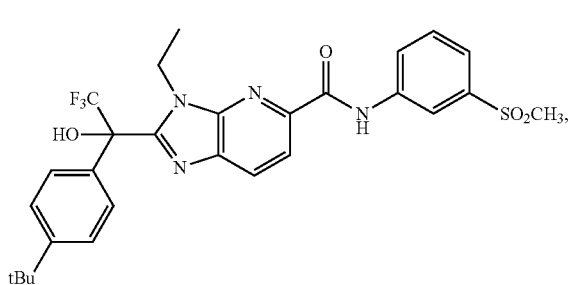 [SMILES: CCn1c(C(O)(c2ccc(C(C)(C)C)cc2)C(F)(F)F)nc2ccc(C(=O)Nc3cccc(S(C)(=O)=O)c3)nc21]

or an enantiomer, diastereoisomer, tautomer, salt, and/or solvate thereof. In certain embodiments, the compound is

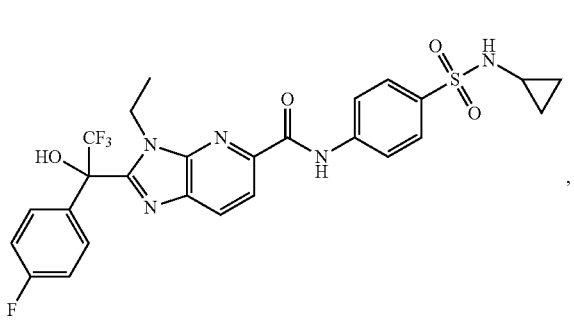 [SMILES: CCn1c(C(O)(c2ccc(F)cc2)C(F)(F)F)nc2ccc(C(=O)Nc3ccc(S(=O)(=O)NC4CC4)cc3)nc21]

or an enantiomer, diastereoisomer, tautomer, salt, and/or solvate thereof. In certain embodiments, the compound is

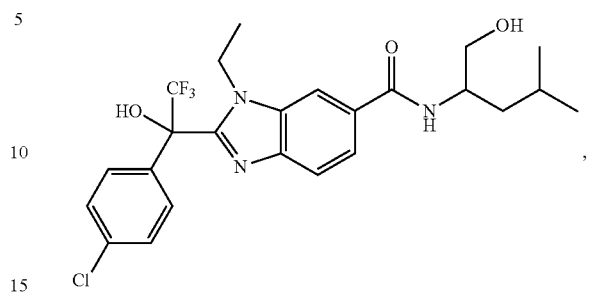

or an enantiomer, diastereoisomer, tautomer, salt, and/or solvate thereof. In certain embodiments, the compound is

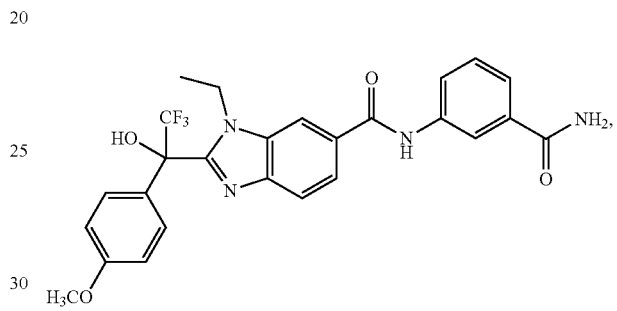

or an enantiomer, diastereoisomer, tautomer, salt, and/or solvate thereof. In certain embodiments, the compound is

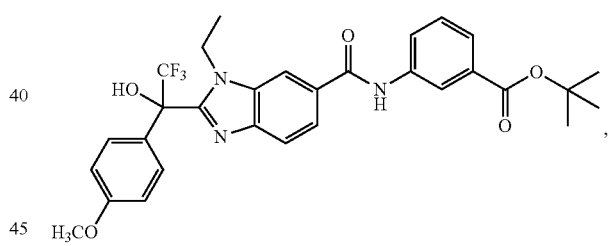

or an enantiomer, diastereoisomer, tautomer, salt, and/or solvate thereof. In certain embodiments, the compound is

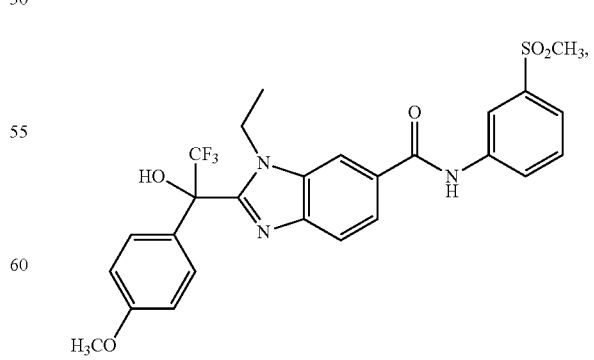

or an enantiomer, diastereoisomer, tautomer, salt, and/or solvate thereof. In certain embodiments, the compound is

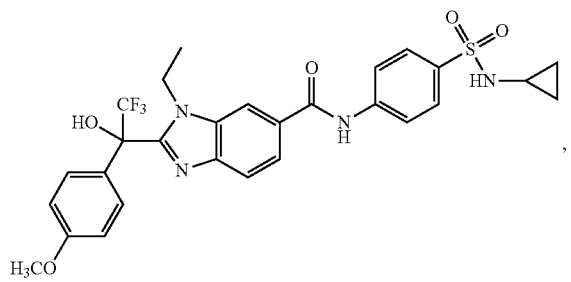 [SMILES: CCn1c(C(O)(c2ccc(OC)cc2)C(F)(F)F)nc2ccc(C(=O)Nc3ccc(S(=O)(=O)NC4CC4)cc3)cc21]

or an enantiomer, diastereoisomer, tautomer, salt, and/or solvate thereof. In certain embodiments, the compound is

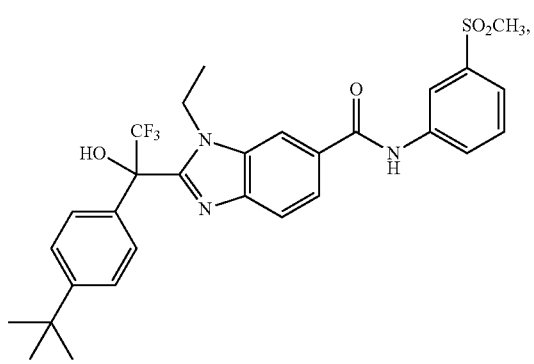 [SMILES: CCn1c(C(O)(c2ccc(C(C)(C)C)cc2)C(F)(F)F)nc2ccc(C(=O)Nc3cccc(S(C)(=O)=O)c3)cc21]

or an enantiomer, diastereoisomer, tautomer, salt, and/or solvate thereof. In certain embodiments, the compound is

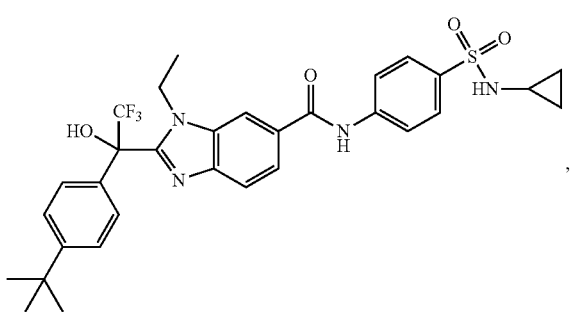 [SMILES: CCn1c(C(O)(c2ccc(C(C)(C)C)cc2)C(F)(F)F)nc2ccc(C(=O)Nc3ccc(S(=O)(=O)NC4CC4)cc3)cc21]

or an enantiomer, diastereoisomer, tautomer, salt, and/or solvate thereof. In certain embodiments, the compound is

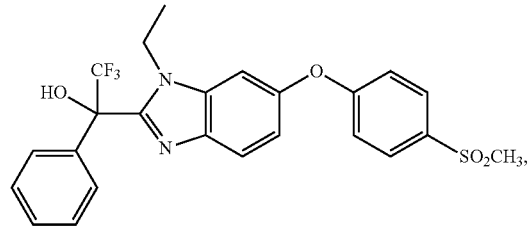 [SMILES: CCn1c(C(O)(c2ccccc2)C(F)(F)F)nc2ccc(Oc3ccc(S(C)(=O)=O)cc3)cc21]

or an enantiomer, diastereoisomer, tautomer, salt, and/or solvate thereof. In certain embodiments, the compound is

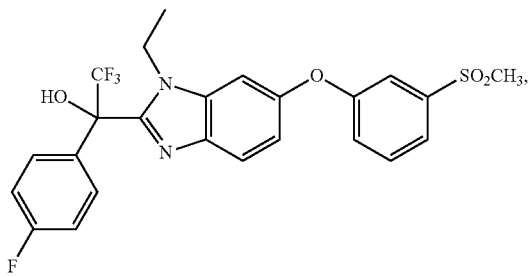 [SMILES: CCn1c(C(O)(c2ccc(F)cc2)C(F)(F)F)nc2ccc(Oc3cccc(S(C)(=O)=O)c3)cc21]

or an enantiomer, diastereoisomer, tautomer, salt, and/or solvate thereof. In certain embodiments, the compound is

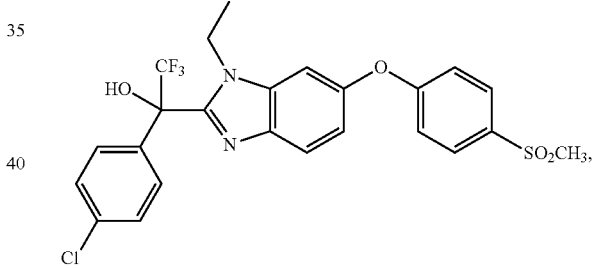

or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is

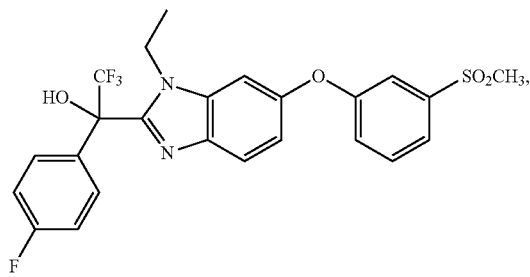 [SMILES: CCn1c(C(O)(c2ccc(F)cc2)C(F)(F)F)nc2ccc(Oc3cccc(S(C)(=O)=O)c3)cc21]

or an enantiomer, diastereoisomer, tautomer, salt, and/or solvate thereof. In certain embodiments, the compound is

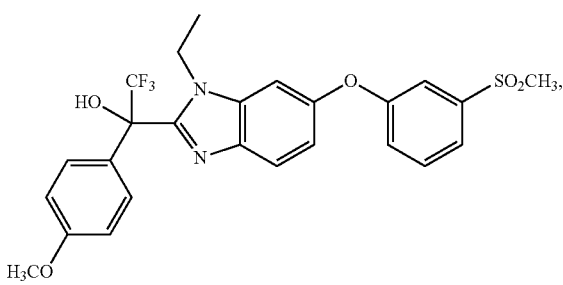 [SMILES: CCn1c(C(O)(c2ccc(OC)cc2)C(F)(F)F)nc2ccc(Oc3cccc(S(C)(=O)=O)c3)cc21]

or an enantiomer, diastereoisomer, tautomer, salt, and/or solvate thereof. In certain embodiments, the compound is

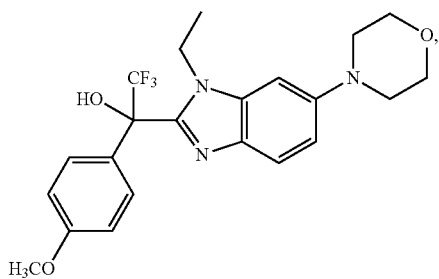 [SMILES: CCn1c(C(O)(c2ccc(OC)cc2)C(F)(F)F)nc2ccc(N3CCOCC3)cc21]

or an enantiomer, diastereoisomer, tautomer, salt and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is or an enantiomer, diastereoisomer, tautomer, salt, and/or solvate thereof. In certain embodiments, the compound is

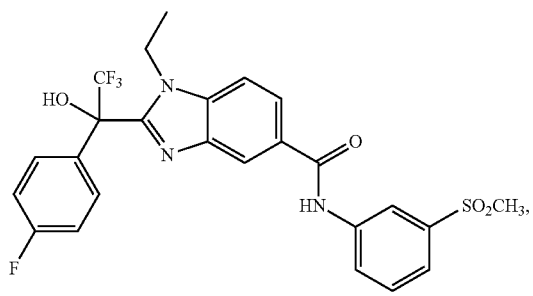 [SMILES: CCn1c(C(O)(c2ccc(F)cc2)C(F)(F)F)nc2cc(C(=O)Nc3cccc(S(C)(=O)=O)c3)ccc21]

or an enantiomer, diastereoisomer, tautomer, salt, and/or solvate thereof. In certain embodiments, the compound is

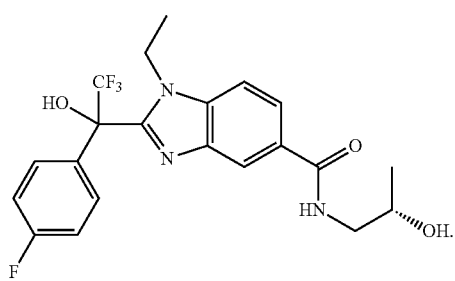 [SMILES: CCn1c(C(O)(c2ccc(F)cc2)C(F)(F)F)nc2cc(C(=O)NC[C@H](C)O)ccc21]

In certain embodiments, compounds of Formula (I) can be prepared according to Scheme 1 below, wherein R³* is R³ or a group that can converted or deprotected to R³.

Scheme 1

As illustrated in a non-limiting manner in Scheme 1, halide (1) can be reacted with an amine to yield aniline (2), which can be cyclized in the presence of an alkyl formate (or a trialkoxymethane) to form bicyclic compound (3). Reaction of (3) with trifluorobenzoyl compound (4) affords (5), wherein R² is —OH. Oxidation of the benzylic position of (5) affords carboxylic acid (6), which can be coupled with an amine to form amide (7), which may be a compound of the disclosure or an intermediate in the preparation of a compound of the disclosure. Tertiary alcohol (7) can be converted to the corresponding fluoride through treatment with DAST, for example.

In certain embodiments, the compound is

or an enantiomer, diastereoisomer, tautomer, salt, and/or solvate thereof.

In certain embodiments, the compound is

or an enantiomer, diastereoisomer, tautomer, salt, and/or solvate thereof.

In certain embodiments, the compound is

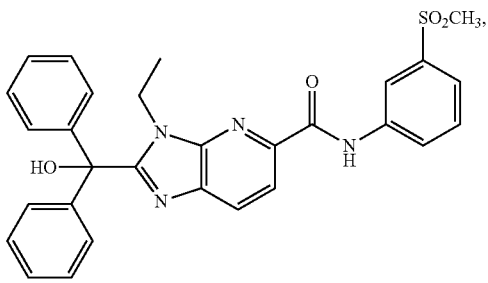 [SMILES: CCn1c(C(O)(c2ccccc2)c2ccccc2)nc2ccc(C(=O)Nc3cccc(S(C)(=O)=O)c3)nc21]

or an enantiomer, diastereoisomer, tautomer, salt, and/or solvate thereof.

In certain embodiments, the compound is

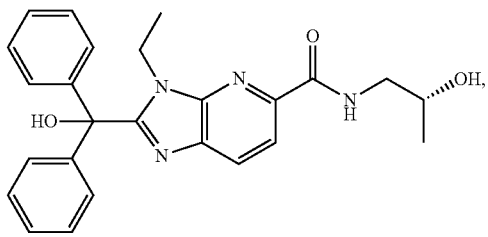 [SMILES: CCn1c(C(O)(c2ccccc2)c2ccccc2)nc2ccc(C(=O)NC[C@@H](C)O)nc21]

or an enantiomer, diastereoisomer, tautomer, salt, and/or solvate thereof.

In certain embodiments, the compound is

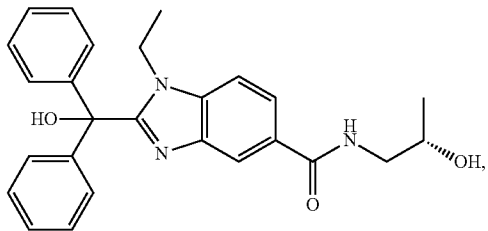 [SMILES: CCn1c(C(O)(c2ccccc2)c2ccccc2)nc2cc(C(=O)NC[C@H](C)O)ccc21]

or an enantiomer, diastereoisomer, tautomer, salt, and/or solvate thereof.

In various embodiments, (I) is an ACSS2 inhibitor with an $IC_{50}$ of at least, less than, or greater than about 1 nM to about 1,000 nM. In various embodiments, (I) is an ACSS2 inhibitor with an $IC_{50}$ of at least, less than, or greater than about 1 nM, 2 nM, 3 nM, 4 nM, 5 nM, 10 nM, 15 nM, 20 nM, 25 nM, 30 nM, 40 nM, 50 nM, 60 nM, 70 nM, 80 nM, 90 nM, 100 nM, 125 nM, 150 nM, 175 nM, 200 nM, 225 nM, 250 nM, 275 nM, 300 nM, 400 nM, 500 nM, 600 nM, 700 nM, 800 nM, 900 nM, or 1,000 nM.

The compounds described herein can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound(s) described herein, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compound(s) described herein can exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compound(s) described herein are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{8}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

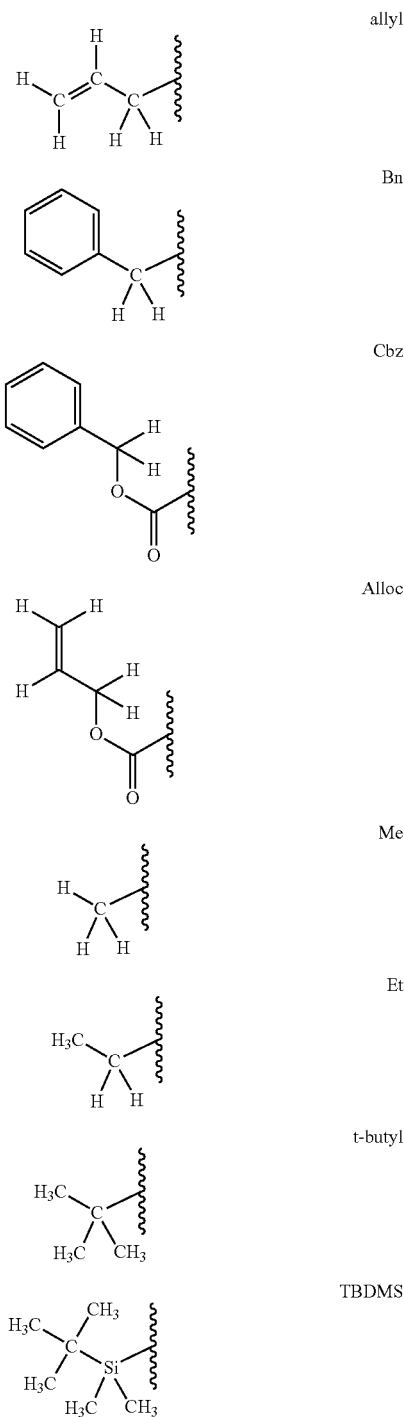

-continued

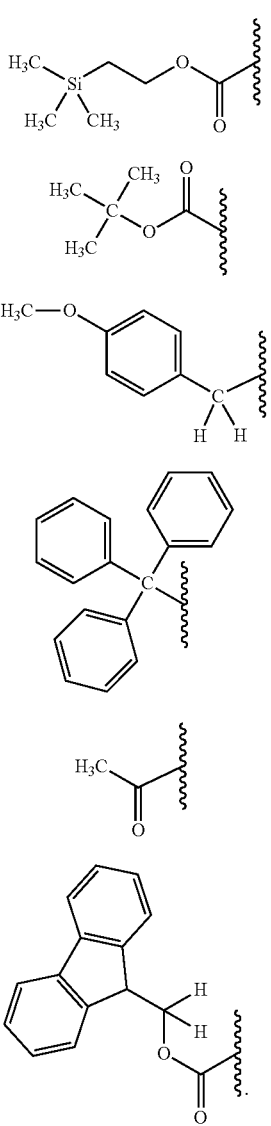

| | |
|---|---|
| | Teoc |
| | Boc |
| | PMB |
| | trityl |
| | acetyl |
| | FMOC |

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Compositions

The compositions containing the compound(s) described herein include a pharmaceutical composition comprising at least one compound as described herein and at least one pharmaceutically acceptable carrier. In certain embodiments, the composition is formulated for an administration route such as oral or parenteral, for example, transdermal, transmucosal (e.g., sublingual, lingual, (trans)buccal, (trans)urethral, vaginal (e.g., trans- and perivaginally), (intra)nasal and (trans)rectal, intravesical, intrapulmonary, intraduodenal, intragastrical, intrathecal, subcutaneous, intramuscular, intradermal, intra-arterial, intravenous, intrabronchial, inhalation, and topical administration.

Methods

Methods of treating, ameliorating, or preventing a disease or disorder that is caused, induced, or characterized by abnormal expression or activity of ACSS2 in a subject.

In certain embodiments, the disclosure provides a method of reducing the rate of, reversing, and/or preventing a cancer cell from becoming metastatic.

In certain embodiments, the disclosure provides a method of reducing the rate of, reversing, and/or preventing development of a hypoxic region in a cancer.

In certain embodiments, the disclosure provides a method of increasing effectiveness of chemotherapy, radiotherapy, and/or immunotherapy administered to a subject suffering from a cancer.

The method includes administering to the subject a therapeutically effective amount of at least one compound described herein, or an enantiomer, diastereoisomer, tautomer, salt, and/or solvate thereof. In certain embodiments, the disease or disorder is cancer, such as but not limited to brain cancer, breast cancer, pancreatic cancer, sarcoma, prostate cancer, colorectal cancer, liver cancer, melanoma, ovarian cancer, and lung cancer. In other embodiments, the breast cancer is triple negative breast cancer. In yet other embodiments, the brain cancer is glioblastoma. In yet other embodiments, the cancer is HER2-positive. In yet other embodiments, the cancer is phosphoinositide 3-kinase (PI3) kinase mutant-positive. In yet other embodiments, the breast cancer is HER2-positive.

The methods described herein include administering to the subject a therapeutically effective amount of at least one compound described herein, which is optionally formulated in a pharmaceutical composition. In various embodiments, a therapeutically effective amount of at least one compound described herein present in a pharmaceutical composition is the only therapeutically active compound in a pharmaceutical composition. In certain embodiments, the method further comprises administering to the subject an additional therapeutic agent that treats or prevents a disease or disorder contemplated herein.

In certain embodiments, administering the compound(s) described herein to the subject allows for administering a lower dose of the additional therapeutic agent as compared to the dose of the additional therapeutic agent alone that is required to achieve similar results in treating or preventing a disease or disorder described as being treatable with at least one compound described herein in the subject. For example, in certain embodiments, the compound(s) described herein enhance(s) the activity of the additional therapeutic compound, thereby allowing for a lower dose of the additional therapeutic compound to provide the same effect.

In certain embodiments, the compound(s) described herein and the therapeutic agent are co-administered to the subject. In other embodiments, the compound(s) described herein and the therapeutic agent are coformulated and co-administered to the subject.

In certain embodiments, the subject is a mammal. In other embodiments, the mammal is a human.

Combination Therapies

The compounds useful within the methods described herein can be used in combination with one or more additional therapeutic agents useful for treating the diseases and disorders described herein. These additional therapeutic agents may comprise compounds that are commercially available or synthetically accessible to those skilled in the art. These additional therapeutic agents are known to treat, prevent, or reduce the symptoms, of at least one disorder described herein.

In various embodiments, a synergistic effect is observed when a compound as described herein is administered with one or more additional therapeutic agents or compounds. A synergistic effect may be calculated, for example, using suitable methods such as, for example, the Sigmoid-$E_{max}$ equation (Holford & Schemer, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a at least one disease or disorder described as being treatable by the compounds described herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions described herein to a patient, preferably a mammal, more preferably a human, may be carried out using known procedures, at dosages and for periods of time effective to treat a at least one disease or disorder described as being treatable by the compounds described herein in the patient. An effective amount of the therapeutic compound necessary to achieve a therapeutic effect may vary according to factors such as the state of the disease or disorder in the patient; the age, sex, and weight of the patient; and the ability of the therapeutic compound to treat a at least one disease or disorder described as being treatable by the compounds described herein in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound described herein is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds described herein employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the compound(s) described herein are dictated by and directly dependent on (a) the unique characteristics of the therapeutic compound and the particular therapeutic effect to be achieved, and (b) the limitations inherent in the art of compounding/formulating such a therapeutic compound.

In certain embodiments, the compositions described herein are formulated using one or more pharmaceutically acceptable excipients or carriers. In certain embodiments, the pharmaceutical compositions described herein comprise a therapeutically effective amount of a compound described herein and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions described herein are administered to the patient in dosages that range from one to five times per day or more. In other embodiments, the compositions described herein are administered to the patient in range of dosages that include, but are not limited to, once every day, every two, days, every three days to once a week, and once every two weeks. It is readily apparent to one skilled in the art that the frequency of administration of the various combination compositions described herein varies from individual to individual depending on many factors including, but not limited to, age, disease or disorder to be treated, gender, overall health, and other factors. Thus, administration of the compounds and compositions described herein should not be construed to be limited to any particular dosage regime and the precise dosage and composition to be administered to any patient is determined by the attending physician taking all other factors about the patient into account.

The compound(s) described herein for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 350 μg to about 6,000 mg, about 500 μg to about 5,000 mg, about 750

µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound described herein is from about 1 mg and about 2,500 mg. In some embodiments, a dose of a compound described herein used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, a composition as described herein is a packaged pharmaceutical composition comprising a container holding a therapeutically effective amount of a compound described herein, alone or in combination with a second pharmaceutical agent; and instructions for using the compound to treat, prevent, or reduce one or more symptoms of a disease or disorder described herein in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions described herein include oral, nasal, rectal, intravaginal, parenteral, buccal, sublingual or topical. The compounds for use in the compositions described herein can be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions described herein are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compound(s) described herein can be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

For parenteral administration, the compounds as described herein may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions.

These oil solutions or suspensions may also contain a long-chain alcohol diluent or dispersant, such as Ph. Helv or similar alcohol.

Additional Administration Forms

Additional dosage forms suitable for use with the compound(s) and compositions described herein include dosage forms as described in U.S. Pat. Nos. 6,340,475; 6,488,962; 6,451,808; 5,972,389; 5,582,837; and 5,007,790. Additional dosage forms suitable for use with the compound(s) and compositions described herein also include dosage forms as described in U.S. Patent Applications Nos. 20030147952; 20030104062; 20030104053; 20030044466; 20030039688; and 20020051820. Additional dosage forms suitable for use with the compound(s) and compositions described herein also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations described herein can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use with the method(s) described herein may be administered in the form of microparticles, for example, by injection or in the form of wafers or discs by implantation.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions described herein. Thus, single unit dosage forms suitable for oral administration, such as tablets, capsules, gelcaps, and caplets, that are adapted for controlled-release are encompassed by the compositions and dosage forms described herein.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" is defined herein as a compound or compounds, including, but not limited to, polymers, polymer matrices, gels, permeable membranes, liposomes, or microspheres or a combination thereof that facilitates the controlled-release of the active ingredient. In one embodiment, the compound(s) described herein are administered to a patient, alone or in combination with another pharmaceutical agent, using a sustained release formulation. In one embodiment, the compound(s) described herein are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound described herein depends on the age, sex and weight of the patient, the current medical condition of the patient and the progression of one or more diseases or disorders mentioned herein in the patient being treated. The skilled artisan is able to determine appropriate dosages depending on these and other factors.

A suitable dose of a compound described herein can be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound(s) described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds described herein can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

EXAMPLES

Various embodiments of the present application can be better understood by reference to the following Examples which are offered by way of illustration. The scope of the present application is not limited to the Examples given herein.

Materials & Methods

Cell Lines and Cell Culture:

BT474c1 cells were a gift of Dr. Jose Baselga (AstraZeneca). Brpkp110 and A7C11 cells were the kind gift of Dr. Jose Conejo-Garcia (Allegrezza, et al., 2016, Cancer Res 76:6253-6265; Rutkowski, et al., 2014, J Vis Exp, doi: 10.3791/51171; Rutkowski, et al., 2015, Cancer Cell 27, 27-40; Sheen, et al., 2016, Oncogenesis 5:e267).

BT474c1, Brpkp110, A7C11, BT20 (ATCC), SKBr3 (ATCC), HCC1806 (ATCC), MDA-MB-468 (ATCC), MDA-MB-231 (ATCC), HCC1954 (ATCC), MDA-MB-231 (ATCC), Cal120 (DSMZ), Cal51 (DSMZ), MCF7 (ATCC), BT549 (ATCC) cells were cultured in 1×DMEM/F-12 50/50 supplemented (Life Technologies) with 10% fetal bovine serum (FBS) (Life Technologies) and 1× penicillin-streptomycin. Hs578t (ATCC) cells were cultured in 1×DMEM/F-12 50/50 supplemented with 0.01 mg/ml bovine insulin (Sigma), 10% FBS, and 1× penicillin-streptomycin. MMTV-PyMT and MMTV-Neu cell lines were provided by Dr. Erica Golemis (Fox Chase Cancer Center) and maintained in low-calcium DMEM supplemented with 5% horse serum.

Lentiviral Transduction:

CRISPR-Cas9 pools of Brpkp110 and A7C11 were generated using single guide RNAs against exon 1 in mouse Acss2. Cas9 and guide RNAs were introduced into Brpkp110 and A7C11 cell by lentiviral infection. Briefly, HEK293T cells were transfected (Lipofectamine 2000) with psPAX2, pVSV-G, and pLentiCRISPRV2-blast containing a single guide RNA cloned into the BsmBI site (GE Healthcare). Transduced pools of Brkp110 and A7C11 cells were selected using blasticidin S.

ACSS2 Biochemical Assay:

ACSS2 enzyme activity was measured using the TRANSCREENER® TRF AMP/GMP assay (Bellbrook Labs). Recombinant ACSS2 was purchased from Origene. The assay was performed in white, opaque, low volume 384 well plates. Test compounds were diluted in 100% DMSO and then 100 nL of each dilution was transferred using the Janus MDT Nanohead to assay plates containing 3 µL ACSS2 (2.5 nM) in assay buffer (30 mM HEPES, pH 7.4, 140 mM NaCl, 2 mM MgCl2, 5 mM sodium acetate, 2 mM DTT, 0.005% Brij35). Three microliters of substrate mix containing 100 µM ATP and 10 µM coenzyme A was added to the plates followed by a 120 min incubation. The final concentrations of enzyme and substrates in the reaction mix was 1.25 nM ACSS2, 50 µM ATP, and 5 µM coenzyme A. After incubation, 3 µL of terbium conjugated AMP antibody and AMP tracer was added to the plates according to the methods described by BellBrook Labs. After an additional 30 min, the HTRF signal was measured using an Envision Plate reader. Data were normalized to % inhibition, where 100% inhibition is equal to the counts obtained in the absence of ACSS2, and 0% inhibition is equal to the counts obtained in the complete reaction including a DMSO control.

Compounds:

All new analogs are fully characterized by LCMS and NMR to ensure purity of greater than 95%.

ADME Drug-Like Properties:

Water-solubility. Approximately 1 mL of PBS buffer (pH 7.4) is added to approximately 10 mg of test compound. The solution is sonicated for 30 minutes and vortexed at a low speed for at least 30 minutes. The solution is kept at room temperature for 16-28 hours. After such time, the solutions are filtered through a 0.22-micron filter followed by diluting 1:10, 1:100, and 1:1000, and 1:10,000 in triplicate in 50% acetonitrile in water (1:1, v/v). The final sample solutions are mixed with an internal standard solution (1:1) followed by LC MS/MS analysis. Solubility is determined according to the calibration curve generated from 5 concentration standards.

Microsomal stability. Representative compounds are evaluated for metabolic stability in mouse and human liver microsomes as a predictive measure for suitable exposure in a mouse pharmacokinetic study. The test compounds at a concentration of 0.5 µM are incubated with 0.5 µg/mL of liver microsomes and an NADPH-regenerating system (cofactor solution) in 50 mM potassium phosphate buffer (pH 7.4) containing 1 mM magnesium chloride solution. At 0, 5, 15, 30, and 45 minutes, an aliquot is taken, and reactions are quenched with an acetonitrile solution containing an internal standard. Additionally, controls are measured that do not contain the cofactor solution. Following completion of the experiment, samples are analyzed by LC-MS/MS. Results are reported as peak area ratios of each analyte to internal standard. The intrinsic clearance (CLint) is determined from the first-order elimination constant by nonlinear regression.

Pharmacokinetic analysis and in vivo exposure. Mouse pharmacokinetic studies are performed on several of the best analogs to confirm in vivo exposure in the plasma. Compound is administered to the mouse by i.p. (10 mg/kg), i.v. (2 mg/kg), and p.o. (10 mg/kg) administration. Samples (blood) are collected through 6 hours after dosing for PK analysis. Six time points are evaluated: 0.25 h, 0.5 h, 1 h, 2 h, 4 h and 6 h. Plasma is obtained, deproteinized and analyzed for compound using LC-MS/MS methods. LC-MS analysis was performed on a Triple Quad 5500 mass spectrometer (Sciex) coupled to a Nexera X2 (Shimadzu) liquid chromatography system. Samples were separated by reverse phase chromatography on a ZORBAX SB C18, 2.1×50 mm, 5 µm column (Agilent) at room temperature with a mobile phase A of 0.1% formic acid in water) and a mobile phase B of 0.1% formic acid in acetonitrile. The LC was run at a flow rate of 0.8 mL/min and the gradient used was as follows: 0.20 min 10% B; 1.10 min, 95% B; 2.10 min, 95% B; 2.15 min, 10% B; and 3.00 min stop. Calculated parameters include, $t_{1/2}$, AUC, Vd, CL, $C_{max}$, $t_{max}$, and % F. Three mice are used for each time point and one control animal.

Antibodies and Western Blotting:

Cells were lysed in 1× Laemmli buffer (BioRad) supplemented with 40 mM dithiothreitol (DTT). Lysates were heated at 95° C. for 5 minutes and resolved using Mini-PROTEAN precast polyacrylamide gels (BioRad) for 30 minutes at 200 volts and blotted onto nitrocellulose membranes for one hour at 20 volts using the Mini Blot Module transfer system (Life Technologies). The blots were then blocked using 5% milk in Tris-buffered saline solution with Tween-20 (TBST) for 1 hour at room temperature. Blots were incubated with primary antibodies overnight at 4° C. Primary antibodies were diluted in a 1% BSA and 0.05% sodium azide in TBST. Antibodies were purchased from the following vendors: ACSS2 (Cell Signaling #3658), GAPDH (Abcam #9485), ACTB (ProteinTech #60008), EGFR (Cell Signaling #3658), and HER2 (Cell Signaling #2165). Secondary antibodies were purchased from Li-Cor Biosciences (goat anti-mouse #926-32210 and donkey anti-rabbit #926-68073) and diluted in TBST. Incubation with the secondary antibody occurred at room temperature for one hour. Blots were imaged using a Li-Cor Odyssey infrared imager.

Nuclear Fractionation:

20×10$^6$ cells were trypsinized, quenched with complete DMEM and pelleted at 1000 rpm for 5 min. The cell pellet was washed in PBS and pelleted at 1000 rpm for 5 min. 10% of the cell pellet was collected as total extract in buffer BC-500 (50 mM Tris pH 7.6, 2 mM EDTA, 500 mM KCl, 10% glycerol) and incubated on ice for 10 minutes, followed by a 10 s sonication. Cell debris were pelleted at 10,000 rpm for 5 min and supernatant was collected as total extract. 5 volumes of buffer A (10 mM Hepes pH7.9, 5 mM $MgCl_2$, 0.25M sucrose, 0.10% NP-40) were added to the remaining cell pellet and incubated on ice for 10 minutes. Nuclei were pelleted at 8000 rpm for 10 minutes and supernatant was collected as cytosolic fraction. 2 volumes of buffer B (10 mM Hepes pH 7.9, 25% Glycerol, 1.5 mM $MgCl_2$, 0.1 mM EDTA, 300 mM NaCl) were added to pelleted nuclei and incubated on ice for 10 minutes. Soluble nuclear proteins were collected as the soluble supernatant following a 15 minute 10000 rpm spin. 1 volume of buffer BC-1000 (50 mM Tris pH 7.6, 2 mM EDTA, 1000 mM KCl, 10% glycerol) was added to remaining chromatin pellet and incubated on ice for 10 minutes. 1 volume of buffer BC-0 (50 mM Tris pH 7.6, 2 mM EDTA, 10% glycerol) was added and the sample was sonicated for 10 s. DNA was pelleted at 10000 rpm for 15 minutes and supernatant was collected as chromatin bound protein fraction. Individual fractions were diluted with buffer BC-0 and equal concentrations of protein loaded onto SDS-PAGE gel.

Bioinformatics and Data Mining:

METABRIC breast cancer database (Curtis, et al., 2012, Nature 486:346-352) was mined using cbioportal dot org. ACSS2 mRNA expression was analyzed in the six different subtypes of breast cancer, including HER2+ breast cancer, and was defined by the PAM50+claudin-low filter. Putative EGFR copy number alterations are generated by GISTIC algorithm which attempts to identify significantly altered regions of amplification or deletion across a set of patients. For mRNA expression of ACSS2 in breast cancer cell lines the Cancer Cell Line Encyclopedia were used to extract the information C(erami, et al., 2012, Cancer Discov 2:401-404; Gao, et al., 2013, Sci Signal 6:pl1). Briefly, the mRNA expression of ACSS2 for all breast cancer cell lines was exported along with whether the cell lines had upregulation or putative copy number gains/amplification of HER2 and EGFR. mRNA expression is computed as the expression of an individual gene and tumor to the gene's expression distribution in a reference population. That reference population is all profiled breast cancer cell lines for the gene in question (ACSS2). The returned value indicates the number of standard deviations away from the mean of expression in the reference population (z-score). This measure is useful to determine whether a gene is up- or down-regulated relative to the normal samples or all other tumor samples. The normalization method is described here: github dot com/cBioPortal/cbioportal/blob/master/docs/Z-Score-normalization-script.m).

Tumor Xenograft Studies:

For BT474 mouse xenograft studies 5-6 week old female NSG (Wistar) were anesthetized and one 17β-estradiol 60 day release pellet (Innovative Research of America Cat. No. SE-121) was injected subcutaneously via 10 gauge precision trochar into the lateral side of the neck between the ear and shoulder. 24 hours later 10$^5$ BT474 luciferase positive cells in 100 µl PBS:matrigel (growth factor reduced) were injected subcutaneously into the hind limb. For A7C11 and Brpkp110 xenografts, 5×10$^5$ cells in 100 µl PBS:Matrigel (growth factor reduced Corning Cat. No. 356231) were subcutaneously injected into the hindlimb of 5-6 week old female NSG mice (Wistar). Following tumor establishment in all groups, mice were randomized and treated intraperitoneally (IP) daily with vehicle (10% DMSO, 10% absolute ethanol, 20% solutol, 60% water containing 0.5% Tween20) or 100 mg/kg VY-3-135 as indicated in the figure legend. Tumors were measured thrice weekly via caliper measurement and tumor volume calculated as $(L \times W^2)/2$ (where L is the longer of the 2 measurements). At the study conclusion all tumors were resected and processed fresh or flash frozen in liquid nitrogen and stored at −80° C. for downstream analysis.

Bioluminescent Imaging:

Mice bearing luciferase positive tumors were injected IP with 150 mg/kg sterile filtered D-luciferin potassium salt (Gold Bio Cat. No. LUCK-1G). Isoflurane anesthetized mice were imaged 15 minutes post substrate injection using the IVIS 200 bioluminescent imager (Perkin Elmer). Images were analyzed using Living Image Software (Perkin Elmer).

Liquid Chromatography Mass Spectrometry Based Metabolomics:

All metabolomic experiments were performed in serum-like modified Eagle's medium (SMEM). SMEM contains 54 different nutrients that are found in the bloodstream at concentrations that are physiologically relevant to humans. SMEM was supplemented with 10% or 1% fetal bovine serum (FBS; Life Technologies). Cells were grown in normoxia (atmospheric oxygen) or hypoxia (1% oxygen) while being incubated in uniformly labeled $^{13}C_2$-acetate (0.100 mM; Cambridge Isotope Laboratories). Lengths of incubation are described in the figure legends. For extraction of metabolites from cultured cells, SMEM medium was aspirated and cells were washed once in ice-cold PBS. Metabolites were extracted by adding a solution of LC-MS grade methanol/acetonitrile/water (5:3:2) to the well. Plates were incubated at 4° C. for 5 minutes on a rocker and then the extraction solution was collected. The metabolite extract was cleared by centrifugation at 15,000×g for 10 minutes at 4° C. Supernatants were transferred to LC-MS silanized glass vials with PTFE caps and either run immediately on the LC-MS or stored at −80° C. For extraction of metabolites from tumors, tumor bearing mice were sacrificed by exsanguination under anesthesia and tumors were immediately excised and flash frozen in liquid nitrogen. Frozen tumors were weighed and then extracted at 40 mg/mL in extraction solution using a tissue homogenizer (Bullet Blender) and stainless steel beads. The metabolite extract was cleared twice by centrifugation at 15,000×g for 10 minutes at 4° C. Supernatants were transferred to LC-MS silanized glass vials with PTFE caps and either run immediately on the LC-MS or stored at −80° C.

LC-MS analysis was performed on a Q Exactive Hybrid Quadrupole-Orbitrap HF-X MS (ThermoFisher Scientific) equipped with a HESI II probe and coupled to a Vanquish Horizon UHPLC system (ThermoFisher Scientific). 0.002 ml of sample is injected and separated by HILIC chromatography on a ZIC-pHILIC 2.1-mm. Samples are separated by ammonium carbonate, 0.1% ammonium hydroxide, pH 9.2, and mobile phase B is acetonitrile. The LC was run at a flow rate of 0.2 ml/min and the gradient used was as follows: 0 min, 85% B; 2 min, 85% B; 17 min, 20% B; 17.1 min, 85% B; and 26 min, 85% B. The column was maintained at 45° C. and the mobile phase was also pre-heated at 45° C. before flowing into the column. The relevant MS parameters were as listed: sheath gas, 40; auxiliary gas, 10; sweep gas, 1; auxiliary gas heater temperature, 350° C.; spray voltage, 3.5 kV for the positive mode and 3.2 kV for the negative mode. Capillary temperature was set at 325° C., and funnel RF level at 40. Samples were analyzed in full MS scan with polarity switching at scan range 65 to 975 m/z; 120,000 resolution; automated gain control (AGC) target of 1E6; and maximum injection time (max IT) of 100 milliseconds. Identification and quantitation of metabolites was performed using an annotated compound library and TraceFinder 4.1 software. The "M+X" nomenclature refers to the isotopolog for that given metabolite. Isotopologs are chemically identical metabolites that differ only in their number of carbon-13 atoms. For instance, "M+2 citrate" means that two of the six carbons in citrate are carbon-13 while the other four are carbon-12. "M+4 citrate" means that four of the six carbons in citrate are carbon-13 while the other two are carbon-12.

Example 1

A robust biochemical screening assay was set up for testing compounds as potential ACSS2 inhibitors. Since this enzyme reaction generates one mole of adenosine monophosphate (AMP) for every mole of acetyl CoA, the transcreener technology was selected as the primary biochemical assay (FIG. 1A). This assay utilizes an antibody that recognizes the AMP product of the reaction, and provides a direct immunodetection of AMP leading to a robust assay method, which eliminates the need for fluorescently labeled substrates, the low signal background ratio in substrate depletion assays, and the potential for interference with coupling enzymes (Staeben, et al., 2010, Drug Dev Technol. 8(3):344-55).

Figure 10A:
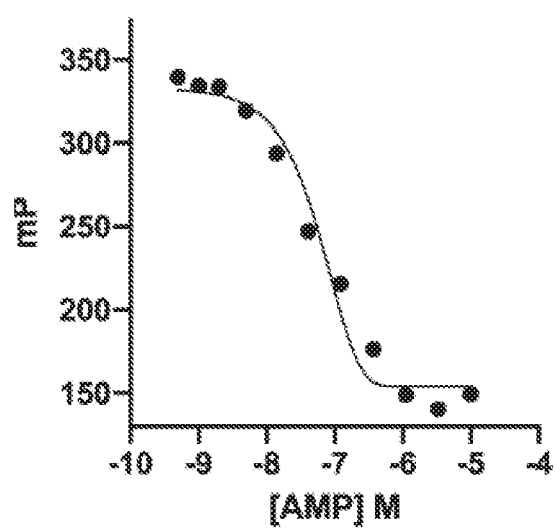
FIGS. 10A-10D illustrate optimization parameters for in vitro ACSS2 biochemical assay.
Figure 10B:
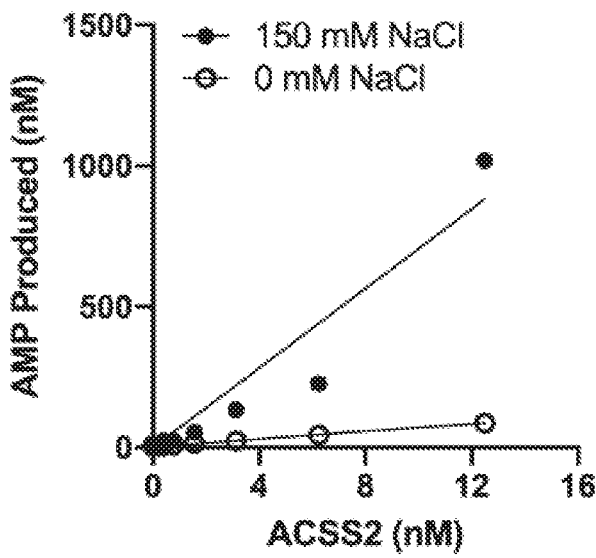
Figure 10D:
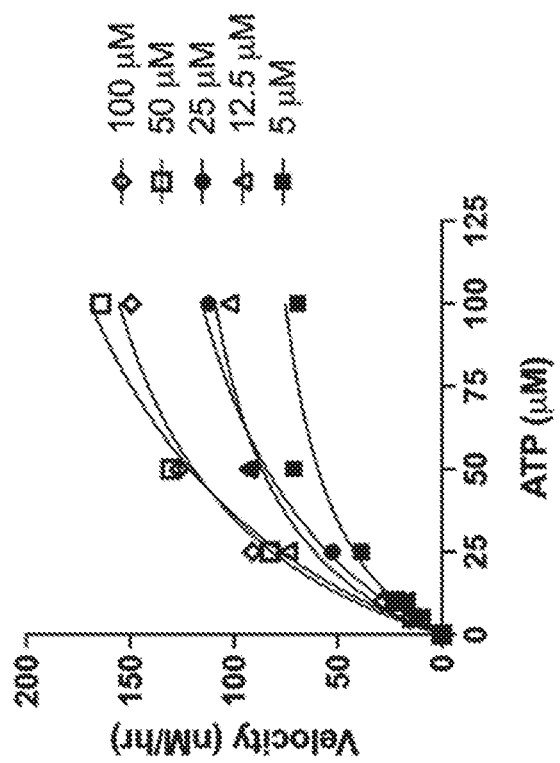
Figure 10C:
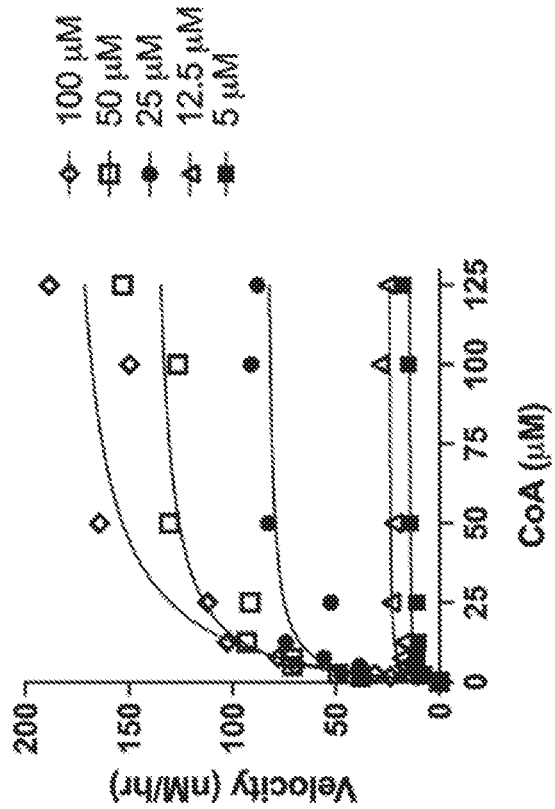

The transcreener AMP FP Assay (Bellbrook Cat #3015) was used to detect the product AMP by displacement of a fluorescent AMP-tracer from an antibody. An AMP standard curve was created, and since salt can affect protein stability and enzyme kinetics, different concentrations of recombinant human ACSS2 were tested in the presence and absence of physiological-like levels of sodium chloride (FIGS. 10A-10B). Sodium chloride boosted ACSS2 activity by five to seven fold and the activity of ACSS2 was linear at lower concentrations of enzyme. Dose response curves were next generated for coenzyme A (CoA) and ATP (FIGS. 10C-10D). Assay optimization resulted in the following conditions: ACSS2 (0.6 nM; Origene cat #TP304260, Lot #30A4DF), Assay buffer conditions; 30 mM HEPES (pH 7.5), 140 mM NaCl, 2 mM $MgCl_2$, 0.01% Brij35, 2 mM DTT, 1% DMSO, 5 mM sodium acetate, CoA (5 μM), and ATP (25-50 μM).

Figure 1C:
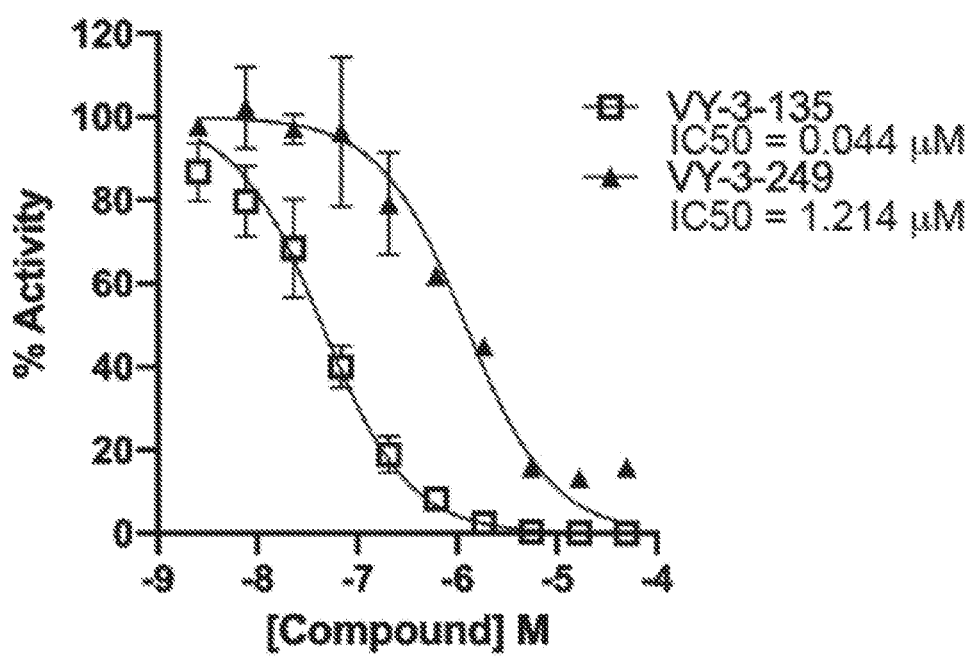

The following tool in vitro inhibitors of ACSS2 activity were used herein: 1-(2,3-di(thiophen-2-yl)quinoxalin-6-yl)-3-(2-methoxyethyl)urea (VY-3-249) and (R)-1-ethyl-2-(hydroxydiphenylmethyl)-N-(2-hydroxypropyl)-1H-benzo[d]imidazole-6-carboxamide (VY-3-135). The in vitro biochemical TranScreener assay indicated that VY-3-249 has an $IC_{50}$ value of 1214±128 nM (FIG. 1C), and VY-3-135 has an $IC_{50}$ value of 44±3.85 nM (FIG. 1C).

Several putative "transition state analogue" inhibitors were designed and tested in the AMP FP assay. At least two of those compounds (Cmpd 1 and Cmpd 2) were identified with activity less than 200 nM. The ADME properties of these compounds were evaluated; both compounds were shown to have very good metabolic stability with half-lives greater than 30 minutes. Such properties are predictive of good metabolic stability in vivo.

Example 3: VY-3-135 and Compounds of Formula (I) are Transition State Mimetics of ACSS2

There are currently no published crystal structures of human ACSS2, but there is an X-ray crystal structure of Salmonella typhimurium AcCoA synthetase complexed with adenosine-5'-propylphosphate and CoA (Gulick, et al., 2003, Biochemistry 42:2866-2873). In certain embodiments, the nucleoside binding site between human, mouse, and salmonella ACSS2 is almost identical, where the only difference is an aromatic tryptophan residue present in salmonella versus an aromatic phenylalanine residue in human and mouse. FIG. 7C depicts the geometry of the transition state of the ACSS2 catalyzed reaction where the sulfur of the CoA attacks the carbonyl carbon of the acetate of acetyl-AMP to form a tetrahedral intermediate. VY-3-135 and compounds of formula (I) resemble this transition state. In certain embodiments, the benzimidazole ring in the compounds mimic the adenine moiety of the acetyl-AMP intermediate, while the tetrahedral carbon bears the hydroxy group potentially mimicking the oxyanion in the transition state. In addition, the S. typhimurium crystal structure suggests that the phenyl rings for VY-3-1-35 (and the phenyl and trifluoromethyl groups for compounds of formula (I)) engage in aromatic binding interactions with residues tryptophan 413 and tryptophan 414 making up the nucleoside binding pocket. Without wishing to be limited by any theory, VY-3-135 and compounds of formula (I) act as transition state mimetic of the acetyl-AMP intermediate of the ACSS2 enzymatic reaction.

Example 4

Figure 7A:
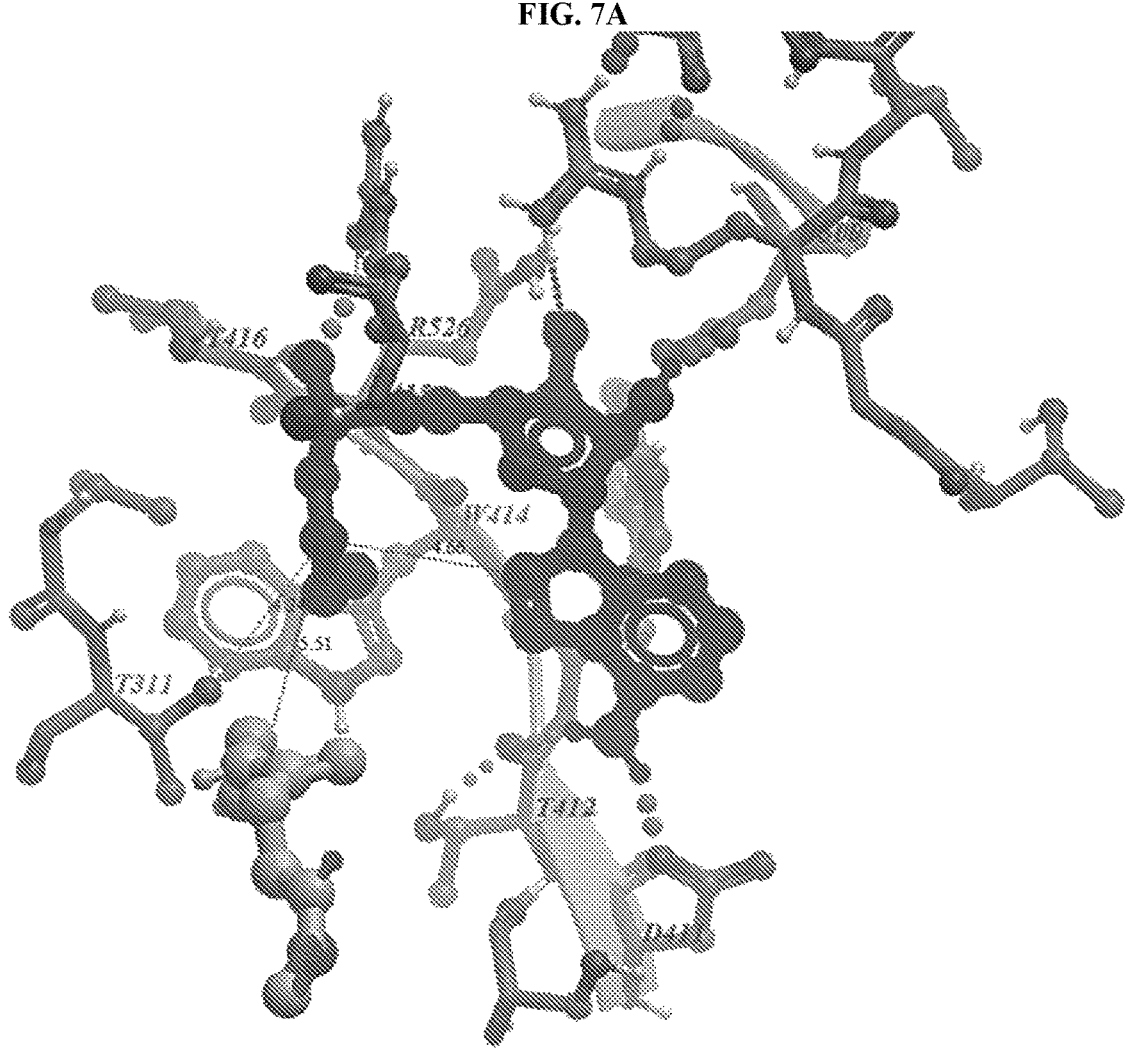

Further optimization of the initially identified ACSS2 inhibitors was performed. FIG. 7A illustrates a non-limiting binding pose for the AMP-Acetyl mimic, AMP-propyl ester in blue complexed with ACSS2 (pdb; 1PG3). In yellow is the CoA moiety with the terminal —SH poised for nucleophilic attack of the acetate carbonyl to generate a tetrahedral transition state, which is stabilized by the Thr 311 —OH moiety through a H-bond to the resulting oxyanion. One of the hit compounds, Cmpd 1, has a chiral center, therefore single enantiomers may be separated and evaluated for potency. In certain non-limiting embodiments, one enantiomer is more potent than the other confirming binding in a stereotopic environment of the active site.

Figure 8:
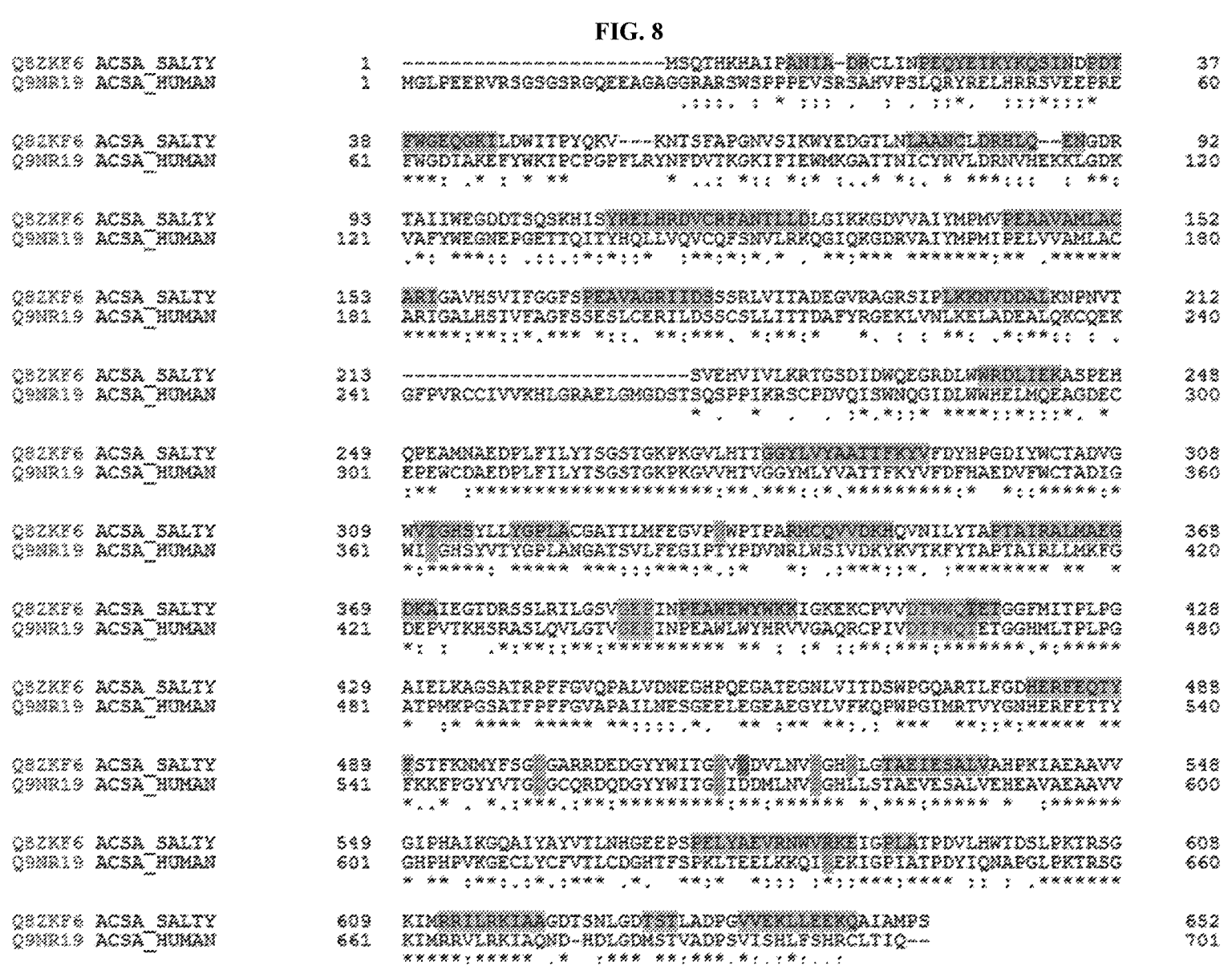
Figure 9:
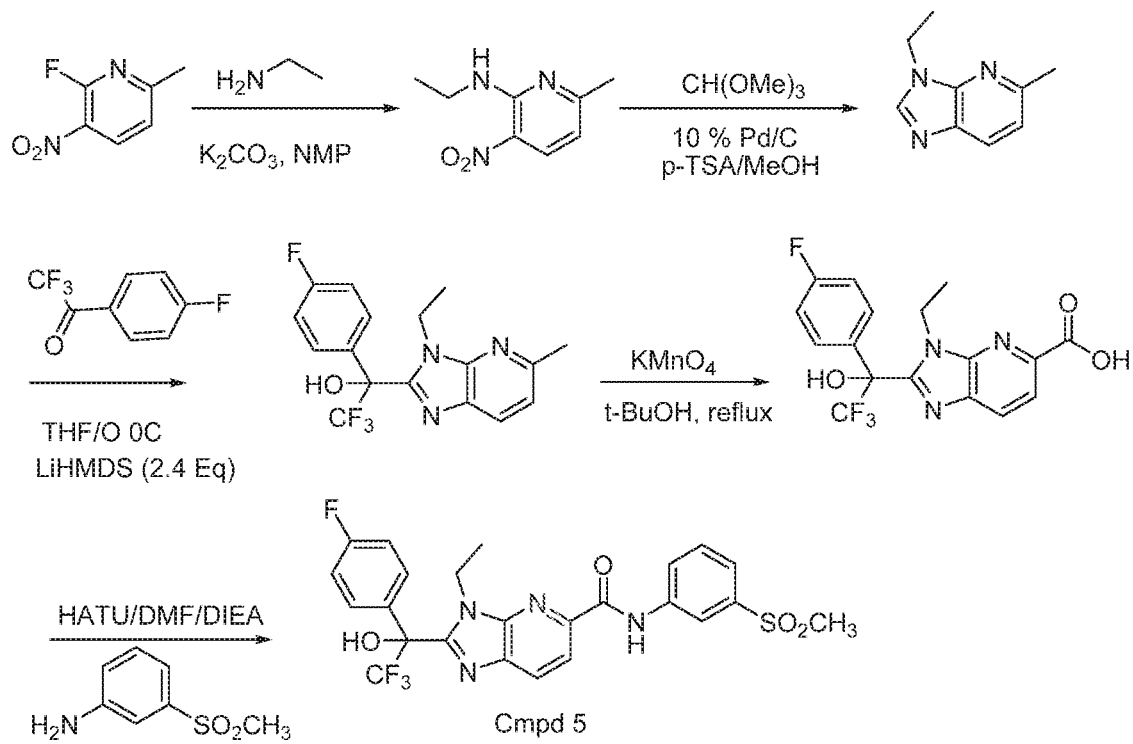
FIG. 9 illustrates a non-limiting synthetic route to a compound contemplated in the disclosure.

The —OH group in Cmpd 1 can be replaced with —CN, —SO$_2$alkyl, or any other group that can H-bond with the Thr 311 residue. The benzimidazole N of Cmpd 1 is N-ethylated. Based on the crystal structure, Asp500, which is conserved in the human enzyme, forms a key H-bond with the ribose ring of AMP-Ac. In certain non-limiting embodiments, the ethyl group is replaced with a —OH, —OMe, or —OCF$_3$, which may engage this Asp500 through an H-bonding interaction (FIG. 8). In other non-limiting embodiments, the amide linker projecting off the benzimidazole is replaced with an ether linkage or a urea linkage to probe the importance of the NH amide bond for H-bonding with Thr412 or Asp411. In yet other non-limiting embodiments, a basic center is incorporated in the aromatic group linked to the benzimidazole ring as to engage the Asp411 through H-bonding or salt bridge interactions. In yet other embodiments, the benzimidazole ring is replaced with aza analogs as to engage the Asp500 moiety through an H-bond or salt bridge interaction. Synthesis of one such aza analogue is shown in FIG. 9.

Figure 2A:
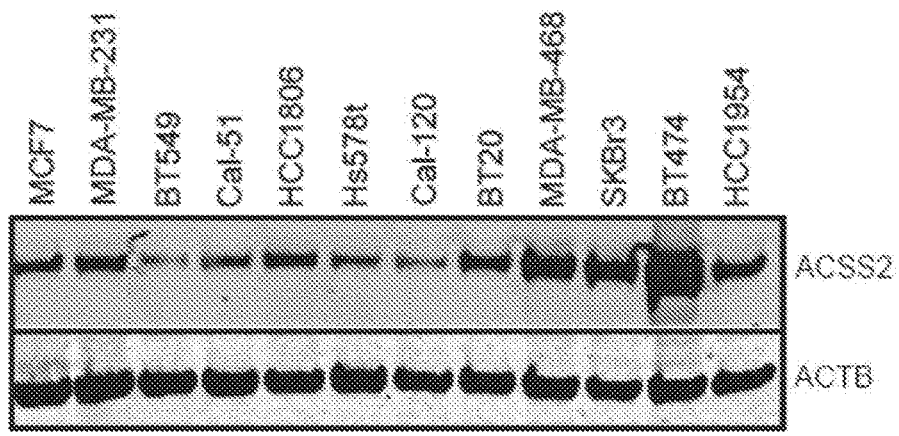

Example 5: VY-3-135 is an Potent Low Nanomolar Inhibitor of ACSS2 in Cancer Cells in Vitro The effectiveness of VY-3-135 was tested in a cell based assay. High ACSS2 expression correlates with high acetate uptake, and thus a panel of 12 breast cancer cell lines was used to identify those with high ACSS2 expression. BT474, MDA-MB-468 and SKBr3 cells all have high basal expression of ACSS2 (FIG. 2A). Acetate uptake and its relative contribution to fatty acid biosynthesis is highest under nutrient and oxygen stressed conditions. Indeed, BT474, MDA-MB-468 and SKBr3 cells can all upregulate ACSS2 at both the mRNA and protein level in response to oxygen and nutrient stress.

Figure 2B:
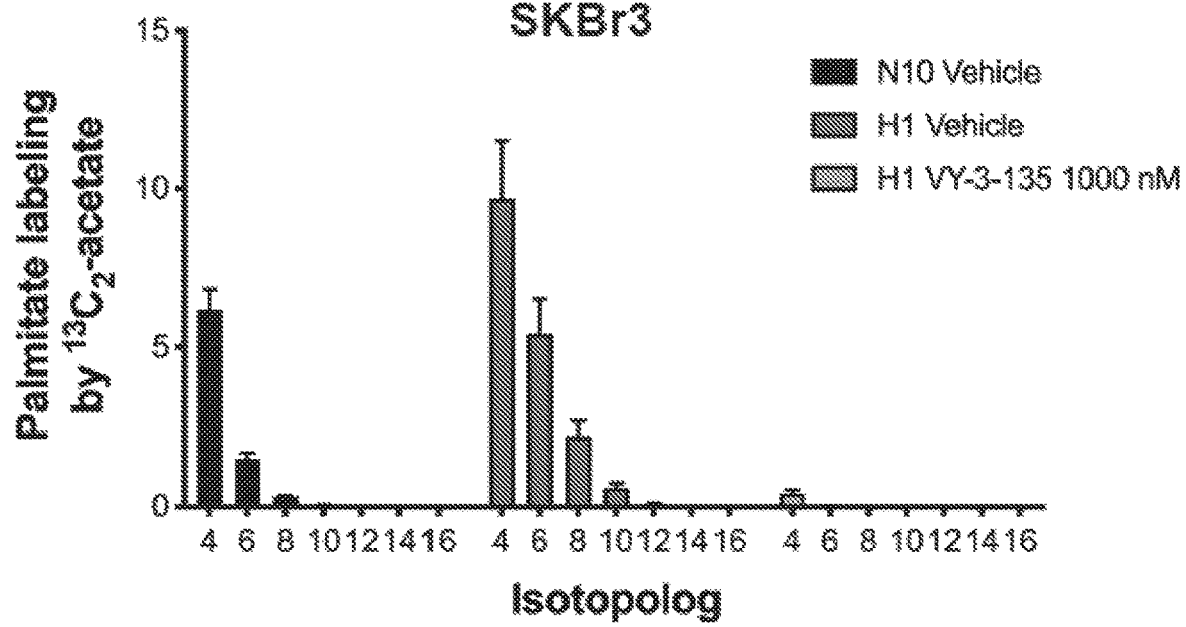
Figure 11A:
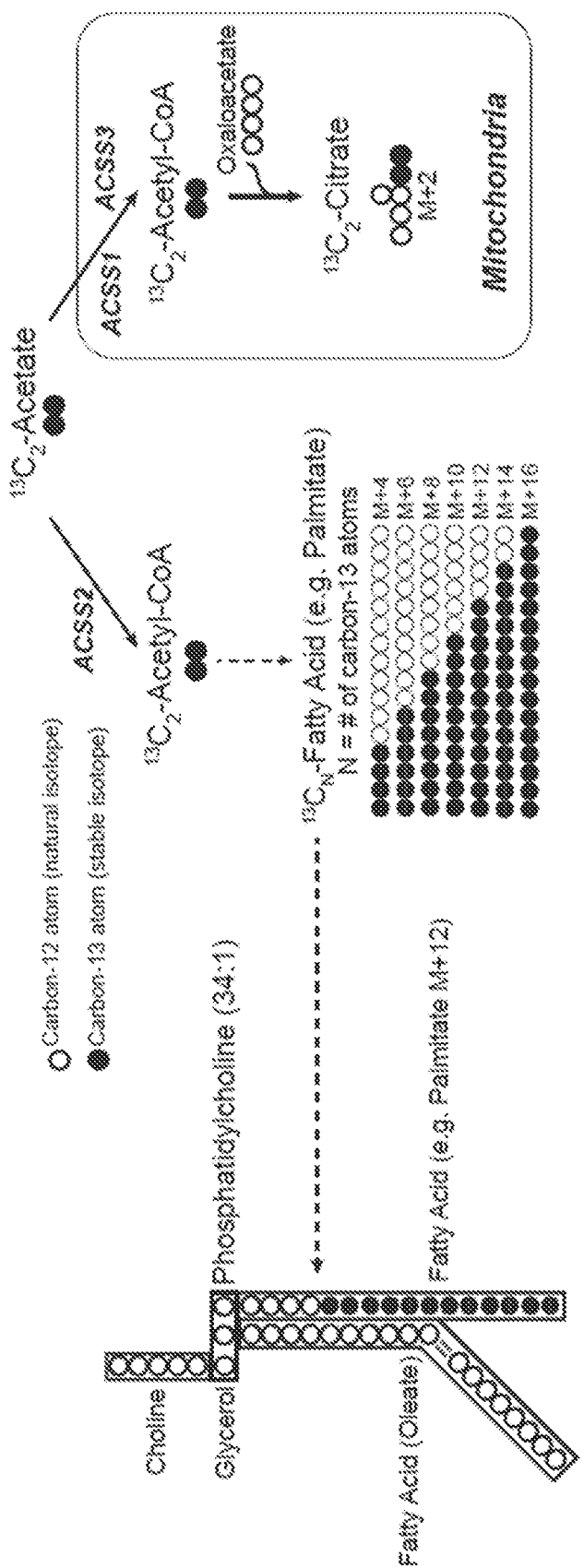
FIGS. 11A-11D depict that an illustrative ACSS2 small molecule inhibitor is a potent inhibitor of ACSS2 in cells.

Thus, SKBr3 cells were incubated for 24 hours in $^{13}C_2$-acetate in normoxic, nutrient replete conditions (N10) and in hypoxic, low lipid conditions (H1). Lipid extracts were saponified and cellular fatty acids were analyzed by LC-MS for carbon-13 labeling from $^{13}C_2$-acetate (FIG. 11A). All in vitro stable isotope tracing experiments are performed in cell culture medium that contains 52 different nutrients at physiologically relevant concentrations (Table 1). $^{13}C_2$-acetate tracing into SKBr3 cells showed that hypoxia and low lipid stress caused a significant increase in carbon-13 labeling of the saturated fatty acid palmitate (FIG. 2B), indicating increased ACSS2 activity in metabolically stressed cancer cells. Addition of an ACSS2 inhibitor, VY-3-135, completely blocked fatty acid synthesis from acetate in SKBr3 cells (FIG. 2B).

Figure 2C:
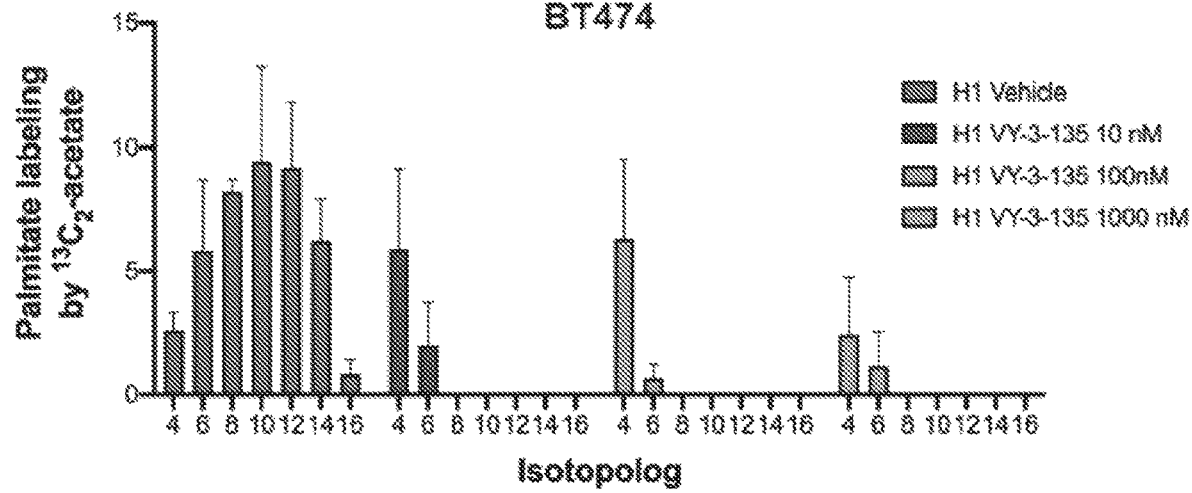
Figure 11B:
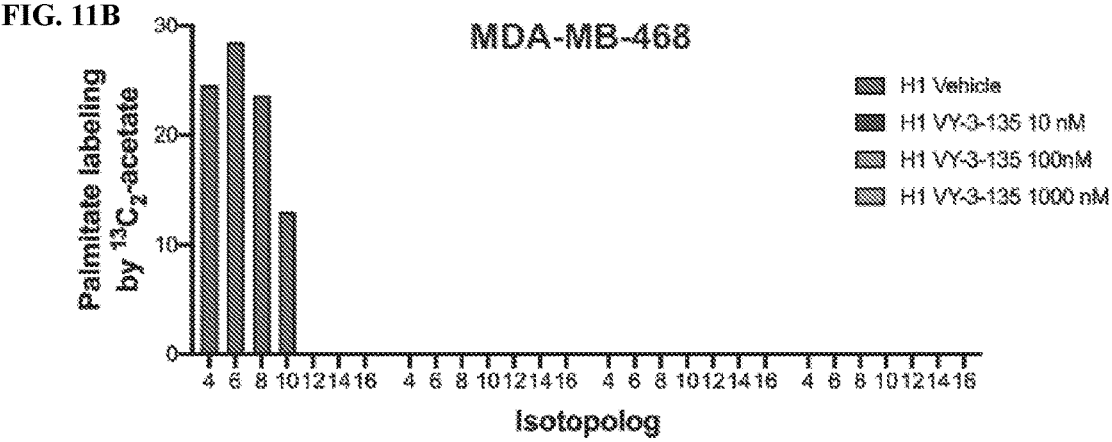

Based on the SKBr3 results, the ability of VY-3-135 to block acetate metabolism in two other breast cancer cell lines was then tested. BT474 cells were exposed to hypoxia and low lipid culture medium supplemented with VY-3-135 and $^{13}C_2$-acetate for 24 hours. Similar to the SKBr3 cells, VY-3-135 markedly inhibits the use of acetate as a substrate for fatty acid synthesis at low nanomolar concentrations (FIG. 2C). Similar results were obtained in MDA-MB-468 cells (FIG. 11B).

Figure 11C:
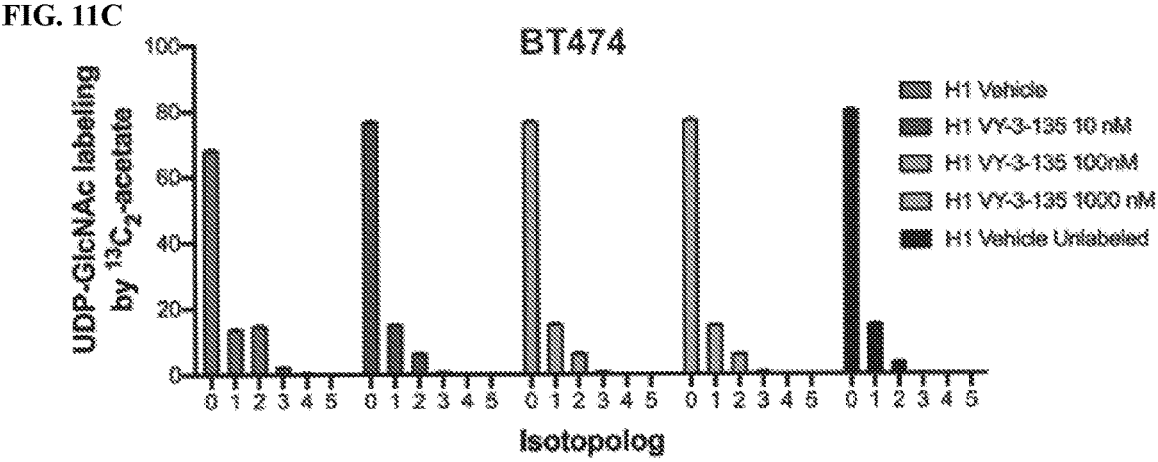
Figure 11D:
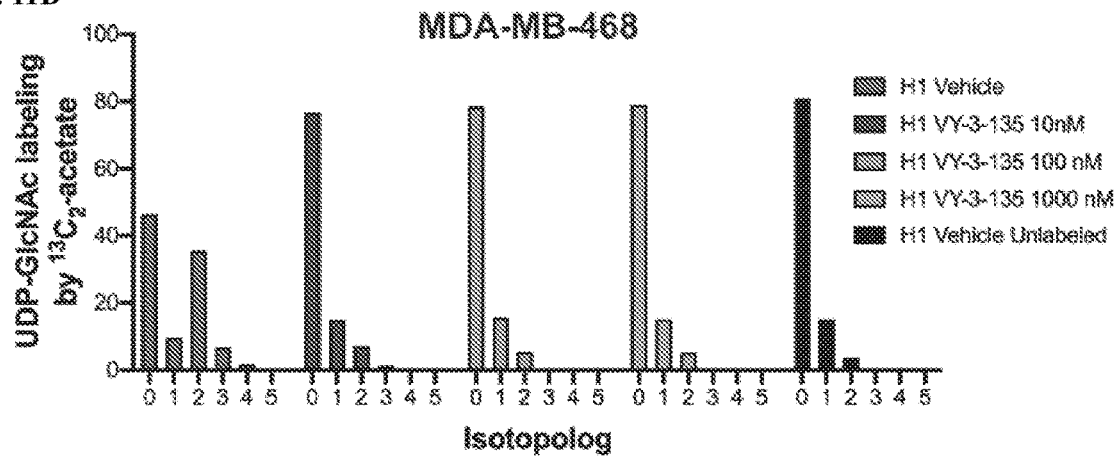

The $^{13}C_2$-acetate tracer studies were repeated in BT474 and MDA-MB-468 cells and polar metabolites were isolated in order to analyze carbon-13 labeling of the cytosolic metabolite UDP-N-acetylglucosamine (UDP-GlcNAc) and the mitochondrial metabolite citrate. Citrate is a readout of ACSS1 and ACSS3 activity in the cells since they are the mitochondria localized AcCoA synthetase family members (FIG. 11A). VY-3-135 is able to block incorporation of $^{13}C_2$-acetate into UDP-GlcNAc to nearly the levels of unlabeled cells (FIGS. 11C-11D). In contrast, VY-3-135 did not decrease incorporation of $^{13}C_2$-acetate into citrate (FIG. 2D). Citrate is strictly synthesized in the mitochondria. In certain non-limiting embodiments, VY-3-135 has little to no activity against the other AcCoA synthetases that localize to the mitochondria, such as ACSS1 and ACSS3. In certain non-limiting embodiments, VY-3-135 cannot enter the mitochondria. In sum, the cell based assays suggested that VY-3-135 is potent on-target ACSS2 inhibitor.

Example 6: Inhibition of ACSS2 has Minimal Effects on Transcriptional Responses to Hypoxia and Low Lipid Stress ACSS2 affects histone and transcription factor acetylation in the nucleus of cells which then affects gene transcription. It was thus tested if inhibition of ACSS2 affects hypoxia and lipid depletion induced transcriptional stress responses. BT474 cells were incubated in normoxic, nutrient replete conditions (N10) and in hypoxic, low lipid conditions (H1). 1075 genes were significantly differentially regulated (FDR<5%) by hypoxia and low lipid conditions with 570 genes upregulated and 505 genes downregulated. Analysis of the gene set using Ingenuity Pathway Analysis (IPA) revealed several significantly changed pathways (FIG. 3A), including activation of cholesterol biosynthesis (FDR=3× $10^{-20}$ activation Z-score=4.2) (FIG. 3B) and glycolysis (FDR=5×$10^{-6}$; activation Z-score=3.2) (FIG. 3C). Additional analysis also found significant upregulation of 30 genes related to fatty acid synthesis (FIG. 3D).

It was then compared how many of the 1075 hypoxia and low lipid stress responsive genes were affected by siRNA mediated knockdown of ACSS2 (siACSS2) and VY-3-135 treatment. Besides ACSS2 itself, only 12 of 570 (2%) of the upregulated genes in hypoxia were also affected by siACSS2, and siACSS2 prevented downregulation of 70 of 505 (14%) genes that had been repressed by hypoxia and low lipid stress (FIGS. 12A-13B). The majority of those genes were not also affected by VY-3-135 treatment (FIGS. 12A-12B) with as few as 21 genes (FIG. 3E) passing nominal significance threshold for VY-3-135 effect (nominal p<0.05) and only one of the 82 genes affected by siACSS2 was also shown to be significantly affected by VY-3-135 at an FDR<5% (RNA binding motif protein 3; RBM3). IPA analysis of the full list of 122 genes significantly regulated by siACSS2 (FDR<5%) showed that those genes were mostly associated with the cell cycle and DNA damage (FIG. 3F). Overall, the RNA sequencing data indicate that inhibition of ACSS2 by siRNA or VY-3-135 has a minimal effect on the transcriptional regulation of genes in response to hypoxia and low lipid stress, and indicates that acetate metabolism can be more important for supporting de novo fatty acid and lipid biosynthesis in BT474 cells.

Figure 4A:
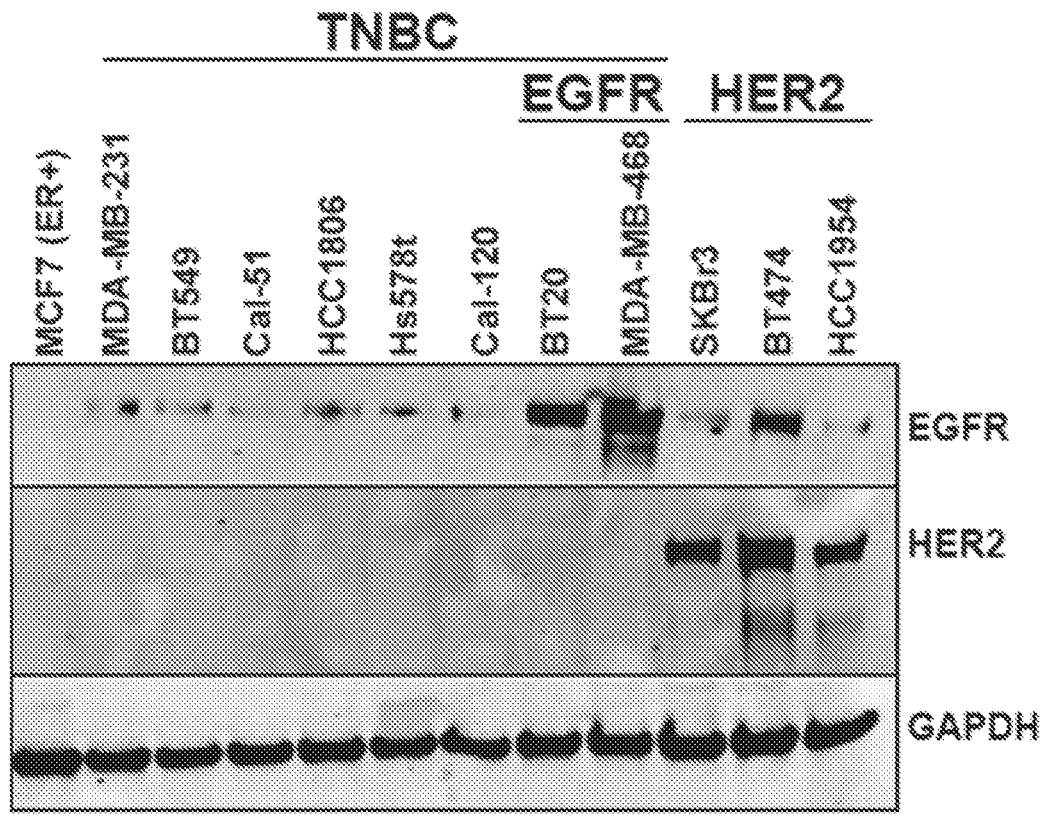
FIGS. 4A-4E illustrate identification of breast cancer cell lines with high expression of ACSS2.
Figure 4B:
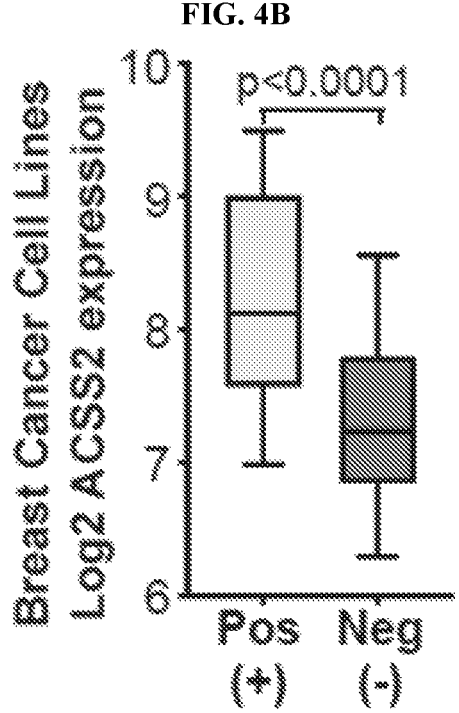

Example 7: ACSS2 is Highly Expressed in HER2 Breast Cancer and EGFR Positive Triple Negative Breast Cancer ACSS2 expression in part dictates whether a cell excretes or consumes acetate. In certain embodiments, ACSS2 expression can also predict sensitivity to ACSS2 inhibitors. FIG. 2A shows that breast cancer cell lines have variable expression of ACSS2, however, the highest expression tended to occur in cell lines with high epidermal growth factor receptor (EGFR) or human epidermal growth factor receptor 2 (HER2) expression, such as BT474, MDA-MB-468 and SKBr3 cells (FIG. 4). Notably, BT474 cells, which have high expression of both EGFR and HER2, also have the highest ACSS2 expression. To further investigate this relationship, mRNA expression of ACSS2 was compared in a panel of 58 breast cancer cell lines, showing that those cell lines with high expression, copy number gains, or amplification of EGFR and/or HER2 had significantly higher expression of ACSS2 compared to breast cancer cell lines with low expression of EGFR and HER2 (FIG. 4B).

Figure 4C:
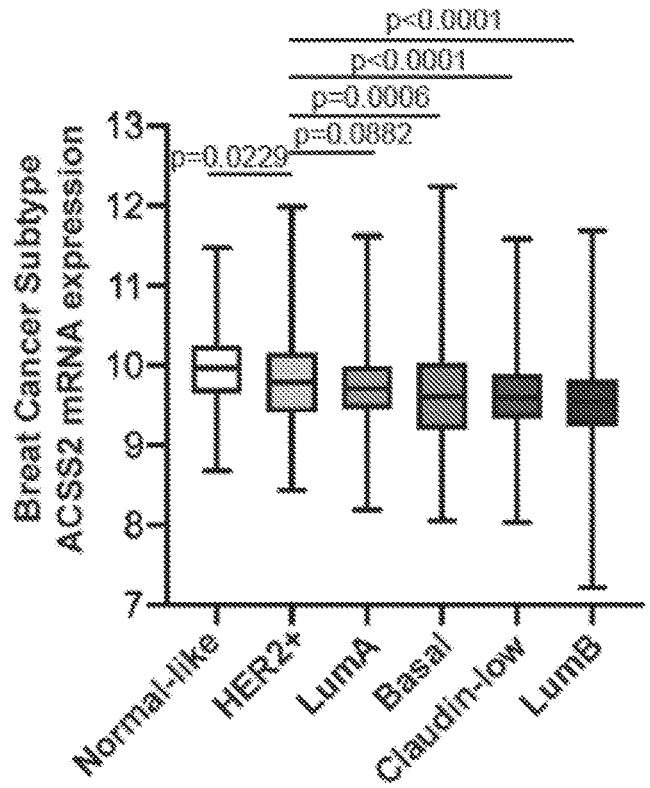
Figure 4D:
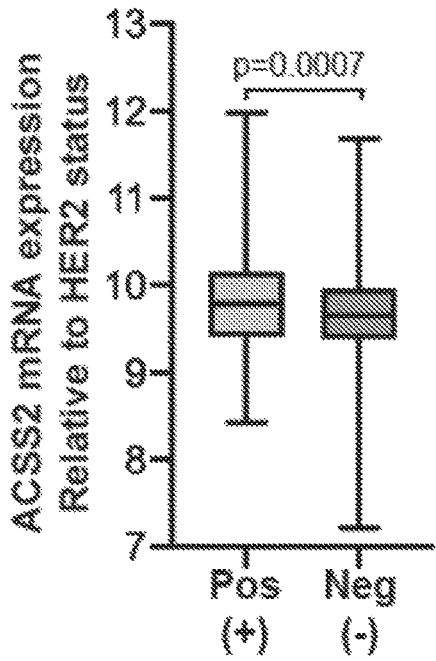
Figure 4E:
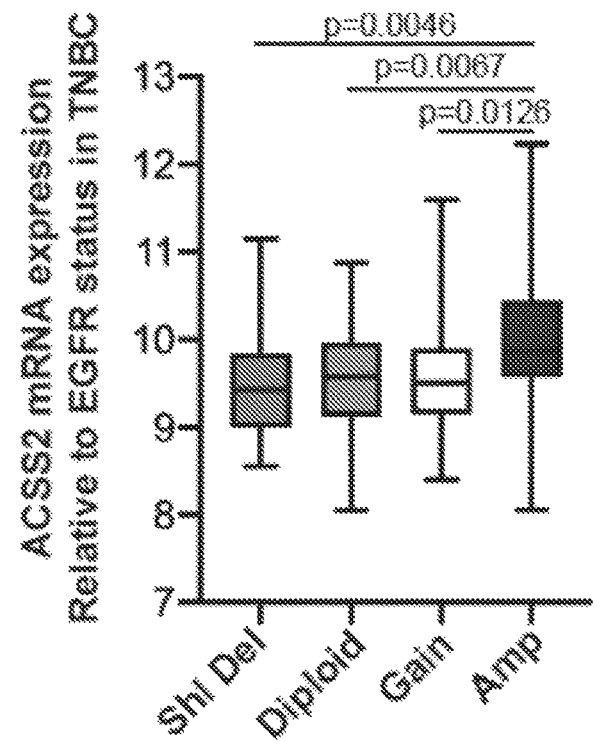

A publicly available breast cancer patient database was mined for ACSS2 expression. Patients were divided into six molecular subtypes according to the PAM50+claudin low filter. Normal-like breast cancers have the highest ACSS2 expression, while HER2+ patient tumors have the second highest ACSS2 expression (FIG. 4C and FIG. 13). Direct comparison of ACSS2 expression in HER2+ tumors versus all other patient tumors showed a significantly higher mRNA expression (FIG. 4D). EGFR is the requisite binding partner of HER2 and is commonly elevated in triple negative breast cancer (TNBC). BT20 and MDA-MB-468 cells are TNBC cells with EGFR amplification and also have relatively high ACSS2 expression (FIGS. 2A and 4A). In line with this finding, TNBC patient tumors that harbor EGFR amplifications also have significantly higher expression of ACSS2 (FIG. 4E). In certain non-limiting embodiments, high ACSS2 predicts poorer survival in HER2+ breast cancer patients (HR 1.77, p=0.007), particularly within the first five years.

Figure 5A:
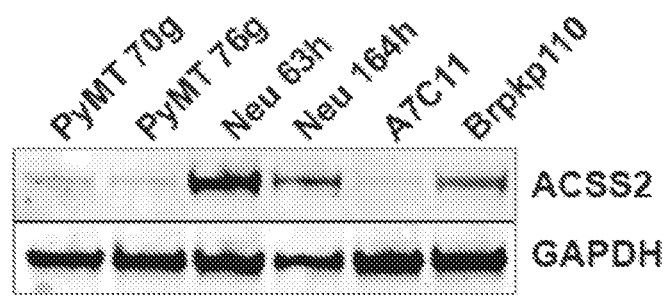
FIGS. 5A-5F depict that knockout or small molecule inhibition of ACSS2 inhibits tumor growth.

FVB/N-Tg(MMTVneu)202Mul/J, also known as the MMTV-Neu mouse model, expresses the wild type rat homolog of HER2 (Neu) in the mouse mammary gland under a mouse mammary tumor virus (MMTV) promoter. The expression of ACSS2 in MMTV-Neu cells was compared to three other mouse breast cancer models. In agreement with the results in FIGS. 4A-4E, HER2+ MMTV-Neu cells (63h and 164h) have the highest expression of ACSS2 (FIG. 5A). p53$^{-/-}$/Kras$^{G12D/+}$/Pik3ca-myr mouse breast cancer cells, hereafter referred to as Brpkp110 cells, also had relatively high expression of ACSS2. In contrast, p53$^{-/-}$/Kras$^{G12D/+}$ mouse breast cancer cells, hereafter referred to as A7C11, and the polyoma middle T (PyMT) driven mouse model of breast cancer (PyMT 70g and 76g) had lower ACSS2 expression (FIG. 5A). RAS and PI3K are two of the most important downstream mediators of EGFR and HER2 signaling; without wishing to be limited by any theory, this indicates a relationship between EGFR/HER2 downstream signaling and ACSS2 expression in breast cancer cells.

Figure 5B:
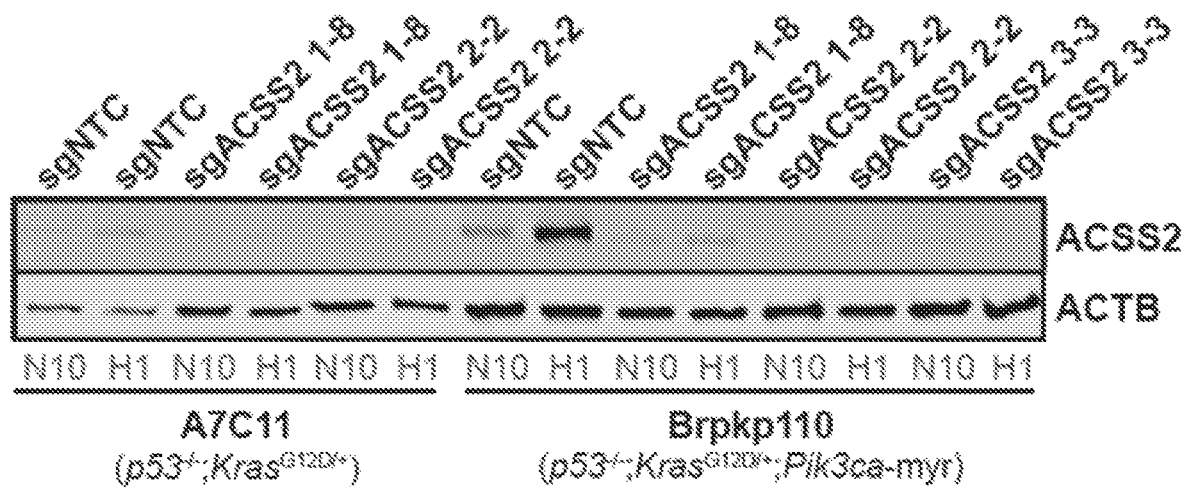
Figure 5C:
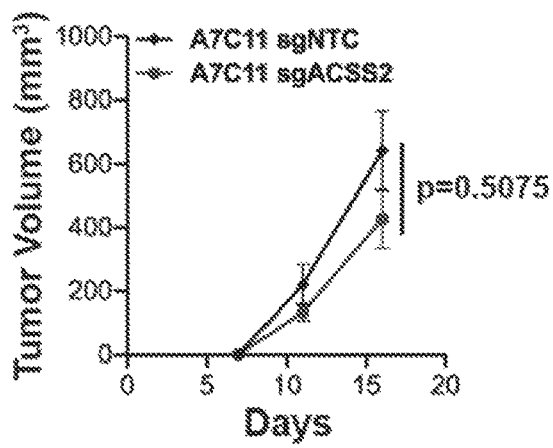
Figure 5D:
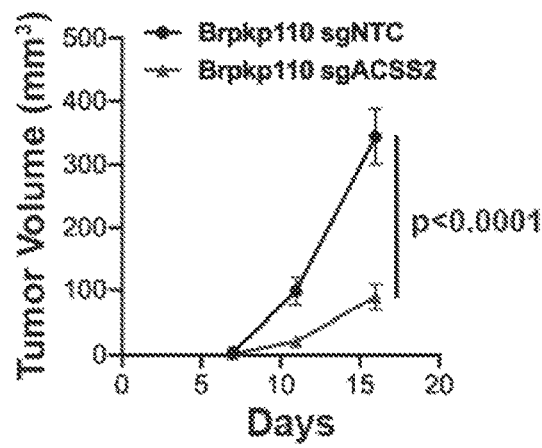

Example 8: Depletion of ACSS2 by CRISPR or ACSS2 Small Molecule Inhibitor Treatment Impairs Breast Tumor Growth CRISPR-Cas9 technology was used to delete Acss2 in Brpkp110 and A7C11 mouse breast cancer cells. Wild type (sgNTC) and CRISPR knockout (sgACSS2) derivatives were cultured in normoxic, nutrient replete conditions (N10) and in hypoxic, low lipid conditions (H1). Cell lysates were checked for ACSS2 expression by western blotting to confirm CRISPR mediated ACSS2 depletion (FIG. 5B). The impact of Acss2 knockout on the growth of A7C11 tumors was then tested, representing a "low ACSS2" expressing model, and Brpkp110 tumors, representing a "high ACSS2" expressing model. A7C11 and Brpkp110 CRISPR knockout pools were injected into the flank of NOD Scid gamma (NSG) mice and tumor growth was monitored. CRISPR mediated depletion of ACSS2 did not significantly affect the growth of A7C11 tumors, but did affect Brpkp110 tumor growth (FIGS. 5C-5D). The strong inhibition of Brpkp110 tumor growth indicates that high ACSS2 expression can dictate sensitivity to ACSS2 inhibitors.

Figure 5E:
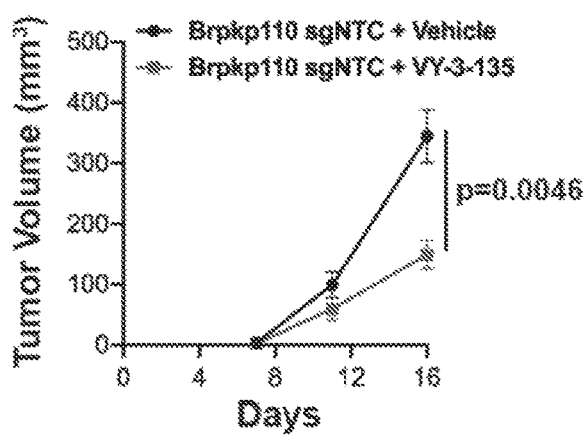
Figure 5F:
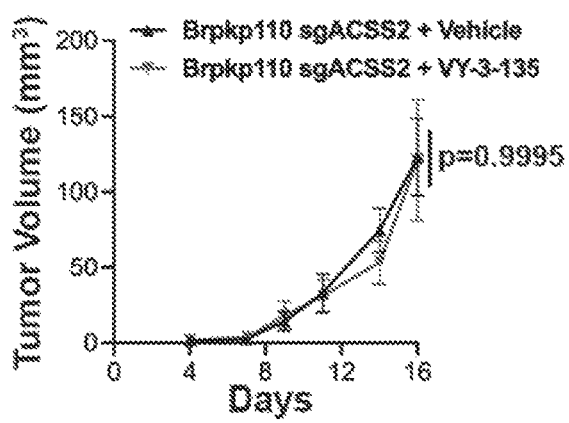

Since significant reduction in tumor growth was observed in sgACSS2 Brpkp110 tumors, it was then tested if VY-3-135 could mimic the effect that ACSS2 knockout has on Brpkp110 tumor growth. Tumor bearing mice were given daily intraperitoneal injection of VY-3-135 for two weeks. Similar to ACSS2 knockout, VY-3-135 treatment caused significant reduction in Brpkp110 tumor growth and is the first evidence that pharmacological inhibition of ACSS2 can cause tumor growth inhibition in vivo (FIG. 5E). In order to validate that tumor growth inhibition was due to the on-target effect of VY-3-135 on ACSS2, sgACSS2 Brpkp110 tumor bearing mice were treated with VY-3-135. Although ACSS2 knockout tumors were smaller and grew more slowly, there was no further effect on tumor growth by VY-3-135, indicating that the anti-tumor growth properties of VY-3-135 are ACSS2 specific (FIG. 5F).

Example 9: ACSS2 Small Molecule Inhibitors Inhibit Human HER2+ Breast Tumor Growth In Vivo Doxycycline induces expression of an shRNA against ACSS2 in BT474 cells inhibits tumor growth. BT474 cells were used as an xenograft model to test the ability of VY-3-135 to inhibit human breast tumor growth. BT474 are derived from an invasive ductal carcinoma of the breast and are positive for estrogen receptor, progesterone receptor and HER2.

Figure 6A:
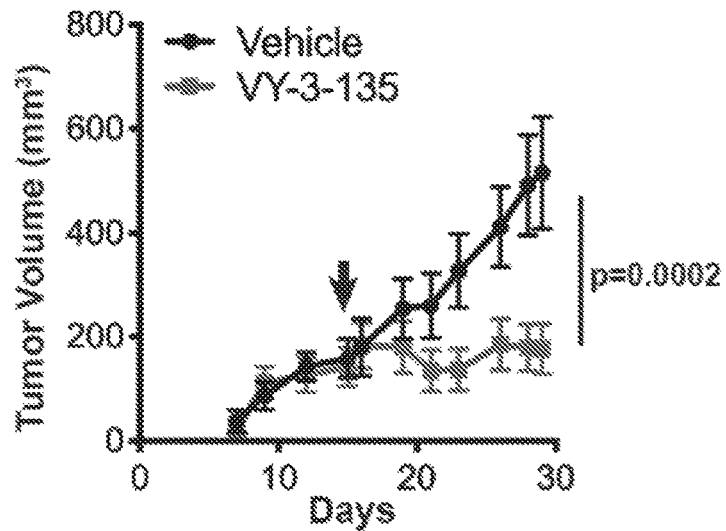
FIGS. 6A-6F depict that an illustrative ACSS2 small molecule inhibitor abrogates the growth of an ER/PR/HER2 triple positive breast tumor and prevents incorporation of acetate carbon in the fatty acids in tumors.
Figure 6B:
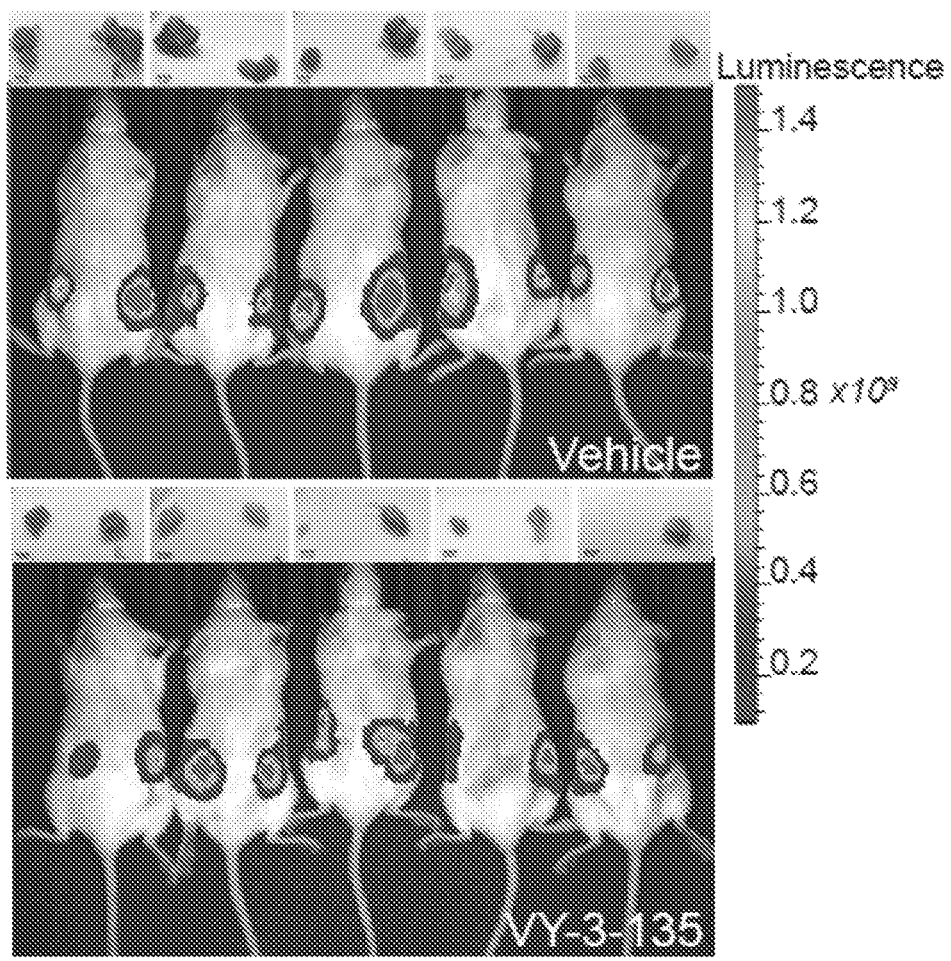
Figure 7B:
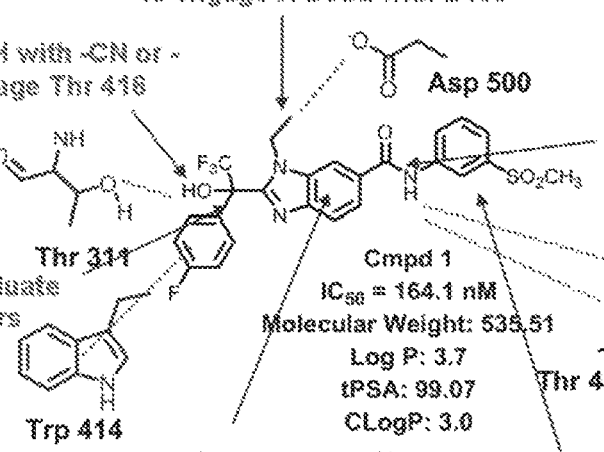

BT474 cells that stably express luciferase were generated and injected into both flanks of female NSG mice with estrogen pellet implants. Tumors were allowed to establish to 200 mm$^3$ before beginning VY-3-135 treatment. Strikingly, VY-3-135 completely abrogated tumor growth over two weeks of treatment (p=0.0002) (FIG. 6A). Although tumors were present in all mice at day 14, as evidenced by bioluminescent imaging (FIG. 7B), two of the tumors in VY-3-135 treated group were not palpable by the end of the regimen, with one tumor fully regressing (FIG. 7B). Conversely, all vehicle treated mice had palpable tumors that progressed over the same period (FIG. 7B). These results demonstrate for the first time that pharmacological targeting of ACSS2 can inhibit human tumor growth in vivo.

Example 10. Gene Expression in VY-3-135 Treated Tumors was not Highly Altered

QuantSeq 3' mRNA sequencing of BT474 tumor tissue from vehicle and VY-3-135 treated mice was performed. Similar to in vitro results in FIG. 3, the effects of VY-3-135 on gene transcription in vivo were minimal. A total of 248 differentially regulated genes had a nominal p<0.05, but no gene passed an FDR<5%. Furthermore, of the 248 differentially regulated genes only 7 changed by more than 2-fold and none by more than 2.5-fold (FIGS. 14A-14B). As such, an IPA of the RNA sequencing data did not predict alteration of any canonical pathways and the activity of only five transcriptional regulators (p<0.05; Z>2.000) were modestly altered, with inactivation of estrogen receptor signaling and activation of p53 as the most significantly altered pathways (FIG. 14C).

Figure 14D:
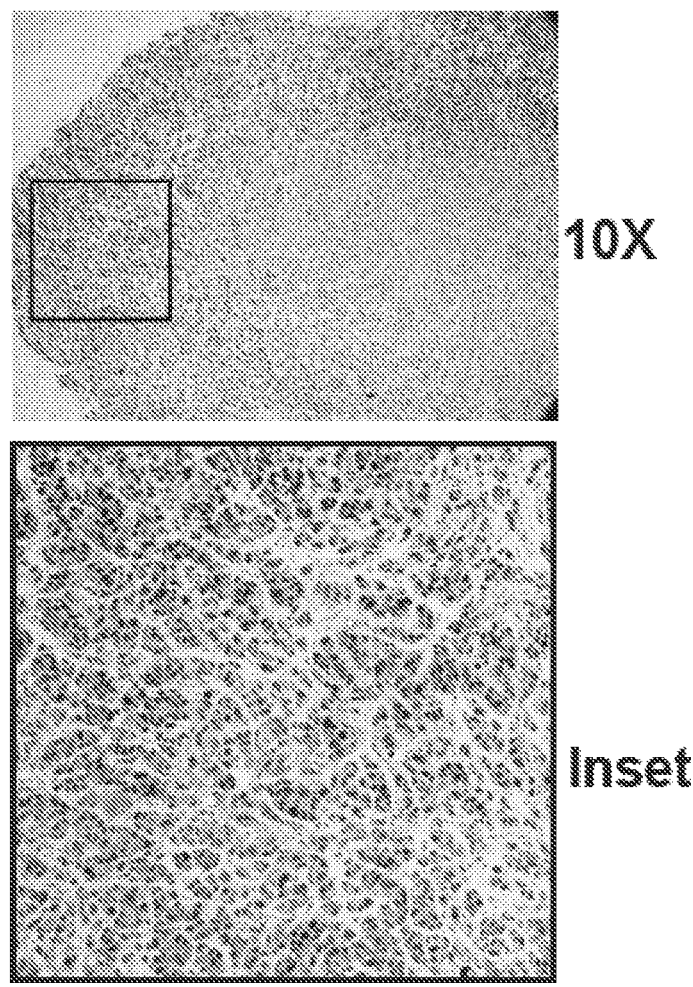
Figure 14E:
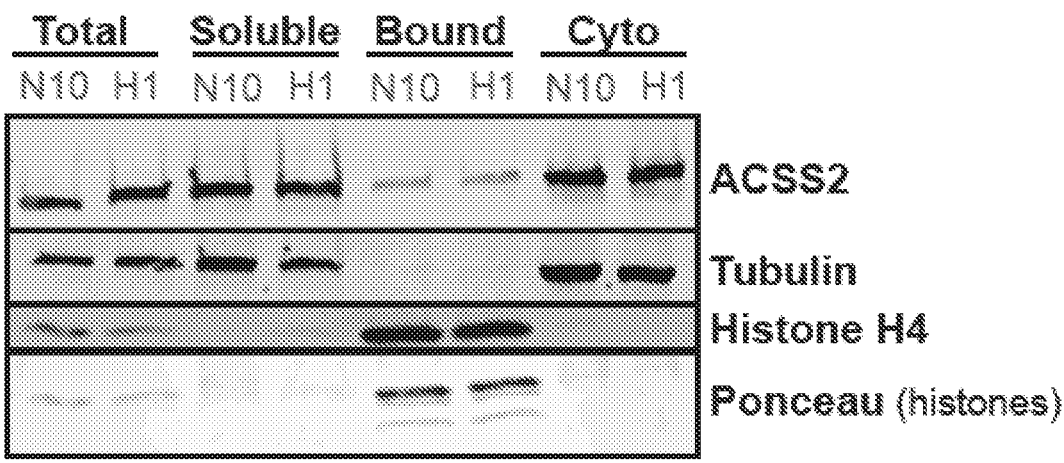

The degree of nuclear ACSS2 accumulation in cells is often regulated by metabolic stress. Immunohistochemical staining for ACSS2 indicated localization to both the nucleus and the cytosol in BT474 tumor cells (FIG. 14D). To further probe the localization of ACSS2 in the nucleus, nuclear extracts subfractionated into soluble and chromatin bound fractions. Overall, ACSS2 was mostly localized to the soluble fraction of the nucleus and the cytosol with very little bound to the chromatin fraction (FIG. 14E).

Figure 6C:
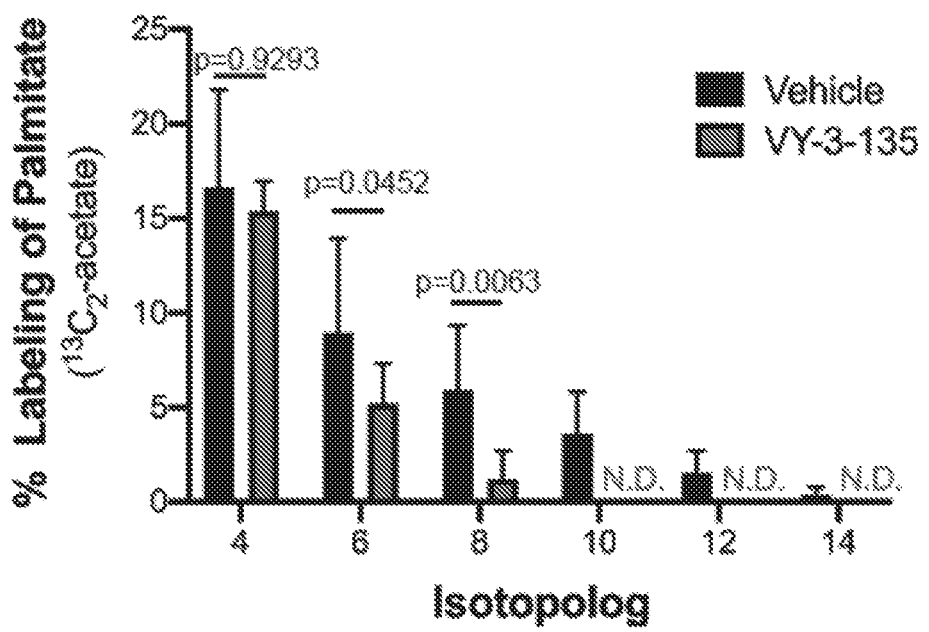
Figure 6D:
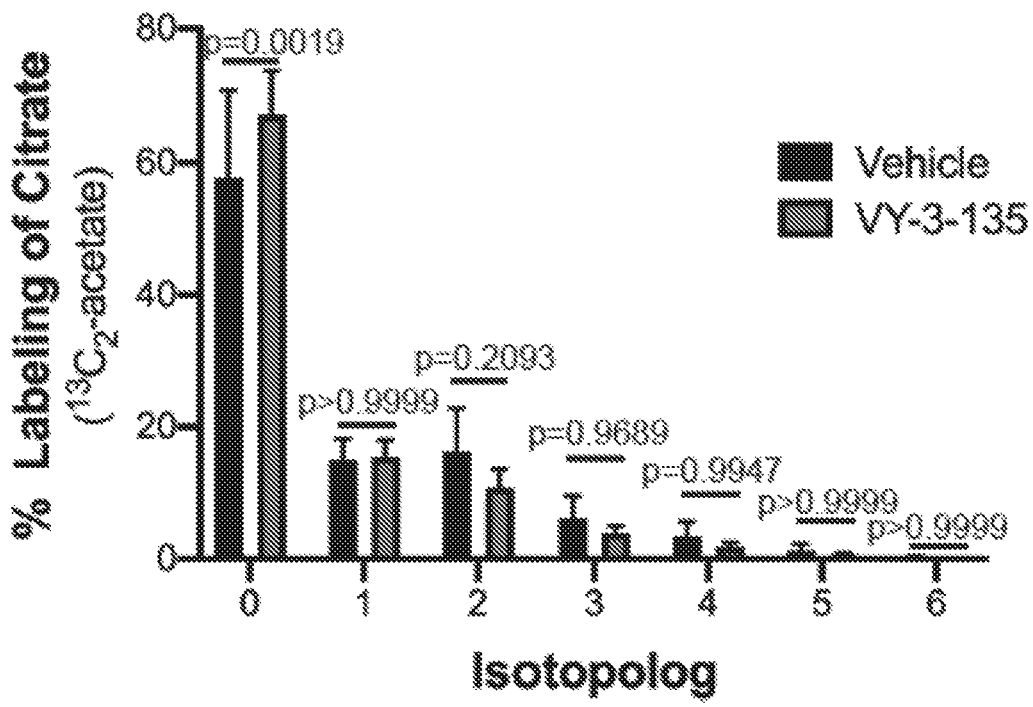

Example 11: ACSS2 Small Molecule Inhibitors Inhibit Acetate Incorporation into Palmitate but not Citrate in the Tumor On-target activity of VY-3-135 in the tumor was probed. The drinking water of the mice was supplemented with carbon-13 labeled sodium acetate ($^{13}C_2$-acetate) for 48 hours to label the lipid fraction in the tumors. In addition, a single IP bolus of $^{13}C_2$-acetate 90 minutes was given prior to tumor harvesting to robustly label TCA cycle intermediates. Tumor lipid extracts were saponified and the resulting fatty acids were analyzed by LC-MS. Likewise, polar metabolites were extracted from matching tumor samples and analyzed by LC-MS. VY-3-135 caused a significant decrease in the $^{13}C$ labeling of palmitate (FIG. 6C). Isotopologs ≥M+10 were not detected in tumors from VY-3-135 treated mice. In accordance with in vitro findings from FIG. 2D, no effect was observed on the $^{13}C_2$-acetate labeling of citrate in the same tumors, indicating that VY-3-135 did not have any off-target effects on ACSS1 or ACSS3 (FIG. 6D). Altogether, these results show that VY-3-135 is active towards ACSS2 in the tumor.

Figure 6E:
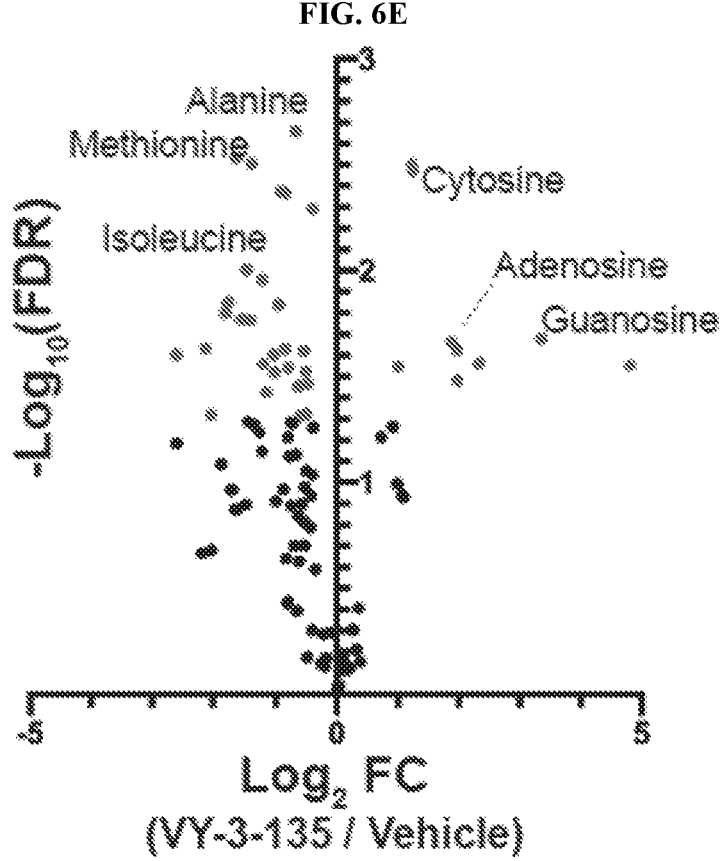
Figure 6F:
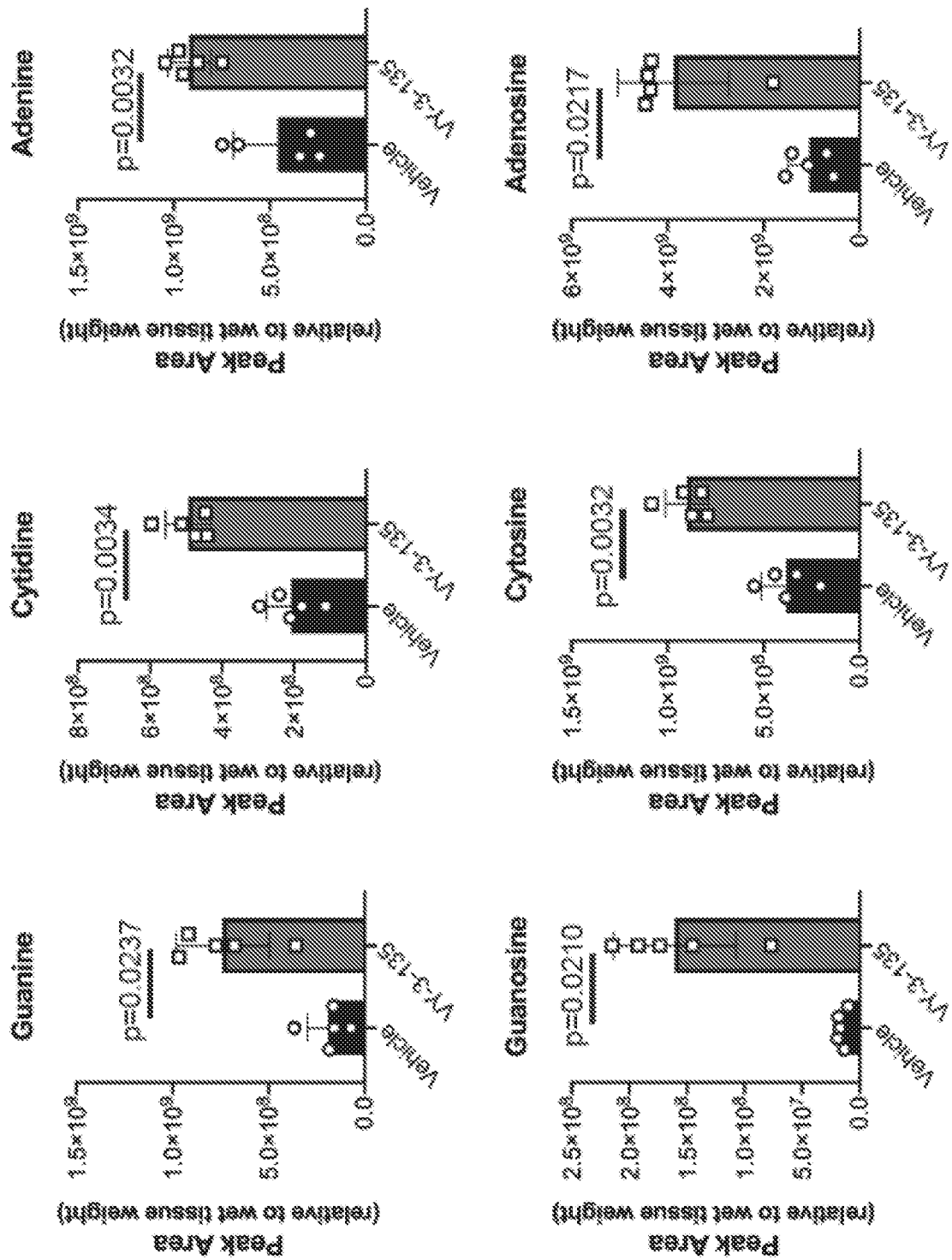

A targeted metabolomic analysis of 99 metabolites in vehicle versus VY-3-135 treated BT474 tumors was performed (FIG. 6E and Table 2). Of the 37 metabolites that were significantly altered, only nine were higher in VY-3-135 treated tumors and interestingly all of these metabolites are associated with nucleotide metabolism (FIG. 6F). In contrast, the majority of downregulated metabolites were protein-coding amino acids (FIG. 6E and Table 2). Without wishing to be limited by any theory, these results indicate that ACSS2 inhibitors can impact pathways outside of acetate metabolism, such as amino acid and nucleotide metabolism.

In certain embodiments, the compounds of the disclosure are effective against multiple different breast cancer cell lines that have relatively high expression of ACSS2. In certain embodiments, the compounds of the disclosure prevent incorporation of acetate into nucleo-cytosolic AcCoA metabolic pathways such as fatty acid biosynthesis and UDP-GlcNAc synthesis. In certain embodiments, the compounds of the disclosure do not have a significant effect on citrate synthesis from acetate-derived AcCoA. In certain embodiments, the compounds of the disclosure are specific for ACSS2 and have minimal to no effect on the mitochondria-localized AcCoA synthetase family member ACSS1 or ACSS3.

In certain embodiments, the compounds of the disclosure as single agents abrogate breast tumor growth and can cause tumor regression. HER2+ and TNBC tumors may have higher ACSS2 expression and in particular TNBC with high EGFR expression or activating mutations in EGFR. HER2 and TNBC also have the poorest survival rates and investigational new drugs are desperately needed for these devastating subtypes of breast cancer. The present in vivo inhibitors studies show that pharmacological inhibition of ACSS2 causes tumor growth inhibition and regression. In certain embodiments, the compounds of the disclosure cause a substantial reduction in the use of $^{13}C_2$-acetate for fatty acid synthesis in tumors, but do not have an inhibitory effect on citrate labeling.

These were also the first studies to show that ACSS2 is necessary for tumors to use acetate for fatty acid synthesis. In certain embodiments, breast tumors with high expression of ACSS2 readily consume and metabolize acetate and are susceptible to ACSS2 inhibitors. In certain embodiments, this metabolic behavior can be used to identify patients in the clinic that are likely to respond to ACSS2 therapy. For example, since acetate uptake and consumption in tumors is strongly linked to ACSS2 expression, clinicians can use $^{11}C$-acetate PET imaging as a tool to identify patients that are "hot" for acetate uptake. $^{11}C$-acetate PET imaging can also be used as a pharmacodynamic biomarker to longitudinally monitor tumor growth and acetate metabolism in patients.

Targeting acetate metabolism represents an unrealized opportunity for improving cancer treatment. Acetate is highly consumed by many different cancer types and even more so under conditions of nutrient and metabolic stress. Given that most normal tissues barely consume acetate as a major nutrient source, it suggests that inhibition of acetate metabolism exploits a unique metabolic vulnerability of many cancers that is both cancer specific and likely to be safe for the patient. In summation, the present disclosure provides ACSS2 inhibitors as a novel therapeutic modality in cancer.

Example 12: Synthesis of ACSS2 Inhibitors

Preparation of Intermediate (I-IX):

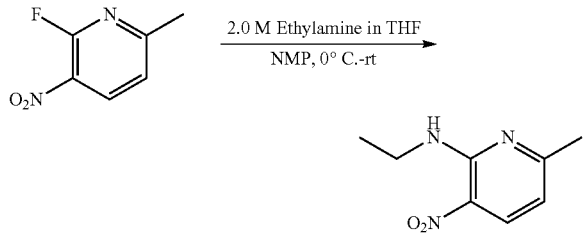

N-ethyl-6-methyl-3-nitropyridin-2-amine: To a stirred solution of 2-fluoro-6-methyl-3-nitropyridine (4683 mg, 30 mmol) in N-Methyl-2-pyrrolidinone (50 mL) was added 2.0 M ethylamine in THF (4057 mg, 90 mmol) at 0° C. dropwise. The reaction mixture was stirred at ambient temperature for 6-8 hours, and after completion of reaction as indicated by TLC water (100 mL) was added and stirred for 30 min. The obtained yellow solid was filtered, washed with water, and dried to give the title compound (5115 mg, 94.09% yield) which was used for the next step without purification. MS (ESI): m/z 182 [M+1]$^+$.

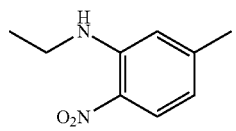

N-ethyl-5-methyl-2-nitroaniline: To a stirred solution of 2-fluoro-4-methyl-1-nitrobenzene (5000 mg, 32.23 mmol) in N-Methyl-2-pyrrolidinone (50 mL) was added 2.0 M ethylamine in THF (3777 mg, 83.80 mmol) at 0° C. dropwise. The reaction mixture was stirred at ambient temperature for 6-8 hours, and after completion of reaction as indicated by TLC water (100 mL) was added and stirred for 30 min. The obtained orange solid was filtered, washed with water, and dried to give the title compound (5347 mg, 92.06% yield) which was used for the next step without purification. MS (ESI): m/z 181 [M+1]$^+$.

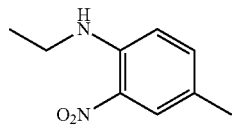

N-ethyl-4-methyl-2-nitroaniline: To a stirred solution of 1-fluoro-4-methyl-2-nitrobenzene (8268 mg, 53.29 mmol) in N-Methyl-2-pyrrolidinone (80 mL) was added 2.0 M ethylamine in THF (6005 mg, 133.24 mmol) at 0° C. dropwise. The reaction mixture was stirred at ambient temperature for 6-8 hours, and after completion of reaction as indicated by TLC water (100 mL) was added and stirred for 30 min. The obtained orange solid was filtered, washed with water and dried to give the title compound (9469 mg, 93.02% yield) which was used for the next step without purification. MS (ESI): m/z 181 [M+1]$^+$.

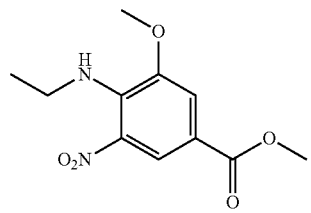 [SMILES: CCNc1c(OC)cc(C(=O)OC)cc1[N+](=O)[O-]]

Methyl 4-(ethylamino)-3-methoxy-5-nitrobenzoate: To a stirred solution of methyl 4-chloro-3-methoxy-5-nitrobenzoate (1586 mg, 6.45 mmol) in DMF (15 mL) was added 2.0 M ethylamine in THF (727 mg, 16.14 mmol) at 0° C. dropwise. The reaction mixture was stirred at ambient temperature for 1 h and then heated at 80° C. for 3 hours. After completion of reaction as indicated by TLC, the reaction mixture was cooled to room temperature, then water (100 mL) was added and stirred for 30 min. The obtained orange solid was filtered, washed with water, and dried to give the title compound (1522 mg, 93.48% yield) which was used for the next step without purification. MS (ESI): m/z 255 [M+1]$^+$.

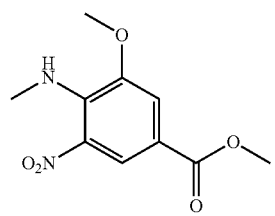

Methyl 3-methoxy-4-(methylamino)-5-nitrobenzoate: To a stirred solution of methyl 4-chloro-3-methoxy-5-nitrobenzoate (2456 mg, 30 mmol) in DMF (20 mL) was added 2.0 M methylamine in THF (4057 mg, 90 mmol) at 0° C. dropwise. The reaction mixture was stirred at ambient temperature for 1 hour and then heated at 80° C. for 3 h. After completion of reaction as indicated by TLC, the reaction mixture was cooled to room temperature then water (100 mL) was added and stirred for 30 min. The obtained orange solid was filtered, washed with water, and dried to give the title compound (2135 mg, 88.88% yield) which was used for the next step without purification. MS (ESI): m/z 241 [M+1]$^+$.

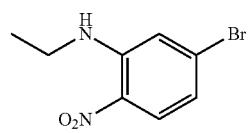

5-bromo-N-ethyl-2-nitroaniline: To a stirred solution of 4-bromo-2-fluoro-1-nitrobenzene (7000 mg, 31.83 mmol) in N-Methyl-2-pyrrolidinone (70 mL) was added 2.0 M ethylamine in THF (3731 mg, 82.73 mmol) at 0° C. dropwise. The reaction mixture was stirred at ambient temperature for 6-8 hours, and after completion of reaction as indicated by TLC water (100 mL) was added and stirred for 30 min. The obtained orange solid was filtered, washed with water and dried to give the title compound (7100 mg, 91.10% yield) which was used for the next step without purification. MS (ESI): m/z 246 [M+1]$^+$.

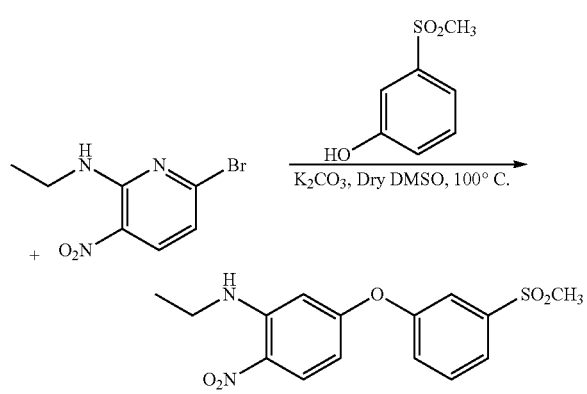

N-ethyl-5-(3-(methylsulfonyl)phenoxy)-2-nitroaniline:
To a stirred solution of 5-bromo-N-ethyl-2-nitroaniline (1423 mg, 5.80 mmol) in anhydrous dimethyl sulfoxide (15 mL) was added 3-(methylsulfonyl)phenol (1000 mg, 5.80 mmol), potassium carbonate (1767 mg, 12.78 mmol) and the reaction mixture was stirred at 100° C. for overnight. After completion of reaction as indicated by TLC reaction mixture cooled to room temperature, potassium carbonate was filtered over filter paper, washed with ethyl acetate (25 mL) and ice cool water was added, and the mixture and aqueous layer were extracted with ethyl acetate (3×25 mL). The combined organic layer was evaporated under vacuum and crude residue was purified by flash chromatography using (0-50% hexane/ethyl acetate) to obtain the pure compound (1825 mg, 93.63% yield) as a white solid. MS (ESI): m/z 337 [M+1]$^+$.

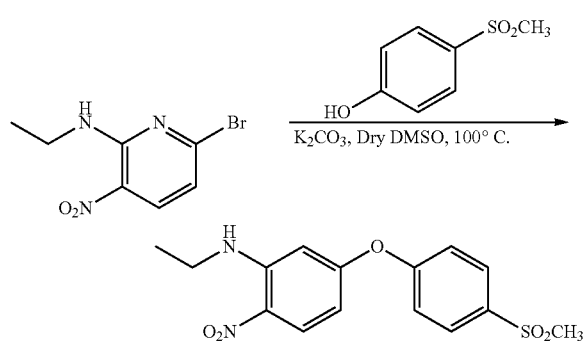

N-ethyl-5-(4-(methylsulfonyl)phenoxy)-2-nitroaniline):
To a stirred solution of 5-bromo-N-ethyl-2-nitroaniline (3279 mg, 13.38 mmol) in anhydrous dimethyl sulfoxide (30 mL) was added 4-(methylsulfonyl)phenol (2535.1 mg, 14.72 mmol), potassium carbonate (4068.3 mg, 29.436 mmol) and the reaction mixture was stirred at 100° C. for overnight. After completion of reaction as indicated by TLC, the reaction mixture was cooled to room temperature, potassium carbonate was filtered over filter paper, washed with ethyl acetate (25 mL) and ice cool water was added, and the mixture and aqueous layer extracted with ethyl acetate (3×25 mL). The combined organic layer was evaporated under vacuum and the crude residue was purified by flash chromatography using (0-50% hexane/ethyl acetate) to obtain the pure compound (4120 mg, 91.65% yield) as a yellow solid. MS (ESI): m/z 337 [M+1]$^+$.

N-Ethyl-5-morpholino-2-nitroaniline: To a stirred solution of 5-bromo-N-ethyl-2-nitroaniline (770 mg, 3.14 mmol) in anhydrous dimethyl sulfoxide (5 mL) was added morpholine (300.77 mg, 3.45 mmol), potassium carbonate (1562 mg, 11.30 mmol) and the reaction mixture stirred at 120° C. for one hour in microwave. After completion of reaction as indicated by TLC reaction, the mixture was cooled to room temperature, potassium carbonate was filtered over filter paper, washed with ethyl acetate (25 mL), and ice cool water was added, aqueous layer extracted with ethyl acetate (3×25 mL). The combined organic layer was evaporated under vacuum and crude residue was purified by flash chromatography using (0-50% hexane/ethyl acetate) to obtain the pure compound (1875 mg, 96.10% yield) as a white solid. MS (ESI): m/z 252 [M+1]$^+$.

General Method for the Synthesis of Benzimidazole Intermediates (X-XV11)

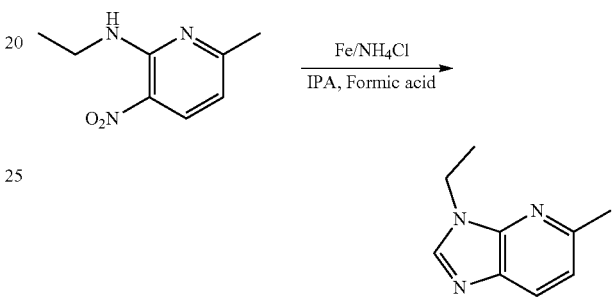

3-Ethyl-5-methyl-3H-imidazo[4,5-b]pyridine: To a stirred solution of N-ethyl-6-methyl-3-nitropyridin-2-amine (5115 mg, 28.22 mmol) in isopropanol (50 mL) were added iron powder (151758 mg, 282.2 mmol), powder ammonium chloride (15084 mg, 53.49 mmol) and formic acid 115 mL, 2882 mmol) and the reaction mixture stirred at reflux for 12 hours. After completion of reaction as indicated by TLC reaction, the mixture was cooled to room temperature, filtered over a bed of celite washed with isopropanol (125 mL), then crude filtrate was evaporated to dryness and washed with saturated sodium bicarbonate solution, aqueous layer extracted with dichloromethane (3×50 mL), the combined organic layer dried over sodium sulfate and evaporated. The crude residue was purified by flash chromatography using 0-15% dichloromethane/methanol to obtain brown color liquid (3963 mg, 87.12% yield) MS (ESI): m/z 162 [M+1]$^+$.

1-Ethyl-6-methyl-1H-benzo[d]imidazole: The title compound was prepared according to the method described for Intermediate X, employing N-ethyl-5-methyl-2-nitroaniline (2500 mg, 13.87 mmol), iron powder (7746 mg, 138.32 mmol), powder ammonium chloride (7420 mg, 138.21 mmol) and formic acid (57.01 mL, 1382.1 mmol) to obtain the pure product as a yellow solid compound (1980g, 89.23% yield) MS (ESI): m/z 161 [M+1]$^+$.

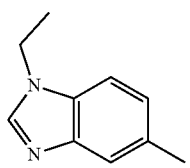

1-Ethyl-5-methyl-1H-benzo[d]imidazole: The title compound was prepared according to the general method described for Intermediate X, employing N-ethyl-4-methyl-2-nitroaniline (9469 mg, 52.60 mmol), iron powder (29418 mg, 526 mmol), powder ammonium chloride (28135 mg, 526 mmol) and formic acid (211 mL, 5260 mmol) to obtain the pure product as a brown orange liquid (7427 mg, 87.70% yield) MS (ESI): m/z 161 [M+1]$^+$.

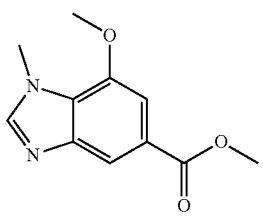 [SMILES: COC(=O)c1cc(OC)c2c(c1)ncn2C]

Methyl 7-methoxy-1-methyl-1H-benzo[d]imidazole-5-carboxylate: The title compound was prepared according to the general method described for Intermediate X, employing methyl 3-methoxy-4-(methylamino)-5-nitrobenzoate (1635 mg, 6.81 mmol), iron powder (3800 mg, 68.06 mmol), powder ammonium chloride (3640 mg, 68.06 mmol) and formic acid (27.34 mL, 680.6 mmol) to obtain the pure product as a white solid (1269 mg, 84.71% yield) MS (ESI): m/z 221 [M+1]$^+$.

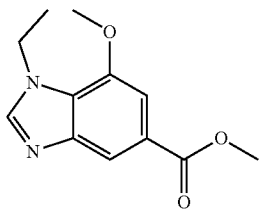 [SMILES: CCn1cnc2cc(C(=O)OC)cc(OC)c21]

Methyl 1-ethyl-7-methoxy-1H-benzo[d]imidazole-5-carboxylate: The title compound was prepared according to the general method described for Intermediate X, employing methyl 4-(ethylamino)-3-methoxy-5-nitrobenzoate (1522 mg, 5.98 mmol), iron powder (3342 mg, 59.86 mmol), powder ammonium chloride (3201 mg, 59.86 mmol) and formic acid (24.05 mL, 598.6 mmol) to obtain the pure product as a yellow solid compound (1194 mg, 85.34% yield) MS (ESI): m/z 235 [M+1]$^+$.

1-Ethyl-6-(3-(methylsulfonyl)phenoxy)-1H-benzo[d]imidazole: The title compound was prepared according to the general method described for Intermediate X, employing N-ethyl-5-(3-(methylsulfonyl)phenoxy)-2-nitroaniline (1977 mg, 5.87 mmol), iron powder (3282 mg, 58.77 mmol), powder ammonium chloride (3143 mg, 58.77 mmol) and formic acid (24.15 mL, 587.7 mmol) to obtain the pure product as a yellow solid compound (1608 mg, 86.59% yield) MS (ESI): m/z 317 [M+1]$^+$.

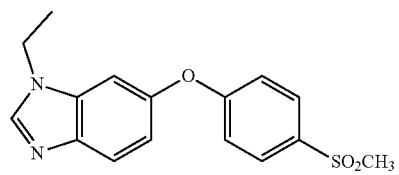 [SMILES: CCn1cnc2ccc(Oc3ccc(S(C)(=O)=O)cc3)cc21]

1-Ethyl-6-(4-(methylsulfonyl)phenoxy)-1H-benzo[d]imidazole: The title compound was prepared according to the general method described for Intermediate X, employing N-ethyl-5-(4-(methylsulfonyl)phenoxy)-2-nitroaniline (4531 mg, 13.47 mmol), iron powder (7522 mg, 130.47 mmol), powder ammonium chloride (6979 mg, 130.47 mmol) and formic acid (52.39 mL, 1304.7 mmol) to obtain the pure product as a yellow solid compound (3623 mg, 85.12% yield) MS (ESI): m/z 317 [M+1]$^+$.

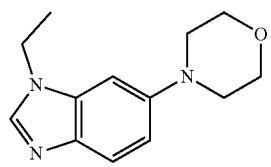 [SMILES: CCn1cnc2ccc(N3CCOCC3)cc21]

4-(1-Ethyl-1H-benzo[d]imidazol-6-yl)morpholine: The title compound was prepared according to the general method described for Intermediate X, employing N-ethyl-5-morpholino-2-nitroaniline (471 mg, 1.87 mmol), iron powder (1046 mg, 18.74 mmol), powder ammonium chloride (1002 mg, 18.74 mmol) and formic acid (7.7 mL, 180.74 mmol) to obtain the pure product as a yellow solid compound (370 mg, 85.84% yield) MS (ESI): m/z 232 [M+1]$^+$.

General Procedure for Intermediate (XVIII):

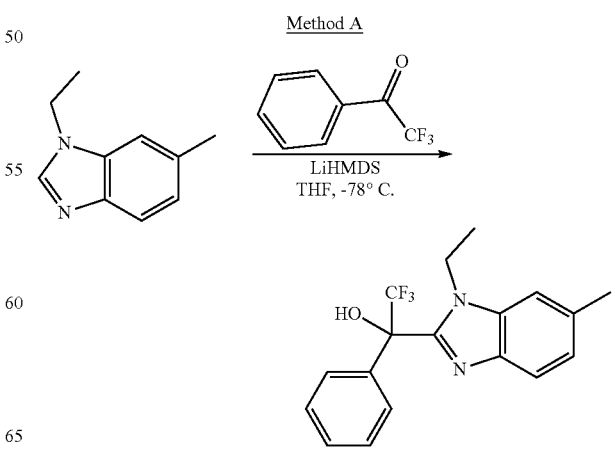

1-(1-Ethyl-6-methyl-1H-benzo[d]imidazol-2-yl)-2,2,2-trifluoro-1-phenylethanol: To a stirred solution of 1-ethyl-6-methyl-1H-benzo[d]imidazole (1679 mg, 9.75 mmol) in anhydrous THF (16 mL) was added 1M solution of lithium bis(trimethylsilyl)amide (1958 mg, 11.70 mmol) at −78° C. dropwise over 5-10 min and stirred for 30 min. To the reaction was added 2,2,2-trifluoro-1-phenylethanone (2122 mg, 12.18 mmol) dissolved in anhydrous THF (5 mL) was added and reaction mixture monitored after 1 hour. After completion of the reaction as indicated by LC-MS. The reaction was quenched with aqueous ammonium chloride solution and aqueous layer extracted with ethyl acetate (3×25 mL) and combined organic layer washed with brine and dried over sodium sulfate. The crude residue was purified by flash chromatography using (0-15% EA/Hexanes) to obtain the pure compound (1124 mg, 34.41% yield) as a pale yellow liquid. MS (ESI): m/z 335 [M+1]+.

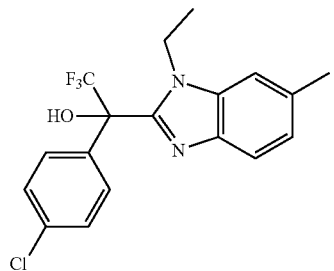 [SMILES: CCn1c(C(O)(c2ccc(Cl)cc2)C(F)(F)F)nc2ccc(C)cc21]

1-(4-chlorophenyl)-1-(1-ethyl-6-methyl-1H-benzo[d]imidazol-2-yl)-2,2,2-trifluoroethanol: The title compound was prepared according to the method B described for intermediate XVIII, employing 1-ethyl-6-methyl-1H-benzo[d]imidazole (859 mg, 5.36 mmol), 1-(4-chlorophenyl)-2,2,2-trifluoroethanone (1130 mg, 5.89 mmol) and n-butyllithium (823 mg, 12.86 mmol) to obtain the pure product as a yellow solid compound (490 mg, 24.78% yield) MS (ESI): m/z 369 [M+1]+.

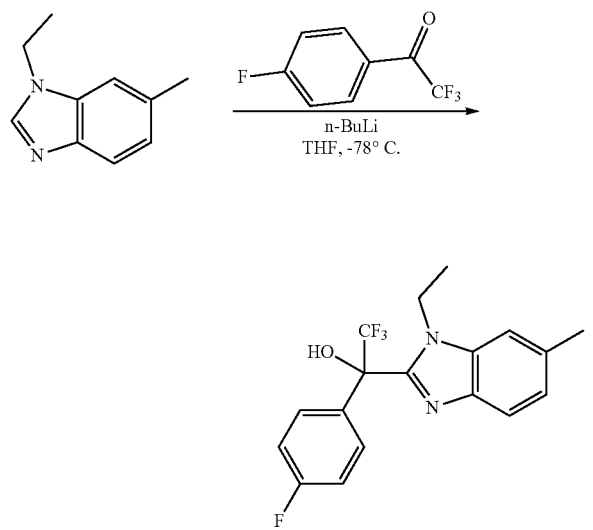

Method B

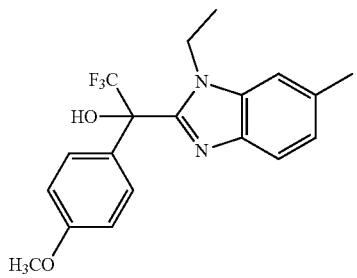 [SMILES: CCn1c(C(O)(c2ccc(OC)cc2)C(F)(F)F)nc2ccc(C)cc21]

1-(1-Ethyl-6-methyl-1H-benzo[d]imidazol-2-yl)-2,2,2-trifluoro-1-(4-methoxyphenyl)ethanol: The title compound was prepared according to the method A described for intermediate XIX, employing 1-ethyl-6-methyl-1H-benzo[d]imidazole (1602 mg, 10 mmol), 2,2,2-trifluoro-1-(4-methoxyphenyl)ethanone (4083 mg, 20 mmol) and lithium bis(trimethylsilyl)amide (4015 mg, 24 mmol) to obtain the pure product as a yellow solid compound (894 mg, 24.53% yield) MS (ESI): m/z 365 [M+1]+.

1-(1-Ethyl-6-methyl-1H-benzo[d]imidazol-2-yl)-2,2,2-trifluoro-1-(4-fluorophenyl)ethanol: To a stirred solution of 1-ethyl-6-methyl-1H-benzo[d]imidazole (1553 mg, 9.69 mmol) in anhydrous THF (16 mL) was added 1.6 M solution of n-butyllithium (1488 mg, 23.25 mmol) at −78° C. dropwise over 5-10 min and stirred for 30 min. To the reaction was added 2,2,2-trifluoro-1-(4-fluorophenyl)ethanone (3724 mg, 19.38 mmol) dissolved in anhydrous THF (5 mL) was added and the reaction mixture monitored after 2-3 hour. After completion of the reaction as indicated by LC-MS, the reaction was quenched with aqueous ammonium chloride solution and the aqueous layer extracted with ethyl acetate (3×25 mL) and combined organic layer washed with brine and dried over sodium sulfate.

The crude residue was purified by flash chromatography using (0-15% EA/Hexanes) to obtain the pure compound (1650 mg, 48.33% yield) as a pale yellow liquid. MS (ESI): m/z 353 [M+1]+.

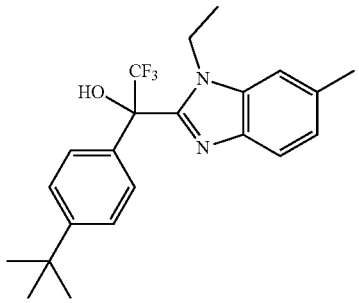 [SMILES: CCn1c(C(O)(c2ccc(C(C)(C)C)cc2)C(F)(F)F)nc2ccc(C)cc21]

1-(4-tert-butylphenyl)-1-(1-ethyl-6-methyl-1H-benzo[d]imidazol-2-yl)-2,2,2-trifluoroethanol: The title compound was prepared according to the method B described for intermediate XIX, employing 1-ethyl-6-methyl-1H-benzo[d]imidazole (696 mg, 4.34 mmol), 1-(4-tert-butylphenyl)-2,2,2-trifluoroethanone (1000 mg, 4.34 mmol) and n-butyllithium (662 mg, 10.42 mmol) to obtain the pure product as a yellow solid compound (714 mg, 42.09% yield) MS (ESI): m/z 391 [M+1]+.

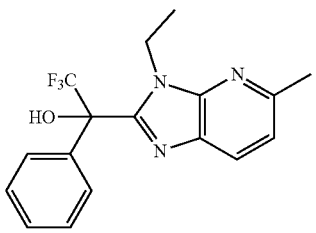 [SMILES: CCn1c(C(O)(c2ccccc2)C(F)(F)F)nc2ccc(C)nc21]

1-(3-Ethyl-5-methyl-3H-imidazo[4,5-b]pyridin-2-yl)-2,2,2-trifluoro-1-phenylethanol: The title compound was prepared according to the method A described for intermediate XVIII, employing 3-ethyl-5-methyl-3H-imidazo[4,5-b]pyridine (450 mg, 2.79 mmol), 2,2,2-trifluoro-1-phenylethanone (590 mg, 3.07 mmol) and lithium bis(trimethylsilyl)amide (560 mg, 3.35 mmol) to obtain the pure product as a yellow solid compound (361 mg, 38.52% yield) MS (ESI): m/z 336 [M+1]+.

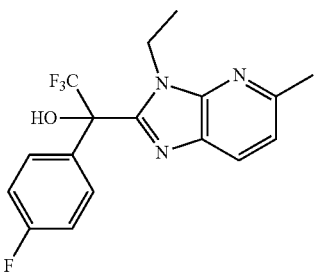 [SMILES: CCn1c(C(O)(c2ccc(F)cc2)C(F)(F)F)nc2ccc(C)nc21]

1-(3-ethyl-5-methyl-3H-imidazo[4,5-b]pyridin-2-yl)-2,2,2-trifluoro-1-(4-fluorophenyl)ethanol: The title compound was prepared according to the method A described for intermediate XVIII, employing 3-ethyl-5-methyl-3H-imidazo[4,5-b]pyridine (806 mg, 5.00 mmol), 2,2,2-trifluoro-1-(4-fluorophenyl)ethanone (1152 mg, 6.00 mmol) and lithium bis(trimethylsilyl)amide (2008 mg, 12.00 mmol) to obtain the pure product as a yellow solid compound (644 mg, 36.53% yield) MS (ESI): m/z 354 [M+1]+.

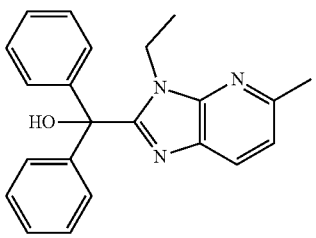 [SMILES: CCn1c(C(O)(c2ccccc2)c2ccccc2)nc2ccc(C)nc21]

(3-Ethyl-5-methyl-3H-imidazo[4,5-b]pyridin-2-yl)diphenylmethanol: The title compound was prepared according to the method described for intermediate XVIII, employing 3-ethyl-5-methyl-3H-imidazo[4,5-b]pyridine (511 mg, 3.16 mmol), benzophenone (722 mg, 3.96 mmol) and lithium bis(trimethylsilyl)amide (635 mg, 3.79 mmol) to obtain the pure product as a yellow solid compound (900 mg, 83.02% yield) MS (ESI): m/z 344 [M+1]+.

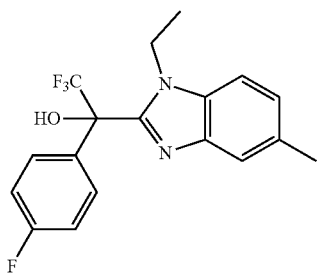 [SMILES: CCn1c(C(O)(c2ccc(F)cc2)C(F)(F)F)nc2cc(C)ccc21]

1-(1-Ethyl-5-methyl-1H-benzo[d]imidazol-2-yl)-2,2,2-trifluoro-1-(4-fluorophenyl)ethanol: The title compound was prepared according to the method A described for intermediate XVIII, employing 1-ethyl-5-methyl-1H-benzo[d]imidazole (1091 mg, 6.81 mmol), 2,2,2-trifluoro-1-(4-fluorophenyl)ethanone (1177 mg, 6.13 mmol) and lithium bis(trimethylsilyl)amide (1367 mg, 8.17 mmol) to obtain the pure product as a yellow solid compound (1005 mg, 41.82% yield) MS (ESI): m/z 353 [M+1]+.

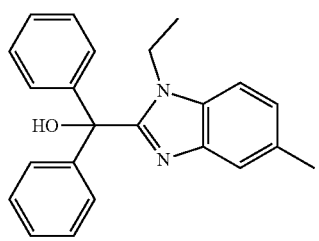 [SMILES: CCn1c(C(O)(c2ccccc2)c2ccccc2)nc2cc(C)ccc21]

(1-Ethyl-5-methyl-1H-benzo[d]imidazol-2-yl)diphenylmethanol: The title compound was prepared according to the method A described for intermediate XVIII, employing 1-ethyl-5-methyl-1H-benzo[d]imidazole (486 mg, 3.03 mmol), benzophenone (553 mg, 3.03 mmol) and lithium bis(trimethylsilyl)amide (608.55 mg, 3.63 mmol) to obtain the pure product as a yellow solid compound (830 mg, 79.88% yield) MS (ESI): m/z 343 [M+1]+.

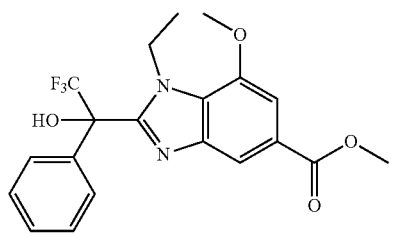 [SMILES: CCn1c(C(O)(c2ccccc2)C(F)(F)F)nc2cc(C(=O)OC)cc(OC)c21]

Methyl 1-ethyl-7-methoxy-2-(2,2,2-trifluoro-1-hydroxy-1-phenylethyl)-1H-benzo[d]imidazole-5-carboxylate: The title compound was prepared according to the method A described for intermediate XVIII, employing methyl 1-ethyl-7-methoxy-1H-benzo[d]imidazole-5-carboxylate (530 mg, 2.26 mmol), 2,2,2-trifluoro-1-phenylethanone (433 mg, 2.48 mmol) and lithium bis(trimethylsilyl)amide (454 mg, 2.71 mmol) to obtain the pure product as a yellow solid compound (420 mg, 45.55% yield) MS (ESI): m/z 409 [M+1]+.

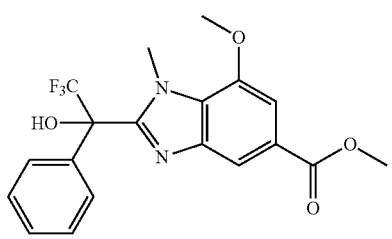 [SMILES: COC(=O)c1cc(OC)c2c(c1)nc(C(O)(c1ccccc1)C(F)(F)F)n2C]

Methyl 7-methoxy-1-methyl-2-(2,2,2-trifluoro-1-hydroxy-1-phenylethyl)-1H-benzo[d]imidazole-5-carboxylate: The title compound was prepared according to the method A described for intermediate XVIII, employing methyl 1-methyl-7-methoxy-1H-benzo[d]imidazole-5-carboxylate (348 mg, 1.58 mmol), 2,2,2-trifluoro-1-phenylethanone (329 mg, 1.89 mmol) and lithium bis(trimethylsilyl)amide (317 mg, 1.89 mmol) to obtain the pure product as a yellow solid compound (289 mg, 46.31% yield) MS (ESI): m/z 395 [M+1]$^+$.

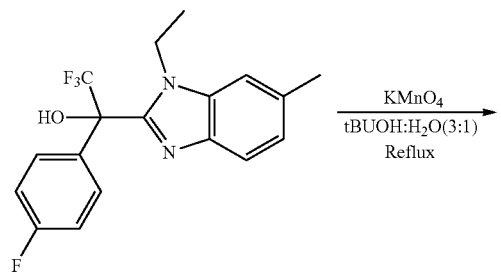

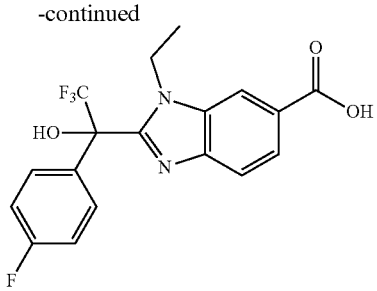

1-Ethyl-2-(2,2,2-trifluoro-1-(4-fluorophenyl)-1-hydroxyethyl)-1H-benzo[d]imidazole-6-carboxylic acid: To a mixture of 1-(1-ethyl-6-methyl-1H-benzo[d]imidazol-2-yl)-2,2,2-trifluoro-1-(4-fluorophenyl)ethanol (1114 mg, 3.16 mmol) in 20:7 mL dissolved in t-BuOH:H$_2$O (3:1) was added potassium permanganate (1998 mg, 12.64 mmol) and reaction mixture stirred at reflux for overnight. After completion of reaction as indicated by TLC reaction mixture cooled to room temperature, filtered through a bed of celite and washed with water (30 mL). To the aqueous filtrate was added diethyl ether, extracted twice with diethyl ether and organic layer was separated. To the aqueous layer was added saturated potassium hydrogen sulfate and adjusted to p$^H$ 4 and then extract the aqueous layer with ethyl acetate (3×50 mL) and combined organic layer dried over sodium sulfate and finally evaporated under vacuum to obtain the a white solid and formed pure compound was used for the next step without purification (811 mg, 67.02% yield). MS (ESI): m/z 383 [M+1]$^+$.

The intermediates 2-10 were prepared according to the general procedure using potassium permanganate in t-butanol and water mixture under reflux conditions for 8-12 h; see Table 3.

TABLE 3

| Intermediate | Structure | Nomenclature | LC-MS |
|---|---|---|---|
| 2 | 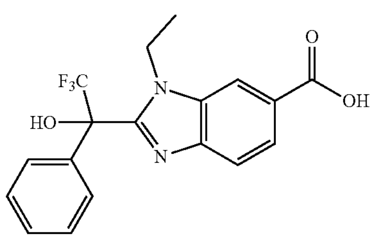 [SMILES: CCn1c(C(O)(c2ccccc2)C(F)(F)F)nc2ccc(C(=O)O)cc21] | 1-Ethyl-2-(2,2,2-trifluoro-1-hydroxy-1-phenylethyl)-1H-benzo[d]imidazole-6-carboxylic acid | 365 [M + 1]$^+$ |
| 3 | 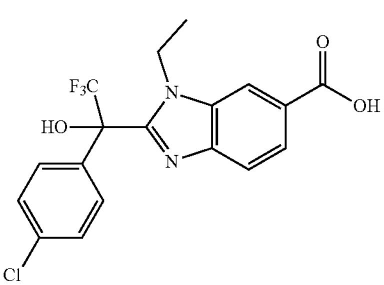 [SMILES: CCn1c(C(O)(c2ccc(Cl)cc2)C(F)(F)F)nc2ccc(C(=O)O)cc21] | 2-(1-(4-Chlorophenyl)-2,2,2-trifluoro-1-hydroxyethyl)-1-ethyl-1H-benzo[d]imidazole-6-carboxylic acid | 399 [M + 1]$^+$ |

TABLE 3-continued

| Intermediate | Structure | Nomenclature | LC-MS |
|---|---|---|---|
| 4 | 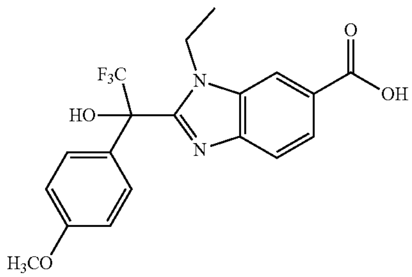 [SMILES: CCn1c(C(O)(c2ccc(OC)cc2)C(F)(F)F)nc2ccc(C(=O)O)cc21] | 1-Ethyl-2-(2,2,2-trifluoro-1-hydroxy-1-(4-methoxyphenyl)ethyl)-1H-benzo[d]imidazole-6-carboxylic acid | 395 [M + 1]+ |
| 5 | 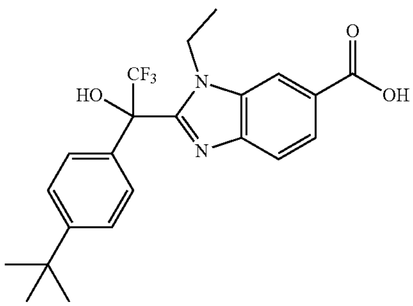 [SMILES: CCn1c(C(O)(c2ccc(C(C)(C)C)cc2)C(F)(F)F)nc2ccc(C(=O)O)cc21] | 2-(1-(4-tert-butylphenyl)-2,2,2-trifluoro-1-hydroxyethyl)-1-ethyl-1H-benzo[d]imidazole-6-carboxylic acid | 421 [M + 1]+ |
| 6 | 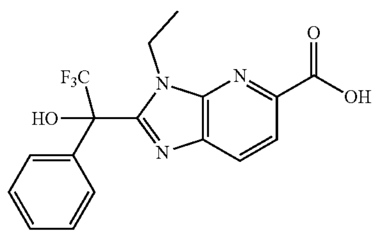 [SMILES: CCn1c(C(O)(c2ccccc2)C(F)(F)F)nc2ccc(C(=O)O)nc21] | 3-Ethyl-2-(2,2,2-trifluoro-1-hydroxy-1-phenylethyl)-3H-imidazo[4,5-b]pyridine-5-carboxylic acid | 366 [M + 1]+ |
| 7 | 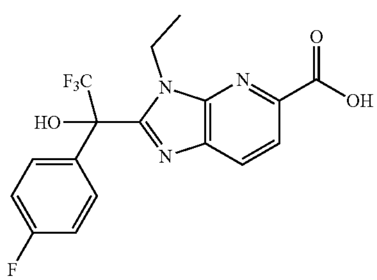 [SMILES: CCn1c(C(O)(c2ccc(F)cc2)C(F)(F)F)nc2ccc(C(=O)O)nc21] | 3-Ethyl-2-(2,2,2-trifluoro-1-(4-fluorophenyl)-1-hydroxyethyl)-3H-imidazo[4,5-b]pyridine-5-carboxylic acid | 384 [M + 1]+ |
| 8 | 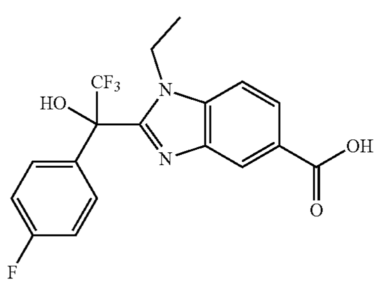 [SMILES: CCn1c(C(O)(c2ccc(F)cc2)C(F)(F)F)nc2cc(C(=O)O)ccc21] | 1-Ethyl-2-(2,2,2-trifluoro-1-(4-fluorophenyl)-1-hydroxyethyl)-1H-benzo[d]imidazole-5-carboxylic acid | 383 [M + 1]+ |

TABLE 3-continued

| Intermediate | Structure | Nomenclature | LC-MS |
|---|---|---|---|
| 9 | 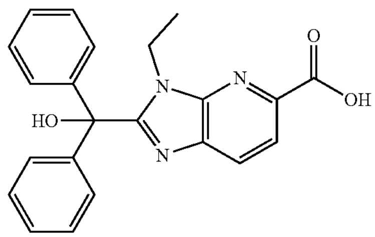 [SMILES: CCn1c(C(O)(c2ccccc2)c2ccccc2)nc2ccc(C(=O)O)nc21] | 3-Ethyl-2-(hydroxydiphenylmethyl)-3H-imidazo[4,5-b]pyridine-5-carboxylic acid | 374 [M + 1]⁺ |
| 10 | 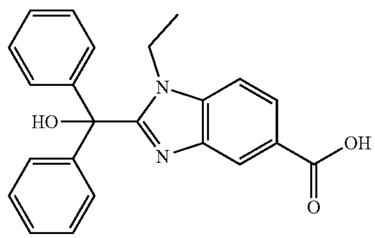 [SMILES: CCn1c(C(O)(c2ccccc2)c2ccccc2)nc2cc(C(=O)O)ccc21] | 1-Ethyl-2-(hydroxydiphenylmethyl)-1H-benzo[d]imidazole-5-carboxylic acid | 373 [M + 1]⁺ |

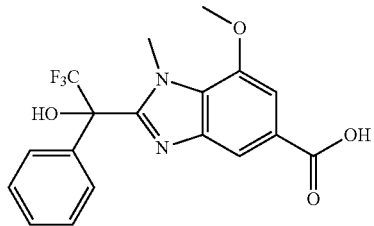 [SMILES: COc1cc(C(=O)O)cc2nc(C(O)(c3ccccc3)C(F)(F)F)n(C)c12]

1-Ethyl-7-methoxy-2-(2,2,2-trifluoro-1-hydroxy-1-phenylethyl)-1H-benzo[d]imidazole-5-carboxylic acid: To a stirred solution of methyl 1-ethyl-7-methoxy-2-(2,2,2-trifluoro-1-hydroxy-1-phenylethyl)-1H-benzo[d]imidazole-5-carboxylate (358 mg, 0.87 mmol) in THF: MeOH: water (3:3:1) was added lithium hydroxide monohydrate (107 mg, 2.629 mmol) and stirred at rt for overnight, after completion of the reaction solvent was evaporated, to the crude residue was added 1-2 mL and acidified with 1N HCl to obtain the white solid which was filtered and washed with water (10 mL), dried to gave pure product as a white solid compound (320 mg, 93.56% yield) MS (ESI): m/z 395 [M+1]⁺.

7-methoxy-1-methyl-2-(2,2,2-trifluoro-1-hydroxy-1-phenylethyl)-1H-benzo[d]imidazole-5-carboxylic acid: The title compound was prepared according to the above method employing methyl 7-methoxy-1-methyl-2-(2,2,2-trifluoro-1-hydroxy-1-phenylethyl)-1H-benzo[d]imidazole-5-carboxylate (250 mg, 0.63 mmol) and lithium hydroxide monohydrate (77 mg, 1.89 mmol) to obtain the pure product as a white solid compound (215 mg, 89.58% yield) MS (ESI): m/z 381 [M+1]⁺.

General Procedure for Synthesis of Final ACSS2 Inhibitor Compounds

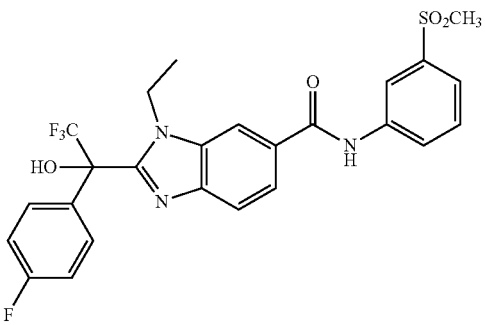 [SMILES: CCn1c(C(O)(c2ccc(F)cc2)C(F)(F)F)nc2ccc(C(=O)Nc3cccc(S(C)(=O)=O)c3)cc21]

1-ethyl-N-(3-(methylsulfonyl)phenyl)-2-(2,2,2-trifluoro-1-(4-fluorophenyl)-1-hydroxyethyl)-1H-benzo[d]imidazole-6-carboxamide: To a stirred solution of 1-ethyl-2-(2,2,2-trifluoro-1-(4-fluorophenyl)-1-hydroxyethyl)-1H-benzo[d]imidazole-6-carboxylic acid (382 mg, 1.00 mmol) in anhydrous DMF (5 mL) was added HATU (760.46 mg, 2.0 mmol) and after 5 min DIPFA (388 mg, 3.0 mmol) was added and reaction mixture was stirred for 10-15 min and then 3-(methylsulfonyl)aniline (205 mg, 1.2 mmol) was added. The reaction mixture was stirred at room temperature for 24-36 hours. After completion of the reaction water was added to the reaction mixture and aqueous layer extracted with ethyl acetate (3×25 mL) and combined organic layer washed with brine and dried over sodium sulfate and crude residue was purified by flash chromatography using (0-80% FA/Hexanes) to obtain the pure compound (786 mg, 69.25% yield) as a pale yellow solid. MS (ESI): m/z 536 [M+1]⁺.

Compounds A1-A53 were prepared similarly to above general procedure, by reacting corresponding intermediate carboxylic acids (10-20) with the appropriate amines, see Table 4 below.

TABLE 4

| No. | Structure | IUPAC Nomenclature | Mass Spectra LC-MS (ESI): m/z |
|---|---|---|---|
| A1 | 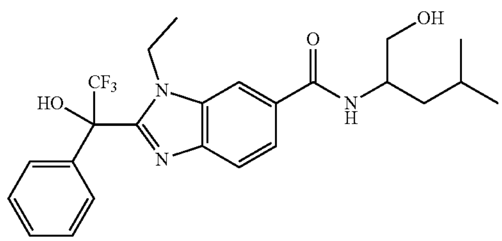 [SMILES: CCn1c(C(O)(c2ccccc2)C(F)(F)F)nc2ccc(C(=O)NC(CO)CC(C)C)cc21] | 1-Ethyl-N-(1-hydroxy-4-methylpentan-2-yl)-2-(2,2,2-trifluoro-1-hydroxy-1-phenylethyl)-1H-benzo[d]imidazole-6-carboxamide | 464 [M + 1]$^+$ |
| A2 | 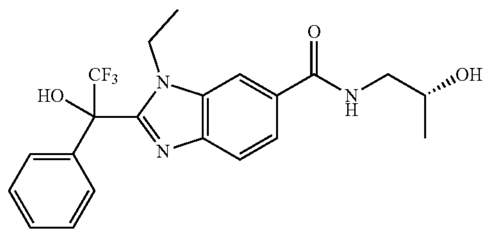 [SMILES: CCn1c(C(O)(c2ccccc2)C(F)(F)F)nc2ccc(C(=O)NC[C@@H](C)O)cc21] | 1-Ethyl-N-((R)-2-hydroxypropyl)-2-(2,2,2-trifluoro-1-hydroxy-1-phenylethyl)-1H-benzo[d]imidazole-6-carboxamide | 422 [M + 1]$^+$ |
| A3 | 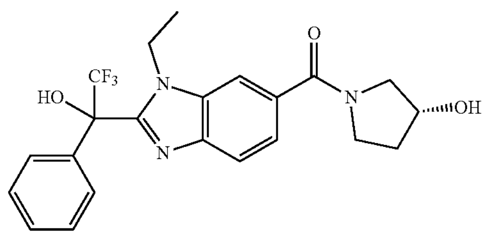 [SMILES: CCn1c(C(O)(c2ccccc2)C(F)(F)F)nc2ccc(C(=O)N3CC[C@@H](O)C3)cc21] | (1-Ethyl-2-(2,2,2-trifluoro-1-hydroxy-1-phenylethyl)-1H-benzo[d]imidazol-6-yl)((R)-3-hydroxypyrrolidin-1-yl)methanone | 434 [M + 1]$^+$ |
| A4 | 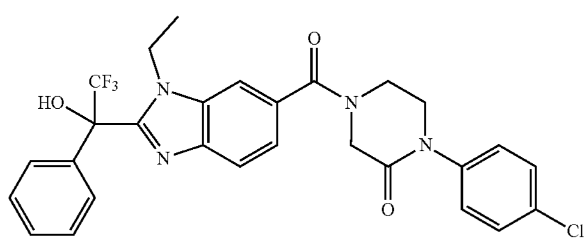 [SMILES: CCn1c(C(O)(c2ccccc2)C(F)(F)F)nc2ccc(C(=O)N3CCN(c4ccc(Cl)cc4)C(=O)C3)cc21] | 1-(4-Chlorophenyl)-4-(1-ethyl-2-(2,2,2-trifluoro-1-hydroxy-1-phenylethyl)-1H-benzo[d]imidazole-6-carbonyl)piperazin-2-one | 557 [M]$^+$ |
| A5 | 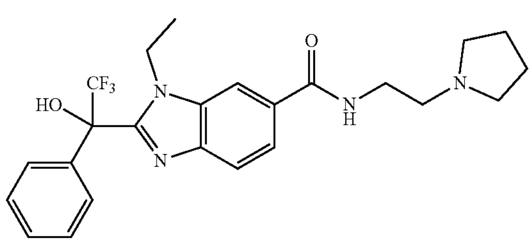 [SMILES: CCn1c(C(O)(c2ccccc2)C(F)(F)F)nc2ccc(C(=O)NCCN3CCCC3)cc21] | 1-Ethyl-N-(2-(pyrrolidin-1-yl)ethyl)-2-(2,2,2-trifluoro-1-hydroxy-1-phenylethyl)-1H-benzo[d]imidazole-6-carboxamide | 461 [M + 1]$^+$ |
| A6 | 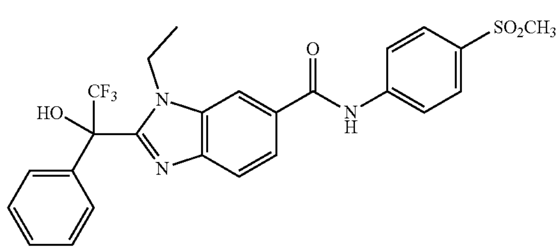 [SMILES: CCn1c(C(O)(c2ccccc2)C(F)(F)F)nc2ccc(C(=O)Nc3ccc(S(C)(=O)=O)cc3)cc21] | 1-Ethyl-N-(4-(methylsulfonyl)phenyl)-2-(2,2,2-trifluoro-1-hydroxy-1-phenylethyl)-1H-benzo[d]imidazole-6-carboxamide | 518 [M + 1]$^+$ |

TABLE 4-continued

| No. | Structure | IUPAC Nomenclature | Mass Spectra LC-MS (ESI): m/z |
|---|---|---|---|
| A7 | 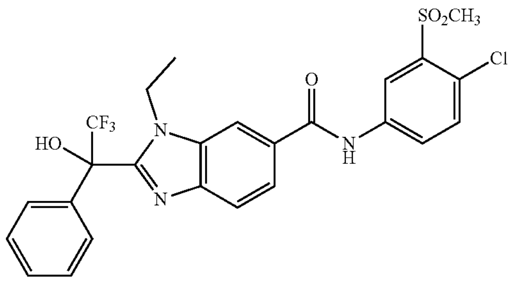 [SMILES: CCn1c(C(O)(c2ccccc2)C(F)(F)F)nc2ccc(C(=O)Nc3ccc(Cl)c(S(C)(=O)=O)c3)cc21] | N-(4-chloro-3-(methylsulfonyl)phenyl)-1-ethyl-2-(2,2,2-trifluoro-1-hydroxy-1-phenylethyl)-1H-benzo[d]imidazole-6-carboxamide | 552 [M]+ |
| A8 | 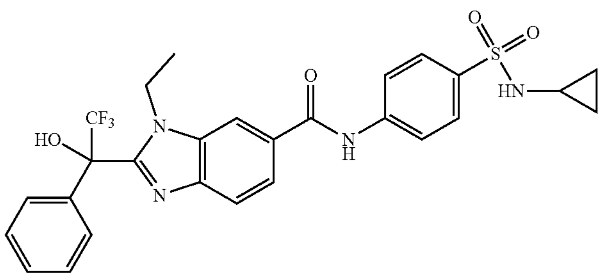 [SMILES: CCn1c(C(O)(c2ccccc2)C(F)(F)F)nc2ccc(C(=O)Nc3ccc(S(=O)(=O)NC4CC4)cc3)cc21] | N-(4-(N-cyclopropylsulfamoyl)phenyl)-1-ethyl-2-(2,2,2-trifluoro-1-hydroxy-1-phenylethyl)-1H-benzo[d]imidazole-6-carboxamide | 559 [M + 1]+ |
| A9 | 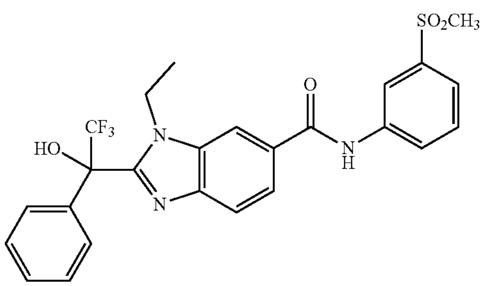 [SMILES: CCn1c(C(O)(c2ccccc2)C(F)(F)F)nc2ccc(C(=O)Nc3cccc(S(C)(=O)=O)c3)cc21] | 1-Ethyl-N-(3-(methylsulfonyl)phenyl)-2-(2,2,2-trifluoro-1-hydroxy-1-phenylethyl)-1H-benzo[d]imidazole-6-carboxamide | 518 [M + 1]+ |
| A10 | 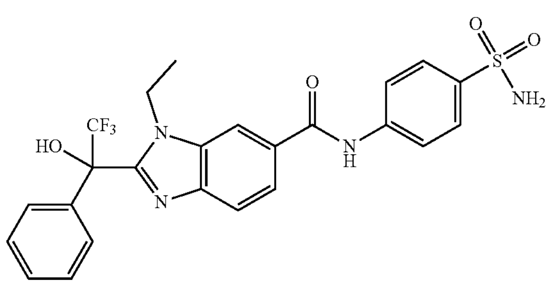 [SMILES: CCn1c(C(O)(c2ccccc2)C(F)(F)F)nc2ccc(C(=O)Nc3ccc(S(N)(=O)=O)cc3)cc21] | 1-Ethyl-N-(4-sulfamoylphenyl)-2-(2,2,2-trifluoro-1-hydroxy-1-phenylethyl)-1H-benzo[d]imidazole-6-carboxamide | 519 [M + 1]+ |
| A11 | 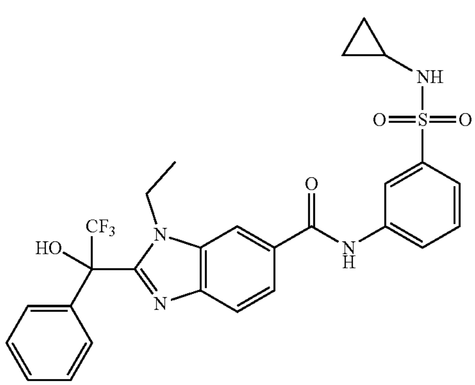 [SMILES: CCn1c(C(O)(c2ccccc2)C(F)(F)F)nc2ccc(C(=O)Nc3cccc(S(=O)(=O)NC4CC4)c3)cc21] | N-(3-(N-cyclopropylsulfamoyl)phenyl)-1-ethyl-2-(2,2,2-trifluoro-1-hydroxy-1-phenylethyl)-1H-benzo[d]imidazole-6-carboxamide | 559 [M + 1]+ |

TABLE 4-continued

| No. | Structure | IUPAC Nomenclature | Mass Spectra LC-MS (ESI): m/z |
|---|---|---|---|
| A12 | 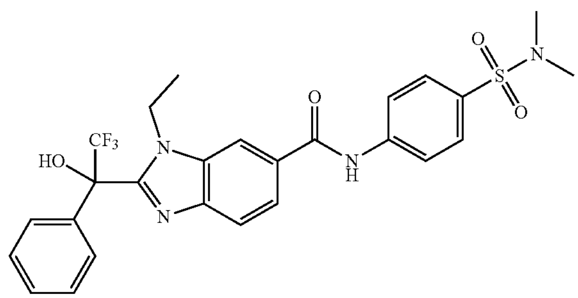 [SMILES: CCn1c(C(O)(c2ccccc2)C(F)(F)F)nc2ccc(C(=O)Nc3ccc(S(=O)(=O)N(C)C)cc3)cc21] | N-(4-(N,N-dimethylsulfamoyl)phenyl)-1-ethyl-2-(2,2,2-trifluoro-1-hydroxy-1-phenylethyl)-1H-benzo[d]imidazole-6-carboxamide | 547 [M + 1]$^+$ |
| A13 | 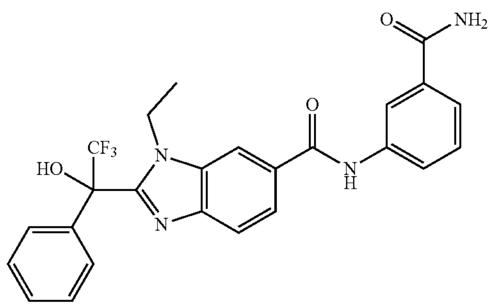 [SMILES: CCn1c(C(O)(c2ccccc2)C(F)(F)F)nc2ccc(C(=O)Nc3cccc(C(N)=O)c3)cc21] | N-(3-carbamoylphenyl)-1-ethyl-2-(2,2,2-trifluoro-1-hydroxy-1-phenylethyl)-1H-benzo[d]imidazole-6-carboxamide | 483 [M + 1]$^+$ |
| A14 | 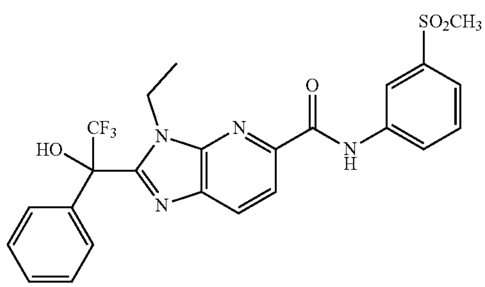 [SMILES: CCn1c(C(O)(c2ccccc2)C(F)(F)F)nc2ccc(C(=O)Nc3cccc(S(C)(=O)=O)c3)nc21] | 3-Ethyl-N-(3-(methylsulfonyl)phenyl)-2-(2,2,2-trifluoro-1-hydroxy-1-phenylethyl)-3H-imidazo[4,5-b]pyridine-5-carboxamide | 519 [M + 1]$^+$ |
| A15 | 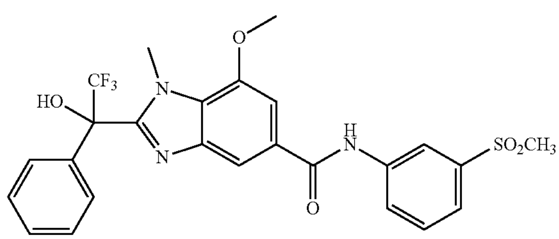 [SMILES: COc1cc(C(=O)Nc2cccc(S(C)(=O)=O)c2)cc2nc(C(O)(c3ccccc3)C(F)(F)F)n(C)c12] | 7-methoxy-1-methyl-N-(3-(methylsulfonyl)phenyl)-2-(2,2,2-trifluoro-1-hydroxy-1-phenylethyl)-1H-benzo[d]imidazole-5-carboxamide | 532 [M + 1]$^+$ |
| A16 | 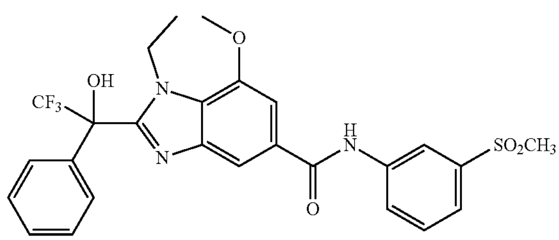 [SMILES: CCn1c(C(O)(c2ccccc2)C(F)(F)F)nc2cc(C(=O)Nc3cccc(S(C)(=O)=O)c3)cc(OC)c21] | 1-ethyl-7-methoxy-N-(3-(methylsulfonyl)phenyl)-2-(2,2,2-trifluoro-1-hydroxy-1-phenylethyl)-1H-benzo[d]imidazole-5-carboxamide | 548 [M + 1]$^+$ |

TABLE 4-continued

| No. | Structure | IUPAC Nomenclature | Mass Spectra LC-MS (ESI): m/z |
|---|---|---|---|
| A17 | 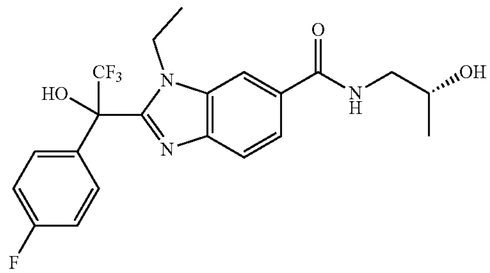 [SMILES: CCn1c(C(O)(c2ccc(F)cc2)C(F)(F)F)nc2ccc(C(=O)NC[C@@H](C)O)cc21] | 1-Ethyl-N-((R)-2-hydroxypropyl)-2-(2,2,2-trifluoro-1-(4-fluorophenyl)-1-hydroxyethyl)-1H-benzo[d]imidazole-6-carboxamide | 440 [M + 1]+ |
| A18 | 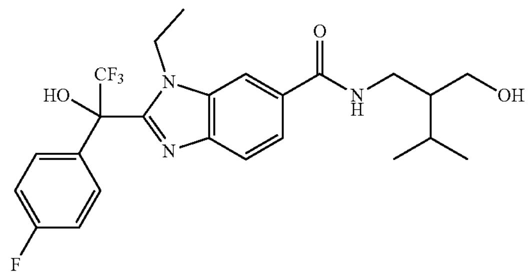 [SMILES: CCn1c(C(O)(c2ccc(F)cc2)C(F)(F)F)nc2ccc(C(=O)NCC(CO)C(C)C)cc21] | 1-Ethyl-N-(2-(hydroxymethyl)-3-methylbutyl)-2-(2,2,2-trifluoro-1-(4-fluorophenyl)-1-hydroxyethyl)-1H-benzo[d]imidazole-6-carboxamide | 482 [M + 1]+ |
| A19 | 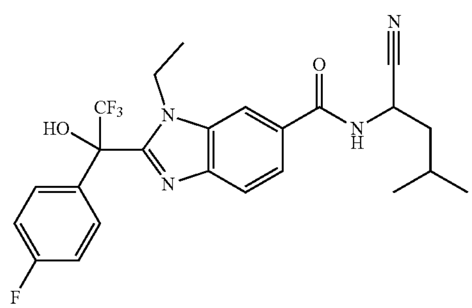 [SMILES: CCn1c(C(O)(c2ccc(F)cc2)C(F)(F)F)nc2ccc(C(=O)NC(C#N)CC(C)C)cc21] | N-(1-Cyano-3-methylbutyl)-1-ethyl-2-(2,2,2-trifluoro-1-(4-fluorophenyl)-1-hydroxyethyl)-1H-benzo[d]imidazole-6-carboxamide | 477 [M + 1]+ |
| A20 | 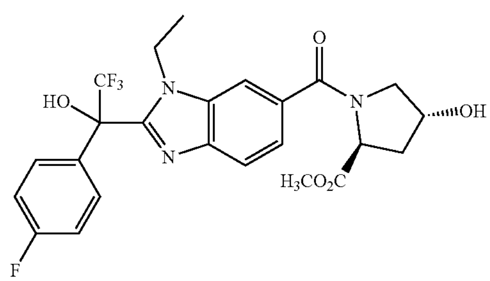 [SMILES: CCn1c(C(O)(c2ccc(F)cc2)C(F)(F)F)nc2ccc(C(=O)N3C[C@H](O)C[C@H]3C(=O)OC)cc21] | (2S,4R)-Methyl 1-(1-ethyl-2-(2,2,2-trifluoro-1-(4-fluorophenyl)-1-hydroxyethyl)-1H-benzo[d]imidazole-6-carbonyl)-4-hydroxypyrrolidine-2-carboxylate | 510 [M + 1]+ |
| A21 | 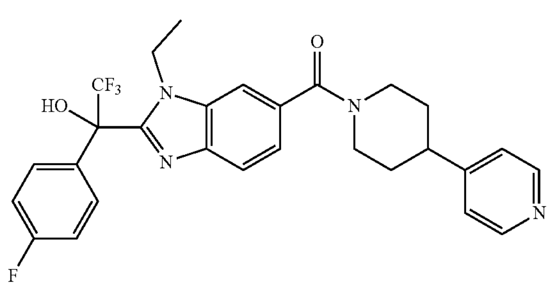 [SMILES: CCn1c(C(O)(c2ccc(F)cc2)C(F)(F)F)nc2ccc(C(=O)N3CCC(c4ccncc4)CC3)cc21] | (1-Ethyl-2-(2,2,2-trifluoro-1-(4-fluorophenyl)-1-hydroxyethyl)-1H-benzo[d]imidazol-6-yl)(4-(pyridin-4-yl)piperidin-1-yl)methanone | 528 [M + 1]+ |

TABLE 4-continued

| No. | Structure | IUPAC Nomenclature | Mass Spectra LC-MS (ESI): m/z |
|---|---|---|---|
| A22 | 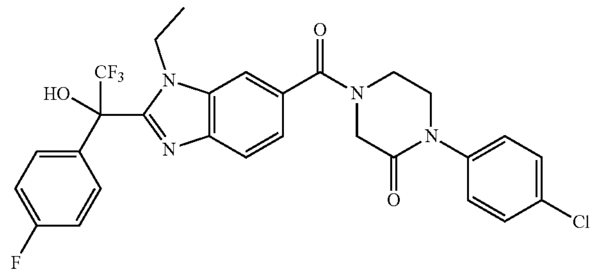 [SMILES: CCn1c(C(O)(c2ccc(F)cc2)C(F)(F)F)nc2ccc(C(=O)N3CCN(c4ccc(Cl)cc4)C(=O)C3)cc21] | 1-(4-Chlorophenyl)-4-(1-ethyl-2-(2,2,2-trifluoro-1-(4-fluorophenyl)-1-hydroxyethyl)-1H-benzo[d]imidazole-6-carbonyl)piperazin-2-one | 575 [M]$^+$ |
| A23 | 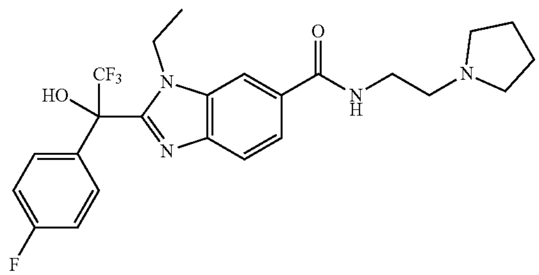 [SMILES: CCn1c(C(O)(c2ccc(F)cc2)C(F)(F)F)nc2ccc(C(=O)NCCN3CCCC3)cc21] | 1-Ethyl-N-(2-(pyrrolidin-1-yl)ethyl)-2-(2,2,2-trifluoro-1-(4-fluorophenyl)-1-hydroxyethyl)-1H-benzo[d]imidazole-6-carboxamide | 479 [M + 1]$^+$ |
| A24 | 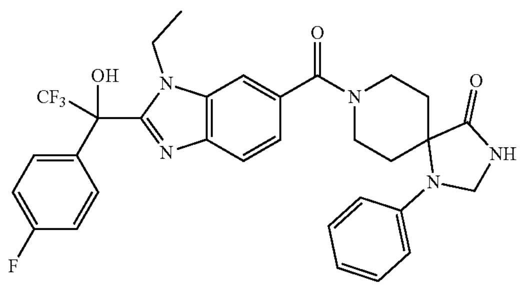 [SMILES: CCn1c(C(O)(c2ccc(F)cc2)C(F)(F)F)nc2ccc(C(=O)N3CCC4(CC3)C(=O)NCN4c3ccccc3)cc21] | 8-(1-Ethyl-2-(2,2,2-trifluoro-1-(4-fluorophenyl)-1-hydroxyethyl)-1H-benzo[d]imidazole-6-carbonyl)-1-phenyl-1,3,8-triazaspiro[4.5]decan-4-one | 596 [M + 1]$^+$ |
| A25 | 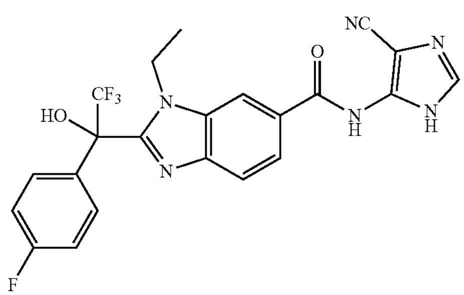 [SMILES: CCn1c(C(O)(c2ccc(F)cc2)C(F)(F)F)nc2ccc(C(=O)Nc3[nH]cnc3C#N)cc21] | N-(4-Cyano-1H-imidazol-5-yl)-1-ethyl-2-(2,2,2-trifluoro-1-(4-fluorophenyl)-1-hydroxyethyl)-1H-benzo[d]imidazole-6-carboxamide | 473 [M + 1]$^+$ |
| A26 | 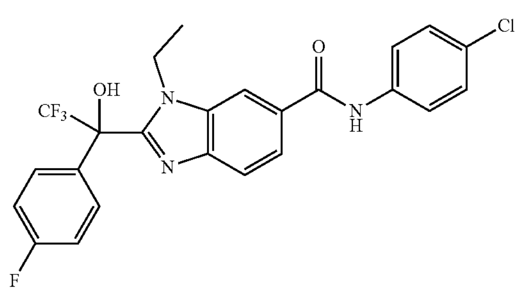 [SMILES: CCn1c(C(O)(c2ccc(F)cc2)C(F)(F)F)nc2ccc(C(=O)Nc3ccc(Cl)cc3)cc21] | N-(4-Chlorophenyl)-1-ethyl-2-(2,2,2-trifluoro-1-(4-fluorophenyl)-1-hydroxyethyl)-1H-benzo[d]imidazole-6-carboxamide | 492 [M]$^+$ |

TABLE 4-continued

| No. | Structure | IUPAC Nomenclature | Mass Spectra LC-MS (ESI): m/z |
|---|---|---|---|
| A27 | 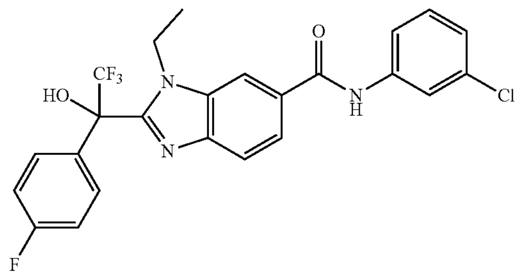 [SMILES: CCn1c(C(O)(c2ccc(F)cc2)C(F)(F)F)nc2ccc(C(=O)Nc3cccc(Cl)c3)cc21] | N-(3-Chlorophenyl)-1-ethyl-2-(2,2,2-trifluoro-1-(4-fluorophenyl)-1-hydroxyethyl)-1H-benzo[d]imidazole-6-carboxamide | 492 [M]+ |
| A28 | 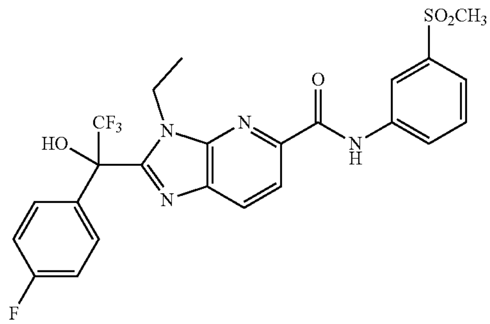 [SMILES: CCn1c(C(O)(c2ccc(F)cc2)C(F)(F)F)nc2ccc(C(=O)Nc3cccc(S(C)(=O)=O)c3)nc21] | 3-Ethyl-N-(3-(methylsulfonyl)phenyl)-2-(2,2,2-trifluoro-1-(4-fluorophenyl)-1-hydroxyethyl)-3H-imidazo[4,5-b]pyridine-5-carboxamide | 537 [M + 1]+ |
| A29 | 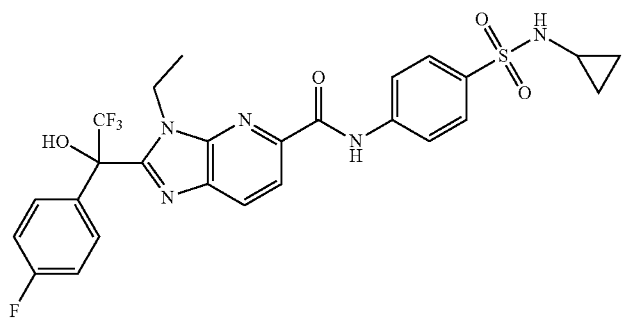 [SMILES: CCn1c(C(O)(c2ccc(F)cc2)C(F)(F)F)nc2ccc(C(=O)Nc3ccc(S(=O)(=O)NC4CC4)cc3)nc21] | N-(4-(N-Cyclopropylsulfamoyl)phenyl)-3-ethyl-2-(2,2,2-trifluoro-1-(4-fluorophenyl)-1-hydroxyethyl)-3H-imidazo[4,5-b]pyridine-5-carboxamide | 578 [M + 1]+ |
| A30 | 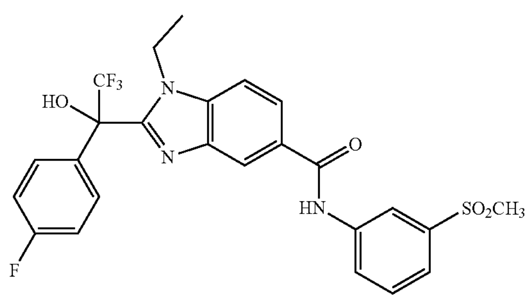 [SMILES: CCn1c(C(O)(c2ccc(F)cc2)C(F)(F)F)nc2cc(C(=O)Nc3cccc(S(C)(=O)=O)c3)ccc21] | 1-Ethyl-N-(3-(methylsulfonyl)phenyl)-2-(2,2,2-trifluoro-1-(4-fluorophenyl)-1-hydroxyethyl)-1H-benzo[d]imidazole-5-carboxamide | 535 [M + 1]+ |
| A31 | 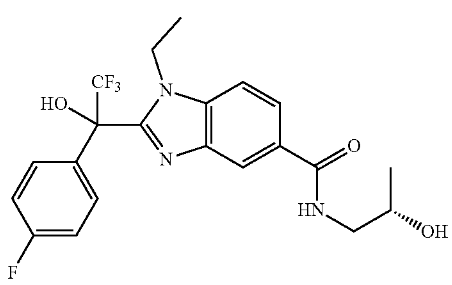 [SMILES: CCn1c(C(O)(c2ccc(F)cc2)C(F)(F)F)nc2cc(C(=O)NC[C@H](C)O)ccc21] | 1-Ethyl-N-(R)-2-hydroxypropyl)-2-(2,2,2-trifluoro-1-(4-fluorophenyl)-1-hydroxyethyl)-1H-benzo[d]imidazole-5-carboxamide | 439 [M + 1]+ |

TABLE 4-continued

| No. | Structure | IUPAC Nomenclature | Mass Spectra LC-MS (ESI): m/z |
|---|---|---|---|
| A32 | 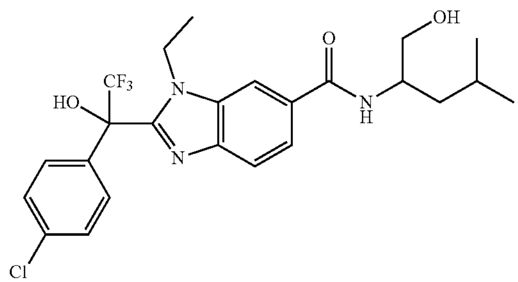 [SMILES: CCn1c(C(O)(c2ccc(Cl)cc2)C(F)(F)F)nc2ccc(C(=O)NC(CO)CC(C)C)cc21] | 2-(1-(4-Chlorophenyl)-2,2,2-trifluoro-1-hydroxyethyl)-1-ethyl-N-(1-hydroxy-4-methylpentan-2-yl)-1H-benzo[d]imidazole-6-carboxamide | 439 [M]+ |
| A33 | 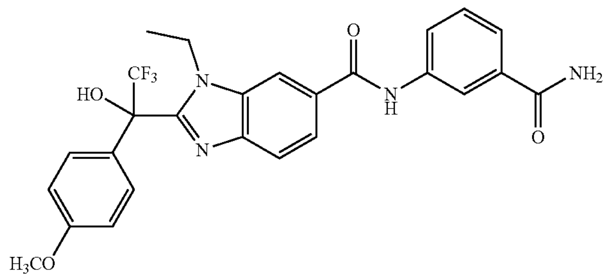 [SMILES: CCn1c(C(O)(c2ccc(OC)cc2)C(F)(F)F)nc2ccc(C(=O)Nc3cccc(C(N)=O)c3)cc21] | N-(3-Carbamoylphenyl)-1-ethyl-2-(2,2,2-trifluoro-1-hydroxy-1-(4-methoxyphenyl)ethyl)-1H-benzo[d]imidazole-6-carboxamide | 513 [M + 1]+ |
| A34 | 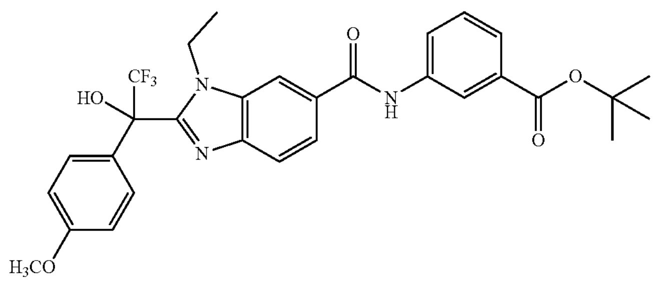 [SMILES: CCn1c(C(O)(c2ccc(OC)cc2)C(F)(F)F)nc2ccc(C(=O)Nc3cccc(C(=O)OC(C)(C)C)c3)cc21] | tert-butyl 3-(1-ethyl-2-(2,2,2-trifluoro-1-hydroxy-1-(4-methoxyphenyl)ethyl)-1H-benzo[d]imidazole-6-carboxamido)benzoate | 570 [M + 1]+ |
| A35 | 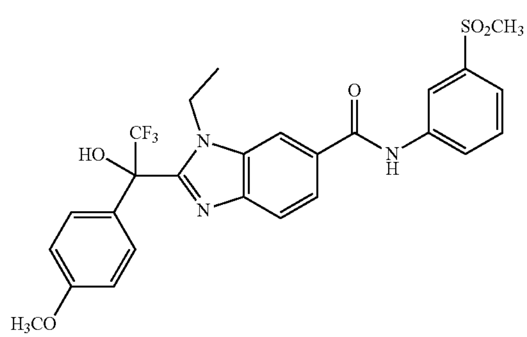 [SMILES: CCn1c(C(O)(c2ccc(OC)cc2)C(F)(F)F)nc2ccc(C(=O)Nc3cccc(S(C)(=O)=O)c3)cc21] | 1-Ethyl-N-(3-(methylsulfonyl)phenyl)-2-(2,2,2-trifluoro-1-hydroxy-1-(4-methoxyphenyl)ethyl)-1H-benzo[d]imidazole-6-carboxamide | 548 [M + 1]+ |
| A36 | 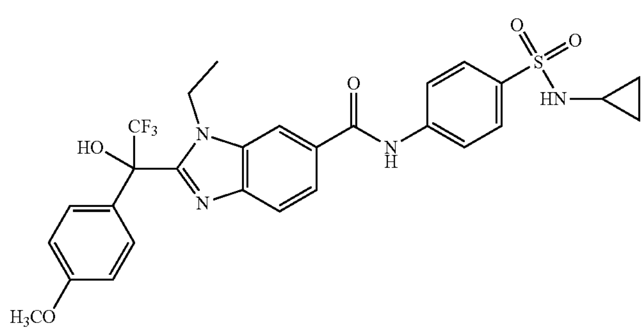 [SMILES: CCn1c(C(O)(c2ccc(OC)cc2)C(F)(F)F)nc2ccc(C(=O)Nc3ccc(S(=O)(=O)NC4CC4)cc3)cc21] | N-(4-(N-cyclopropylsulfamoyl)phenyl)-1-ethyl-2-(2,2,2-trifluoro-1-hydroxy-1-(4-methoxyphenyl)ethyl)-1H-benzo[d]imidazole-6-carboxamide | 589 [M + 1]+ |

TABLE 4-continued

| No. | Structure | IUPAC Nomenclature | Mass Spectra LC-MS (ESI): m/z |
|---|---|---|---|
| A37 | 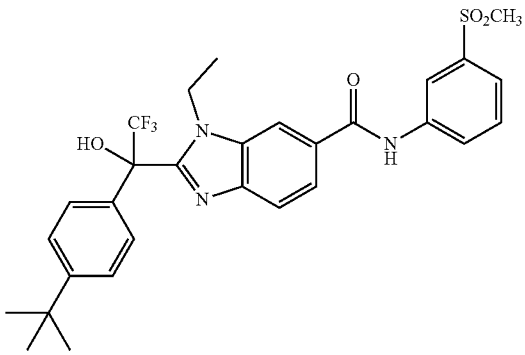 [SMILES: CCn1c(C(O)(c2ccc(C(C)(C)C)cc2)C(F)(F)F)nc2ccc(C(=O)Nc3cccc(S(C)(=O)=O)c3)cc21] | 2-(1-(4-tert-butylphenyl)-2,2,2-trifluoro-1-hydroxyethyl)-1-ethyl-N-(3-(methylsulfonyl)phenyl)-1H-benzo[d]imidazole-6-carboxamide | 574 [M + 1]+ |
| A38 | 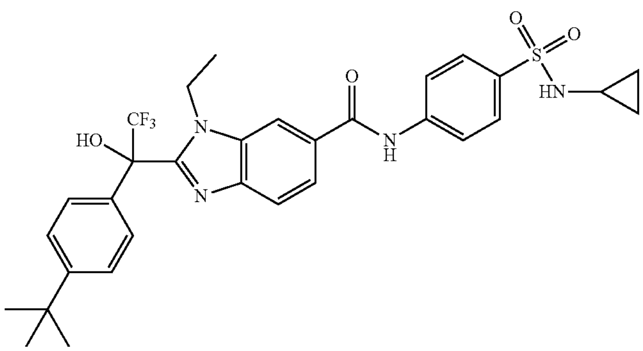 [SMILES: CCn1c(C(O)(c2ccc(C(C)(C)C)cc2)C(F)(F)F)nc2ccc(C(=O)Nc3ccc(S(=O)(=O)NC4CC4)cc3)cc21] | 2-(1-(4-tert-butylphenyl)-2,2,2-trifluoro-1-hydroxyethyl)-N-(4-(N-cyclopropylsulfamoyl)phenyl)-1-ethyl-1H-benzo[d]imidazole-6-carboxamide | 615 [M + 1]+ |
| A39 | 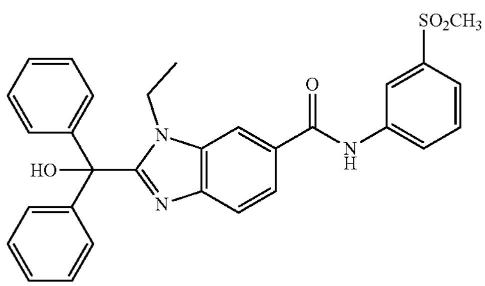 [SMILES: CCn1c(C(O)(c2ccccc2)c2ccccc2)nc2ccc(C(=O)Nc3cccc(S(C)(=O)=O)c3)cc21] | 1-Ethyl-2-(hydroxydiphenylmethyl)-N-(3-(methylsulfonyl)phenyl)-1H-benzo[d]imidazole-6-carboxamide | 526 [M + 1]+ |
| A40 | 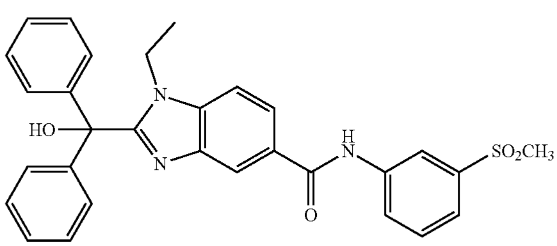 [SMILES: CCn1c(C(O)(c2ccccc2)c2ccccc2)nc2cc(C(=O)Nc3cccc(S(C)(=O)=O)c3)ccc21] | 1-Ethyl-2-(hydroxydiphenylmethyl)-N-(3-(methylsulfonyl)phenyl)-1H-benzo[d]imidazole-5-carboxamide | 526 [M + 1]+ |
| A41 | 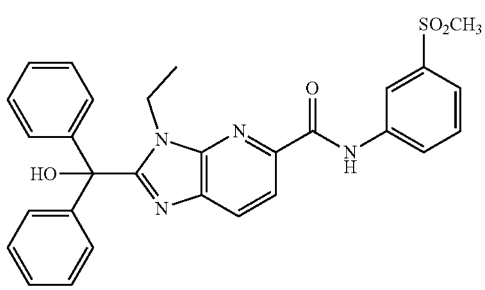 [SMILES: CCn1c(C(O)(c2ccccc2)c2ccccc2)nc2ccc(C(=O)Nc3cccc(S(C)(=O)=O)c3)nc21] | 3-Ethyl-2-(hydroxydiphenylmethyl)-N-(3-(methylsulfonyl)phenyl)-3H-imidazo[4,5-b]pyridine-5-carboxamide | 527 [M + 1]+ |

TABLE 4-continued

| No. | Structure | IUPAC Nomenclature | Mass Spectra LC-MS (ESI): m/z |
|---|---|---|---|
| A42 | 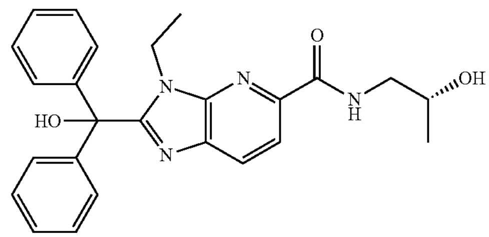 [SMILES: CCn1c(C(O)(c2ccccc2)c2ccccc2)nc2ccc(C(=O)NC[C@@H](C)O)nc21] | (R)-3-Ethyl-2-(hydroxydiphenylmethyl)-N-(2-hydroxypropyl)-3H-imidazo[4,5-b]pyridine-5-carboxamide | 431 [M + 1]+ |
| A43 | 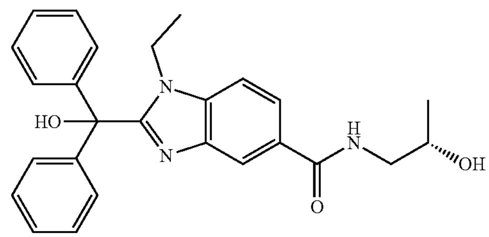 [SMILES: CCn1c(C(O)(c2ccccc2)c2ccccc2)nc2cc(C(=O)NC[C@H](C)O)ccc21] | (S)-1-ethyl-2-(hydroxydiphenylmethyl)-N-(2-hydroxypropyl)-1H-benzo[d]imidazole-5-carboxamide | 430 [M + 1]+ |

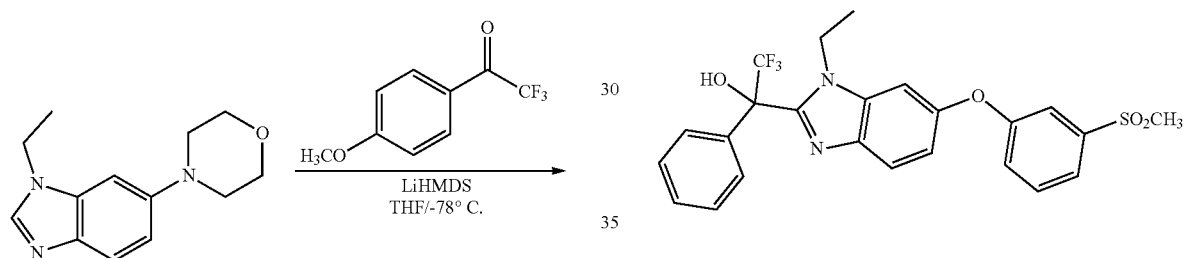

1-(1-Ethyl-6-(3-(methylsulfonyl)phenoxy)-1H-benzo[d]imidazol-2-yl)-2,2,2-trifluoro-1-phenylethanol: The title compound was prepared according to the method A employing 1-ethyl-6-(3-(methylsulfonyl)phenoxy)-1H-benzo[d]imidazole (316 mg, 1.00 mmol), 2,2,2-trifluoro-1-phenylethanone (209 mg, 1.20 mmol) and lithium bis(trimethylsilyl)amide (402 mg, 2.40 mmol) to obtain the pure product as a white solid. (303 mg, 61.71% yield) MS (ESI): m/z 491 [M+1]+.

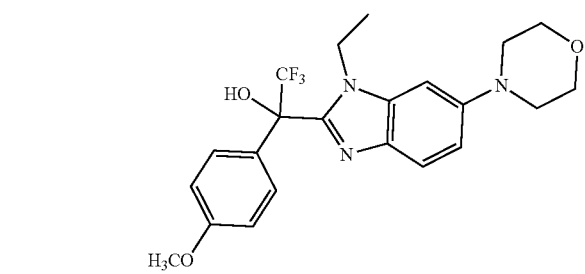

1-(1-ethyl-6-morpholino-1H-benzo[d]imidazol-2-yl)-2,2,2-trifluoro-1-(4-methoxyphenyl)ethanol: The title compound was prepared according to the method described for compound 1-(1-ethyl-6-(3-(methylsulfonyl)phenoxy)-1H-benzo[d]imidazol-2-yl)-2,2,2-trifluoro-1-phenylethanol, employing 4-(1-ethyl-1H-benzo[d]imidazol-6-yl)morpholine (90 mg, 0.389 mmol), 2,2,2-trifluoro-1-(4-methoxyphenyl)ethanone (95 mg, 0.47 mmol) and lithium bis(trimethylsilyl)amide (0.467 mL, 0.47 mmol) to obtain the pure product as a yellow solid compound (33 mg, 19.52% yield) MS (ESI): m/z 436 [M+1]+.

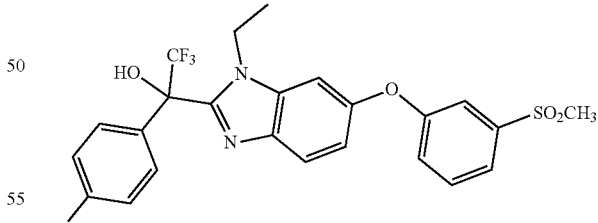

2-(1-Ethyl-6-(3-(methylsulfonyl)phenoxy)-1H-benzo[d]imidazol-2-yl)-2,2,2-trifluoro-1-(4-fluorophenyl)ethanol: The title compound was prepared according to the method A described for compound 1-(1-ethyl-6-(3-(methylsulfonyl)phenoxy)-1H-benzo[d]imidazol-2-yl)-2,2,2-trifluoro-1-phenylethanol, employing 1-ethyl-6-(3-(methylsulfonyl)phenoxy)-1H-benzo[d]imidazole (316 mg, 1.00 mmol) and 2,2,2-trifluoro-1-(4-fluorophenyl)ethanone (231 mg, 1.20 mmol,) and lithium bis(trimethylsilyl) amide (402 mg, 2.40 mmol) to obtain the pure product as a white solid. (295 mg, 58.01% yield) MS (ESI): m/z 509 [M+1]⁺.

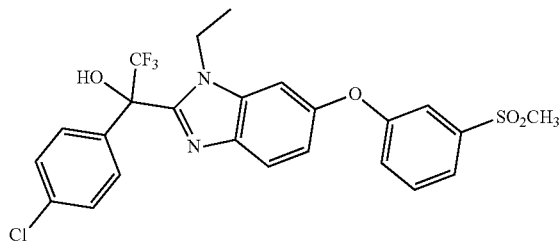 [SMILES: CCn1c(C(O)(c2ccc(Cl)cc2)C(F)(F)F)nc2ccc(Oc3cccc(S(C)(=O)=O)c3)cc21]

1-(4-Chlorophenyl)-1-(1-ethyl-6-(3-(methylsulfonyl)phenoxy)-1H-benzo[d]imidazol-2-yl)-2,2,2-trifluoroethanol:
The title compound was prepared according to the method described for compound 1-(1-ethyl-6-(3-(methylsulfonyl)phenoxy)-1H-benzo[d]imidazol-2-yl)-2,2,2-trifluoro-1-phenylethanol, employing 1-ethyl-6-(3-(methylsulfonyl)phenoxy)-1H-benzo[d]imidazole (316 mg, 1.00 mmol) and 1-(4-chlorophenyl)-2,2,2-trifluoroethanone (250 mg, 1.20 mmol)) and lithium bis(trimethylsilyl) amide (402 mg, 2.40 mmol) to obtain the pure product 11f as a white solid compound (308 mg, 58.66% yield) MS (ESI): m/z 526 [M+1]⁺.

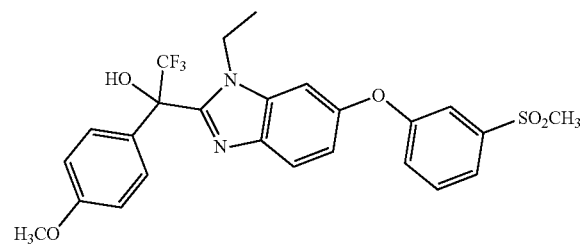 [SMILES: CCn1c(C(O)(c2ccc(OC)cc2)C(F)(F)F)nc2ccc(Oc3cccc(S(C)(=O)=O)c3)cc21]

1-(1-ethyl-6-(3-(methylsulfonyl)phenoxy)-1H-benzo[d]imidazol-2-yl)-2,2,2-trifluoro-1-(4-methoxyphenyl)ethanol:
The title compound was prepared according to the method A described for compound 1-(1-ethyl-6-(3-(methylsulfonyl)phenoxy)-1H-benzo[d]imidazol-2-yl)-2,2,2-trifluoro-1-phenylethanol, employing 1-ethyl-6-(3-(methylsulfonyl)phenoxy)-1H-benzo[d]imidazole (316 mg, 1.00 mmol) and 2,2,2-trifluoro-1-(4-methoxyphenyl)ethanone (245 mg, 1.20 mmol)) and lithium bis(trimethylsilyl) amide (402 mg, 2.40 mmol) to obtain to obtain the pure compound (384 mg, 73.84% yield) as a pale yellow solid. MS (ESI): m/z 521 [M+1]⁺.

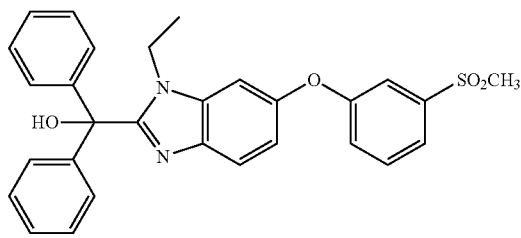 [SMILES: CCn1c(C(O)(c2ccccc2)c2ccccc2)nc2ccc(Oc3cccc(S(C)(=O)=O)c3)cc21]

(1-Ethyl-6-(3-(methylsulfonyl)phenoxy)-1H-benzo[d]imidazol-2-yl)diphenylmethanol: The title compound was prepared according to the method A described for compound 1-(1-ethyl-6-(3-(methylsulfonyl)phenoxy)-1H-benzo[d]imidazol-2-yl)-2,2,2-trifluoro-1-phenylethanol, employing 1-ethyl-6-(3-(methylsulfonyl)phenoxy)-1H-benzo[d]imidazole (180 mg, 0.57 mmol), benzophenone (130 mg, 0.71 mmol) and lithium bis(trimethylsilyl)amide (114 mg, 0.68 mmol) to obtain the pure product as a yellow solid compound (230 mg, 80.98% yield) MS (ESI): m/z 499 [M+1]⁺.

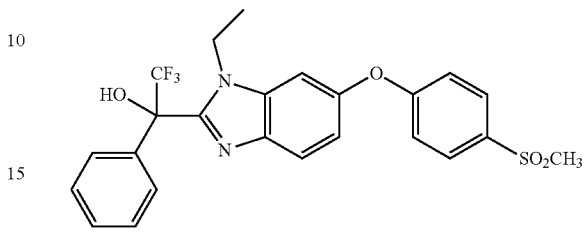

1-(1-ethyl-6-(4-(methylsulfonyl)phenoxy)-1H-benzo[d]imidazol-2-yl)-2,2,2-trifluoro-1-phenylethanol: The title compound was prepared according to the method described for compound 1-(1-ethyl-6-(3-(methylsulfonyl)phenoxy)-1H-benzo[d]imidazol-2-yl)-2,2,2-trifluoro-1-phenylethanol, employing 1-ethyl-6-(4-(methylsulfonyl)phenoxy)-1H-benzo[d]imidazole (306 mg, 0.97 mmol) and 2,2,2-trifluoro-1-phenylethanone (202 mg, 1.16 mmol) and lithium bis(trimethylsilyl)amide (388 mg, 2.32 mmol) to obtain to obtain the pure compound (345 mg, 72.93% yield) as a pale yellow solid. MS (ESI): m/z 491 [M+1]⁺.

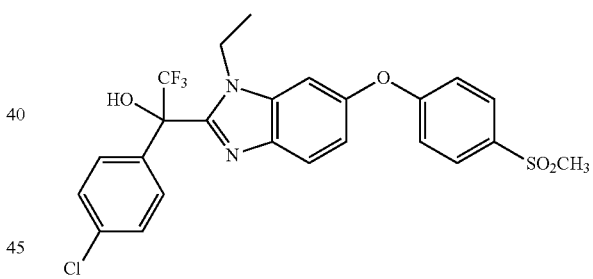

1-(4-chlorophenyl)-1-(1-ethyl-6-(4-(methylsulfonyl)phenoxy)-1H-benzo[d]imidazol-2-yl)-2,2,2-trifluoroethanol:
The title compound was prepared according to the method described for compound 1-(1-ethyl-6-(3-(methylsulfonyl)phenoxy)-1H-benzo[d]imidazol-2-yl)-2,2,2-trifluoro-1-phenylethanol, employing 1-ethyl-6-(4-(methylsulfonyl)phenoxy)-1H-benzo[d]imidazole (300 mg, 0.95 mmol) and 1-(4-chlorophenyl)-2,2,2-trifluoroethanone (236 mg, 1.13 mmol) and Lithium bis(trimethylsilyl)amide (380 mg, 2.27 mmol) to obtain to obtain the pure compound (351 mg, 70.42% yield) as a pale yellow solid. MS (ESI): m/z 526 [M+1]⁺.

| No. | Structure | IUPAC Nomenclature | Mass Spectra LC-MS (ESI): m/z |
|---|---|---|---|
| A44 | 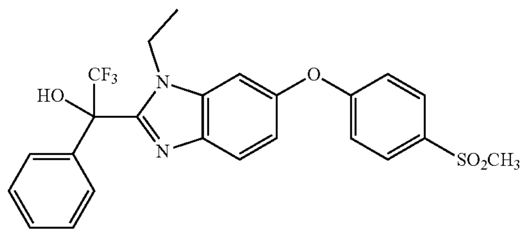 [SMILES: CCn1c(C(O)(c2ccccc2)C(F)(F)F)nc2ccc(Oc3ccc(S(C)(=O)=O)cc3)cc21] | 1-(1-Ethyl-6-(4-(methylsulfonyl)phenoxy)-1H-benzo[d]imidazol-2-yl)-2,2,2-trifluoro-1-phenylethanol | 491 [M + 1]+ |
| A46 | 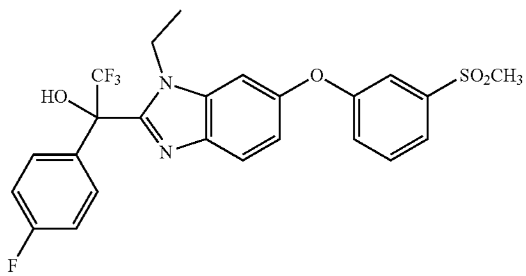 [SMILES: CCn1c(C(O)(c2ccc(F)cc2)C(F)(F)F)nc2ccc(Oc3cccc(S(C)(=O)=O)c3)cc21] | 1-(1-Ethyl-6-(3-(methylsulfonyl)phenoxy)-1H-benzo[d]imidazol-2-yl)-2,2,2-trifluoro-1-(4-fluorophenyl)ethanol | 509 [M + 1]+ |
| A47 | 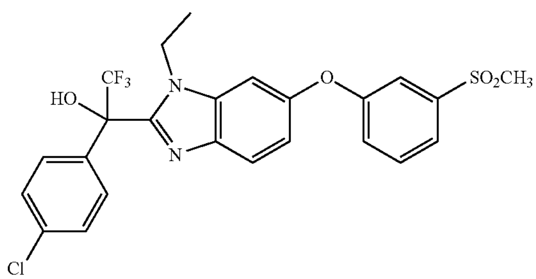 [SMILES: CCn1c(C(O)(c2ccc(Cl)cc2)C(F)(F)F)nc2ccc(Oc3cccc(S(C)(=O)=O)c3)cc21] | 1-(4-Chlorophenyl)-1-(1-ethyl-6-(3-(methylsulfonyl)phenoxy)-1H-benzo[d]imidazol-2-yl)-2,2,2-trifluoroethanol | 525 [M]+ |
| A48 | 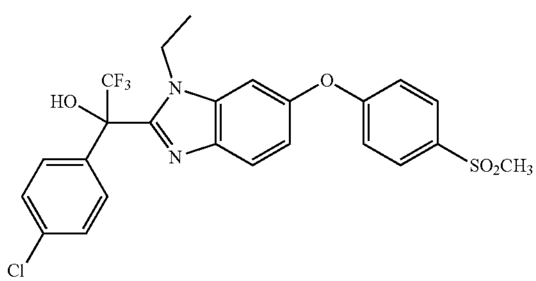 [SMILES: CCn1c(C(O)(c2ccc(Cl)cc2)C(F)(F)F)nc2ccc(Oc3ccc(S(C)(=O)=O)cc3)cc21] | 1-(4-Chlorophenyl)-1-(1-ethyl-6-(4-(methylsulfonyl)phenoxy)-1H-benzo[d]imidazol-2-yl)-2,2,2-trifluoroethanol | 525 [M]+ |
| A49 | 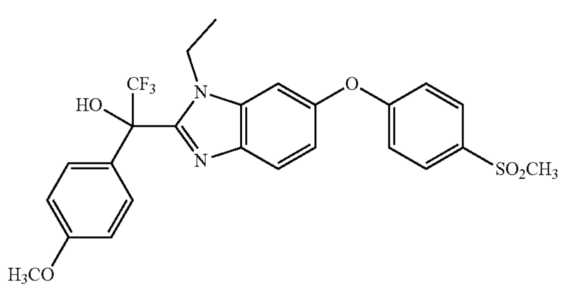 [SMILES: CCn1c(C(O)(c2ccc(OC)cc2)C(F)(F)F)nc2ccc(Oc3ccc(S(C)(=O)=O)cc3)cc21] | 1-(1-Ethyl-6-(4-(methylsulfonyl)phenoxy)-1H-benzo[d]imidazol-2-yl)-2,2,2-trifluoro-1-(4-methoxyphenyl)ethanol | 521 [M + 1]+ |

-continued

| No. | Structure | IUPAC Nomenclature | Mass Spectra LC-MS (ESI): m/z |
|---|---|---|---|
| A46 | 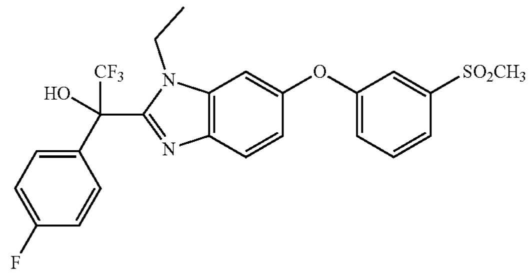 [SMILES: CCn1c(C(O)(c2ccc(F)cc2)C(F)(F)F)nc2ccc(Oc3cccc(S(C)(=O)=O)c3)cc21] | 1-(1-Ethyl-6-(3-(methylsulfonyl)phenoxy)-1H-benzo[d]imidazol-2-yl)-2,2,2-trifluoro-1-(4-fluorophenyl)ethanol | 509 [M + 1]+ |
| A47 | 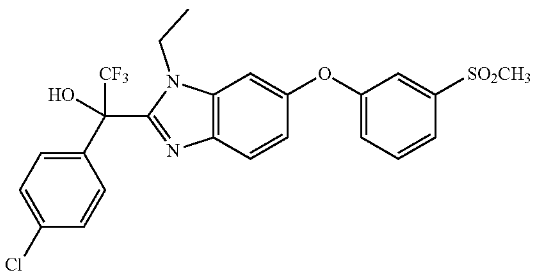 [SMILES: CCn1c(C(O)(c2ccc(Cl)cc2)C(F)(F)F)nc2ccc(Oc3cccc(S(C)(=O)=O)c3)cc21] | 1-(4-Chlorophenyl)-1-(1-ethyl-6-(3-(methylsulfonyl)phenoxy)-1H-benzo[d]imidazol-2-yl)-2,2,2-trifluoroethanol | 525 [M]+ |
| A50 | 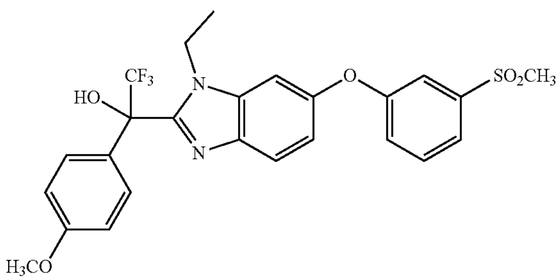 [SMILES: CCn1c(C(O)(c2ccc(OC)cc2)C(F)(F)F)nc2ccc(Oc3cccc(S(C)(=O)=O)c3)cc21] | 1-(1-Ethyl-6-(3-(methylsulfonyl)phenoxy)-1H-benzo[d]imidazol-2-yl)-2,2,2-trifluoro-1-(4-methoxyphenyl)ethanol | 521 [M + 1]+ |
| A51 | 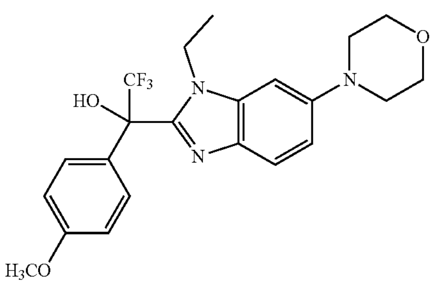 [SMILES: CCn1c(C(O)(c2ccc(OC)cc2)C(F)(F)F)nc2ccc(N3CCOCC3)cc21] | 1-(1-Ethyl-6-morpholino-1H-benzo[d]imidazol-2-yl)-2,2,2-trifluoro-1-(4-methoxyphenyl)ethanol | 436 [M + 1]+ |
| A52 | 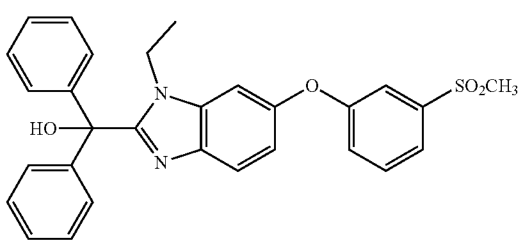 [SMILES: CCn1c(C(O)(c2ccccc2)c2ccccc2)nc2ccc(Oc3cccc(S(C)(=O)=O)c3)cc21] | (1-Ethyl-6-(3-(methylsulfonyl)phenoxy)-1H-benzo[d]imidazol-2-yl)diphenylmethanol | 499 [M + 1]+ |

| No. | Structure | IUPAC Nomenclature | Mass Spectra LC-MS (ESI): m/z |
|---|---|---|---|
| A53 | 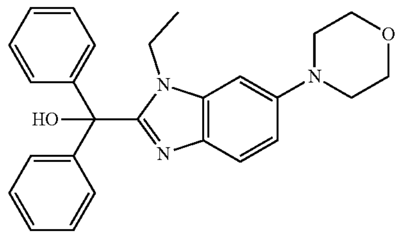 [SMILES: CCn1c(C(O)(c2ccccc2)c2ccccc2)nc2ccc(N3CCOCC3)cc21] | (1-Ethyl-6-morpholino-1H-benzo[d]imidazol-2-yl)diphenylmethanol | 414 [M + 1]$^+$ |

TABLE 1

SMEM 2.0 Formulation (all concentrations in μM)

| Materials | Concentration | Material | Concentration |
|---|---|---|---|
| Glucose | 5500 | Vitamins | |
| Amino Acids | | Biotin | 0.82 |
| Alanine | 510 | Choline | 21.49 |
| Arginine | 64 | Folate | 2.27 |
| Asparagine | 41 | myo-Inositol | 194.27 |
| Aspartate | 6 | Niacinamide | 8.19 |
| Citrulline | 55 | p-Aminobenzoate | 7.29 |
| Cystine | 65 | Pantothenate | 1.05 |
| Glutamate | 98 | Pyridoxine | 4.86 |
| Glutamine | 650 | Riboflavin | 0.53 |
| Glycine | 330 | Thiamine | 2.96 |
| Histidine | 120 | Vitamin B-12 | 0.0037 |
| Isoleucine | 140 | Additional polar metabolites | |
| Leucine | 170 | 2-hydroxybutyrate | 50 |
| Lysine | 220 | 3-hydroxybutyrate | 50 |
| Methionine | 30 | 4-hydroxyproline | 20 |
| Ornithine HCl | 80 | Acetate | 100 |
| Phenylalanine | 68 | Acetone | 60 |
| Proline | 360 | Acetylglycine | 90 |
| Serine | 140 | Alpha-aminobutyrate | 20 |
| Taurine | 130 | Betaine | 70 |
| Threonine | 240 | Carnitine | 40 |
| Tryptophan | 78 | Citrate | 130 |
| Tyrosine | 74 | Creatine | 40 |
| Valine | 230 | Creatinine | 75 |
| Salts | | Formate | 50 |
| CaCl2 | 1000 | Fructose | 40 |
| KCl | 4100 | Galactose | 60 |
| MgCl2 | 480 | Glutathione | 25 |
| MgSO4 | 350 | Glycerol | 120 |
| NaCl | 105000 | Hypoxanthine | 10 |
| NaHCO3 | 26200 | Lactate | 500 |
| NaH2PO4•H2O | 1010 | Malonate | 10 |
| Ca(NO3)2•4H2O | 40 | Pyruvate | 100 |
| NH4Cl | 40 | Succinate | 20 |
| CuSO4•5H2O | 0.0052 | Urea | 5000 |
| FeSO4•7H2O | 0.0015 | Uric acid | 350 |
| ZnSO4•7H2O | 0.0015 | | |
| Other | | | |
| Phenol red | 14 | | |

TABLE 2

| Metabolite | Log2 FC (VY/Veh) | Log10(FDR) |
|---|---|---|
| 2-aminobutyrate | −0.516553004 | 1.522754201 |
| 3-hydroxybutryate | −1.00099771 | 0.911171175 |
| 3-phosphoglycerate | −0.580152855 | 0.898512865 |

TABLE 2-continued

| Metabolite | Log2 FC (VY/Veh) | Log10(FDR) |
|---|---|---|
| 4-hydroxyproline | −0.725002399 | 1.278547532 |
| acetyl-aspartate | −0.757490553 | 1.282381508 |
| acetyl-carnitine | −0.544897859 | 0.813353075 |
| acetyl-glycine | −1.037080441 | 1.603749149 |
| acetyl-putrescine | −1.423121544 | 1.766382627 |
| adenine | 1.002905853 | 1.546469799 |
| adenosine | 1.879224904 | 1.663161068 |
| ADP | −1.451677879 | 1.285309267 |
| aketoglutarate | 0.919163653 | 1.262512578 |
| alanine | −0.673889537 | 2.657962952 |
| AMP | −0.655511702 | 0.393160283 |
| arginine | 0.722944623 | 1.213412503 |
| arginosuccinate | −0.174104243 | 0.172326021 |
| asparagine | −1.225227883 | 1.959025839 |
| aspartate | 0.009996063 | 0.022142038 |
| ATP | −2.025796069 | 0.680376177 |
| betaine | −0.473866341 | 1.46560948 |
| carbamoyl-asp | −0.787031927 | 1.122428165 |
| carnitine | −0.676820395 | 1.131149479 |
| CDP | −1.642481741 | 0.871059188 |
| CDP-choline | −2.603092075 | 1.602709197 |
| CDP-ethanolamine | −1.552184579 | 1.770696821 |
| choline | −0.530356596 | 0.703488716 |
| cis-aconitate | −0.224684845 | 0.283238018 |
| citrate | −0.113395569 | 0.290131279 |
| citrulline | −0.393711573 | 1.259586081 |
| CMP | −0.81994789 | 0.427968208 |
| creatine | −0.532131363 | 0.977108751 |
| creatinine | 0.018688869 | 0.042941965 |
| cystathionine | −1.232418624 | 1.14707421 |
| cystine | −0.483724693 | 0.176181066 |
| cytidine | 1.244426861 | 2.47247476 |
| cytosine | 1.231919419 | 2.501380332 |
| DHAP/G3P | −2.0289327 | 1.319207101 |
| ethanolamine-P | −1.36436005 | 1.273116992 |
| FBP | −1.709884561 | 0.964483612 |
| GDP | −2.599350531 | 1.185221897 |
| glucose-6-P | 0.036913143 | 0.042735253 |
| glucose/hexose | 0.990763773 | 0.993526171 |
| glutamate | −0.542927225 | 1.620050357 |
| glutamine | 0.092025373 | 0.177936654 |
| glycerol | 0.107870817 | 0.157549003 |
| glycerol-3-P | −0.848678106 | 1.628444537 |
| glycine | −0.403422516 | 1.035276377 |
| GMP | −1.275434573 | 1.236429764 |
| GSH | −0.690339599 | 0.701606503 |
| GSSG | 0.209353771 | 0.123854786 |
| guanine | 1.968560568 | 1.625321816 |
| guanosine | 3.355927811 | 1.677369058 |
| histidine | −0.423782717 | 0.935910509 |
| hypoxanthine | 0.354788155 | 0.406096236 |
| IMP | 1.066923015 | 0.93984291 |
| isoleucine | −1.48307935 | 2.001681837 |
| lactate | −1.76093763 | 1.850862916 |
| leucine | −0.63606589 | 1.454229262 |
| lysine | −1.025510347 | 1.520665385 |
| malate | 0.023896918 | 0.034037325 |

TABLE 2-continued

| Metabolite | Log2 FC (VY/Veh) | Log10(FDR) |
|---|---|---|
| malonate | 0.125351543 | 0.119467504 |
| methionine | −1.631109594 | 2.532787221 |
| methyl-lysine | −1.395840325 | 2.504601059 |
| myo-inositol | −0.430688866 | 0.786430828 |
| niacin/nicotinate | 1.977109082 | 1.481742958 |
| nicotinamide | 0.125374841 | 0.119651393 |
| nicotinamide N-oxide | 4.80846869 | 1.552292304 |
| ornithine | −0.751609609 | 0.890518634 |
| pantothenate | −0.61811587 | 0.626634757 |
| PEP | −1.207035778 | 1.560404487 |
| phenylalanine | −0.509115619 | 1.324323793 |
| phosphocholine | −0.792444035 | 1.540118978 |
| phosphocreatine | 0.324023569 | 0.208333414 |
| proline | −0.402412257 | 2.292639088 |
| pyridoxine | 0.380756907 | 0.154088841 |
| pyruvate | −0.803677056 | 0.43783138 |
| riboflavin | −2.119500694 | 1.630976529 |
| ribose | −0.50263879 | 1.053536279 |
| ribose-P | 0.263403846 | 0.30465532 |
| SAH | −0.353180744 | 0.589081797 |
| SAM | −1.159905849 | 1.424879269 |
| sedoheptulose-P | −0.258442333 | 0.14403213 |
| serine | 1.090150708 | 0.930550522 |
| succinate | −1.793439331 | 1.798544434 |
| succinyladenosine | −0.873773357 | 0.966783354 |
| succinylcysteine | −0.956140296 | 1.838644939 |
| succinylglutathione | −1.861195418 | 1.085790365 |
| taurine | 0.115949169 | 0.159868862 |
| threonine | −0.91861989 | 2.373029421 |
| thymidine | 2.327882232 | 1.562648808 |
| tryptophan | −0.204540727 | 0.130015122 |
| tyrosine | −0.843220906 | 2.366254999 |
| UDP | −1.494658876 | 0.894932279 |
| UDP-GlcNAc | −0.800656705 | 1.214482768 |
| UMP | −0.402362097 | 0.302441287 |
| urate | −0.628792709 | 0.842261619 |
| UTP | −2.181937613 | 0.665273886 |
| valine | −0.594206575 | 1.313982352 |
| xanthine | −0.828594683 | 0.639440467 |

Enumerated Embodiments

The following exemplary embodiments are provided, the numbering of which is not to be construed as designating levels of importance.

Embodiment 1 provides a compound of Formula (I), or an enantiomer, diastereoisomer, tautomer, salt, and/or solvate thereof:

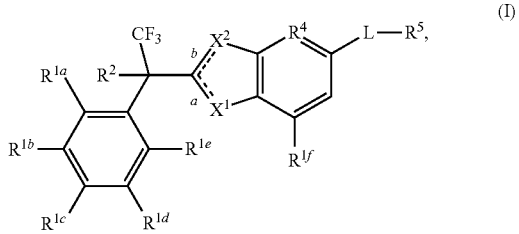

(I)

wherein:
one of the following applies: (a) $X^1$ is N, $X^2$ is N(CH$_2$—$R^3$), bond a is a double bond, and bond b is a single bond; or (b) $X^1$ is N(CH$_2$—$R^3$), $X^2$ is N, bond a is a single bond, and bond b is a double bond;
each occurrence of $R^{1a}$, $R^{1b}$, $R^{1c}$, $R^{1d}$, $R^{1e}$, $R^{1f}$, and $R^{1g}$ is independently selected from the group consisting of: H; $C_1$-$C_6$ alkyl; $C_3$-$C_8$ cycloalkyl; $C_1$-$C_6$ haloalkyl (such as, but not limited to, trifluoromethyl); —OH; $C_1$-$C_6$ alkoxy; halogen; —C≡N; —NR'R'; —C(=O)OR'; —C(=O)NR'R'; —S($C_1$-$C_6$ alkyl); —S(=O)($C_1$-$C_6$ alkyl); —S(=O)$_2$($C_1$-$C_6$ alkyl); —SO$_2$NR'R'; —C(=NR')—NR'R'; —NO$_2$; and $C_1$-$C_6$ alkyl optionally substituted with at least one selected from halogen, —OH, $C_1$-$C_6$ alkoxy, and —NR'R'; wherein each occurrence of R' is independently H, $C_1$-$C_6$ alkyl, or $C_3$-$C_8$ cycloalkyl;
$R^2$ is selected from the group consisting of —OH, —CN, and —SO$_2$($C_1$-$C_6$ alkyl);
$R^3$ is selected from the group consisting of H, $C_1$-$C_6$ alkyl, $C_3$-$C_8$ cycloalkyl, —OH, $C_1$-$C_6$ haloalkyl, $C_1$-$C_6$ alkoxy, and $C_1$-$C_6$ haloalkoxy;
$R^4$ is selected from the group consisting of $CR^{1g}$ and N;
L is selected from the group consisting of —O—*, —C(=O)NR—*, and —NR$^c$—(C=O)—NR—*, wherein each occurrence of R and $R^c$ is independently selected from the group consisting of H, $C_1$-$C_6$ alkyl, and $C_3$-$C_8$ cycloalkyl, and wherein the bond marked as * is to $R^5$;
$R^5$ is selected from the group consisting of $C_1$-$C_{10}$ alkyl, phenyl, and heteroaryl, any of each optionally independently substituted with at least one substituent independently selected from the group consisting of: H; $C_1$-$C_6$ alkyl; $C_3$-$C_8$ cycloalkyl; $C_1$-$C_6$ haloalkyl (such as, but not limited to, trifluoromethyl); —OH; optionally substituted phenyl; optionally substituted heterocyclyl; optionally substituted heteroaryl; $C_1$-$C_6$ alkoxy; heterocyclyl; halogen; —C≡N; —N"R"; —C(=O)OR"; —C(=O)N"R"; —S($C_1$-$C_6$ alkyl); —S(=O)($C_1$-$C_6$ alkyl); —S(=O)$_2$($C_1$-$C_6$ alkyl); —SO$_2$N"R"; —C(=NR")—N"R"; —NO$_2$; and $C_1$-$C_6$ alkyl optionally substituted with at least one selected from halogen, —OH, $C_1$-$C_6$ alkoxy, and —N"R"; wherein each occurrence of R" is independently H, $C_1$-$C_6$ alkyl, or $C_3$-$C_8$ cycloalkyl;
or -L-$R^5$ is optionally substituted heterocyclyl or —C(=O)(optionally substituted heterocyclyl).

Embodiment 2 provides the compound of Embodiment 1, wherein $R^{1c}$ is not H, i.e., $R^{1c}$ is $C_1$-$C_6$ alkyl; $C_3$-$C_8$ cycloalkyl; $C_1$-$C_6$ haloalkyl (such as, but not limited to, trifluoromethyl); —OH; $C_1$-$C_6$ alkoxy; halogen; —C≡N; —NR'R'; —C(=O)OR'; —C(=O)NR'R'; —S($C_1$-$C_6$ alkyl); —S(=O)($C_1$-$C_6$ alkyl); —S(=O)$_2$($C_1$-$C_6$ alkyl); —SO$_2$NR'R'; —C(=NR')—NR'R'; —NO$_2$; or $C_1$-$C_6$ alkyl optionally substituted with at least one selected from halogen, —OH, $C_1$-$C_6$ alkoxy, and —NR'R'; wherein each occurrence of R' is independently H, $C_1$-$C_6$ alkyl, or $C_3$-$C_8$ cycloalkyl.

Embodiment 3 provides the compound of any of Embodiments 1-2, which is a compound of Formula (Ia):

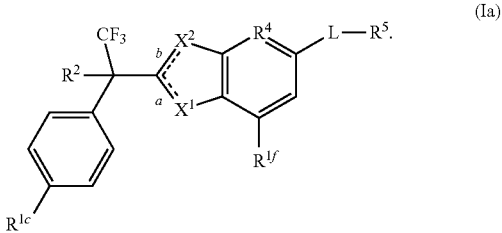

(Ia)

Embodiment 4 provides the compound of any of Embodiments 1-3, which is selected from the group consisting of:

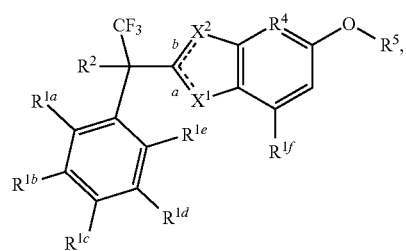
(Ib)
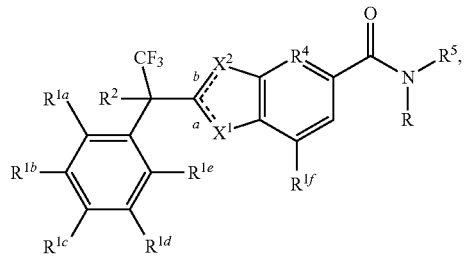
(Ic)
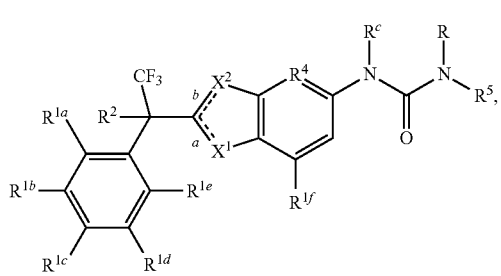
(Id)
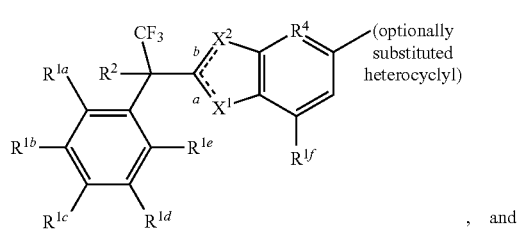
(Ie)
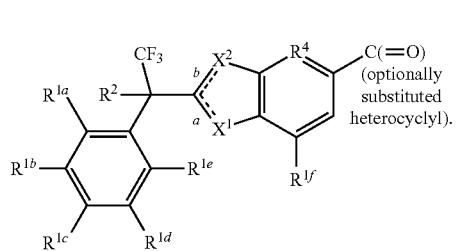
(If)
Embodiment 5 provides the compound of any of Embodiments 1-4, which is selected from the group consisting of:
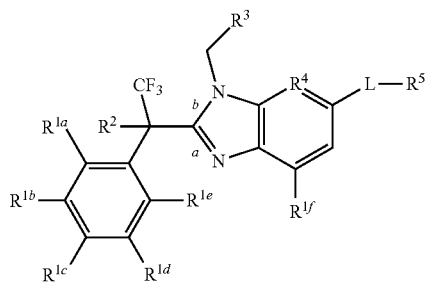
(Ig)
and
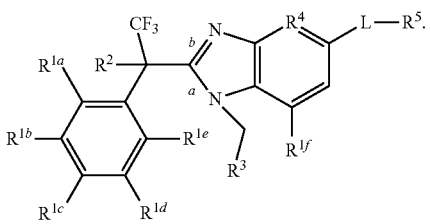
(Ih)
Embodiment 6 provides the compound of any of Embodiments 1-4, which is selected from the group consisting of:
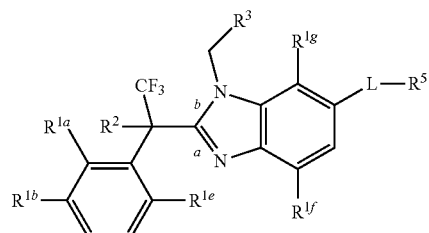
(Ii)
and
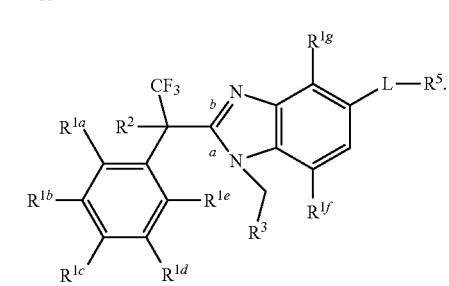
(Ij)
Embodiment 7 provides the compound of any of Embodiments 1-4, which is selected from the group consisting of:
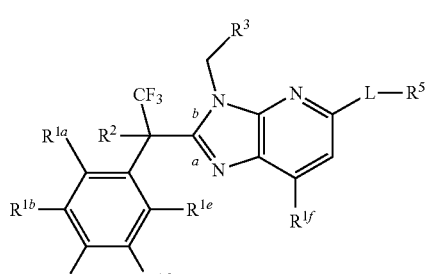
(Ik)
and

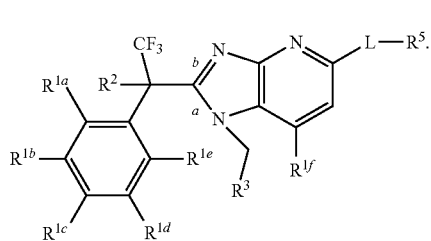
Embodiment 8 provides the compound of any of Embodiments 1-7, which is selected from the group consisting of:
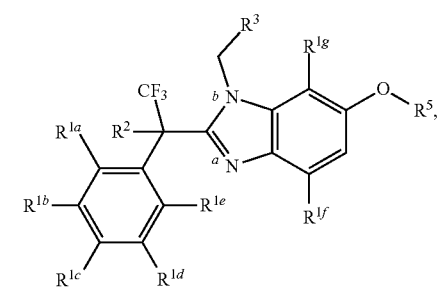
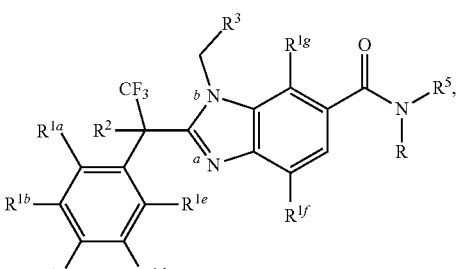
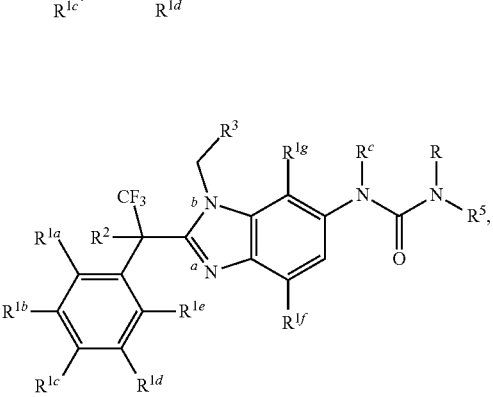
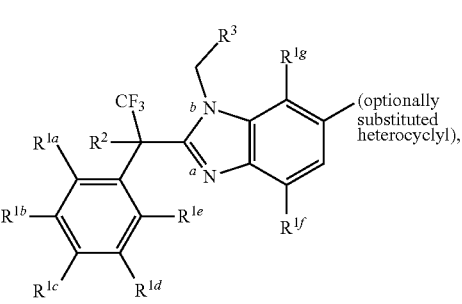
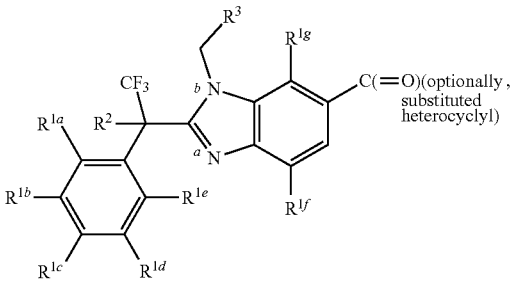
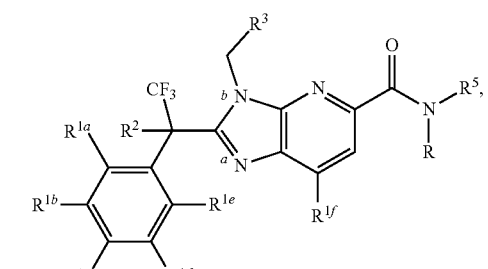
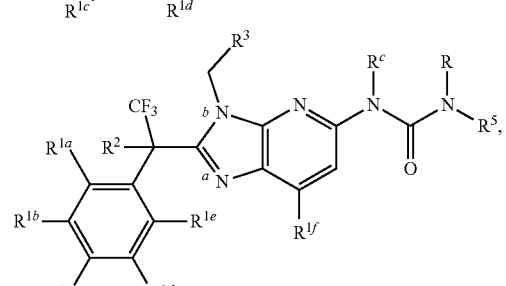
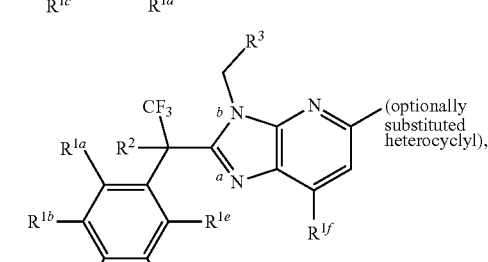
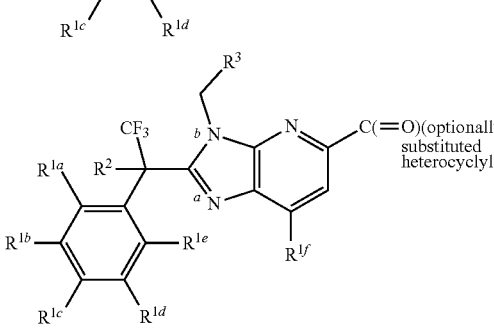

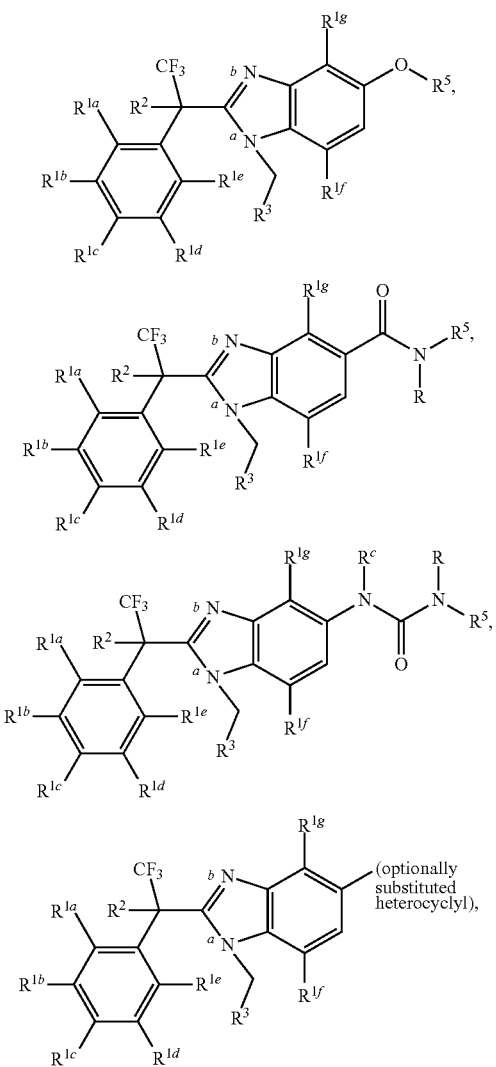
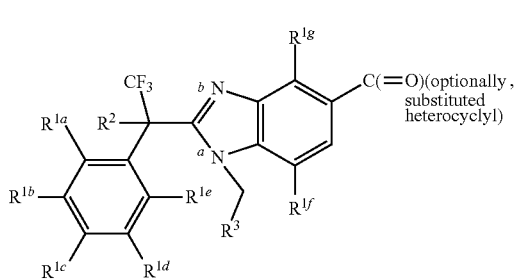
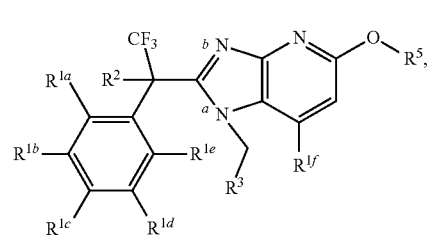
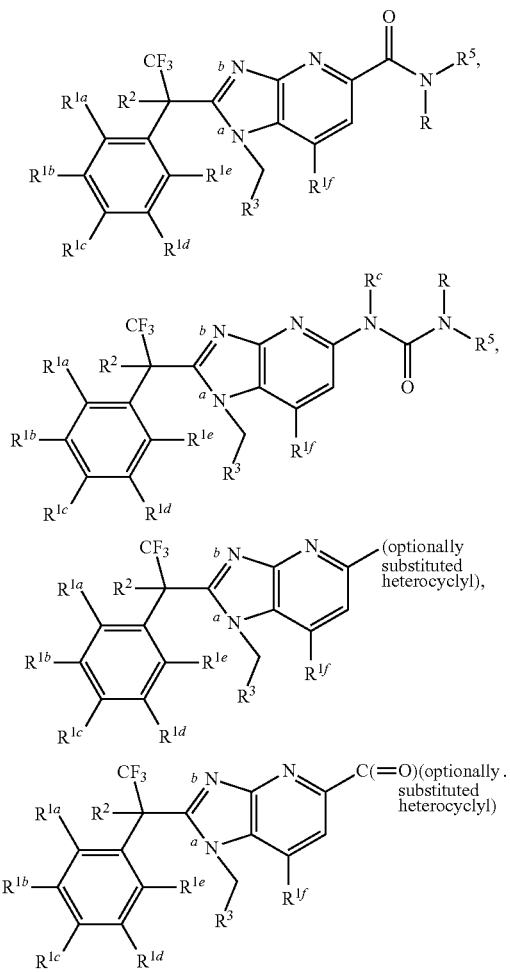
Embodiment 9 provides the compound of any of Embodiments 1-8, which is selected from the group consisting of:
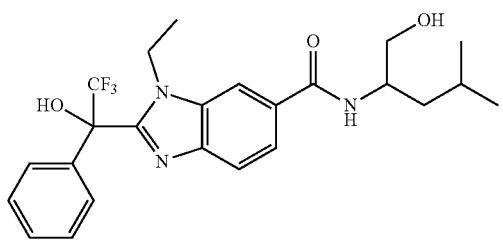
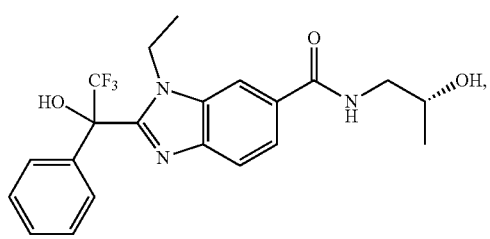

119
-continued
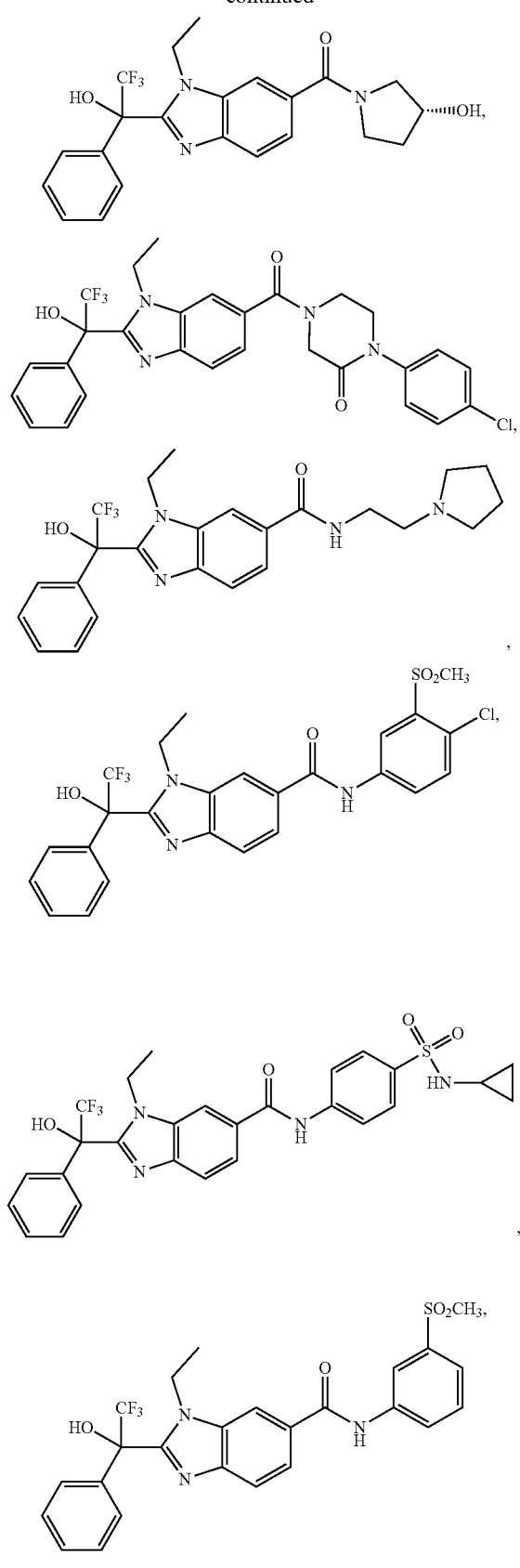
120
-continued
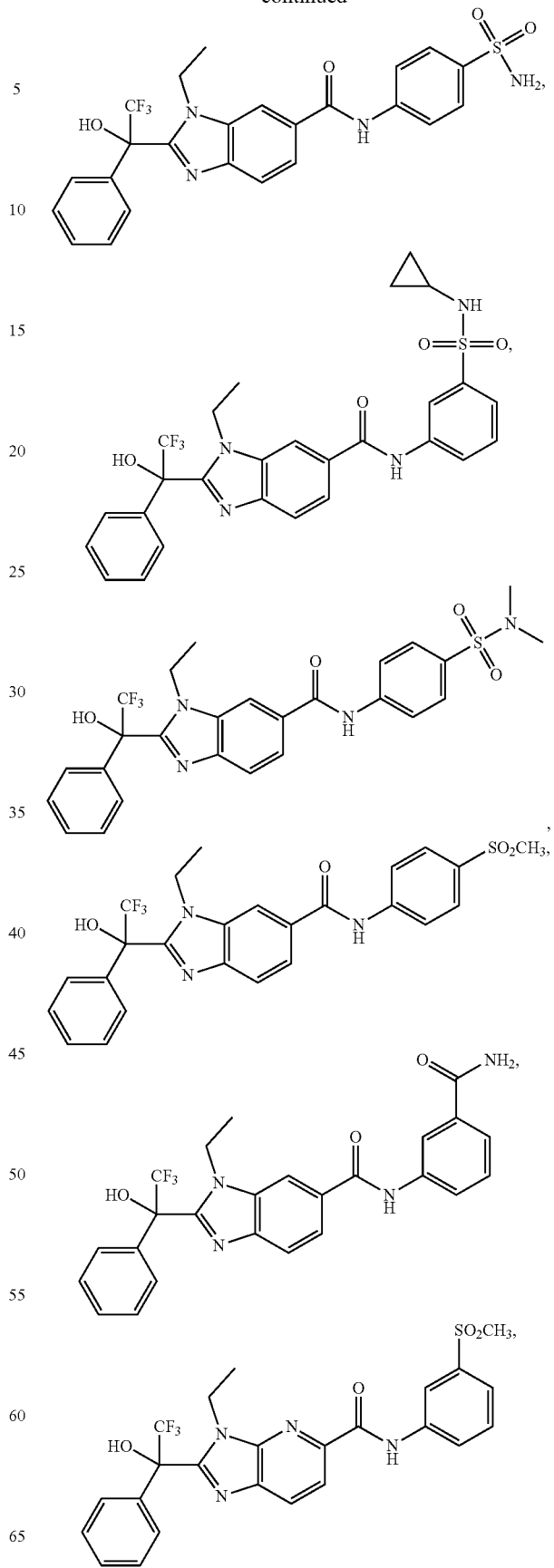

121
-continued
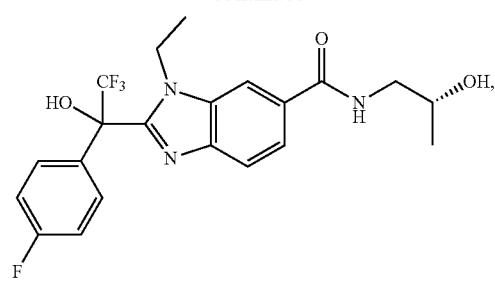
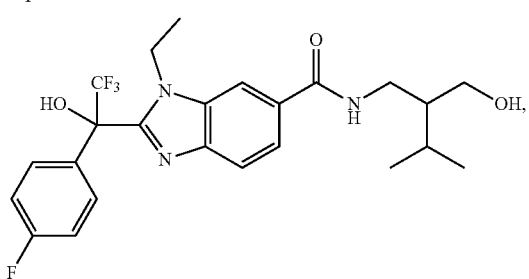
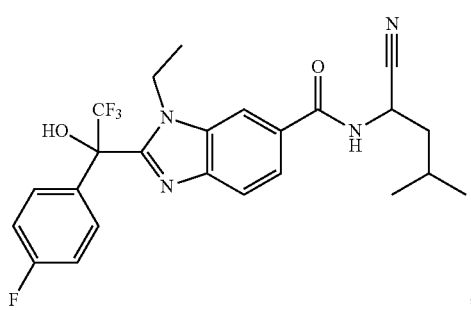
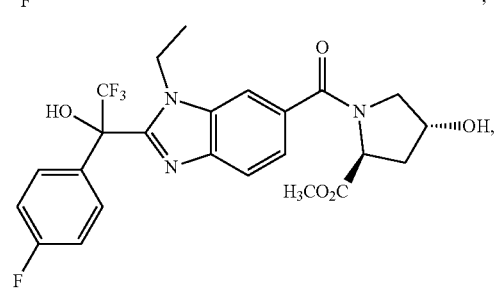
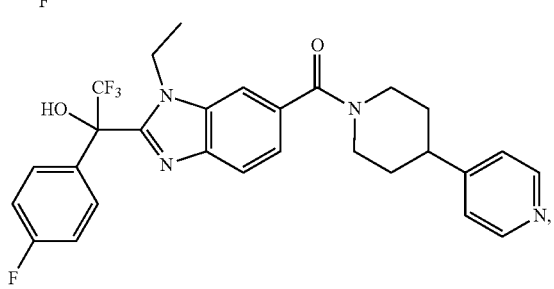
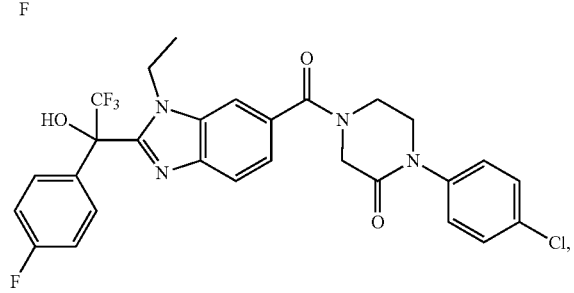
122
-continued
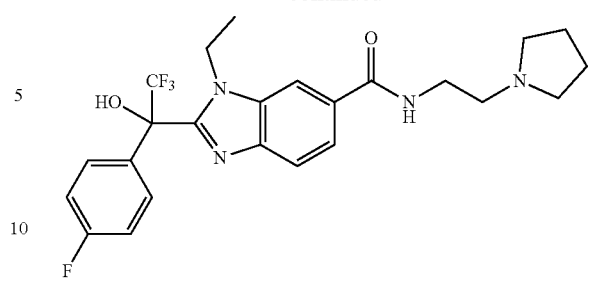
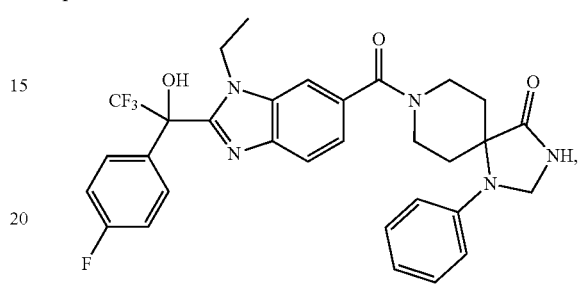
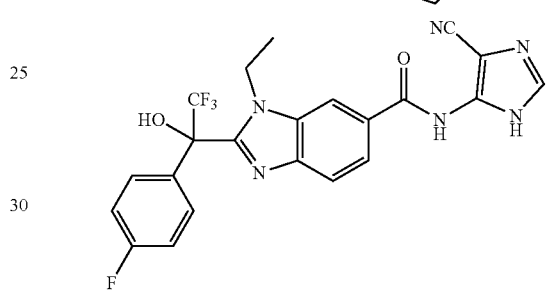
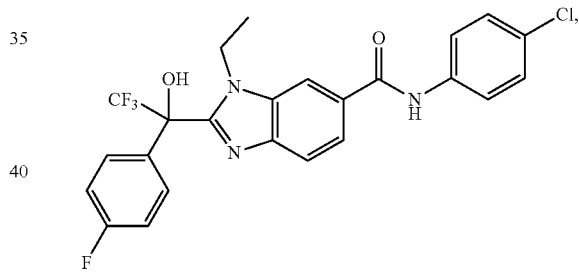
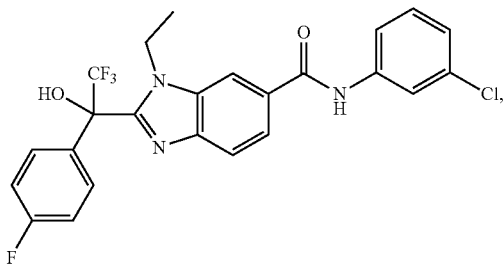
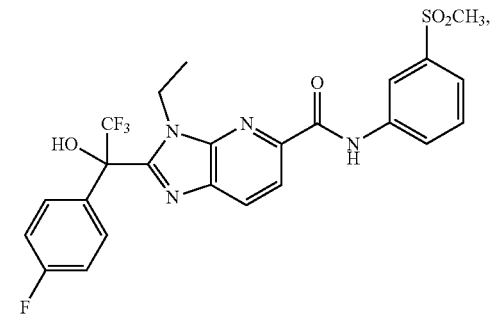

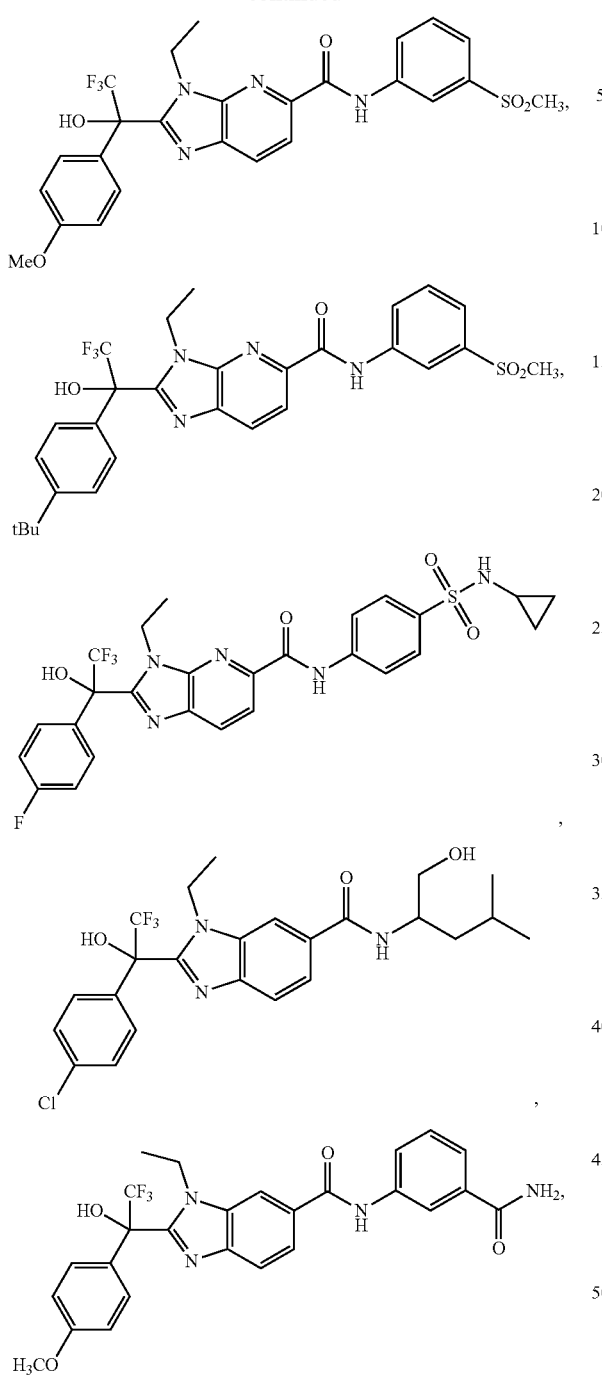
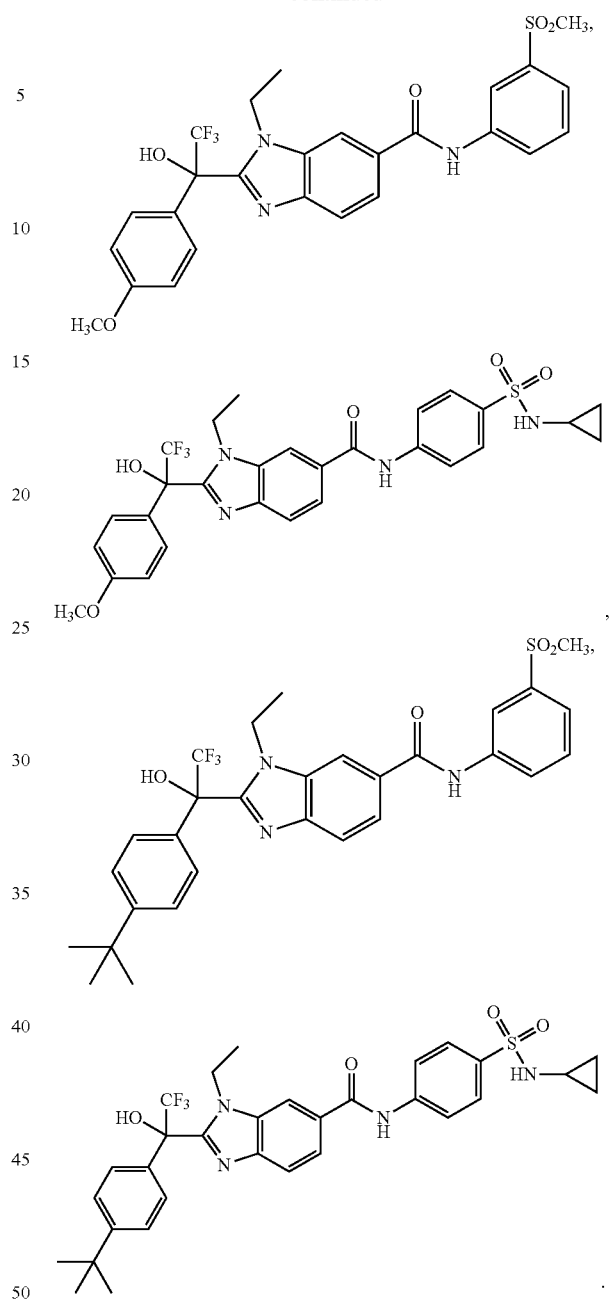
Embodiment 10 provides the compound of any of Embodiments 1-8, which is selected from the group consisting of:
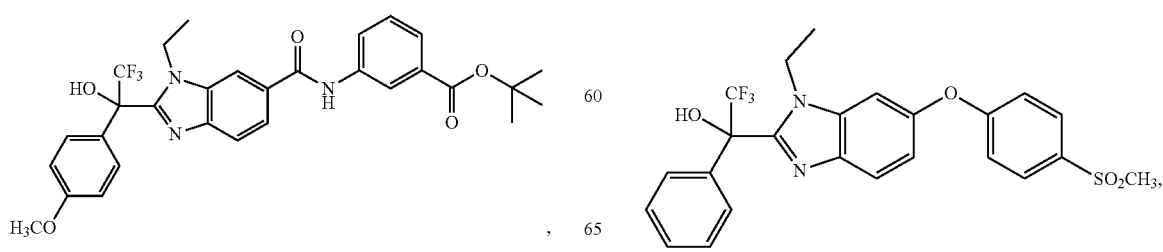

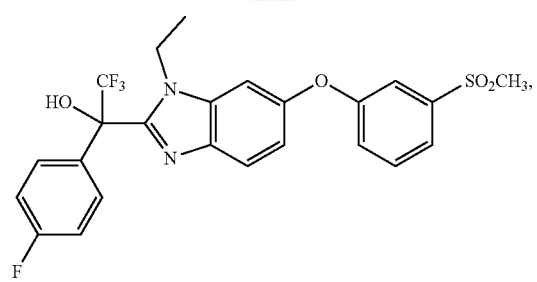
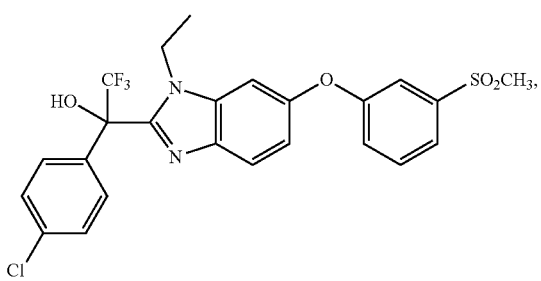
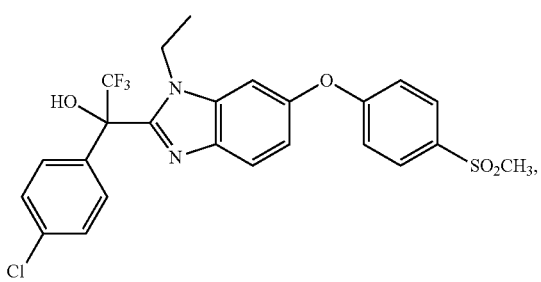
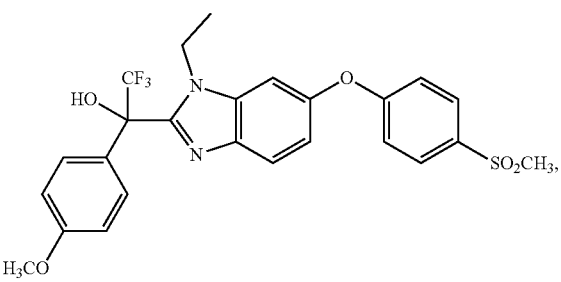
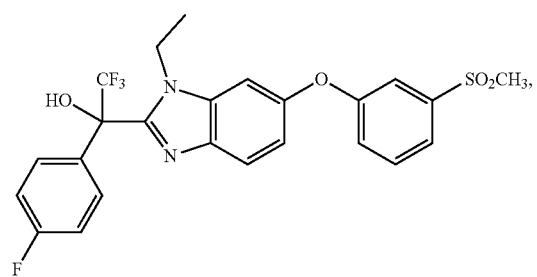
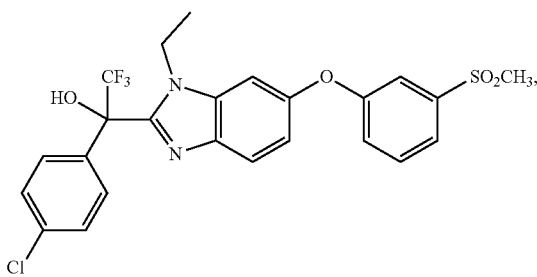
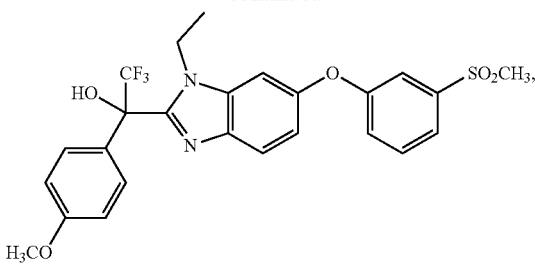
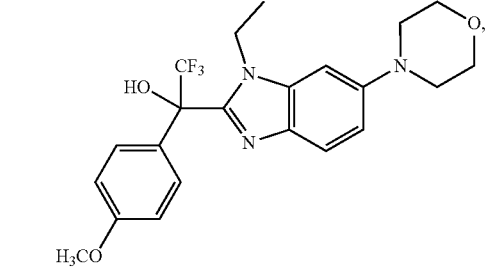
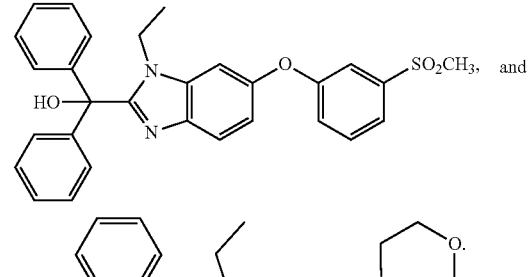
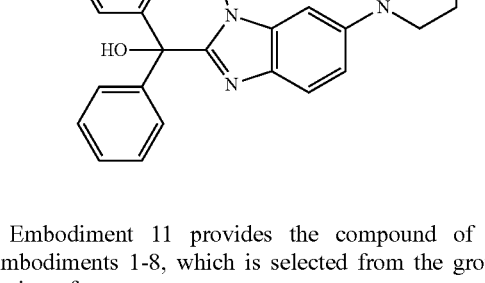
Embodiment 11 provides the compound of any of Embodiments 1-8, which is selected from the group consisting of:
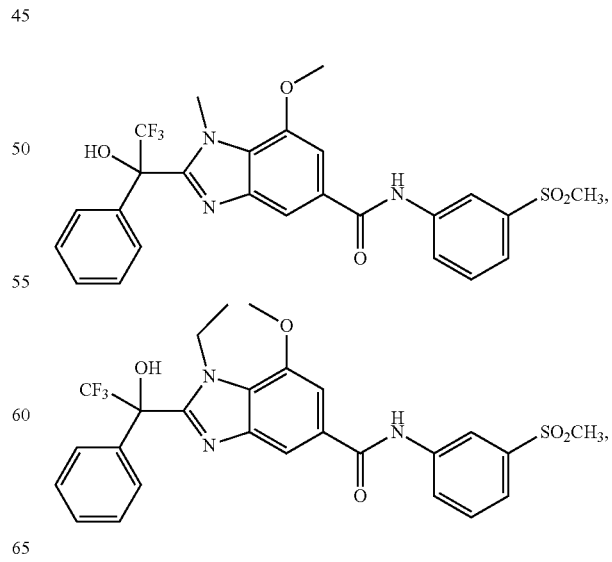

127
-continued
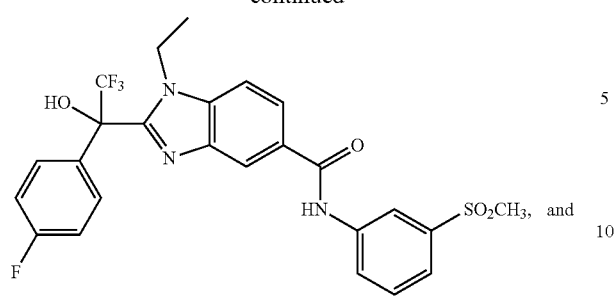
and
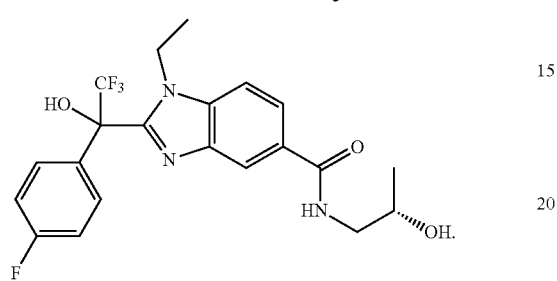
Embodiment 12 provides the compound of any of Embodiments 1-11, wherein L-R⁵ is selected from the group consisting of:
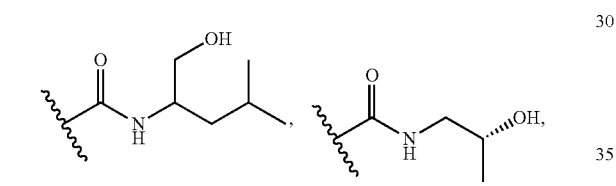
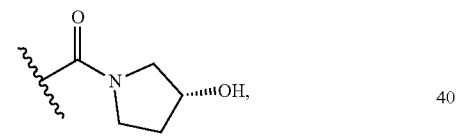
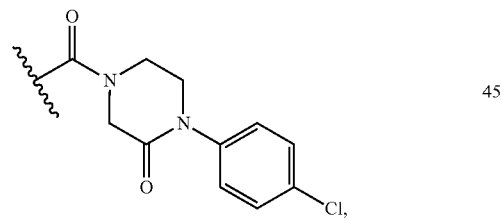
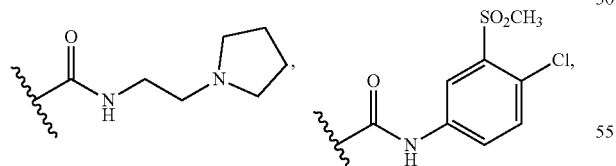
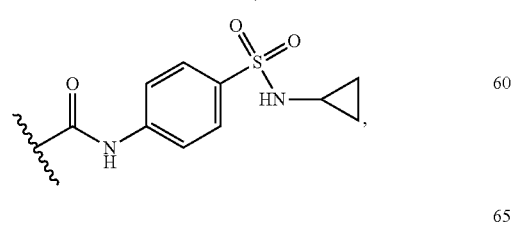
128
-continued
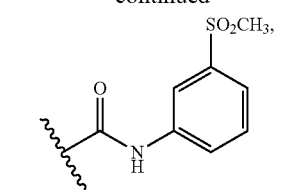
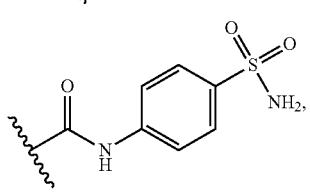
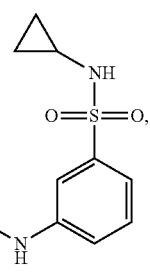
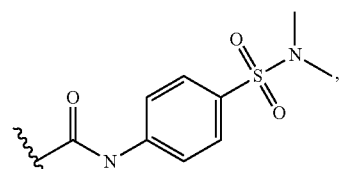
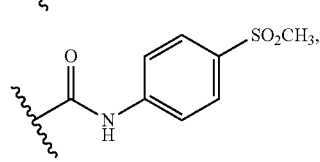
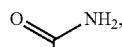
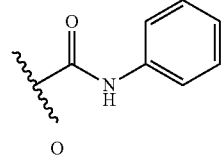
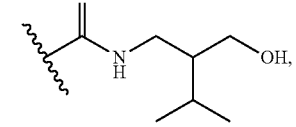
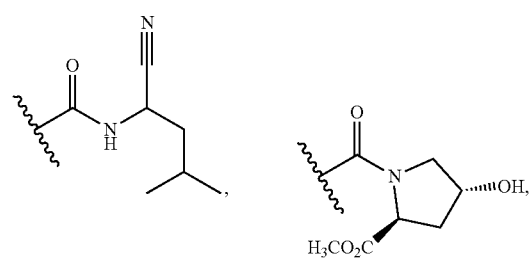

-continued

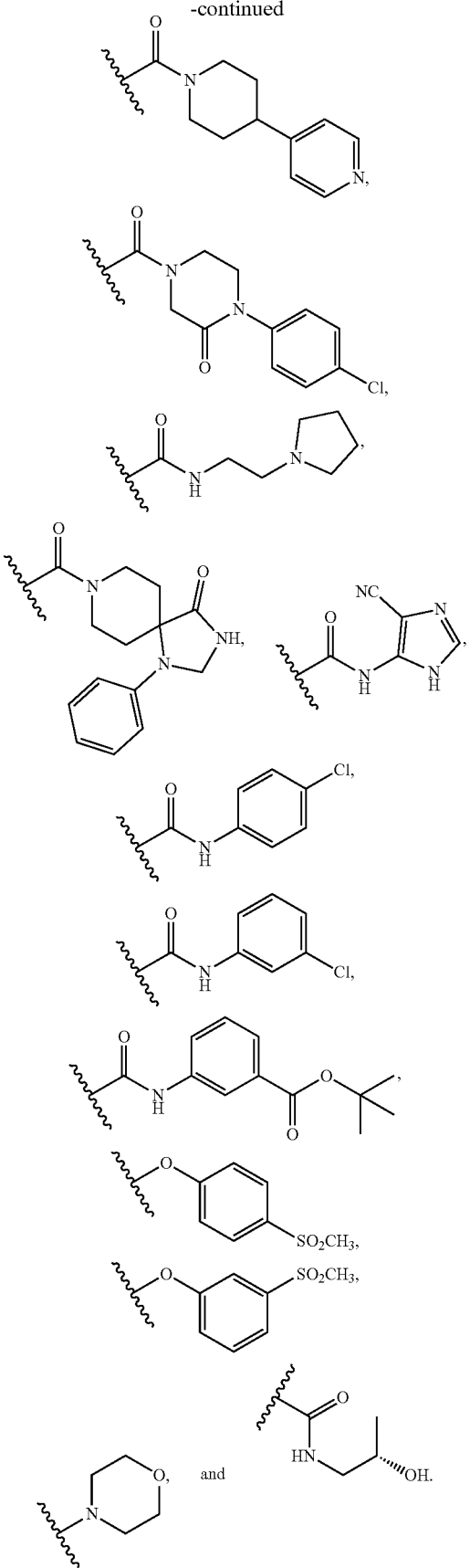

Embodiment 13 provides a method of treating, ameliorating, and/or preventing a disease or disorder that is caused, induced, or characterized by abnormal expression or activity of ACSS2 in a subject, the method comprising administering to the subject a therapeutically effective amount of the compound of any one of Embodiments 1-12.

Embodiment 14 provides a method of reducing the rate of, reversing, and/or preventing conversion of a non-metastatic cancer cell to a metastatic cancer cell, the method comprising contacting the cell with an effective amount of the compound of any one of Embodiments 1-12.

Embodiment 15 provides the method of Embodiment 14, wherein the cell is in vivo in a subject.

Embodiment 16 provides a method of reducing the rate of, reversing, and/or preventing development of a hypoxic region in a cancer in a subject, the method comprising administering to the subject a therapeutically effective amount of the compound of any one of Embodiments 1-12.

Embodiment 17 provides a method of increasing effectiveness of chemotherapy, radiotherapy, and/or immunotherapy administered to a subject suffering from a cancer, the method comprising administering to the subject a therapeutically effective amount of the compound of any one of Embodiments 1-12 and at least one of chemotherapy, radiotherapy, and immunotherapy.

Embodiment 18 provides the method of Embodiment 13, wherein the disease or disorder is cancer.

Embodiment 19 provides the method of any of Embodiments 14-18, wherein the cancer comprises at least one of brain cancer, breast cancer, pancreatic cancer, sarcoma, prostate cancer, colorectal cancer, liver cancer, melanoma, ovarian cancer, or lung cancer.

Embodiment 20 provides the method of any of Embodiments 18-19, wherein the breast cancer is ER/PR/HER2 triple negative breast cancer.

Embodiment 21 provides the method of Embodiment 19, wherein the brain cancer is glioblastoma.

Embodiment 22 provides the method of any of Embodiments 18-21, wherein the cancer is HER2-positive.

Embodiment 23 provides the method of Embodiment 22, wherein the HER2-positive cancer is breast cancer.

Embodiment 24 provides the method of any of Embodiments 19-20 and 22-23, wherein the breast cancer is ER/PR/HER2 triple positive.

Embodiment 25 provides the method of any of Embodiments 18-24, wherein the cancer is EGFR-positive.

Embodiment 26 provides the method of any of Embodiments 18-19 and 22-25, wherein the cancer is breast cancer.

Embodiment 27 provides the method of any of Embodiments 18-26, wherein the cancer is PI3 kinase mutant-positive Embodiment 28 provides the method of any of Embodiments 13-26, wherein the compound is formulated in a pharmaceutical composition.

Embodiment 28 provides the method of any of Embodiments 13 and 15-28, wherein the subject is further administered at least one additional anticancer agent.

Embodiment 30 provides the method of any of Embodiments 13 and 15-29, wherein the subject is a mammal.

Embodiment 31 provides the method of Embodiment 30, wherein the mammal is human.

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

What is claimed is:

1. A compound of Formula (I), or an enantiomer, diastereoisomer, tautomer, salt, and/or solvate thereof:

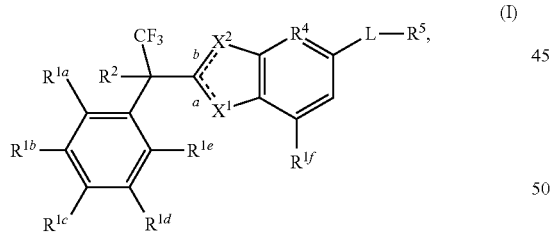

wherein:
one of the following applies:
(a) $X^1$ is N, $X^2$ is $N(CH_2-R^3)$, bond a is a double bond, and bond b is a single bond; or
(b) $X^1$ is $N(CH_2-R^3)$, $X^2$ is N, bond a is a single bond, and bond b is a double bond;
each occurrence of $R^{1a}$, $R^{1b}$, $R^{1c}$, $R^{1d}$, $R^{1e}$, $R^{1f}$, and $R^{1g}$ is independently selected from the group consisting of: H; $C_1$-$C_6$ alkyl; $C_3$-$C_8$ cycloalkyl; $C_1$-$C_6$ haloalkyl; —OH; $C_1$-$C_6$ alkoxy; halogen; —C≡N; —NR'R'; —C(=O)OR'; —C(=O) NR'R'; —S($C_1$-$C_6$ alkyl); —S(=O)($C_1$-$C_6$ alkyl); —S(=O)$_2$($C_1$-$C_6$ alkyl); —SO$_2$NR'R'; —C(=NR')—NR'R'; —NO$_2$; and $C_1$-$C_6$ alkyl optionally substituted with at least one selected from halogen, —OH, $C_1$-$C_6$ alkoxy, and —NR'R';
wherein each occurrence of R' is independently H, $C_1$-$C_6$ alkyl, or $C_3$-$C_8$ cycloalkyl;
$R^2$ is selected from the group consisting of —OH, —CN, and —SO$_2$($C_1$-$C_6$ alkyl);
$R^3$ is selected from the group consisting of H, $C_1$-$C_6$ alkyl, $C_3$-$C_8$ cycloalkyl, —OH, $C_1$-$C_6$ haloalkyl, $C_1$-$C_6$ alkoxy, and $C_1$-$C_6$ haloalkoxy;
$R^4$ is selected from the group consisting of $CR^{1g}$ and N;
L is selected from the group consisting of —O—*, —C(=O)NR—*, and —NR$^e$—(C=O)—NR—*,
wherein each occurrence of R and R$^e$ is independently selected from the group consisting of H, $C_1$-$C_6$ alkyl, and $C_3$-$C_8$ cycloalkyl, and
wherein the bond marked as * is to $R^5$;
$R^5$ is selected from the group consisting of $C_1$-$C_{10}$ alkyl, phenyl, and heteroaryl, any of each optionally independently substituted with at least one substituent independently selected from the group consisting of: H; $C_1$-$C_6$ alkyl; $C_3$-$C_8$ cycloalkyl; $C_1$-$C_6$ haloalkyl; optionally substituted phenyl; optionally substituted heterocyclyl; optionally substituted heteroaryl; —OH; $C_1$-$C_6$ alkoxy; heterocyclyl; halogen; —C≡N; —NR"R"; —C(=O)OR"; —C(=O) NR"R"; —S($C_1$-$C_6$ alkyl); —S(=O)($C_1$-$C_6$ alkyl); —S(=O)$_2$($C_1$-$C_6$ alkyl); —SO$_2$NR"R"; —C(=NR")—NR"R"; —NO$_2$; and $C_1$-$C_6$ alkyl optionally substituted with at least one selected from halogen, —OH, $C_1$-$C_6$ alkoxy, and —NR"R";

wherein each occurrence of R" is independently H, $C_1$-$C_6$ alkyl, or $C_3$-$C_8$ cycloalkyl; or -L-$R^5$ is optionally substituted heterocyclyl or —C(=O)(optionally substituted heterocyclyl).

2. The compound of claim 1, wherein $R^{1c}$ is $C_1$-$C_6$ alkyl; $C_3$-$C_8$ cycloalkyl; $C_1$-$C_6$ haloalkyl; —OH; $C_1$-$C_6$ alkoxy; halogen; —C≡N; —NR'R'; —C(=O)OR'; —C(=O)NR'R'; —S($C_1$-$C_6$ alkyl); —S(=O)($C_1$-$C_6$ alkyl); —S(=O)$_2$($C_1$-$C_6$ alkyl); —SO$_2$NR'R'; —C(=NR')—NR'R'; —NO$_2$; and $C_1$-$C_6$ alkyl optionally substituted with at least one selected from halogen, —OH, $C_1$-$C_6$ alkoxy, and —NR'R.

3. The compound of claim 1, which is a compound of Formula (Ia):

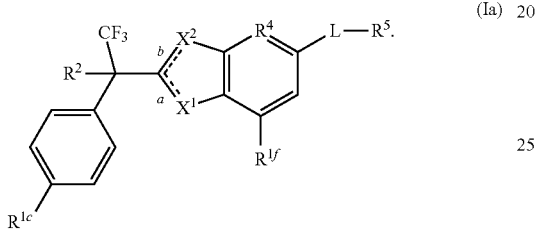

4. The compound of claim 1, which is selected from the group consisting of:

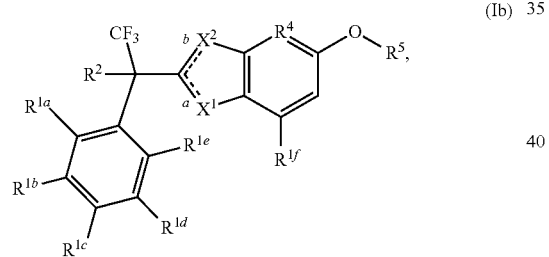

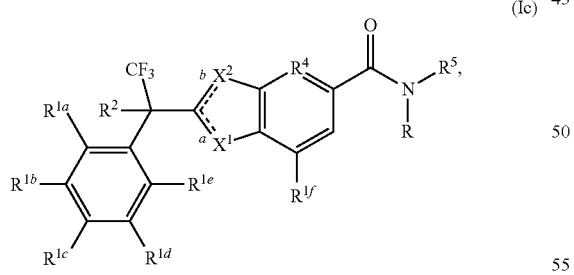

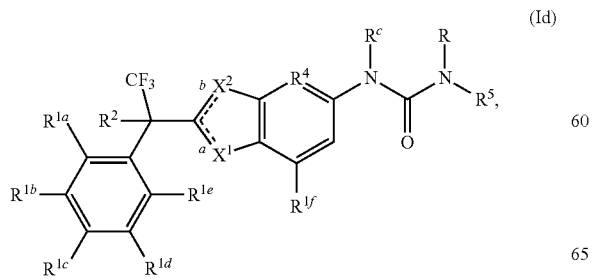

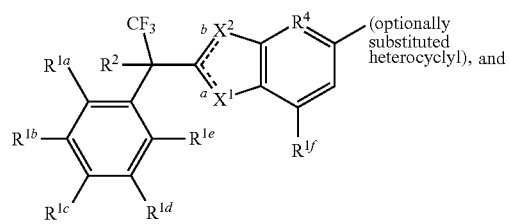

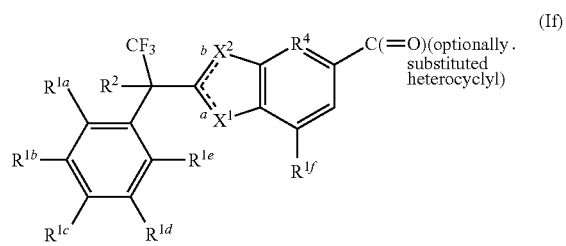

5. The compound of claim 1, which is selected from the group consisting of:

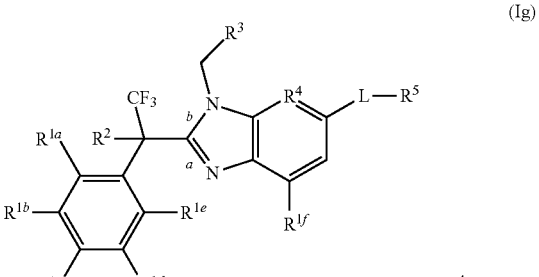

and

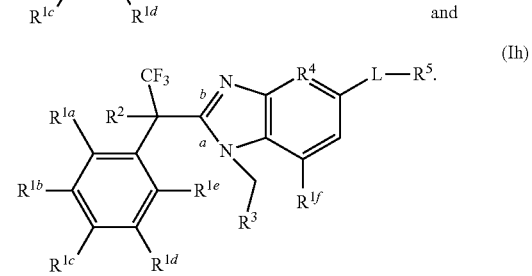

6. The compound of claim 1, which is selected from the group consisting of:

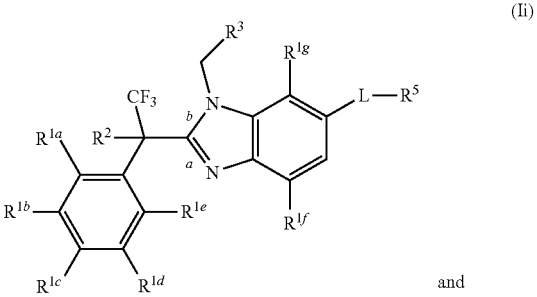

and

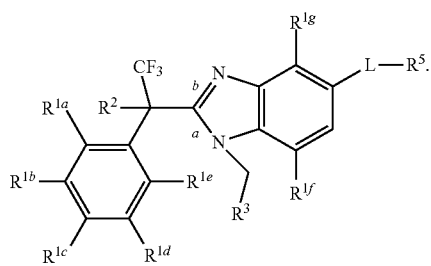
(Ij)
7. The compound of claim 1, which is selected from the group consisting of:
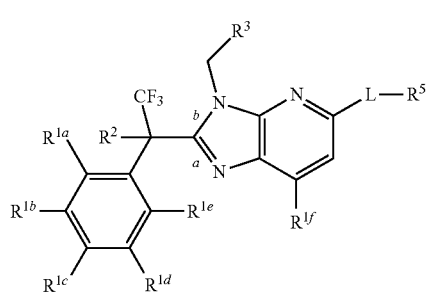
(Ik)
and
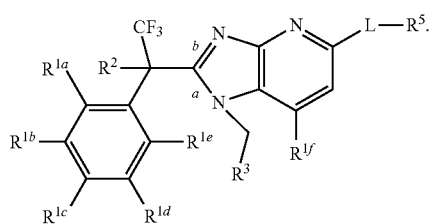
(Il)
8. The compound of claim 1, which is selected from the group consisting of:
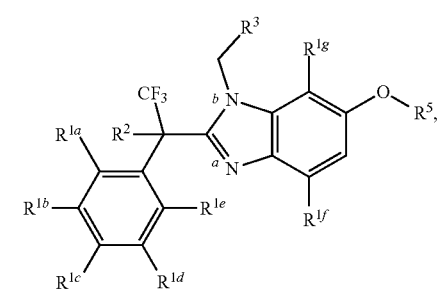
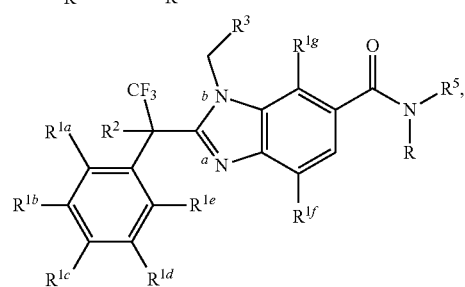
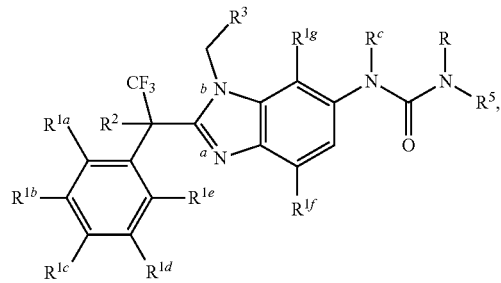
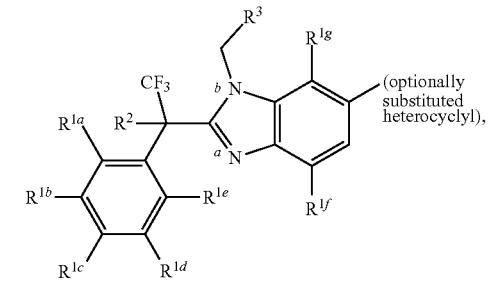
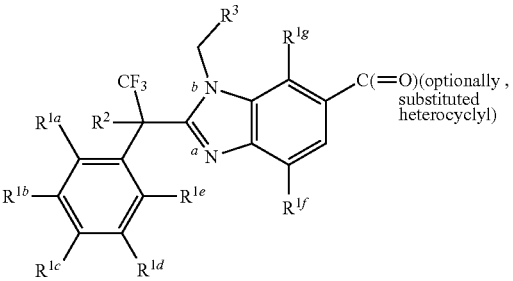
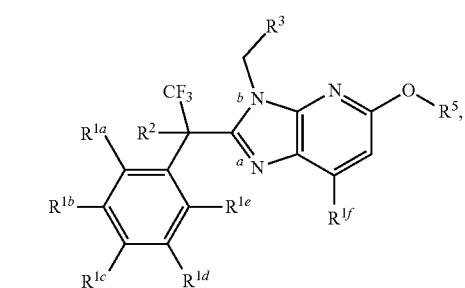
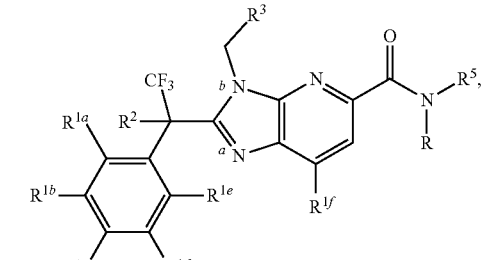
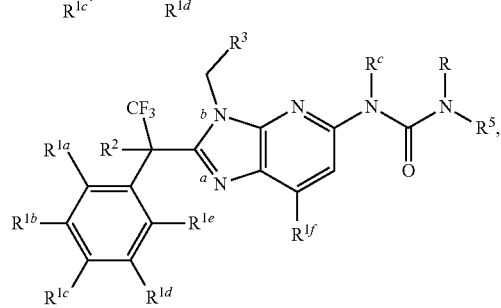

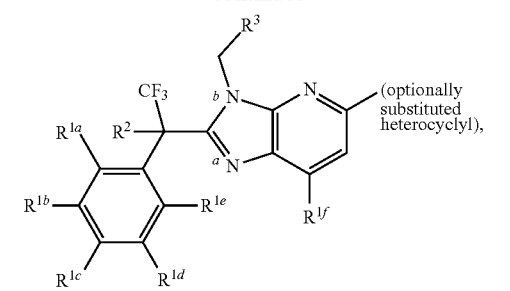
(optionally substituted heterocyclyl),
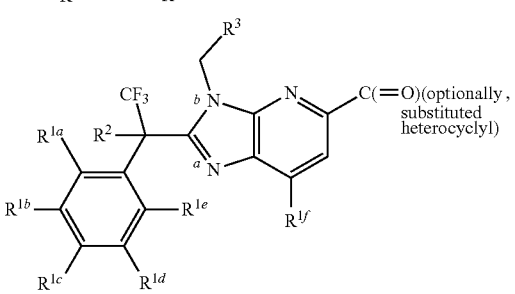
C(=O)(optionally, substituted heterocyclyl)
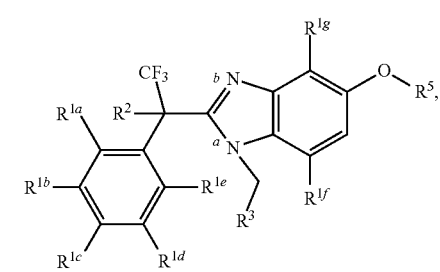
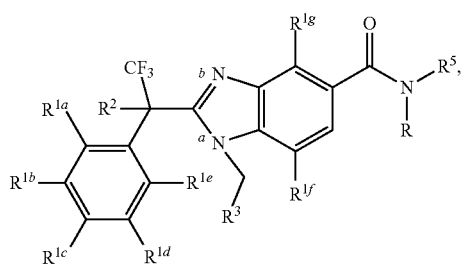
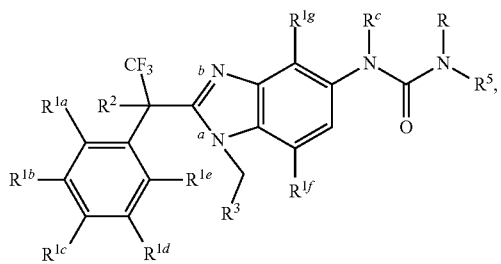
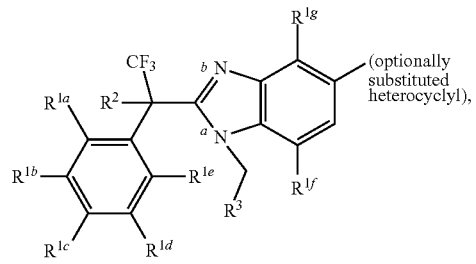
(optionally substituted heterocyclyl),
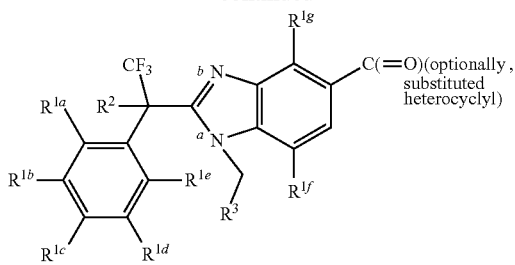
C(=O)(optionally, substituted heterocyclyl)
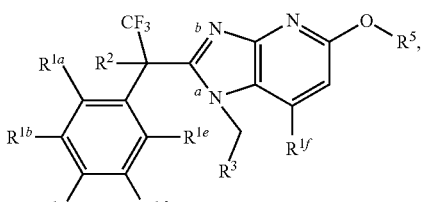
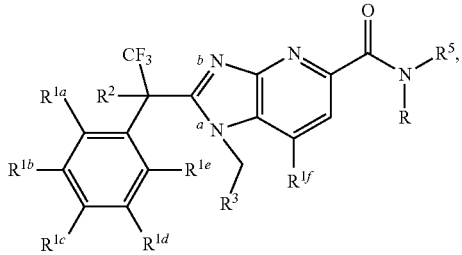
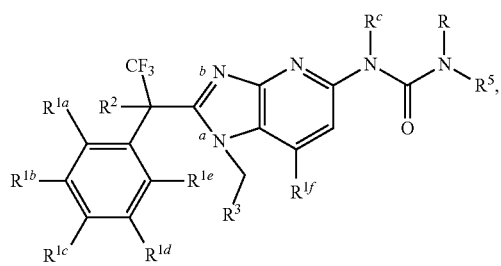
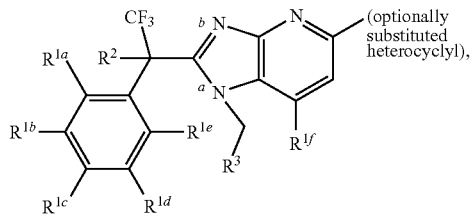
(optionally substituted heterocyclyl),
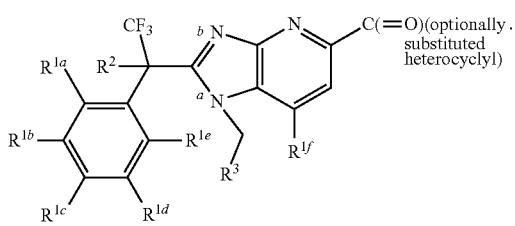
C(=O)(optionally. substituted heterocyclyl)
9. The compound of claim 1, which is selected from the group consisting of:

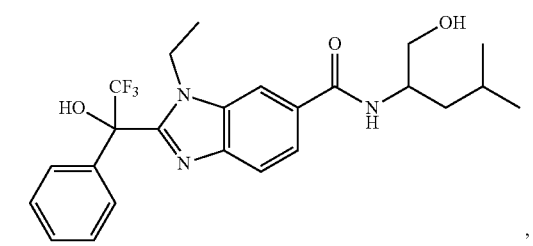
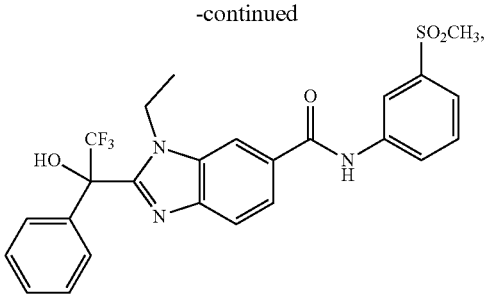
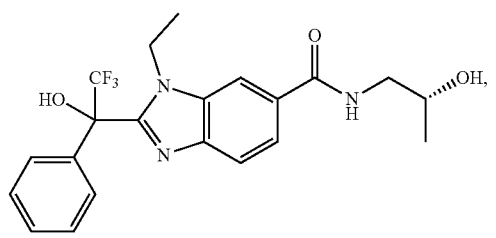
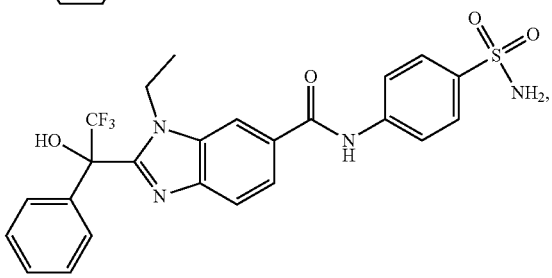
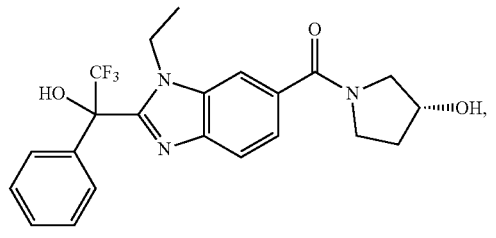
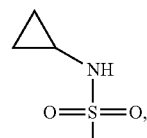
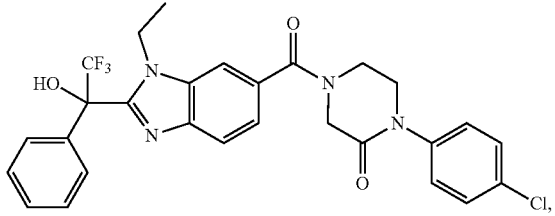
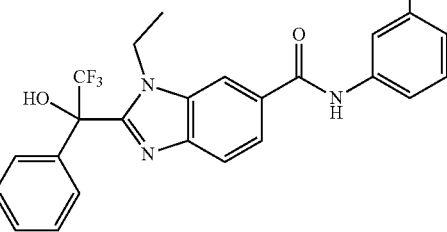
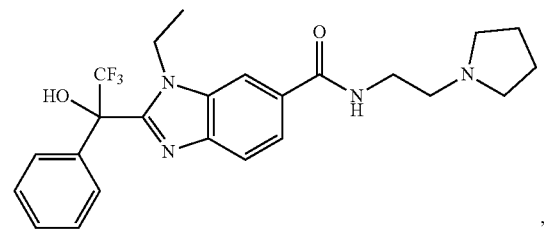
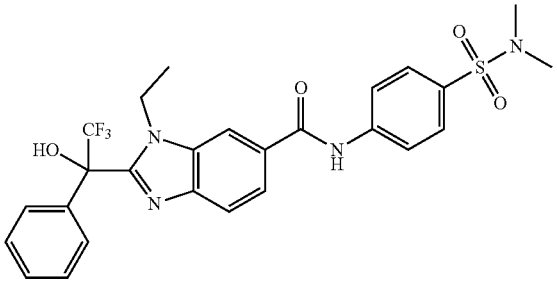
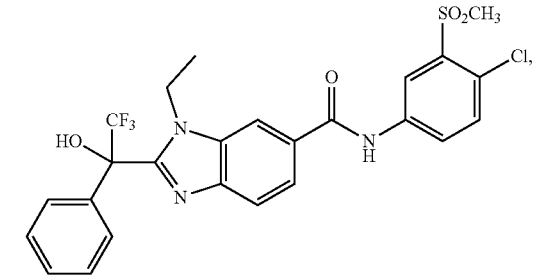
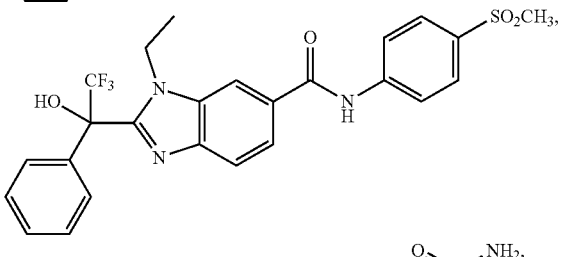
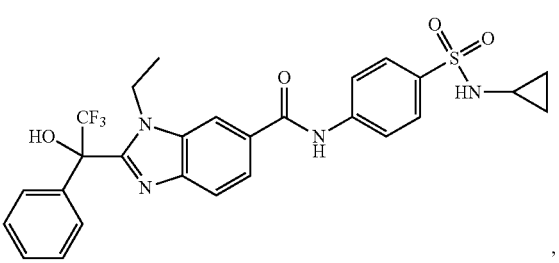
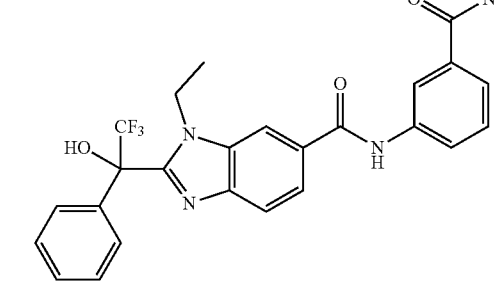

147
-continued
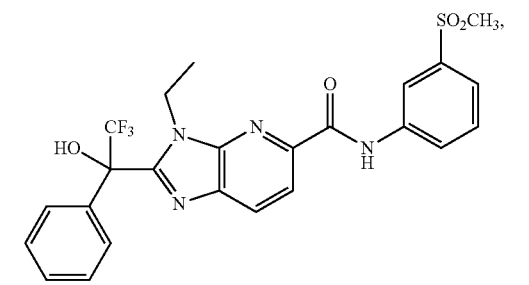
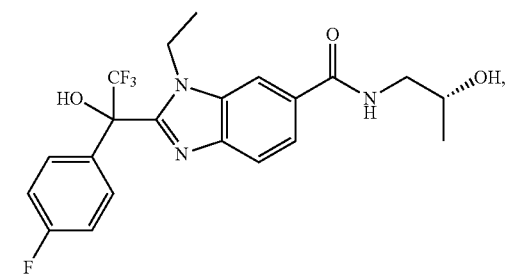
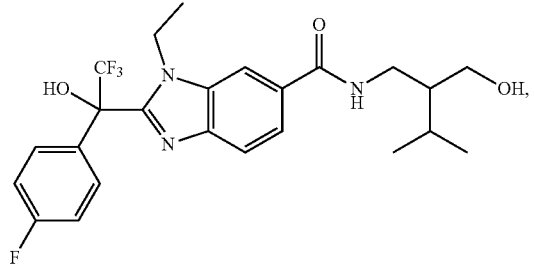
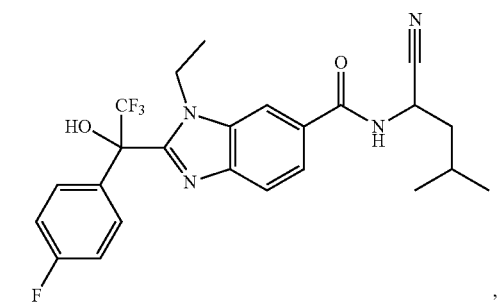
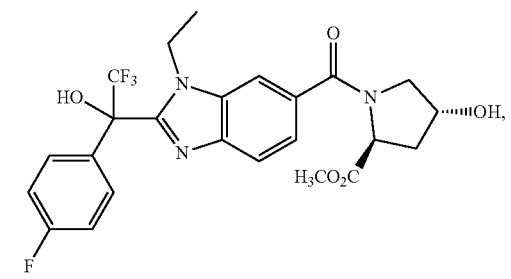
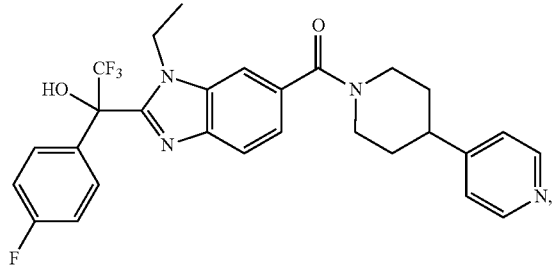
148
-continued
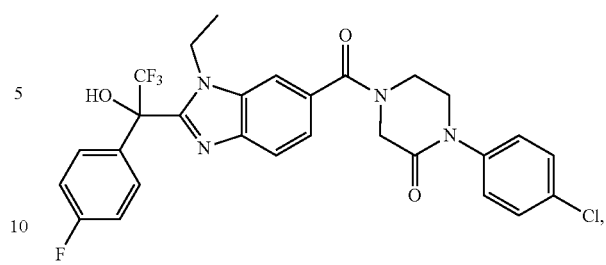
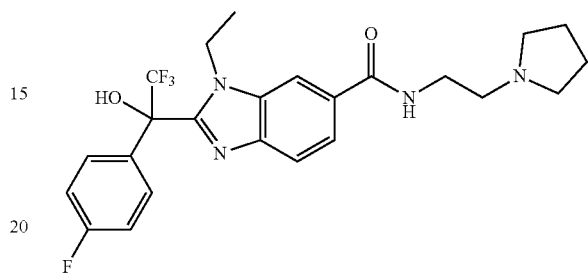
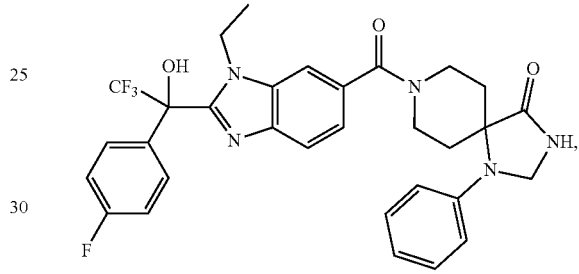
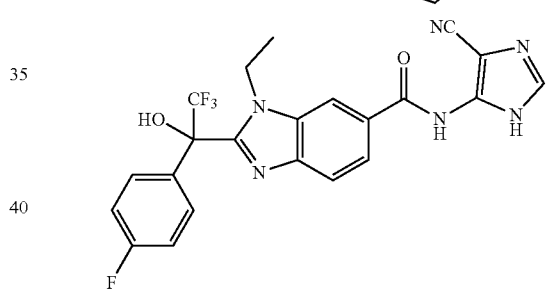
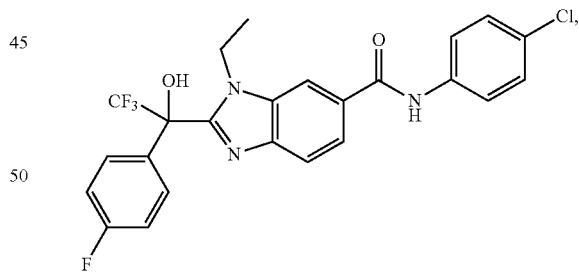
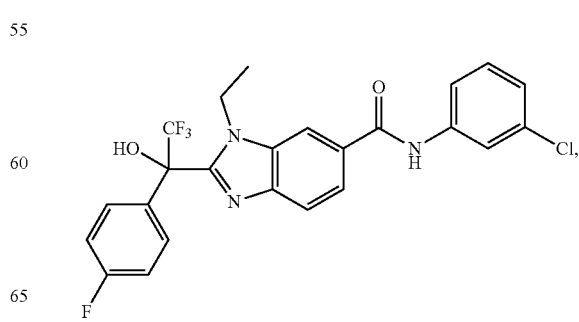

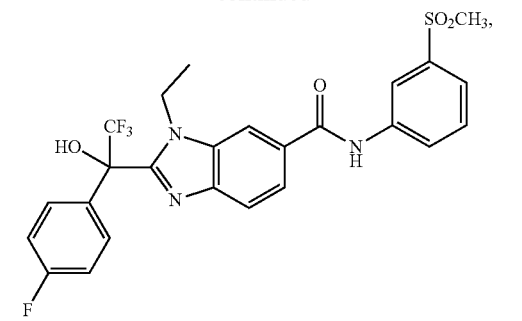
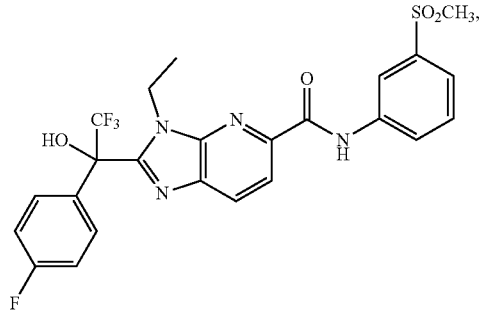
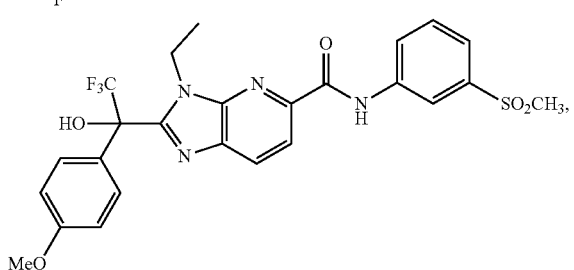
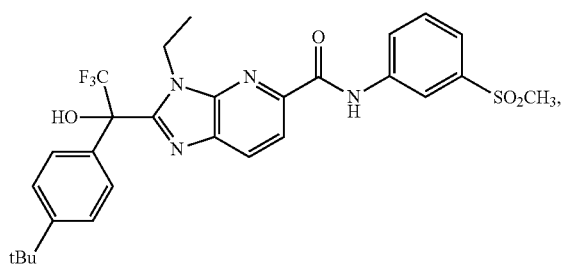
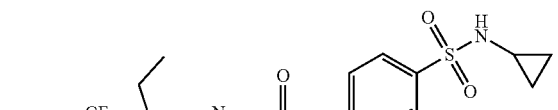
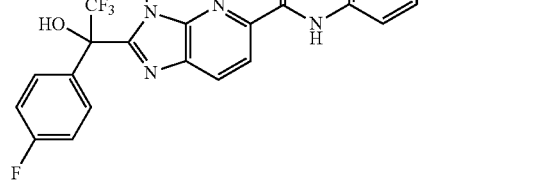
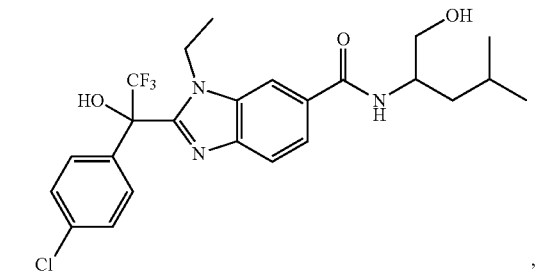
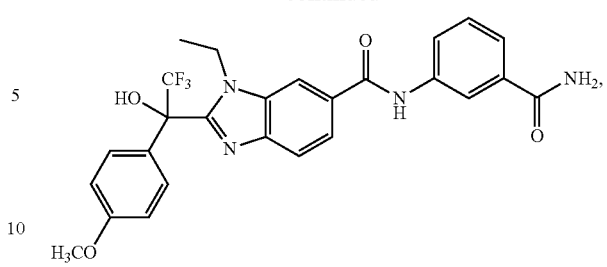
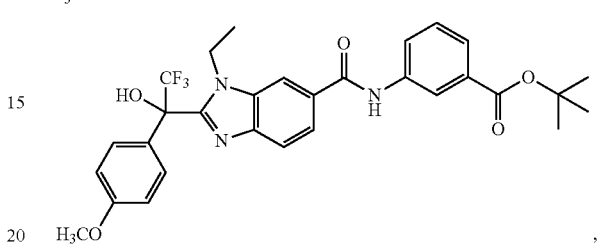
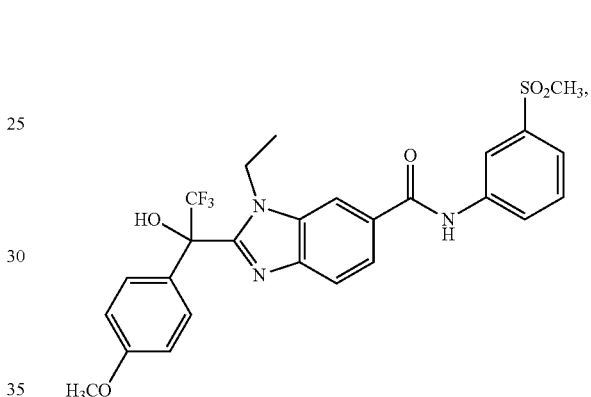
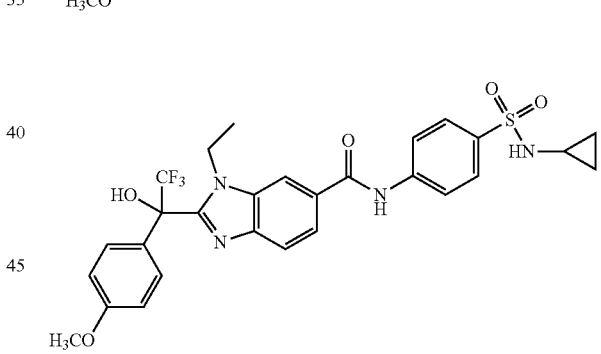
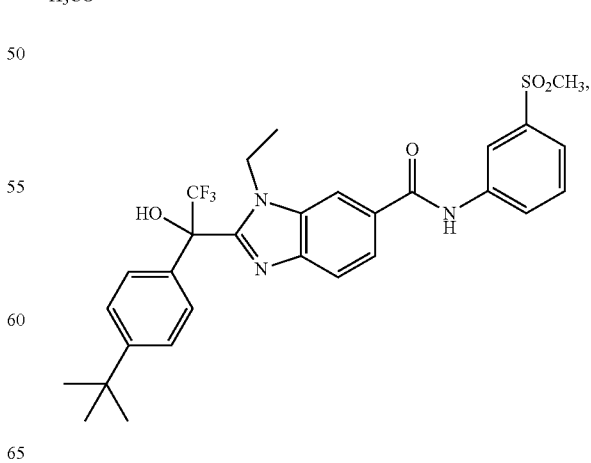

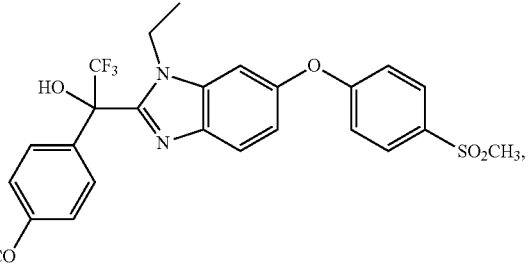
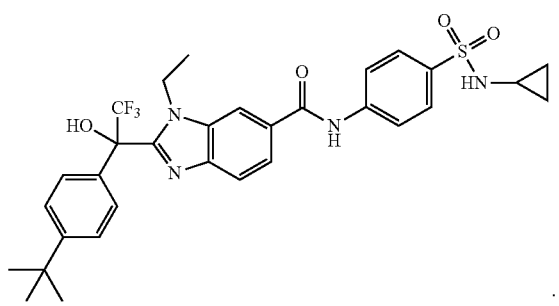 [SMILES: CCn1c(C(O)(c2ccc(C(C)(C)C)cc2)C(F)(F)F)nc2ccc(C(=O)Nc3ccc(S(=O)(=O)NC4CC4)cc3)cc21]
10. The compound of claim 1, which is selected from the group consisting of:
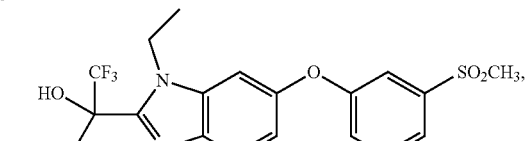
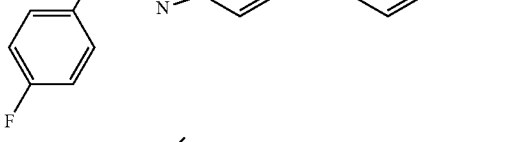
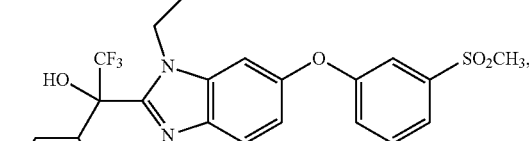
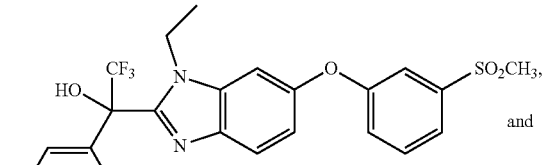
and
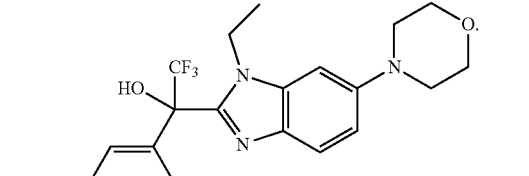
11. The compound of claim 1, which is selected from the group consisting of:
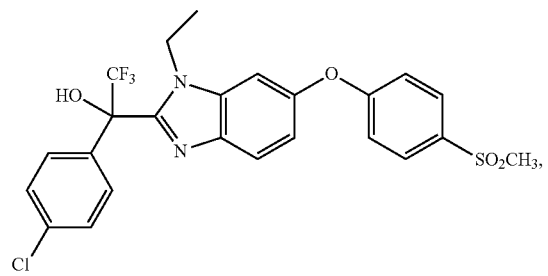
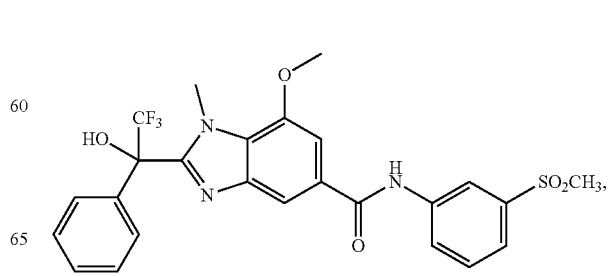

-continued
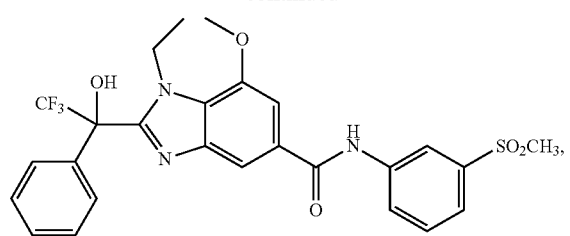
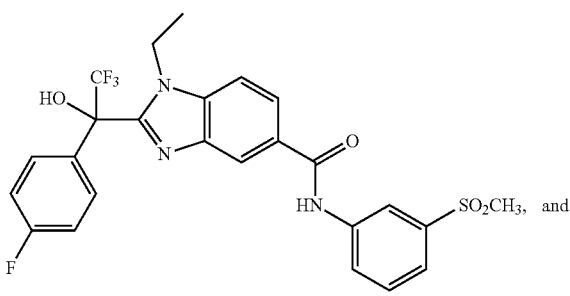
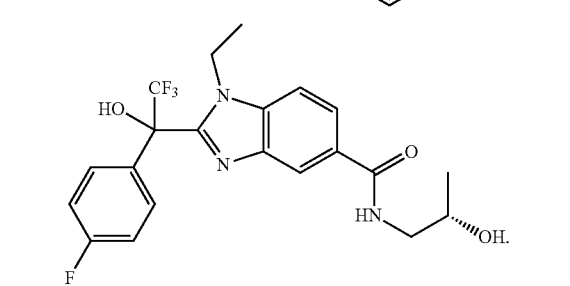
12. The compound of claim 1, wherein L-R$^5$ is selected from the group consisting of:
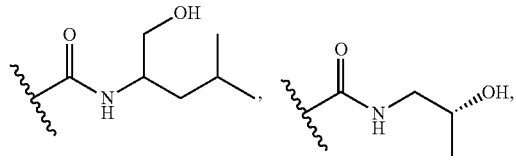
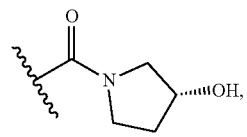
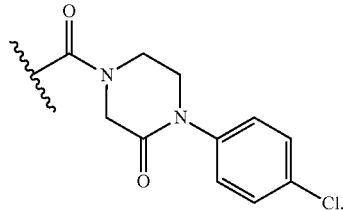
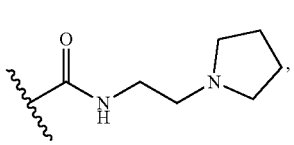
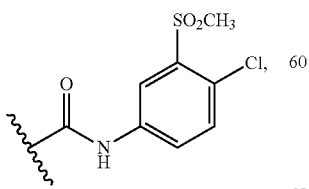
-continued
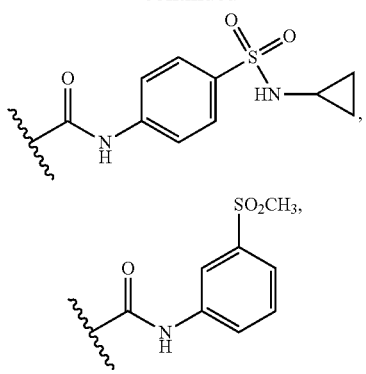
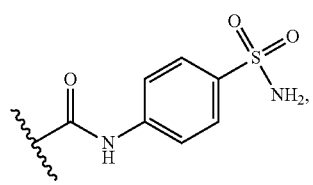
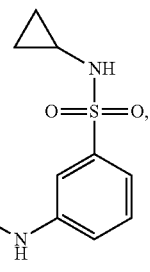
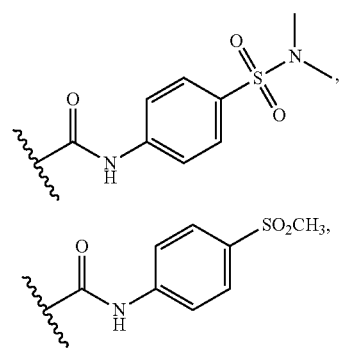

-continued

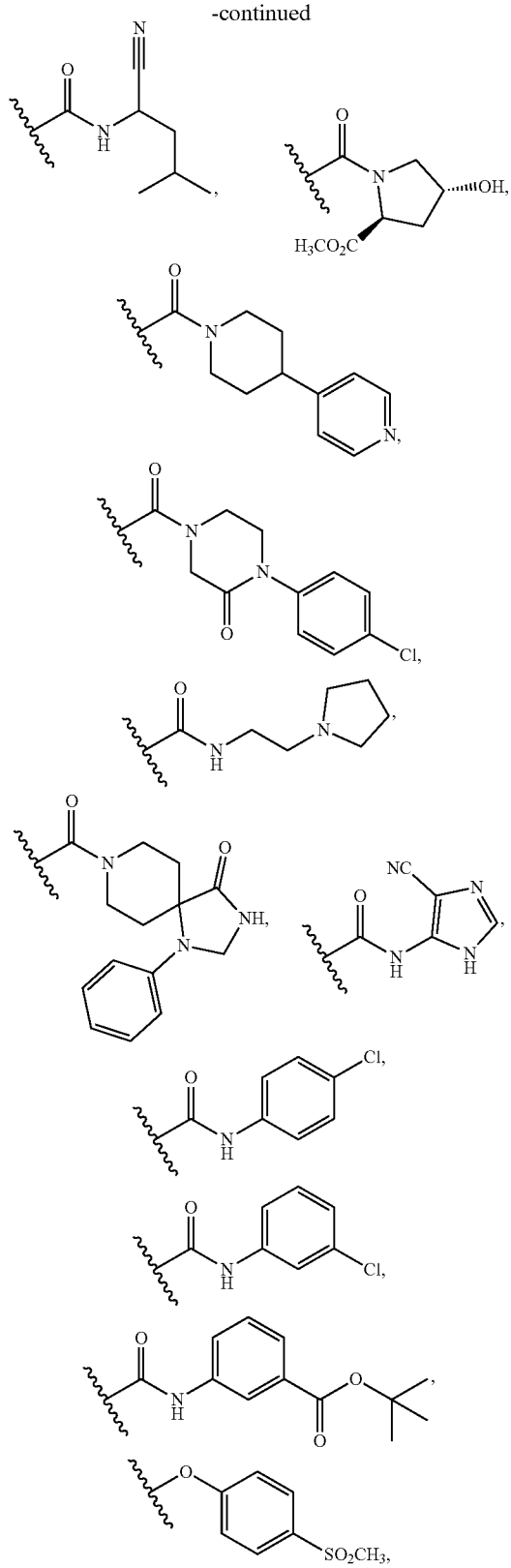

-continued

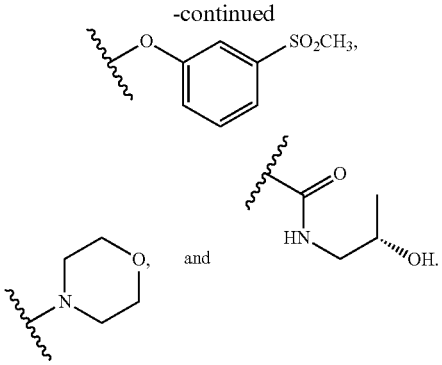

13. A method of treating, ameliorating, or preventing a disease or disorder that is caused, induced, or characterized by abnormal expression or activity of ACSS2 in a subject, the method comprising administering to the subject a therapeutically effective amount of the compound of claim 1.

14. A method of reducing the rate of, reversing, or preventing conversion of a non-metastatic cancer cell to a metastatic cancer cell, the method comprising contacting the cell with an effective amount of the compound of claim 1, optionally wherein the cell is in vivo in a subject.

15. A method of reducing the rate of, reversing, or preventing development of a hypoxic region in a cancer in a subject, the method comprising administering to the subject a therapeutically effective amount of the compound of claim 1.

16. A method of increasing effectiveness of chemotherapy, radiotherapy, or immunotherapy administered to a subject suffering from a cancer, the method comprising administering to the subject a therapeutically effective amount of the compound of claim 1 and at least one of chemotherapy, radiotherapy, and immunotherapy.

17. The method of claim 13, wherein the disease or disorder is cancer.

18. The method of claim 14, wherein the cancer comprises at least one of brain cancer, breast cancer, pancreatic cancer, sarcoma, prostate cancer, colorectal cancer, liver cancer, melanoma, ovarian cancer, and lung cancer.

19. The method of claim 18, wherein at least one of the following applies:
the cancer is breast cancer,
    optionally wherein the breast cancer is ER/PR/HER2 triple negative breast cancer;
the brain cancer is glioblastoma;
the cancer is HER2-positive,
    optionally wherein the HER2-positive cancer is breast cancer;
the cancer is EGFR-positive;
the cancer is PI3 kinase mutant-positive.

20. The method of claim 13, wherein at least one of the following applies:
the compound is formulated in a pharmaceutical composition;
the subject is further administered at least one additional anticancer agent;
the subject is a mammal,
    optionally wherein the mammal is a human.

* * * * *

SEQUENCE LISTING

<160> NUMBER OF SEQ ID NOS: 2

<210> SEQ ID NO 1
<211> LENGTH: 652
<212> TYPE: PRT
<213> ORGANISM: Salmonella typhimurium

<400> SEQUENCE: 1

```
Met Ser Gln Thr His Lys His Ala Ile Pro Ala Asn Ile Ala Asp Arg
1               5                   10                  15

Cys Leu Ile Asn Pro Glu Gln Tyr Glu Thr Lys Tyr Lys Gln Ser Ile
                20                  25                  30

Asn Asp Pro Asp Thr Phe Trp Gly Glu Gln Gly Lys Ile Leu Asp Trp
            35                  40                  45

Ile Thr Pro Tyr Gln Lys Val Lys Asn Thr Ser Phe Ala Pro Gly Asn
    50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
                85                  90                  95

Trp Glu Gly Asp Asp Thr Ser Gln Ser Lys His Ile Ser Tyr Arg Glu
                100                 105                 110

Leu His Arg Asp Val Cys Arg Phe Ala Asn Thr Leu Leu Asp Leu Gly
            115                 120                 125

Ile Lys Lys Gly Asp Val Val Ala Ile Tyr Met Pro Met Val Pro Glu
    130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Ser Ser Arg Leu Val Ile Thr Ala Asp Glu Gly Val Arg Ala
                180                 185                 190

Gly Arg Ser Ile Pro Leu Lys Lys Asn Val Asp Asp Ala Leu Lys Asn
            195                 200                 205

Pro Asn Val Thr Ser Val Glu His Val Ile Val Leu Lys Arg Thr Gly
    210                 215                 220

Ser Asp Ile Asp Trp Gln Glu Gly Arg Asp Leu Trp Trp Arg Asp Leu
225                 230                 235                 240

Ile Glu Lys Ala Ser Pro Glu His Gln Pro Glu Ala Met Asn Ala Glu
                245                 250                 255

Asp Pro Leu Phe Ile Leu Tyr Thr Ser Gly Ser Thr Gly Lys Pro Lys
                260                 265                 270

Gly Val Leu His Thr Thr Gly Gly Tyr Leu Val Tyr Ala Ala Thr Thr
            275                 280                 285

Phe Lys Tyr Val Phe Asp Tyr His Pro Gly Asp Ile Tyr Trp Cys Thr
    290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335
```

Pro Thr Pro Ala Arg Met Cys Gln Val Val Asp Lys His Gln Val Asn
                340                 345                 350

Ile Leu Tyr Thr Ala Pro Thr Ala Ile Arg Ala Leu Met Ala Glu Gly
            355                 360                 365

Asp Lys Ala Ile Glu Gly Thr Asp Arg Ser Ser Leu Arg Ile Leu Gly
        370                 375                 380

Ser Val Gly Glu Pro Ile Asn Pro Glu Ala Trp Glu Trp Tyr Trp Lys
385                 390                 395                 400

Lys Ile Gly Lys Lys Cys Pro Val Val Asp Thr Trp Trp Gln Thr
                405                 410                 415

Glu Thr Gly Gly Phe Met Ile Thr Pro Leu Pro Gly Ala Ile Glu Leu
            420                 425                 430

Lys Ala Gly Ser Ala Thr Arg Pro Phe Phe Gly Val Gln Pro Ala Leu
        435                 440                 445

Val Asp Asn Glu Gly His Pro Gln Glu Gly Ala Thr Glu Gly Asn Leu
    450                 455                 460

Val Ile Thr Asp Ser Trp Pro Gly Gln Ala Arg Thr Leu Phe Gly Asp
465                 470                 475                 480

His Glu Arg Phe Glu Gln Thr Tyr Phe Ser Thr Phe Lys Asn Met Tyr
                485                 490                 495

Phe Ser Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Leu Gly
        515                 520                 525

Thr Ala Glu Ile Glu Ser Ala Leu Val Ala His Pro Lys Ile Ala Glu
    530                 535                 540

Ala Ala Val Val Gly Ile Pro His Ala Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
            580                 585                 590

Pro Asp Val Leu His Trp Thr Asp Ser Leu Pro Lys Thr Arg Ser Gly
        595                 600                 605

Lys Ile Met Arg Arg Ile Leu Arg Lys Ile Ala Ala Gly Asp Thr Ser
    610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650

<210> SEQ ID NO 2
<211> LENGTH: 701
<212> TYPE: PRT
<213> ORGANISM: Homo sapiens

<400> SEQUENCE: 2

Met Gly Leu Pro Glu Glu Arg Val Arg Ser Gly Ser Gly Ser Arg Gly
1               5                   10                  15

Gln Glu Glu Ala Gly Ala Gly Gly Arg Ala Arg Ser Trp Ser Pro Pro
            20                  25                  30

Pro Glu Val Ser Arg Ser Ala His Val Pro Ser Leu Gln Arg Tyr Arg
        35                  40                  45

Glu Leu His Arg Arg Ser Val Glu Glu Pro Arg Glu Phe Trp Gly Asp
    50                  55                  60

```
Ile Ala Lys Glu Phe Tyr Trp Lys Thr Pro Cys Pro Gly Pro Phe Leu
65                  70                  75                  80

Arg Tyr Asn Phe Asp Val Thr Lys Gly Lys Ile Phe Ile Glu Trp Met
                85                  90                  95

Lys Gly Ala Thr Thr Asn Ile Cys Tyr Asn Val Leu Asp Arg Asn Val
            100                 105                 110

His Glu Lys Lys Leu Gly Asp Lys Val Ala Phe Tyr Trp Glu Gly Asn
        115                 120                 125

Glu Pro Gly Glu Thr Thr Gln Ile Thr Tyr His Gln Leu Leu Val Gln
    130                 135                 140

Val Cys Gln Phe Ser Asn Val Leu Arg Lys Gly Ile Gln Lys Gly
145                 150                 155                 160

Asp Arg Val Ala Ile Tyr Met Pro Met Ile Pro Glu Leu Val Val Ala
                165                 170                 175

Met Leu Ala Cys Ala Arg Ile Gly Ala Leu His Ser Ile Val Phe Ala
            180                 185                 190

Gly Phe Ser Ser Glu Ser Leu Cys Glu Arg Ile Leu Asp Ser Ser Cys
        195                 200                 205

Ser Leu Leu Ile Thr Thr Asp Ala Phe Tyr Arg Gly Glu Lys Leu Val
    210                 215                 220

Asn Leu Lys Glu Leu Ala Asp Glu Ala Leu Gln Lys Cys Gln Glu Lys
225                 230                 235                 240

Gly Phe Pro Val Arg Cys Ile Val Val Lys His Leu Gly Arg Ala
                245                 250                 255

Glu Leu Gly Met Gly Asp Ser Thr Ser Gln Ser Pro Pro Ile Lys Arg
            260                 265                 270

Ser Cys Pro Asp Val Gln Ile Ser Trp Asn Gln Gly Ile Asp Leu Trp
        275                 280                 285

Trp His Glu Leu Met Gln Glu Ala Gly Asp Glu Cys Glu Pro Glu Trp
    290                 295                 300

Cys Asp Ala Glu Asp Pro Leu Phe Ile Leu Tyr Thr Ser Gly Ser Thr
305                 310                 315                 320

Gly Lys Pro Lys Gly Val Val His Thr Val Gly Gly Tyr Met Leu Tyr
                325                 330                 335

Val Ala Thr Thr Phe Lys Tyr Val Phe Asp Phe His Ala Glu Asp Val
            340                 345                 350

Phe Trp Cys Thr Ala Asp Ile Gly Trp Ile Thr Gly His Ser Tyr Val
        355                 360                 365

Thr Tyr Gly Pro Leu Ala Asn Gly Ala Thr Ser Val Leu Phe Glu Gly
    370                 375                 380

Ile Pro Thr Tyr Pro Asp Val Asn Arg Leu Trp Ser Ile Val Asp Lys
385                 390                 395                 400

Tyr Lys Val Thr Lys Phe Tyr Thr Ala Pro Thr Ala Ile Arg Leu Leu
                405                 410                 415

Met Lys Phe Gly Asp Glu Pro Val Thr Lys His Ser Arg Ala Ser Leu
            420                 425                 430

Gln Val Leu Gly Thr Val Gly Glu Pro Ile Asn Pro Glu Ala Trp Leu
        435                 440                 445

Trp Tyr His Arg Val Val Gly Ala Gln Arg Cys Pro Ile Val Asp Thr
    450                 455                 460

Phe Trp Gln Thr Glu Thr Gly Gly His Met Leu Thr Pro Leu Pro Gly
465                 470                 475                 480
```

```
Ala Thr Pro Met Lys Pro Gly Ser Ala Thr Phe Pro Phe Phe Gly Val
            485                 490                 495
Ala Pro Ala Ile Leu Asn Glu Ser Gly Glu Glu Leu Glu Gly Glu Ala
            500                 505                 510
Glu Gly Tyr Leu Val Phe Lys Gln Pro Trp Pro Gly Ile Met Arg Thr
            515                 520                 525
Val Tyr Gly Asn His Glu Arg Phe Glu Thr Thr Tyr Phe Lys Lys Phe
    530                 535                 540
Pro Gly Tyr Tyr Val Thr Gly Asp Gly Cys Gln Arg Asp Gln Asp Gly
545                 550                 555                 560
Tyr Tyr Trp Ile Thr Gly Arg Ile Asp Asp Met Leu Asn Val Ser Gly
                565                 570                 575
His Leu Leu Ser Thr Ala Glu Val Glu Ser Ala Leu Val Glu His Glu
            580                 585                 590
Ala Val Ala Glu Ala Ala Val Val Gly His Pro His Pro Val Lys Gly
            595                 600                 605
Glu Cys Leu Tyr Cys Phe Val Thr Leu Cys Asp Gly His Thr Phe Ser
    610                 615                 620
Pro Lys Leu Thr Glu Glu Leu Lys Lys Gln Ile Arg Glu Lys Ile Gly
625                 630                 635                 640
Pro Ile Ala Thr Pro Asp Tyr Ile Gln Asn Ala Pro Gly Leu Pro Lys
                645                 650                 655
Thr Arg Ser Gly Lys Ile Met Arg Arg Val Leu Arg Lys Ile Ala Gln
                660                 665                 670
Asn Asp His Asp Leu Gly Asp Met Ser Thr Val Ala Asp Pro Ser Val
            675                 680                 685
Ile Ser His Leu Phe Ser His Arg Cys Leu Thr Ile Gln
    690                 695                 700
```